US010206941B2

(12) United States Patent
von Andrian et al.

(10) Patent No.: US 10,206,941 B2
(45) Date of Patent: Feb. 19, 2019

(54) VENULE ENDOTHELIAL CELL GENES AND USES THEREOF

(71) Applicants: President and Fellows of Harvard College, Cambridge, MA (US); The Brigham and Women's Hospital, Inc., Boston, MA (US)

(72) Inventors: Ulrich H. von Andrian, Brookline, MA (US); Aude Thiriot, Brookline, MA (US); Omid Farokhzad, Waban, MA (US); Jinjun Shi, Boston, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/903,899

(22) PCT Filed: Jul. 9, 2014

(86) PCT No.: PCT/US2014/046037
§ 371 (c)(1),
(2) Date: Jan. 8, 2016

(87) PCT Pub. No.: WO2015/006500
PCT Pub. Date: Jan. 15, 2015

(65) Prior Publication Data
US 2016/0354403 A1 Dec. 8, 2016

Related U.S. Application Data

(60) Provisional application No. 61/844,372, filed on Jul. 9, 2013.

(51) Int. Cl.
*C12N 15/11* (2006.01)
*A61K 31/713* (2006.01)
*C07K 14/47* (2006.01)
*C12Q 1/6881* (2018.01)
*A61K 47/54* (2017.01)
*A61K 47/69* (2017.01)
*A61K 48/00* (2006.01)

(52) U.S. Cl.
CPC .......... *A61K 31/713* (2013.01); *A61K 47/543* (2017.08); *A61K 47/6929* (2017.08); *C07K 14/47* (2013.01); *C12Q 1/6881* (2013.01); *A61K 48/00* (2013.01); *C12Q 2600/136* (2013.01); *C12Q 2600/158* (2013.01); *C12Q 2600/16* (2013.01)

(58) Field of Classification Search
CPC ............................ C12N 15/111; C12N 15/113
See application file for complete search history.

(56) References Cited

U.S. PATENT DOCUMENTS

| 5,605,821 | A | 2/1997 | McEver et al. |
| 5,660,827 | A | 8/1997 | Thorpe et al. |
| 5,747,470 | A * | 5/1998 | Becherer ............ C12N 15/1138 424/450 |
| 5,767,241 | A | 6/1998 | McEver |
| 6,020,196 | A | 2/2000 | Hu et al. |
| 6,096,722 | A * | 8/2000 | Bennett ............. C12N 15/1138 435/325 |
| 6,528,487 | B1 | 3/2003 | Heavner et al. |
| 7,449,186 | B1 | 11/2008 | Masinovsky et al. |
| 8,231,895 | B2 | 7/2012 | De Almeida Moreira et al. |
| 8,377,440 | B2 | 2/2013 | McEver et al. |
| 2004/0220129 | A1* | 11/2004 | Reich ................. C12N 15/1138 514/44 A |
| 2005/0048529 | A1* | 3/2005 | McSwiggen ..... A61K 47/48092 435/6.16 |

(Continued)

FOREIGN PATENT DOCUMENTS

WO   WO 2000/053236 A2   9/2000
WO   WO 2006/086639      8/2006

(Continued)

OTHER PUBLICATIONS

Palombella et al., Role of the proteasome and NF-kappaB in streptococcal cell wall-induced polyarthritis, 1998, PNAS, vol. 95, pp. 15671-15676.*
Kang et al., Regulation of early adipose commitment by Zfp521, 2012, PLOS Biology, vol. 10, issue 11, e1001433, pp. 1-9.*
Xu et al., Discovery of a novel orally active small-molecule gp130 inhibitor for the treatment of ovarian cancer, 2013, Molecular Cancer Therapeutics, vol. 12, pp. 937-949.*
Mantovani et al., Turning inflammation and immunity by chemokine sequestration: decoys and more, Nature Reviews Immunology, vol. 6, pp. 907-918. (Year: 2006).*
Benson et al., Deletion of the Duffy antigen receptor for chemokines (DARC) promotes insulin resistance and adipose tissue inflammation during high fact feeding, Molecular and Cellular Endocrinology, 10 pages. (Year: 2018).*

(Continued)

*Primary Examiner* — Dana H Shin
(74) *Attorney, Agent, or Firm* — Clark & Elbing LLP

(57) ABSTRACT

Disclosed herein are genes which are differentially expressed in venule endothelial cells (V-ECs) compared to non-venule endothelial cells (NV-ECs) and methods and compositions relating to those genes. Also disclosed herein are methods of modulating the venuleness of an endothelial cell or microvessel, methods of modulating leukocyte trafficking, methods of modulating inflammation, methods of targeting agents to tissues based on their ability to bind to surface markers expressed in a microvessel (e.g., venules and non-venules), methods of identifying the venuleness of endothelial cells or microvessels, methods of identifying agents that modulate the venuleness of endothelial cells or microvessels, methods of identifying agents that target microvessels, methods for treating diseases associated with leukocyte trafficking, methods for treating inflammatory diseases, and compositions and kits for use in the methods.

2 Claims, 26 Drawing Sheets
(23 of 26 Drawing Sheet(s) Filed in Color)

(56) References Cited

U.S. PATENT DOCUMENTS

| 2005/0118164 | A1 | 6/2005 | Herman |
| 2006/0024231 | A1 | 2/2006 | Schnitzer et al. |
| 2007/0160531 | A1 | 7/2007 | Schnitzer |
| 2008/0107621 | A1 | 5/2008 | Dreano et al. |
| 2009/0017030 | A1 | 1/2009 | St Croix et al. |
| 2009/0092663 | A1 | 4/2009 | Ponzoni et al. |
| 2013/0102546 | A1* | 4/2013 | Feinberg ............ A61K 31/7105 514/20.9 |
| 2013/0109737 | A1 | 5/2013 | Young et al. |
| 2015/0232837 | A1* | 8/2015 | Thibonnier .......... C12N 15/113 514/44 A |
| 2016/0339113 | A1 | 11/2016 | Von Andrian |

FOREIGN PATENT DOCUMENTS

| WO | WO 2010/103118 | A1 | 9/2010 | |
| WO | WO-2011127175 | A1 * | 10/2011 | ......... C12N 15/1138 |
| WO | WO 2015/006500 | | 1/2015 | |
| WO | WO 2015/006501 | | 1/2015 | |

OTHER PUBLICATIONS

Lacorre, et al., "Plasticity of Endothelial Cells: Rapid Dedifferentiation of Freshly Isolated High Endothelial Venule Endothelial Cells Outside the Lymphoid Tissue Microenvironment," *Blood*, 103(11):4164-4172, (Jun. 2004).
Supplementary Partial European Search Report from EP 14 82 2681, dated Dec. 8, 2016.
Dahlman et al., "In vivo endothelial siRNA delivery using polymeric nanoparticles with low molecular weight," *Nature Nanotechnology*, Published Online: May 11, 2014:1-6.
Gp130/CD130 Phycoerythrin-Labeled Mouse Monoclonal Antibody. Neuromics catalog No. FC15014.
Hadley et al., "Postcapillary venule endothelial cells in kidney express a multispecific chemokine receptor that is structurally and functionally Identical to the erythroid isoform, which is the Duffy blood group antigen," *J Clion Invest.*, 94:985-991, (1994).
Halin et al., "In vivo imaging of lymphocyte trafficking," *Annu Rev Cell Dev Biol.*, 21:581-603, (2005).
Jo et al., "VEGF-binding aptides and the inhibition of choroidal and retinal Neovascularization," *Biomaterials*, 35(9):3052-3059, Abstract, (2014).
Jon et al., "Aptide-based Nanomedicine for Cancer Imaging and Therapy," *Cell Dynamics Research Center, School of Life Sciences, Gwangju Institute of Science and Technology (GIST)*, Gwangju pp. 500-712, Korea.
Kang et al., "Regulation of Early Adipose Commitment by Zfp521," *PLOS Biology*, 10(11):1-9, (2012).
Ley et al., "Endothelial, not hemodynamic, differences are responsible for preferential leukocyte rolling in rat mesenteric venules," *Circulation Research*, 69:1034-1041, (1991).

Luster et al., "Immune cell migration in inflammation: present and future therapeutic targets," *Nature Immunology* 6(12):1182-1190, (2005).
Nielsen et al, "Sequence-selective recognition of DNA by strand displacement with a thymine-substituted polyamide," *Science*, 254(5037):1497-1500, Abstract, (1991).
Park et al., "Fibronectin extra domain B-specific aptide conjugated nanoparticles for targeted cancer imaging," *J. Control Release*, 163(2):111-118, Abstract, (2012).
Park et al., "HER2-specific aptide conjugated magneto-nanoclusters for potential breast cancer imaging and therapy," *J. Mater. Chem. B.*, 1:4576-4583, Abstract, (2013).
Peiper et al., "The Duffy antigen/receptor for chemokines (DARC) is expressed in endothelial cells of Duffy negative individuals who lack the erythrocyte receptor," *J. Exp Med.*, 181:1311-1317, (1995).
von Andrian et al., "T-cell function and migration. Two sides of the same coin," *New Engl Jour Med.*, 343(14):1020-1034, (2000).
von Andrian, "Segmental specialization of endothelial cells: A new approach to drug discovery and anti-inflammatory therapy," *UCB Meeting*, HMS, Boston, Feb. 13, 2013.
Yao et al, "Elevated CXCL1 expression in gp130-deficient endothelial cells impairs neutrophil migration in mice," *Blood*, 122(23):3832-3842, (2013).
von Andrian, Ulrich H. Abstract "T Cell Activation in Lymph Nodes." National Institutes of Health Grant No. 1R01AI069259-01 (Funding Start Date Mar. 1, 2006).
von Andrian, Ulrich H. Abstract "Anti-Viral Immune Responses in Lymph Node." National Institutes of Health Grant No. 1P01AI078897-01 (Funding Start Date Aug. 15, 2008).
International Search Report for International Application PCT/US2014/46037, dated Dec. 24, 2014.
International Search Report for International Application PCT/US2014/46039, dated Dec. 30, 2014.
Malik, "Targeting Endothelial Cell Surface Receptors: Novel Mechanisms of Microvascular Endothelial Barrier Transport," *Journal of Medical Sciences*, 2(2):13-17, (2009).
Massey, et al., "Targeting and Imaging Signature Caveolar Molecules in Lungs," *Proceedings of the American Thoracic Society*, 6:419-430, (2009).
Simone, et al., "Targeted Delivery of Therapeutics to Endothelium," *Cell and Tissue Research*, 335(1):283-300, (Sep. 25, 2008).
Muzykantov, et al., "Dynamic Factors Controlling Targeting Nanocarriers to Vascular Endothelium," *Curr. Drug Metab.*, 13(1):70-81, (Jan. 1, 2012).
Extended European Search Report from EP 14823750.6, dated Feb. 14, 2017.
Taga, et al., "GP130 and the Interleukin-6-Family of Cytokines," *Annu. Rev. Immunol.*, 15:797-819, (1997).
Wang, et al., "CD44 Antibody-Targeted Liposomal Nanoparticles for Molecular Imaging and Therapy of Hepatocellular Carcinoma," *Biomaterial*, 33:5107-5114, (2012).
Extended European Search Report from EP 14822681.4, dated Mar. 24, 2017.
Non-Final Office Action from U.S. Appl. No. 14/903,964 dated May 5, 2017.

* cited by examiner

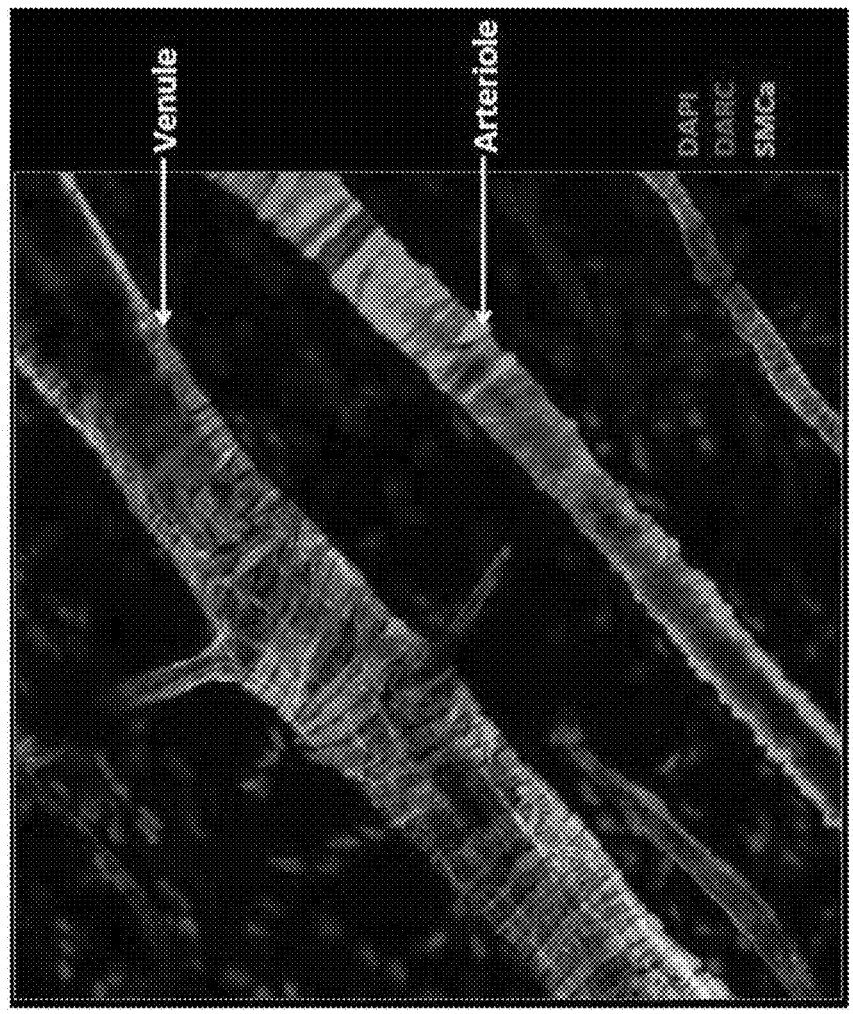

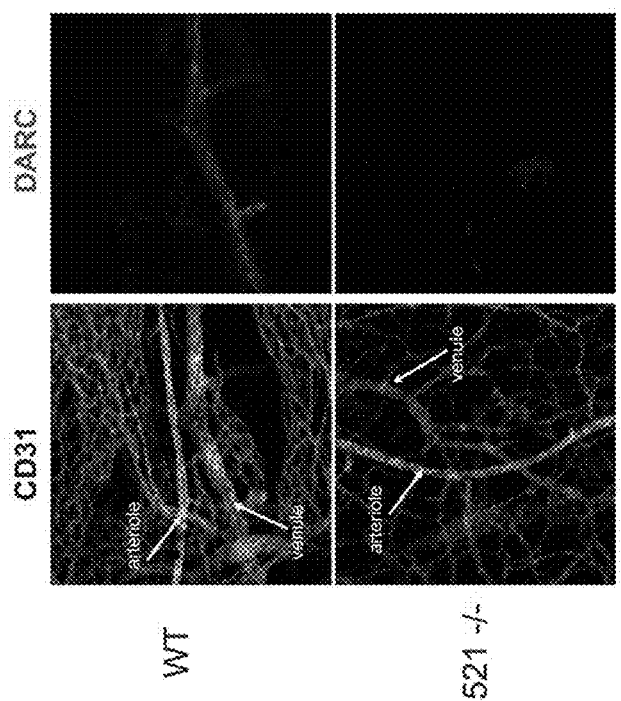
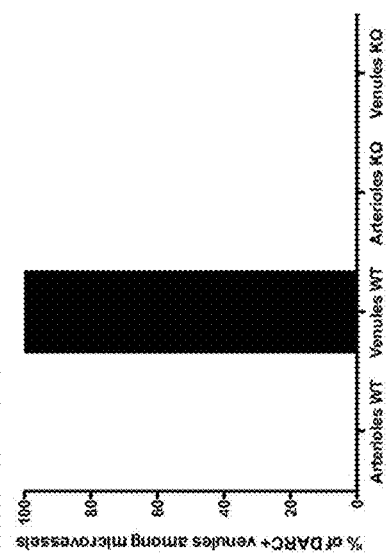
Figure 22
Absence of DARC expression on venules from Zfp521 ko newborn mice at day 1

VENULE ENDOTHELIAL CELL GENES AND USES THEREOF

RELATED APPLICATIONS

This application is a national stage filing under 35 U.S.C. 371 of International Application No. PCT/US2014/46037, filed Jul. 9, 2014, which claims the benefit of U.S. Provisional Application Ser. No. 61/844,372, filed Jul. 9, 2013, the teachings of which are incorporated herein by reference in their entirety. International Application PCT/US2014/46037 was published under PCT Article 21(2) in English

GOVERNMENT SUPPORT

This invention was made with government support under RO1 AI069259 and PO1 AI078897 awarded by the National Institute of Allergy and Infectious Diseases of the National Institutes of Health. The government has certain rights in the invention.

BACKGROUND OF THE INVENTION

Current anti-inflammatory drugs, such as corticoids, non-steroidal drugs and biologics, typically act systemically and thus affect both healthy and damaged tissues. Adverse side effects include gastrointestinal and renal effects as well as, in some cases, an increased susceptibility to infection linked to impaired leukocyte interactions with healthy tissue. There are currently no FDA-approved anti-inflammatory agents that selectively target the endothelium, much less tissue-specific vascular beds that promote inflammation. Accordingly, there is a need for agents (e.g., anti-inflammatory agents) that specifically target venular endothelium, either globally or in a tissue-specific manner.

SUMMARY OF THE INVENTION

In some aspects, disclosed herein is a method of modulating the venuleness of an endothelial cell, comprising contacting the endothelial cell with an effective amount of an agent that modulates expression of at least one gene that is differentially expressed in venule endothelial cells compared to non-venule endothelial cells.

In some embodiments, modulating the venuleness of the endothelial cell comprises changing the endothelial cell from a venule endothelial cell to a non-venule endothelial cell.

In some embodiments, the agent: (a) decreases expression of at least one gene exhibiting higher expression levels in venule endothelial cells compared to non-venule endothelial cells; (b) increases expression of at least one gene exhibiting lower expression levels in venule endothelial cells compared to non-venule endothelial cells; (c) increases expression of at least one gene exhibiting higher expression levels in non-venule endothelial cells compared to venule endothelial cells; or (d) decreases expression of at least one gene exhibiting lower expression levels in non-venule endothelial cells compared to venule endothelial cells.

In some embodiments, the at least one gene exhibiting higher expression levels in venule endothelial cells compared to non-venule endothelial cells is selected from the group consisting of a gene, or combination of genes, listed in Table 1. In some embodiments, the at least one gene exhibiting lower expression levels in venule endothelial cells compared to non-venule endothelial cells is selected from the group consisting of a gene, or combination of genes, listed in Table 8. In some embodiments, the at least one gene exhibiting higher expression levels in non-venule endothelial cells compared to venule endothelial cells is selected from the group consisting of a gene, or combination of genes, listed in Table 8. In some embodiments, the at least one gene exhibiting lower expression levels in non-venule endothelial cells compared to venule endothelial cells is selected from the group consisting of a gene, or combination of genes, listed in Table 1.

In some embodiments, modulating the venuleness of the endothelial cell comprises changing the endothelial cell from a non-venule endothelial cell to a venule endothelial cell. In some embodiments, the agent: (a) increases expression of at least one gene exhibiting higher expression levels in venule endothelial cells compared to non-venule endothelial cells; (b) decreases expression of at least one gene exhibiting lower expression levels in venule endothelial cells compared to non-venule endothelial cells; (c) decreases expression of at least one gene exhibiting higher expression levels in non-venule endothelial cells compared to venule endothelial cells; or (d) increases expression of at least one gene exhibiting lower expression levels in non-venule endothelial cells compared to venule endothelial cells.

In some embodiments, the at least one gene exhibiting higher expression levels in venule endothelial cells compared to non-venule endothelial cells is selected from the group consisting of a gene, or combination of genes, listed in Table 1. In some embodiments, the at least one gene exhibiting lower expression levels in venule endothelial cells compared to non-venule endothelial cells is selected from the group consisting of a gene, or combination of genes, listed in Table 8. In some embodiments, the at least one gene exhibiting higher expression levels in non-venule endothelial cells compared to venule endothelial cells is selected from the group consisting of a gene, or combination of genes, listed in Table 8. In some embodiments, the at least one gene exhibiting lower expression levels in non-venule endothelial cells compared to venule endothelial cells is selected from the group consisting of a gene, or combination of genes, listed in Table 1.

In some embodiments, the venuleness of the endothelial cells is modulated in a tissue-specific manner. In some embodiments, the endothelial cell is a skin endothelial cell. In some embodiments, the skin endothelial cell changes from a skin venule endothelial cell to a skin non-venule endothelial cell.

In some embodiments, the agent: (a) decreases expression of at least one gene exhibiting higher expression levels in skin venule endothelial cells compared to skin non-venule endothelial cells; (b) increases expression of at least one gene exhibiting lower expression levels in skin venule endothelial cells compared to skin non-venule endothelial cells; (c) increases expression of at least one gene exhibiting higher expression levels in skin non-venule endothelial cells compared to skin venule endothelial cells; or (d) decreases expression of at least one gene exhibiting lower expression levels in skin non-venule endothelial cells compared to skin venule endothelial cells.

In some embodiments, the at least one gene exhibiting higher expression levels in skin venule endothelial cells compared to skin non-venule endothelial cells is selected from the group consisting of a gene, or combination of genes, listed in Table 2. In some embodiments, the at least one gene exhibiting lower expression levels in venule endothelial cells compared to non-venule endothelial cells is selected from the group consisting of a gene, or combination of genes, listed in Table 9. In some embodiments, the at least one gene exhibiting higher expression levels in non-venule endothelial cells compared to venule endothelial cells is selected from the group consisting of a gene, or combination of genes, listed in Table 9. In some embodiments, the at least one gene exhibiting lower expression levels in non-venule endothelial cells compared to venule endothelial cells is selected from the group consisting of a gene, or combination of genes, listed in Table 2.

In some embodiments, the skin endothelial cell changes from a skin non-venule endothelial cell to a skin venule endothelial cell.

In some embodiments, the agent: (a) increases expression of at least one gene exhibiting higher expression levels in skin venule endothelial cells compared to skin non-venule endothelial cells; (b) decreases expression of at least one gene exhibiting lower expression levels in skin venule endothelial cells compared to skin non-venule endothelial cells; (c) decreases expression of at least one gene exhibiting higher expression levels in skin non-venule endothelial cells compared to skin venule endothelial cells; or (d) increases expression of at least one gene exhibiting lower expression levels in skin non-venule endothelial cells compared to skin venule endothelial cells.

In some embodiments, the at least one gene exhibiting higher expression levels in venule endothelial cells compared to non-venule endothelial cells is selected from the group consisting of a gene, or combination of genes, listed in Table 2. In some embodiments, the at least one gene exhibiting lower expression levels in venule endothelial cells compared to non-venule endothelial cells is selected from the group consisting of a gene, or combination of genes, listed in Table 9. In some embodiments, the at least one gene exhibiting higher expression levels in non-venule endothelial cells compared to venule endothelial cells is selected from the group consisting of a gene, or combination of genes, listed in Table 9. In some embodiments, the at least one gene exhibiting lower expression levels in non-venule endothelial cells compared to venule endothelial cells is selected from the group consisting of a gene, or combination of genes, listed in Table 2.

In some embodiments, the endothelial cell is an adipose tissue endothelial cell. In some embodiments, the adipose tissue endothelial cell changes from an adipose tissue venule endothelial cell to an adipose tissue non-venule endothelial cell.

In some embodiments, the agent: (a) decreases expression of at least one gene exhibiting higher expression levels in adipose tissue venule endothelial cells compared to adipose tissue non-venule endothelial cells; (b) increases expression of at least one gene exhibiting lower expression levels in adipose tissue venule endothelial cells compared to adipose tissue non-venule endothelial cells; (c) increases expression of at least one gene exhibiting higher expression levels in adipose tissue non-venule endothelial cells compared to adipose tissue venule endothelial cells; or (d) decreases expression of at least one gene exhibiting lower expression levels in adipose tissue non-venule endothelial cells compared to adipose tissue venule endothelial cells.

In some embodiments, the at least one gene exhibiting higher expression levels in adipose tissue venule endothelial cells compared to adipose tissue non-venule endothelial cells is selected from the group consisting of a gene, or combination of genes, listed in Table 3. In some embodiments, the at least one gene exhibiting lower expression levels in adipose tissue venule endothelial cells compared to adipose tissue non-venule endothelial cells is selected from the group consisting of a gene, or combination of genes, listed in Table 10. In some embodiments, the at least one gene exhibiting higher expression levels in adipose tissue non-venule endothelial cells compared to adipose tissue venule endothelial cells is selected from the group consisting of a gene, or combination of genes, listed in Table 10. In some embodiments, the at least one gene exhibiting lower expression levels in adipose tissue non-venule endothelial cells compared to adipose tissue venule endothelial cells is selected from the group consisting of a gene, or combination of genes, listed in Table 3.

In some embodiments, the adipose tissue endothelial cell changes from an adipose tissue non-venule endothelial cell to an adipose tissue venule endothelial cell.

In some embodiments, the agent: (a) increases expression of at least one gene exhibiting higher expression levels in adipose tissue venule endothelial cells compared to adipose tissue non-venule endothelial cells; (b) decreases expression of at least one gene exhibiting lower expression levels in adipose tissue venule endothelial cells compared to adipose tissue non-venule endothelial cells; (c) decreases expression of at least one gene exhibiting higher expression levels in adipose tissue non-venule endothelial cells compared to adipose tissue venule endothelial cells; or (d) increases expression of at least one gene exhibiting lower expression levels in adipose tissue non-venule endothelial cells compared to adipose tissue venule endothelial cells.

In some embodiments, the at least one gene exhibiting higher expression levels in adipose tissue venule endothelial cells compared to adipose tissue non-venule endothelial cells is selected from the group consisting of a gene, or combination of genes, listed in Table 3. In some embodiments, the at least one gene exhibiting lower expression levels in adipose tissue venule endothelial cells compared to adipose tissue non-venule endothelial cells is selected from the group consisting of a gene, or combination of genes, listed in Table 10. In some embodiments, the at least one gene exhibiting higher expression levels in adipose tissue non-venule endothelial cells compared to adipose tissue venule endothelial cells is selected from the group consisting of a gene, or combination of genes, listed in Table 10. In some embodiments, the at least one gene exhibiting lower expression levels in adipose tissue non-venule endothelial cells compared to adipose tissue venule endothelial cells is selected from the group consisting of a gene, or combination of genes, listed in Table 3.

In some embodiments, the endothelial cell is a lymph node endothelial cell. In some embodiments, the lymph node endothelial cell changes from a lymph node venule endothelial cell to a lymph node non-venule endothelial cell.

In some embodiments, the agent: (a) decreases expression of at least one gene exhibiting higher expression levels in lymph node venule endothelial cells compared to lymph node non-venule endothelial cells; (b) increases expression of at least one gene exhibiting lower expression levels in lymph node venule endothelial cells compared to lymph node non-venule endothelial cells; (c) increases expression of at least one gene exhibiting higher expression levels in lymph node non-venule endothelial cells compared to lymph node venule endothelial cells; or (d) decreases expression of at least one gene exhibiting lower expression levels in lymph node non-venule endothelial cells compared to lymph node venule endothelial cells.

In some embodiments, the at least one gene exhibiting higher expression levels in lymph node venule endothelial cells compared to lymph node non-venule endothelial cells is selected from the group consisting of a gene, or combination of genes, listed in Table 4. In some embodiments, the at least one gene exhibiting lower expression levels in lymph node venule endothelial cells compared to lymph node non-venule endothelial cells is selected from the group consisting of a gene, or combination of genes, listed in Table 11. In some embodiments, the at least one gene exhibiting higher expression levels in lymph node non-venule endothelial cells compared to lymph node venule endothelial cells is selected from the group consisting of a gene, or combination of genes, listed in Table 11. In some embodiments, the at least one gene exhibiting lower expression levels in lymph node non-venule endothelial cells compared to lymph node venule endothelial cells is selected from the group consisting of a gene, or combination of genes, listed in Table 4.

In some embodiments, the lymph node endothelial cell changes from a lymph node non-venule endothelial cell to a lymph node venule endothelial cell.

In some embodiments, the agent: (a) increases expression of at least one gene exhibiting higher expression levels in lymph node venule endothelial cells compared to lymph node non-venule endothelial cells; (b) decreases expression of at least one gene exhibiting lower expression levels in lymph node venule endothelial cells compared to lymph node non-venule endothelial cells; (c) decreases expression of at least one gene exhibiting higher expression levels in lymph node non-venule endothelial cells compared to lymph node venule endothelial cells; or (d) increases expression of at least one gene exhibiting lower expression levels in lymph node non-venule endothelial cells compared to lymph node venule endothelial cells.

In some embodiments, the at least one gene exhibiting higher expression levels in lymph node venule endothelial cells compared to lymph node non-venule endothelial cells is selected from the group consisting of a gene, or combination of genes, listed in Table 4. In some embodiments, the at least one gene exhibiting lower expression levels in lymph node venule endothelial cells compared to lymph node non-venule endothelial cells is selected from the group consisting of a gene, or combination of genes, listed in Table 11. In some embodiments, the at least one gene exhibiting higher expression levels in lymph node non-venule endothelial cells compared to lymph node venule endothelial cells is selected from the group consisting of a gene, or combination of genes, listed in Table 11. In some embodiments, the at least one gene exhibiting lower expression levels in lymph node non-venule endothelial cells compared to lymph node venule endothelial cells is selected from the group consisting of a gene, or combination of genes, listed in Table 4.

In some embodiments, changing the endothelial cell from a venule endothelial cell to a non-venule endothelial cell interferes with leukocyte interactions with leukocyte interactions with the endothelial cell. In some embodiments, changing the endothelial cell from a venule endothelial cell to a non-venule endothelial cell interferes with extravasation of leukocytes to the extravascular compartment in the tissue in which the endothelial cell resides. In some embodiments, changing the endothelial cell from a venule endothelial cell to non-venule endothelial cell decreases a local inflammatory response in the tissue in which the endothelial cell resides. In some embodiments, changing the endothelial cell from a non-venule endothelial cell to a venule endothelial cell enables leukocyte interactions with leukocyte interactions with the endothelial cell. In some embodiments, changing the endothelial cell from a non-venule endothelial cell to a venule endothelial cell enables extravasation of leukocytes to the extravascular compartment in the tissue in which the endothelial cell resides. In some embodiments, changing the endothelial cell from a non-venule endothelial cell to a venule endothelial cell enables a local inflammatory response in the tissue in which the endothelial cell resides.

In some embodiments, the gene encodes a protein selected from the group consisting of an enzyme, a protein kinase, a transcriptional regulator, and an endothelial cell surface protein.

In some embodiments, the agent inhibits enzymatic activity of the enzyme. In some embodiments, the agent inhibits the level or activity of phosphorylation of the protein kinase. In some embodiments, the agent inhibits activation of transcription or a signaling pathway. In some embodiments, the agent inhibits leukocyte adhesion to the endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is coupled to an endothelial cell targeting agent that binds to a protein expressed on the surface of the endothelial cell. In some embodiments, the agent is coupled to a venule endothelial cell targeting agent that binds to a protein expressed on the surface of venule endothelial cells.

In some embodiments, the protein is encoded by a gene selected from the group consisting of Sele, Selp, Il6st, Plxnb2, Lepr, Bst1, and Icam1. In some embodiments, the protein is not encoded by the Darc gene. In some embodiments, the protein is encoded by the Bst1 gene. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the protein is not encoded by the Sele gene. In some embodiments, the protein is not encoded by the Selp gene.

In some embodiments, the agent is coupled to a non-venule endothelial cell targeting agent that binds to a protein expressed on the surface of non-venule endothelial cells. In some embodiments, the protein is encoded by a gene selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a.

In some embodiments, the agent is coupled to a skin venule endothelial cell targeting agent that binds to a protein expressed on the surface of skin venule endothelial cells. In some embodiments, the protein is encoded by a gene selected from the group consisting of Nrp2, Gpr1, C630004H02Rik, Fndc1, 2310046K01Rik, Insr, and Slco2a1. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1.

In some embodiments, the agent is coupled to a skin non-venule endothelial cell targeting agent that binds to a protein expressed on the surface of skin non-venule endothelial cells. In some embodiments, the protein is encoded by a gene selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the protein is not encoded by the Sell gene. In some embodiments, the protein is not encoded by the Cd44 gene. In some embodiments, the protein is not encoded by the Siglech (also known as Siglec-h) gene.

In some embodiments, the agent is coupled to an adipose tissue venule endothelial cell targeting agent that binds to a protein expressed on the surface of adipose tissue venule endothelial cells. In some embodiments, the protein is encoded by a gene selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the protein is encoded by a gene selected from the group consisting of Tnfrsf11a, Mpz, Dnm3os, Icosl, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the protein is encoded by the Fcer1a gene.

In some embodiments, the agent is coupled to an adipose tissue non-venule endothelial cell targeting agent that binds to a protein expressed on the surface of adipose tissue non-venule endothelial cells. In some embodiments, the protein is encoded by a gene selected from the group consisting of Adora2a, H2-Ab1, Hspg2, Gpr81, Kcna5, Jam3, and Gpc4. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the agent is coupled to a lymph node venule endothelial cell targeting agent that binds to a protein expressed on the surface of lymph node venule endothelial cells. In some embodiments, the protein is encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the protein is encoded by a gene selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the agent is coupled to a lymph node non-venule endothelial cell targeting agent that binds to a protein expressed on the surface of lymph node non-venule endothelial cells. In some embodiments, protein is encoded by a gene selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Pmp22 gene.

In some aspects, disclosed herein is a method of modulating the venuleness of a microvessel, comprising contacting at least one endothelial cell of a microvessel with an effective amount of an agent that modulates expression of at least one gene that is differentially expressed in venule endothelial cells compared to non-venule endothelial cells.

In some embodiments, modulating the venuleness of a microvessel comprises changing the venular phenotype of a majority of the endothelial cells lining the microvessel. In some embodiments, modulating the venuleness of the microvessel comprises changing endothelial cells lining the microvessel from venule endothelial cells to non-venule endothelial cells.

In some embodiments, the agent: (a) decreases expression of at least one gene exhibiting higher expression levels in venule endothelial cells compared to non-venule endothelial cells; (b) increases expression of at least one gene exhibiting lower expression levels in venule endothelial cells compared to non-venule endothelial cells; (c) increases expression of at least one gene exhibiting higher expression levels in non-venule endothelial cells compared to venule endothelial cells; or (d) decreases expression of at least one gene exhibiting lower expression levels in non-venule endothelial cells compared to venule endothelial cells.

In some embodiments, the at least one gene exhibiting higher expression levels in venule endothelial cells compared to non-venule endothelial cells is selected from the group consisting of a gene, or combination of genes, listed in Table 1. In some embodiments, the at least one gene exhibiting lower expression levels in venule endothelial cells compared to non-venule endothelial cells is selected from the group consisting of a gene, or combination of genes, listed in Table 8. In some embodiments, the at least one gene exhibiting higher expression levels in non-venule endothelial cells compared to venule endothelial cells is selected from the group consisting of a gene, or combination of genes, listed in Table 8. In some embodiments, the at least one gene exhibiting lower expression levels in non-venule endothelial cells compared to venule endothelial cells is selected from the group consisting of a gene, or combination of genes, listed in Table 1.

In some embodiments, modulating the venuleness of the microvessel comprises changing endothelial cells lining the microvessel from non-venule endothelial cells to venule endothelial cells. In some embodiments, the agent: (a) increases expression of at least one gene exhibiting higher expression levels in venule endothelial cells compared to non-venule endothelial cells; (b) decreases expression of at least one gene exhibiting lower expression levels in venule endothelial cells compared to non-venule endothelial cells; (c) decreases expression of at least one gene exhibiting higher expression levels in non-venule endothelial cells compared to venule endothelial cells; or (d) increases expression of at least one gene exhibiting lower expression levels in non-venule endothelial cells compared to venule endothelial cells. In some embodiments, the at least one gene exhibiting higher expression levels in venule endothelial cells compared to non-venule endothelial cells is selected from the group consisting of a gene, or combination of genes, listed in Table 1. In some embodiments, the at least one gene exhibiting lower expression levels in venule endothelial cells compared to non-venule endothelial cells is selected from the group consisting of a gene, or combination of genes, listed in Table 8. In some embodiments, the at least one gene exhibiting higher expression levels in non-venule endothelial cells compared to venule endothelial cells is selected from the group consisting of a gene, or combination of genes, listed in Table 8. In some embodiments, the at least one gene exhibiting lower expression levels in non-venule endothelial cells compared to venule endothelial cells is selected from the group consisting of a gene, or combination of genes, listed in Table 1.

In some embodiments, the venuleness of the microvessel is modulated in a tissue-specific manner. In some embodiments, the venuleness of the microvessel is modulated in skin. In some embodiments, endothelial cells lining the microvessel in the skin change from skin venule endothelial cells to skin non-venule endothelial cells.

In some embodiments, the agent: (a) decreases expression of at least one gene exhibiting higher expression levels in skin venule endothelial cells compared to skin non-venule endothelial cells; (b) increases expression of at least one gene exhibiting lower expression levels in skin venule endothelial cells compared to skin non-venule endothelial cells; (c) increases expression of at least one gene exhibiting higher expression levels in skin non-venule endothelial cells compared to skin venule endothelial cells; or (d) decreases expression of at least one gene exhibiting lower expression levels in skin non-venule endothelial cells compared to skin venule endothelial cells.

In some embodiments, the at least one gene exhibiting higher expression levels in skin venule endothelial cells compared to skin non-venule endothelial cells is selected from the group consisting of a gene, or combination of genes, listed in Table 2. In some embodiments, the at least one gene exhibiting lower expression levels in skin venule endothelial cells compared to skin non-venule endothelial cells is selected from the group consisting of a gene, or combination of genes, listed in Table 9. In some embodiments, the at least one gene exhibiting higher expression levels in skin non-venule endothelial cells compared to skin venule endothelial cells is selected from the group consisting of a gene, or combination of genes, listed in Table 9. In some embodiments, the at least one gene exhibiting lower expression levels in skin non-venule endothelial cells compared to skin venule endothelial cells is selected from the group consisting of a gene, or combination of genes, listed in Table 2.

In some embodiments, the endothelial cells lining the microvessel in the skin change from a skin non-venule endothelial cells to a skin venule endothelial cells.

In some embodiments, the agent: (a) increases expression of at least one gene exhibiting higher expression levels in skin venule endothelial cells compared to skin non-venule endothelial cells; (b) decreases expression of at least one gene exhibiting lower expression levels in skin venule endothelial cells compared to skin non-venule endothelial cells; (c) decreases expression of at least one gene exhibiting higher expression levels in skin non-venule endothelial cells compared to skin venule endothelial cells; or (d) increases expression of at least one gene exhibiting lower expression levels in skin non-venule endothelial cells compared to skin venule endothelial cells.

In some embodiments, the at least one gene exhibiting higher expression levels in skin venule endothelial cells compared to skin non-venule endothelial cells is selected from the group consisting of a gene, or combination of genes, listed in Table 2. In some embodiments, the at least one gene exhibiting lower expression levels in skin venule endothelial cells compared to skin non-venule endothelial cells is selected from the group consisting of a gene, or combination of genes, listed in Table 9. In some embodiments, the at least one gene exhibiting higher expression levels in skin non-venule endothelial cells compared to skin venule endothelial cells is selected from the group consisting of a gene, or combination of genes, listed in Table 9. In some embodiments, the at least one gene exhibiting lower expression levels in skin non-venule endothelial cells compared to skin venule endothelial cells is selected from the group consisting of a gene, or combination of genes, listed in Table 2.

In some embodiments, the venuleness of the microvessel is modulated in adipose tissue. In some embodiments, endothelial cells lining the microvessel change from adipose tissue venule endothelial cells to an adipose tissue non-venule endothelial cells.

In some embodiments, the agent: (a) decreases expression of at least one gene exhibiting higher expression levels in adipose tissue venule endothelial cells compared to adipose tissue non-venule endothelial cells; (b) increases expression of at least one gene exhibiting lower expression levels in adipose tissue venule endothelial cells compared to adipose tissue non-venule endothelial cells; (c) increases expression of at least one gene exhibiting higher expression levels in adipose tissue non-venule endothelial cells compared to adipose tissue venule endothelial cells; or (d) decreases expression of at least one gene exhibiting lower expression levels in adipose tissue non-venule endothelial cells compared to adipose tissue venule endothelial cells.

In some embodiments, the at least one gene exhibiting higher expression levels in adipose tissue venule endothelial cells compared to adipose tissue non-venule endothelial cells is selected from the group consisting of a gene, or combination of genes, listed in Table 3. In some embodiments, the at least one gene exhibiting lower expression levels in adipose tissue venule endothelial cells compared to adipose tissue non-venule endothelial cells is selected from the group consisting of a gene, or combination of genes, listed in Table 10. In some embodiments, the at least one gene exhibiting higher expression levels in adipose tissue non-venule endothelial cells compared to adipose tissue venule endothelial cells is selected from the group consisting of a gene, or combination of genes, listed in Table 10. In some embodiments, the at least one gene exhibiting lower expression levels in adipose tissue non-venule endothelial cells compared to adipose tissue venule endothelial cells is selected from the group consisting of a gene, or combination of genes, listed in Table 3.

In some embodiments, endothelial cells lining the microvessel change from adipose tissue non-venule endothelial cells to adipose tissue venule endothelial cells.

In some embodiments, the agent: (a) increases expression of at least one gene exhibiting higher expression levels in adipose tissue venule endothelial cells compared to adipose tissue non-venule endothelial cells; (b) decreases expression of at least one gene exhibiting lower expression levels in adipose tissue venule endothelial cells compared to adipose tissue non-venule endothelial cells; (c) decreases expression of at least one gene exhibiting higher expression levels in adipose tissue non-venule endothelial cells compared to adipose tissue venule endothelial cells; or (d) increases expression of at least one gene exhibiting lower expression levels in adipose tissue non-venule endothelial cells compared to adipose tissue venule endothelial cells.

In some embodiments, the at least one gene exhibiting higher expression levels in adipose tissue venule endothelial cells compared to adipose tissue non-venule endothelial cells is selected from the group consisting of a gene, or combination of genes, listed in Table 3. In some embodiments, the at least one gene exhibiting lower expression levels in adipose tissue venule endothelial cells compared to adipose tissue non-venule endothelial cells is selected from the group consisting of a gene, or combination of genes, listed in Table 10. In some embodiments, the at least one gene exhibiting higher expression levels in adipose tissue non-venule endothelial cells compared to adipose tissue venule endothelial cells is selected from the group consisting of a gene, or combination of genes, listed in Table 10. In some embodiments, the at least one gene exhibiting lower expression levels in adipose tissue non-venule endothelial cells compared to adipose tissue venule endothelial cells is selected from the group consisting of a gene, or combination of genes, listed in Table 3.

In some embodiments, the venuleness of the microvessel is modulated in lymph nodes. In some embodiments, the endothelial cells lining the microvessel change from lymph node venule endothelial cells to lymph node non-venule endothelial cells.

In some embodiments, the agent: (a) decreases expression of at least one gene exhibiting higher expression levels in lymph node venule endothelial cells compared to lymph node non-venule endothelial cells; (b) increases expression of at least one gene exhibiting lower expression levels in lymph node venule endothelial cells compared to lymph node non-venule endothelial cells; (c) increases expression of at least one gene exhibiting higher expression levels in lymph node non-venule endothelial cells compared to lymph node venule endothelial cells; or (d) decreases expression of at least one gene exhibiting lower expression levels in lymph node non-venule endothelial cells compared to lymph node venule endothelial cells.

In some embodiments, the at least one gene exhibiting higher expression levels in lymph node venule endothelial cells compared to lymph node non-venule endothelial cells is selected from the group consisting of a gene, or combination of genes, listed in Table 4. In some embodiments, the at least one gene exhibiting lower expression levels in lymph node venule endothelial cells compared to lymph node non-venule endothelial cells is selected from the group consisting of a gene, or combination of genes, listed in Table 11. In some embodiments, the at least one gene exhibiting higher expression levels in lymph node non-venule endothelial cells compared to lymph node venule endothelial cells is selected from the group consisting of a gene, or combination of genes, listed in Table 11. In some embodiments, the at least one gene exhibiting lower expression levels in lymph node non-venule endothelial cells compared to lymph node venule endothelial cells is selected from the group consisting of a gene, or combination of genes, listed in Table 4.

In some embodiments, endothelial cells lining the microvessel change from a lymph node non-venule endothelial cells to a lymph node venule endothelial cells.

In some embodiments, the agent: (a) increases expression of at least one gene exhibiting higher expression levels in lymph node venule endothelial cells compared to lymph node non-venule endothelial cells; (b) decreases expression of at least one gene exhibiting lower expression levels in lymph node venule endothelial cells compared to lymph node non-venule endothelial cells; (c) decreases expression of at least one gene exhibiting higher expression levels in lymph node non-venule endothelial cells compared to lymph node venule endothelial cells; or (d) increases expression of at least one gene exhibiting lower expression levels in lymph node non-venule endothelial cells compared to lymph node venule endothelial cells.

In some embodiments, the at least one gene exhibiting higher expression levels in lymph node venule endothelial cells compared to lymph node non-venule endothelial cells is selected from the group consisting of a gene, or combination of genes, listed in Table 4. In some embodiments, the at least one gene exhibiting lower expression levels in lymph node venule endothelial cells compared to lymph node non-venule endothelial cells is selected from the group consisting of a gene, or combination of genes, listed in Table 11. In some embodiments, the at least one gene exhibiting higher expression levels in lymph node non-venule endothelial cells compared to lymph node venule endothelial cells is selected from the group consisting of a gene, or combination of genes, listed in Table 11. In some embodiments, the at least one gene exhibiting lower expression levels in lymph node non-venule endothelial cells compared to lymph node venule endothelial cells is selected from the group consisting of a gene, or combination of genes, listed in Table 4.

In some embodiments, changing the endothelial cells from venule endothelial cells to a non-venule endothelial cells interferes with leukocyte interactions with leukocyte interactions with the microvessel. In some embodiments, changing the endothelial cells from venule endothelial cells to non-venule endothelial cells interferes with extravasation of leukocytes to the extravascular compartment in the tissue in which the microvessel resides. In some embodiments, changing the endothelial cells from venule endothelial cells to non-venule endothelial cells decreases a local inflammatory response in the tissue in which the microvessel resides. In some embodiments, changing the endothelial cells from venule endothelial cells to non-venule endothelial cells inhibits leukocyte adhesion to the microvessel. In some embodiments, changing the endothelial cells from non-venule endothelial cells to venule endothelial cells enables leukocyte interactions with leukocyte interactions with the microvessel. In some embodiments, changing the endothelial cells from non-venule endothelial cells to venule endothelial cells enables extravasation of leukocytes to the extravascular compartment in the tissue in which the microvessel resides. In some embodiments, changing the endothelial cells from non-venule endothelial cells to venule endothelial cells enables a local inflammatory response in the tissue in which the microvessel resides.

In some embodiments, the gene encodes a protein selected from the group consisting of an enzyme, a protein kinase, a transcriptional regulator, and a venule endothelial cell surface protein.

In some embodiments, the agent inhibits enzymatic activity of the enzyme. In some embodiments, the agent inhibits the level or activity of phosphorylation of the protein kinase. In some embodiments, the agent inhibits activation of transcription or a signaling pathway.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is coupled to an endothelial cell targeting agent that binds to a protein expressed on the surface of the endothelial cell lining the microvessel. In some embodiments, the agent is coupled to a venule endothelial cell targeting agent that binds to a protein expressed on the surface of venule endothelial cells lining the microvessel.

In some embodiments, the protein is encoded by a gene selected from the group consisting of Sele, Selp, Il6st, Plxnb2, Lepr, Bst1, and Icam1. In some embodiments, the protein is not encoded by the Darc gene. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the protein is not encoded by the Sele gene. In some embodiments, the protein is not encoded by the Selp gene. In some embodiments, the protein is encoded by the Bst1 gene. In some embodiments, the agent is coupled to a non-venule endothelial cell targeting agent that binds to a protein expressed on the surface of non-venule endothelial cells lining the microvessel.

In some embodiments, the protein is encoded by a gene selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a.

In some embodiments, the agent is coupled to a skin venule endothelial cell targeting agent that binds to a protein expressed on the surface of skin venule endothelial cells lining the microvessel. In some embodiments, the protein is encoded by a gene selected from the group consisting of Nrp2, Gpr1, C630004H02Rik, Fndc1, 2310046K01Rik, Insr, and Slco2a1. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1. In some embodiments, the agent is coupled to a skin non-venule endothelial cell targeting agent that binds to a protein expressed on the surface of skin non-venule endothelial cells lining the microvessel. In some embodiments, the protein is encoded by a gene selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the protein is not encoded by the Sell gene. In some embodiments, the protein is not encoded by the Cd44 gene. In some embodiments, the protein is not encoded by the Siglech gene. In some embodiments, the agent is coupled to an adipose tissue venule endothelial cell targeting agent that binds to a protein expressed on the surface of adipose tissue venule endothelial cells lining the microvessel. In some embodiments, the protein is encoded by a gene selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the protein is encoded by the Fcer1a gene. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the agent is coupled to an adipose tissue non-venule endothelial cell targeting agent that binds to a protein expressed on the surface of adipose tissue non-venule endothelial cells lining the microvessel. In some embodiments, the protein is encoded by a gene selected from the group consisting of Adora2a, H2-Ab1, Hspg2, Gpr81, Kcna5, Jam3, and Gpc4. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the agent is coupled to a lymph node venule endothelial cell targeting agent that binds to a protein expressed on the surface of lymph node venule endothelial cells lining the microvessel. In some embodiments, the protein is encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the protein is encoded by a gene selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the agent is coupled to a lymph node non-venule endothelial cell targeting agent that binds to a protein expressed on the surface of lymph node non-venule endothelial cells lining the microvessel. In some embodiments, the protein is encoded by a gene selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Pmp22 gene.

In some aspects, disclosed herein is a method of targeting an agent to microvessel endothelial cells in a subject, comprising administering to the subject a therapeutically effective amount of an agent to be targeted to microvessel endothelial cells, wherein the agent is coupled to a microvessel endothelial cell targeting agent.

In some embodiments, the microvessel endothelial cell targeting agent binds to a protein expressed on the surface of a microvessel endothelial cell. In some embodiments, the protein is encoded by a gene exhibiting higher expression levels in venule endothelial cells compared to non-venule endothelial cells. In some embodiments, the gene is selected from the group consisting of Sele, Selp, Il6st, Plxnb2, Lepr, Bst1, and Icam1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the gene is not Darc. In some embodiments, the gene is not Sele. In some embodiments, the gene is not Selp. In some embodiments, the gene is Bst1.

In some embodiments, the gene exhibits higher expression levels in venule endothelial cells in skin compared to venule endothelial cells in other tissues. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mrl, Lifr, Anxa1, Lphn2, Vamp5, Olr1, Eps8, Slco2b1, and Slco2a1. In some embodiments, the gene exhibits higher expression levels in venule endothelial cells in adipose tissue compared to venule endothelial cells in other tissues.

In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the gene is Fcer1a. In some embodiments, the gene exhibits higher expression levels in venule endothelial cells in lymph nodes compared to venule endothelial cells in other tissues. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the gene is selected from the group of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the gene exhibits higher expression levels in venule endothelial cells in skin and lymph nodes compared to venule endothelial cells in other tissues. In some embodiments, the gene is selected from the group consisting of Gpr182 and Slco2b1. In some embodiments, the gene is Gpr182. In some embodiments, the gene exhibits higher expression levels in venule endothelial cells in adipose tissue and lymph nodes compared to venule endothelial cells in other tissues. In some embodiments, the gene is selected from the group consisting of Cd63, Sirpa, Slc2a1, Vmn1r100, Vmn1r148, Vmn1r132, and Vmn1r125. In some embodiments, the gene is selected from the group consisting of H60b, Ppap2c, Celsr1, Glycam1, Slc37a1, Cd59a, Slc2a1, Tnfrsf9, Tes, Pglyrp1, Il27ra, and Eda2r. In some embodiments, gene exhibits higher expression levels in venule endothelial cells in adipose tissue and skin compared to venule endothelial cells in other tissues. In some embodiments, the gene is selected from the group consisting of Il1rl, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Il1rl, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is encoded by a gene exhibiting higher expression levels in non-venule endothelial cells compared to venule endothelial cells. In some embodiments, the gene is selected from the group consisting of Flt4, Jup, Lgals3bp, Ednrb, Ptp4a3, Gpihbp1, Notch4, Slc9a3r2, Pmd, Sdc3, Alpl, Cldn15, Kdr, Slc6a6, Podxl, Efnb2, Sema7a, and Itm2a. In some embodiments, the gene is selected from the group consisting of Cxcr4, Unc5b, Flt4, Ednrb, Notch4, Prnd, Gja5, Gja4, Alpl, Kcna5, P2ry2, Efnb2, and Itm2a. In some embodiments, the gene exhibits higher expression levels in non-venule endothelial cells in skin compared to venule endothelial cells in skin. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the gene is not Sell. In some embodiments, the gene is not Cd44. In some embodiments, the gene is not Siglech. In some embodiments, the gene exhibits higher expression levels in non-venule endothelial cells in adipose tissue compared to venule endothelial cells in adipose tissue. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the gene exhibits higher expression levels in non-venule endothelial cells in lymph nodes compared to venule endothelial cells lymph nodes. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the gene is not Pmp22. In some embodiments, the gene exhibits higher expression levels in non-venule endothelial cells in skin and lymph nodes compared to venule endothelial cells in skin and lymph nodes. In some embodiments, the gene is selected from the group consisting of Tns1, Cxcr4, Atp1b1, Car4, Cd7, Itga1, Gja5, Laptm5, Aqp7, Gja4, Mlec, P2ry2, and Cd97. In some embodiments, the gene is selected from the group consisting of Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4. In some embodiments, the gene exhibits higher expression levels in non-venule endothelial cells in adipose tissue and lymph nodes compared to venule endothelial cells in adipose tissue and lymph nodes. In some embodiments, the gene is selected from the group consisting of Unc5b, Lpar6, Sema6d, Ppap2b, and Lpar4. In some embodiments, the gene is selected from the group consisting of Ramp3, Olfr1396, Slc1a1, Cldn15, and Cd109. In some embodiments, the gene exhibits higher expression levels in non-venule endothelial cells in adipose tissue and skin compared to venule endothelial cells in adipose tissue and skin. In some embodiments, the gene is selected from the group consisting of Ly86, H2-Aa, and Cd74. In some embodiments, the gene is selected from the group consisting of Sell, Cd79b, Ly86, Chrm3, Ptger4, and Sema7a.

In some embodiments, the microvessel endothelial cell targeting agent is internalized into the endothelial cells lining the microvessel. In some embodiments, internalization of the microvessel endothelial cell targeting agent into the endothelial cells lining the microvessel causes the microvessel endothelial cell targeting agent to accumulate in the tissue in which the microvessel resides. In some embodiments, the microvessel endothelial cell targeting agent accumulates in the subject's skin. In some embodiments, the microvessel endothelial cell targeting agent accumulates in the subject's adipose tissue. In some embodiments, the microvessel endothelial cell targeting agent accumulates in the venule endothelial cells in the subject's lymph nodes. In some embodiments, the microvessel endothelial cell targeting agent does not accumulate in non-target tissues. In some embodiments, internalization of the microvessel endothelial cell targeting agent into the endothelial cells lining the microvessel causes the agent to accumulate in the tissue in which the microvessel resides. In some embodiments, the agent accumulates in the subject's skin. In some embodiments, the agent accumulates in the subject's adipose tissue. In some embodiments, the agent accumulates in the subject's lymph nodes. In some embodiments, the agent does not accumulate in non-target tissue.

In some embodiments, the microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the microvessel endothelial cell targeting agent is coupled to the agent via a linker. In some embodiments, the microvessel endothelial cell targeting agent or the agent is coupled to a detectable reporter. In some embodiments, the microvessel endothelial cell targeting agent and/or the agent is encapsulated in a nanoparticle. In some embodiments, the nanoparticle comprises a lipid nanoparticle or microparticle.

In some embodiments, targeting an agent to microvessel endothelial cells of the subject treats, prevents, or ameliorates a symptom of, an inflammatory disease in the subject. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parasitic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis *nodosa*, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, the inflammatory disease is not or does not involve sickle cell disease. In some embodiments, the inflammatory disease is not, or does not involve, sickle cell disease mediated by, or involving, Sele. In some embodiments, the inflammatory disease is not, or does not involve, sickle cell disease mediated by, or involving, Sell. In some embodiments, the inflammatory disease is not, or does not involve, sickle cell disease mediated by, or involving, Selp. In some embodiments, the inflammatory disease is not, or does not involve, sickle cell disease mediated by, or involving, Cd44. In some embodiments, the inflammatory disease is not, or does not involve, sickle cell disease mediated by, or involving, Cd130.

In some embodiments, the inflammatory disease is not, or does not involve, pain crisis associated with sickle cell disease mediated by, or involving, Sele. In some embodiments, the inflammatory disease is not, or does not involve, pain crisis associated with sickle cell disease mediated by, or involving, Sell. In some embodiments, the inflammatory disease is not, or does not involve, pain crisis associated with sickle cell disease mediated by, or involving, Selp. In some embodiments, the inflammatory disease is not, or does not involve, pain crisis associated with sickle cell disease mediated by, or involving, Cd44. In some embodiments, the inflammatory disease is not, or does not involve, pain crisis associated with sickle cell disease mediated by, or involving, Cd130.

In some embodiments, the inflammatory disease is not, or does not involve, deep vein thrombosis. In some embodiments, the inflammatory disease is not, or does not involve, deep vein thrombosis mediated by, or involving, Sele. In some embodiments, the inflammatory disease is not, or does not involve, deep vein thrombosis mediated by, or involving, Sell. In some embodiments, the inflammatory disease is not, or does not involve, deep vein thrombosis mediated by, or involving, Selp. In some embodiments, the inflammatory disease is not, or does not involve, deep vein thrombosis mediated by, or involving, Cd44. In some embodiments, the inflammatory disease is not, or does not involve, deep vein thrombosis mediated by, or involving, Cd130.

In some embodiments, the inflammatory disease is not, or does not involve, asthma. In some embodiments, the inflammatory disease is not, or does not involve, asthma mediated by, or involving, Sele. In some embodiments, the inflammatory disease is not, or does not involve, asthma mediated by, or involving, Sell. In some embodiments, the inflammatory disease is not, or does not involve, asthma mediated by, or involving, Selp. In some embodiments, the inflammatory disease is not, or does not involve, asthma mediated by, or involving, Cd44. In some embodiments, the inflammatory disease is not, or does not involve, asthma mediated by, or involving, Cd130.

In some embodiments, the inflammatory disease is not, or does not involve, rheumatoid arthritis. In some embodiments, the inflammatory disease is not, or does not involve, rheumatoid arthritis mediated by, or involving, Sele. In some embodiments, the inflammatory disease is not, or does not involve, rheumatoid arthritis mediated by, or involving, Selp. In some embodiments, the inflammatory disease is not, or does not involve, rheumatoid arthritis mediated by, or involving, Sell. In some embodiments, the inflammatory disease is not, or does not involve, rheumatoid arthritis mediated by, or involving, Cd44. In some embodiments, the inflammatory disease is not, or does not involve, rheumatoid arthritis mediated by, or involving, Cd130.

In some embodiments, the inflammatory disease is not, or does not involve, psoriasis. In some embodiments, the inflammatory disease is not, or does not involve, psoriasis mediated by, or involving, Sele. In some embodiments, the inflammatory disease is not, or does not involve, psoriasis mediated by, or involving, Sell. In some embodiments, the inflammatory disease is not, or does not involve, psoriasis mediated by, or involving, Selp. In some embodiments, the inflammatory disease is not, or does not involve, psoriasis mediated by, or involving, Cd44. In some embodiments, the inflammatory disease is not, or does not involve, psoriasis mediated by, or involving, Cd130.

In some embodiments, the inflammatory disease is not or does not involve ischemia reperfusion injury. In some embodiments, the inflammatory disease is not, or does not involve, ischemia reperfusion injury mediated by, or involving, Sele. In some embodiments, the inflammatory disease is not, or does not involve, ischemia reperfusion injury mediated by, or involving, Sell. In some embodiments, the inflammatory disease is not, or does not involve, ischemia reperfusion injury mediated by, or involving, Selp. In some embodiments, the inflammatory disease is not, or does not involve, ischemia reperfusion injury mediated by, or involving, Cd44. In some embodiments, the inflammatory disease is not, or does not involve, ischemia reperfusion injury mediated by, or involving, Cd130.

In some embodiments, the inflammatory disease is not, or does not involve, tumor metastasis mediated by, or involving, Sele. In some embodiments, the inflammatory disease is not, or does not involve, tumor metastasis mediated by, or involving, Sell. In some embodiments, the inflammatory disease is not, or does not involve, tumor metastasis mediated by, or involving, Selp. In some embodiments, the inflammatory disease is not, or does not involve, tumor metastasis mediated by, or involving, Cd44. In some embodiments, the inflammatory disease is not, or does not involve, tumor metastasis mediated by, or involving, Cd130.

In some embodiments, the inflammatory disease is not, or does not involve an immune response, mediated by, or involving, Sele. In some embodiments, the inflammatory disease is not, or does not involve an immune response, mediated by, or involving, Sell. In some embodiments, the inflammatory disease is not, or does not involve an immune response, mediated by, or involving, Selp. In some embodiments, the inflammatory disease is not, or does not involve an immune response, mediated by, or involving, Cd44. In some embodiments, the inflammatory disease is not, or does not involve an immune response, mediated by, or involving, Cd130.

In some embodiments, the inflammatory disease is not, or does not involve inflammation mediated by, or involving, Sele. In some embodiments, the inflammatory disease is not, or does not involve inflammation mediated by, or involving, Sell. In some embodiments, the inflammatory disease is not, or does not involve an inflammation mediated by, or involving, Selp. In some embodiments, the inflammatory disease is not, or does not involve inflammation mediated by, or involving, Cd44. In some embodiments, the inflammatory disease is not, or does not involve inflammation mediated by, or involving, Cd130.

In some embodiments, the inflammatory disease is not, or does not involve, leukocyte trafficking mediated by, or involving, Sele. In some embodiments, the inflammatory disease is not, or does not involve, leukocyte trafficking mediated by, or involving, Sell. In some embodiments, the inflammatory disease is not, or does not involve, leukocyte trafficking mediated by, or involving, Selp. In some embodiments, the inflammatory disease is not, or does not involve, leukocyte trafficking mediated by, or involving, Cd44. In some embodiments, the inflammatory disease is not, or does not involve, leukocyte trafficking mediated by, or involving, Cd130.

In some embodiments, the inflammatory disease is not, or does not involve, leukocyte adherence mediated by, or involving, Sele. In some embodiments, the inflammatory disease is not, or does not involve, leukocyte adherence mediated by, or involving, Sell. In some embodiments, the inflammatory disease is not, or does not involve, leukocyte adherence mediated by, or involving, Selp. In some embodiments, the inflammatory disease is not, or does not involve, leukocyte adherence mediated by, or involving, Cd44. In some embodiments, the inflammatory disease is not, or does not involve, leukocyte adherence mediated by, or involving, Cd130.

In some embodiments, the inflammatory disease is not, or does not involve, leukocyte-mediated inflammation mediated by, or involving, Sele. In some embodiments, the inflammatory disease is not, or does not involve, leukocyte-mediated inflammation mediated by, or involving, Sell. In some embodiments, the inflammatory disease is not, or does not involve, leukocyte-mediated inflammation mediated by, or involving, Selp. In some embodiments, the inflammatory disease is not, or does not involve, leukocyte-mediated inflammation mediated by, or involving, Cd44. In some embodiments, the inflammatory disease is not, or does not involve, leukocyte-mediated inflammation mediated by, or involving, Cd130.

In some embodiments, the inflammatory disease is not, or does not involve, diseases in which ischemia and reperfusion result in organ injury mediated by adherence of leukocytes to vascular surfaces, including stroke, mediated by, or involving, Sele. In some embodiments, the inflammatory disease is not, or does not involve, diseases in which ischemia and reperfusion result in organ injury mediated by adherence of leukocytes to vascular surfaces, including stroke, mediated by, or involving, Sell. In some embodiments, the inflammatory disease is not, or does not involve, diseases in which ischemia and reperfusion result in organ injury mediated by adherence of leukocytes to vascular surfaces, including stroke, mediated by, or involving, Selp. In some embodiments, the inflammatory disease is not, or does not involve, diseases in which ischemia and reperfusion result in organ injury mediated by adherence of leukocytes to vascular surfaces, including stroke, mediated by, or involving, Cd44. In some embodiments, the inflammatory disease is not, or does not involve, circulatory shock mediated by, or involving, Cd130.

In some embodiments, the inflammatory disease is not mesenteric vascular disease mediated by, or involving, Sele. In some embodiments, the inflammatory disease is not mesenteric vascular disease mediated by, or involving, Sell. In some embodiments, the inflammatory disease is not mesenteric vascular disease mediated by, or involving, Selp. In some embodiments, the inflammatory disease is not mesenteric vascular disease mediated by, or involving, Cd44. In some embodiments, the inflammatory disease is not, or does not involve, circulatory shock mediated by, or involving, Cd130.

In some embodiments, the inflammatory disease is not, or does not involve, circulatory shock mediated by, or involving, Sele. In some embodiments, the inflammatory disease is not, or does not involve, circulatory shock mediated by, or involving, Sell. In some embodiments, the inflammatory disease is not, or does not involve, circulatory shock mediated by, or involving, Selp. In some embodiments, the inflammatory disease is not, or does not involve, circulatory shock mediated by, or involving, Cd44. In some embodiments, the inflammatory disease is not, or does not involve, circulatory shock mediated by, or involving, Cd130.

In some embodiments, the inflammatory disease is not, or does not involve, adult respiratory distress syndrome. In some embodiments, the inflammatory disease is not, or does not involve, adult respiratory distress syndrome mediated by, or involving, Sele. In some embodiments, the inflammatory disease is not, or does not involve, adult respiratory distress syndrome mediated by, or involving, Sell. In some embodiments, the inflammatory disease is not, or does not involve, adult respiratory distress syndrome mediated by, or involving, Selp. In some embodiments, the inflammatory disease is not, or does not involve, adult respiratory distress syndrome mediated by, or involving, Cd44. In some embodiments, the inflammatory disease is not, or does not involve, adult respiratory distress syndrome mediated by, or involving, Cd130.

In some embodiments, the inflammatory disease is not, or does not involve, adult respiratory distress syndrome in patients with sepsis or following trauma mediated by, or involving, Sele. In some embodiments, the inflammatory disease is not, or does not involve, adult respiratory distress syndrome in patients with sepsis or following trauma mediated by, or involving, Sell. In some embodiments, the inflammatory disease is not, or does not involve, adult respiratory distress syndrome in patients with sepsis or following trauma mediated by, or involving, Selp. In some embodiments, the inflammatory disease is not, or does not involve, adult respiratory distress syndrome in patients with sepsis or following trauma mediated by, or involving, Cd44. In some embodiments, the inflammatory disease is not, or does not involve, adult respiratory distress syndrome in patients with sepsis or following trauma mediated by, or involving, Cd130.

In some embodiments, the inflammatory disease is not, or does not involve, atherosclerosis mediated by, or involving, Sele. In some embodiments, the inflammatory disease is not, or does not involve, atherosclerosis mediated by, or involving, Sell. In some embodiments, the inflammatory disease is not, or does not involve, atherosclerosis mediated by, or involving, Selp. In some embodiments, the inflammatory disease is not, or does not involve, atherosclerosis mediated by, or involving, Cd44. In some embodiments, the inflammatory disease is not, or does not involve, atherosclerosis mediated by, or involving, Cd130.

In some embodiments, the inflammatory disease is not, or does not involve, bacterial sepsis mediated by, or involving, Sele. In some embodiments, the inflammatory disease is not, or does not involve, bacterial sepsis mediated by, or involving, Sell. In some embodiments, the inflammatory disease is not, or does not involve, bacterial sepsis mediated by, or involving, Selp. In some embodiments, the inflammatory disease is not, or does not involve, bacterial sepsis mediated by, or involving, Cd44. In some embodiments, the inflammatory disease is not, or does not involve, bacterial sepsis mediated by, or involving, Cd130.

In some embodiments, the inflammatory disease is not, or does not involve, disseminated intravascular coagulation mediated by, or involving, Sele. In some embodiments, the inflammatory disease is not, or does not involve, disseminated intravascular coagulation mediated by, or involving, Sell. In some embodiments, the inflammatory disease is not, or does not involve, disseminated intravascular coagulation mediated by, or involving, Selp. In some embodiments, the inflammatory disease is not, or does not involve, disseminated intravascular coagulation mediated by, or involving, Cd44. In some embodiments, the inflammatory disease is not, or does not involve, disseminated intravascular coagulation mediated by, or involving, CD130.

In some embodiments, the inflammatory disease is not, or does not involve, coagulation, such as disseminated intravascular coagulation, mediated by, or involving, Sele. In some embodiments, the inflammatory disease is not, or does not involve, coagulation, such as disseminated intravascular coagulation, mediated by, or involving, Sell. In some embodiments, the inflammatory disease is not, or does not involve, coagulation, such as disseminated intravascular coagulation, mediated by, or involving, Selp. In some embodiments, the inflammatory disease is not, or does not involve, coagulation, such as disseminated intravascular coagulation, mediated by, or involving, Cd44. In some embodiments, the inflammatory disease is not, or does not involve, coagulation, such as disseminated intravascular coagulation, mediated by, or involving, Cd130.

In some embodiments, the inflammatory disease is not, or does not involve, leukocyte adherence mediated by, or involving, Sele. In some embodiments, the inflammatory disease is not, or does not involve, leukocyte adherence mediated by, or involving, Sell. In some embodiments, the inflammatory disease is not, or does not involve, leukocyte adherence mediated by, or involving, Selp. In some embodiments, the inflammatory disease is not, or does not involve, leukocyte adherence mediated by, or involving, Cd44. In some embodiments, the inflammatory disease is not, or does not involve, leukocyte adherence mediated by, or involving, Cd130.

In some aspects, disclosed herein is a method of targeting an agent to microvessel endothelial cells in skin, comprising administering to a subject a therapeutically effective amount of an agent to be targeted to microvessel endothelial cells in skin, wherein the agent is coupled to a skin microvessel endothelial cell targeting agent. In some embodiments, the skin microvessel endothelial cell targeting agent binds to a protein expressed on the surface of an endothelial cell lining a microvessel in the subject's skin. In some embodiments, the protein is encoded by a gene exhibiting higher expression levels in skin venule endothelial cells compared to skin non-venule endothelial cells. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1. In some embodiments, the protein is encoded by a gene exhibiting higher expression levels in skin non-venule endothelial cells compared to skin venule endothelial cells. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap11, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the gene is not Sell. In some embodiments, the gene is not Cd44. In some embodiments, the gene is not Siglech. In some embodiments, the skin microvessel endothelial cell targeting agent is internalized into the endothelial cells lining a microvessel in the subject's skin. In some embodiments, internalization of the skin microvessel endothelial cell targeting agent into the endothelial cells lining the microvessel in the subject's skin causes the skin microvessel endothelial cell targeting agent to accumulate in subject's skin. In some embodiments, the skin microvessel endothelial cell targeting agent does not accumulate in tissues other than skin. In some embodiments, internalization of the skin microvessel endothelial cell targeting agent into the endothelial cells lining the microvessel in the subject's skin causes the agent to be internalized into the endothelial cells lining the microvessel in the subject's skin. In some embodiments, internalization of the agent causes the agent to accumulate in the subject's skin. In some embodiments, the agent does not accumulate in tissues other than skin.

In some embodiments, the skin microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the microvessel endothelial cell targeting agent is coupled to the agent via a linker. In some embodiments, the skin microvessel endothelial cell targeting agent or agent is coupled to a detectable reporter. In some embodiments, targeting an agent to skin microvessel endothelial cells of the subject treats, prevents, or ameliorates a symptom of, a skin inflammatory disease. In some embodiments, the skin inflammatory disease is selected from the group consisting of acne, dermatitis, eczema, oily skin, rosacea, cutaneus lymphoma and urticaria.

In some embodiments, the dermatitis is selected from the group consisting of atopic dermatitis, psoriasis and contact dermatitis. In some aspects, disclosed herein is, a method of targeting an agent to microvessel endothelial cells in adipose tissue, comprising administering to a subject a therapeutically effective amount of an agent to be targeted to microvessel endothelial cells in the subject's adipose tissue, wherein the agent is coupled to an adipose tissue microvessel endothelial cell targeting agent. In some embodiments, the adipose tissue microvessel endothelial cell targeting agent binds to a protein expressed on the surface of an endothelial cell lining a microvessel in the subject's adipose tissue. In some embodiments, the protein is encoded by a gene exhibiting higher expression levels in adipose tissue venule endothelial cells compared to adipose tissue non-venule endothelial cells. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the gene is Fcer1a. In some embodiments, the protein is encoded by a gene exhibiting higher expression levels in adipose tissue non-venule endothelial cells compared to adipose tissue venule endothelial cells. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the adipose tissue microvessel endothelial cell targeting agent is internalized into the endothelial cells lining a microvessel in the subject's adipose tissue. In some embodiments, internalization of the adipose tissue microvessel endothelial cell targeting agent into the endothelial cells lining the microvessel in the subject's adipose tissue causes the adipose tissue microvessel endothelial cell targeting agent to accumulate in subject's adipose tissue. In some embodiments, the adipose tissue microvessel endothelial cell targeting agent does not accumulate in tissues other than adipose tissue. In some embodiments, internalization of the adipose tissue microvessel endothelial cell targeting agent into the endothelial cells lining the microvessel in the subject's adipose tissue causes the agent to be internalized into the endothelial cells lining the microvessel in the subject's adipose tissue. In some embodiments, internalization of the agent causes the agent to accumulate in the subject's adipose tissue. In some embodiments, the agent does not accumulate in tissues other than adipose tissue.

In some embodiments, the adipose tissue microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the adipose tissue microvessel endothelial cell targeting agent is coupled to the agent via a linker. In some embodiments, the adipose tissue microvessel endothelial cell targeting agent or agent is coupled to a detectable reporter.

In some embodiments, targeting an agent to the subject's adipose tissue microvessel endothelial cells treats, prevents, or ameliorates a symptom of, a disease characterized by inflammation in the subject's visceral fat.

In some embodiments, the disease is selected from the group consisting of cancer, CVHD, fibrosis, hypertension, lypodystrophy, obesity, metabolic syndrome, and type II diabetes.

In some aspects, disclosed herein is a method of targeting an agent to microvessel endothelial cells in lymph nodes, comprising administering to a subject a therapeutically effective amount of an agent to be targeted to microvessel endothelial cells in the subject's lymph nodes, wherein the agent is coupled to a lymph node microvessel endothelial cell targeting agent. In some embodiments, the lymph node microvessel endothelial cell targeting agent binds to a protein expressed on the surface of an endothelial cell lining a microvessel in the subject's lymph nodes. In some embodiments, the protein is encoded by a gene exhibiting higher expression levels in lymph node venule endothelial cells compared to lymph node non-venule endothelial cells. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the gene is selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the protein is encoded by a gene exhibiting higher expression levels in lymph node non-venule endothelial cells compared to lymph node venule endothelial cells. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the gene is not Pmp22. In some embodiments, the lymph node microvessel endothelial cell targeting agent is internalized into the endothelial cells lining a microvessel in the subject's lymph nodes. In some embodiments, internalization of the lymph node microvessel endothelial cell targeting agent into the endothelial cells lining the microvessel in the subject's lymph nodes causes the lymph node microvessel endothelial cell targeting agent to accumulate in subject's lymph nodes. In some embodiments, the lymph node microvessel endothelial cell targeting agent does not accumulate in tissues other than lymph nodes. In some embodiments, internalization of the lymph node microvessel endothelial cell targeting agent into the endothelial cells lining the microvessel in the subject's lymph nodes causes the agent to be internalized into the endothelial cells lining the microvessel in the subject's lymph nodes. In some embodiments, internalization of the agent causes the agent to accumulate in the subject's lymph nodes. In some embodiments, the agent does not accumulate in tissues other than lymph nodes.

In some embodiments, the lymph node microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises a cytotoxic agent. In some embodiments, the cytotoxic agent is selected from the group consisting of taxol; a nitrogen mustard selected from the group consisting of mechlorethamine, cyclophosphamide, melphalan, uracil mustard and chlorambucil; thiotepa; busulfan; a nitrosourea selected from the group consisting of carmustine, lomustine, semustine and streptozocin; dacarbazine; methotrexate; fluorouracil, cytarabine, azaribine; a purine analogs selected from the group consisting of mercaptopurine and thioguanine; a vinca alkaloids selected from the group consisting of vinblastine and vincristine; an antibiotic selected from the group consisting of dactinomycin, daunorubicin, doxorubicin, bleomycin, mithramycin and mitomycin; L-asparaginase; cisplatin; hydroxyurea; procarbazine; anti-virals; vaccines; and photodynamic dyes. In some embodiments, the agent comprises a chemotherapeutic agent. In some embodiments, the chemotherapeutic agent is selected from the group consisting of vinblastine, doxorubicin, bleomycin, methotrexate, 5-fluorouracil, 6-thioguanine, cytarabine, cyclophosphamide and cisplatinum. In some embodiments, the agent comprises a diagnostic agent. In some embodiments, the agent comprises an imaging agent. In some embodiments, the lymph node microvessel endothelial cell targeting agent is coupled to the agent via a linker. In some embodiments, the microvessel endothelial cell targeting agent is coupled to a detectable reporter.

In some embodiments, targeting an agent to lymph node microvessel endothelial cells of the subject treats, prevents, or ameliorates a symptom of, a disease characterized by lymphadenopathy or lymphadenitis. In some embodiments, the disease is selected from the group consisting of cancer, a connective tissue disorder, and infection. In some embodiments, the cancer is selected from the group consisting of leukemias, lymphomas, and metastatic cancer. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome.

In some aspects, disclosed herein is a method of identifying the venuleness of an endothelial cell or a population of endothelial cells, comprising: (a) obtaining an endothelial cell or a population of endothelial cells to be identified; (b) detecting an expression level in the endothelial cell or the population of endothelial cells of at least one gene which is differentially expressed in venule endothelial cells compared to non-venule endothelial cells; and (c) identifying the venuleness of the endothelial cell, wherein: (i) an elevated level of expression in the endothelial cell or the population of endothelial cells of at least one gene exhibiting higher expression levels in venule endothelial cells compared to non-venule endothelial cells indicates that the endothelial cells comprise venule endothelial cells; (ii) a reduced level of expression in the endothelial cell or the population of endothelial cells of at least one gene exhibiting lower expression levels in venule endothelial cells compared to non-venule endothelial cells indicates that the endothelial cells comprise venule endothelial cells; (iii) an elevated level of expression in the endothelial cell or the population of endothelial cells of at least one gene exhibiting higher expression levels in non-venule endothelial cells compared to venule endothelial cells indicates that the endothelial cells comprise non-venule endothelial cells; and (iv) a reduced level of expression in the endothelial cell or the population of endothelial cells of at least one gene exhibiting lower expression levels in non-venule endothelial cells compared to venule endothelial cells indicates that the endothelial cells comprise non-venule endothelial cells.

In some aspects, disclosed herein is a method of identifying the venuleness of a microvessel, comprising: (a) obtaining an endothelial cell or a population of endothelial cells lining a microvessel to be identified; (b) detecting an expression level in the endothelial cell or the population of endothelial cells of at least one gene which is differentially expressed in venule endothelial cells compared to non-venule endothelial cells; and (c) identifying the venuleness of the microvessel, wherein: (i) an elevated level of expression in the endothelial cell or the population of endothelial cells of at least one gene exhibiting higher expression levels in venule endothelial cells compared to non-venule endothelial cells indicates that the indicates that the microvessel is a venule; (2) a reduced level of expression in the endothelial cell or the population of endothelial cells of at least one gene exhibiting lower expression levels in venule endothelial cells compared to non-venule endothelial cells indicates that the microvessel is a venule (iii) an elevated level of expression in the endothelial cell or the population of endothelial cells of at least one gene exhibiting higher expression levels in non-venule endothelial cells compared to venule endothelial cells indicates that the microvessel is a non-venule; or (iv) a reduced level of expression in the endothelial cell or the population of endothelial cells of at least one gene exhibiting lower expression levels in non-venule endothelial cells compared to venule endothelial cells indicates that the microvessel is a non-venule.

In some aspects, disclosed herein is a method of identifying a candidate agent that modulates the venuleness of an endothelial cell, comprising: (a) contacting an endothelial cell or a population of endothelial cells with a test agent; (b) detecting expression levels in the endothelial cell or the population of endothelial cells, in the presence of the test agent, of at least one gene which is differentially expressed in venule endothelial cells compared to non-venule endothelial cells; and (c) identifying a candidate agent that modulates the venuleness of an endothelial cell, wherein: the test agent is a candidate agent that induces endothelial cells to become venule endothelial cells if, in the presence of the test agent, the endothelial cell or the population of endothelial cells exhibit elevated levels of expression of at least one gene exhibiting higher expression levels in venule endothelial cells compared to non-venule endothelial cells; the test agent is a candidate agent that induces endothelial cells to become venule endothelial cells if, in the presence of the test agent, the endothelial cell or the population of endothelial cells exhibit reduced levels of expression of at least one gene exhibiting lower expression levels in venule endothelial cells compared to non-venule endothelial cells; (i) the test agent is a candidate agent that induces endothelial cells to become non-venule endothelial cells if, in the presence of the test agent, the endothelial cell or the population of endothelial cells exhibit elevated levels of expression of at least one gene exhibiting higher expression levels in non-venule endothelial cells compared to venule endothelial cells; or (ii) the test agent is a candidate agent that induces endothelial cells to become non-venule endothelial cells if, in the presence of the test agent, the endothelial cell or the population of endothelial cells exhibit reduced levels of expression of at least one gene exhibiting lower expression levels in non-venule endothelial cells compared to venule endothelial cells.

In some embodiments, the at least one gene exhibiting higher expression levels in venule endothelial cells compared to non-venule endothelial cells is selected from the group consisting of a gene or combination of genes listed in Table 1. In some embodiments, the at least one gene exhibiting reduced expression levels in venule endothelial cells compared to non-venule endothelial cells is selected from the group consisting of a gene or combination of genes listed in Table 8. In some embodiments, the at least one gene exhibiting higher expression levels in non-venule endothelial cells compared to venule endothelial cells is selected from the group consisting of a gene or combination of genes listed in Table 8. In some embodiments, the at least one gene exhibiting lower expression levels in non-venule endothelial cells compared to venule endothelial cells is selected from the group consisting of a gene or combination of genes listed in Table 1. In some embodiments, wherein the at least one gene is differentially expressed in skin venule endothelial cells compared to skin non-venule endothelial cells. In some embodiments, wherein the at least one gene exhibiting higher expression levels in venule endothelial cells compared to non-venule endothelial cells is selected from the group consisting of a gene or combination of genes listed in Table 2. In some embodiments, the at least one gene exhibiting lower expression levels in venule endothelial cells compared to non-venule endothelial cells is selected from the group consisting of a gene or combination of genes listed in Table 9. In some embodiments, the at least one gene exhibiting higher expression levels in non-venule endothelial cells compared to venule endothelial cells is selected from the group consisting of a gene or combination of genes listed in Table 9. In some embodiments, the at least one gene exhibiting lower expression levels in non-venule endothelial cells compared to venule endothelial cells is selected from the group consisting of a gene or combination of genes listed in Table 2. In some embodiments, the at least one gene is differentially expressed in adipose tissue venule endothelial cells compared to adipose tissue non-venule endothelial cells. In some embodiments, at least one gene exhibiting higher expression levels in venule endothelial cells compared to non-venule endothelial cells is selected from the group consisting of a gene or combination of genes listed in Table 3.

In some embodiments, the at least one gene exhibiting lower expression levels in venule endothelial cells compared to non-venule endothelial cells is selected from the group consisting of a gene or combination of genes listed in Table 10. In some embodiments, the at least one gene exhibiting higher expression levels in non-venule endothelial cells compared to venule endothelial cells is selected from the group consisting of a gene or combination of genes listed in Table 10. In some embodiments, the at least one gene exhibiting lower expression levels in non-venule endothelial cells compared to venule endothelial cells is selected from the group consisting of a gene or combination of genes listed in Table 3. In some embodiments, the at least one gene is differentially expressed in lymph node venule endothelial cells compared to lymph node non-venule endothelial cells. In some embodiments, the at least one gene exhibiting higher expression levels in venule endothelial cells compared to non-venule endothelial cells is selected from the group consisting of a gene or combination of genes listed in Table 4. In some embodiments, the at least one gene exhibiting lower expression levels in venule endothelial cells compared to non-venule endothelial cells is selected from the group consisting of a gene or combination of genes listed in Table 11. In some embodiments, the at least one gene exhibiting higher expression levels in non-venule endothelial cells compared to venule endothelial cells is selected from the group consisting of a gene or combination of genes listed in Table 11. In some embodiments, the at least one gene exhibiting lower expression levels in non-venule endothelial cells compared to venule endothelial cells is selected from the group consisting of a gene or combination of genes listed in Table 4.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the endothelial cell or the population of endothelial cells are obtained from an in vitro source. In some embodiments, the in vitro source is a culture of differentiating stem cells. In some embodiments, the stem cells are selected from the group consisting of human embryonic stem cells (hESCs), induced pluripotent stem cells (iPSCs), and combinations thereof. In some embodiments, the in vitro source is selected from the group consisting of a cell bank, cell line, cell culture, cell population, and combinations thereof.

In some embodiments, the in vitro source is an artificial tissue or organ. In some embodiments, the in vitro source is an artificial tissue selected from the group consisting of skin, adipose tissue, and lymph nodes. In some embodiments, the endothelial cell or population of endothelial cells are obtained from an in vivo source. In some embodiments, the in vivo source is an individual that has received an administration of a microvessel targeting agent.

In some embodiments, the microvessel targeting agent is selected from the group consisting of a skin microvessel targeting agent, an adipose tissue microvessel targeting agent, and a lymph node microvessel targeting agent. In some embodiments, the skin microvessel targeting agent is selected from the group consisting of a skin venule endothelial cell targeting agent and a skin non-venule endothelial cell targeting agent. In some embodiments, the adipose tissue microvessel targeting agent is selected from the group consisting of an adipose tissue venule endothelial cell targeting agent and an adipose tissue non-venule endothelial cell targeting agent. In some embodiments, the lymph node microvessel targeting agent is selected from the group consisting of a lymph node venule endothelial cell targeting agent and a lymph node non-venule endothelial cell targeting agent.

In some embodiments, in vivo source is an individual suffering from a disease selected from the group consisting of a disease associated with leukocyte trafficking, an inflammatory disease, a disease characterized by visceral fat inflammation, a disease characterized by lymphadenitis, an infection, and cancer. In some embodiments, the in vivo source is an individual suffering from a disease involving leukocyte trafficking. In some embodiments, the in vivo source is an individual suffering from a disease involving leukocyte adhesion to endothelial cells. In some embodiments, the in vivo source is a tissue or organ obtained from a donor individual. In some embodiments, the individual is a human or animal individual.

In some embodiments, detecting expression comprises utilizing a technique selected from the group consisting of a microarray analysis, Nanostring technology, RNA-seq, RT-PCR, and q-RT-PCR. In some embodiments, detecting expression comprises conducting at least one binding assay to determine the expression level of the one or more genes. In some embodiments, the method further comprises sorting the venule and non-venule endothelial cells. In some embodiments, sorting comprises fluorescence-activated cell sorting (FACS). In some embodiments, FACS comprises staining at least one antibody specific for an endothelial cell surface marker selected from the group consisting of: (1) a venule endothelial cell surface marker selected from the group consisting of Sele, Selp, Il6st, Plxnb2, Lepr, Bst1, and Icam1; (2) a skin venule endothelial cell surface marker selected from the group consisting of Nrp2, Gpr1, C630004H02Rik, Fndc1, 2310046K01Rik, Insr, and Slco2a1; (3) an adipose tissue endothelial cell surface marker selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; (4) a lymph node endothelial cell surface marker selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; (5) a multi-tissue skin and lymph node venule endothelial cell surface marker selected from the group consisting of Gpr182 and Slco2b1; (6) a multi-tissue adipose tissue and lymph node venule endothelial cell surface marker selected from the group consisting of Cd63, Sirpa, Slc2a1, Vmn1r100, Vmn1r148, Vmn1r132, and Vmn1r125; (7) a multi-tissue adipose tissue and skin venule endothelial cell surface marker selected from the group consisting of Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; (8) a non-venule endothelial cell surface marker selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; (9) a skin non-venule endothelial cell surface marker selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; (10) an adipose tissue non-venule endothelial cell surface marker selected from the group consisting of Adora2a, H2-Ab1, Hspg2, Gpr81, Kcna5, Jam3, and Gpc4; (11) a lymph node non-venule endothelial cell surface marker selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; (12) a multi-tissue skin and lymph node non-venule endothelial cell surface marker selected from the group consisting of Tns1, Cxcr4, Atp1b1, Car4, Cd7, Itga1, Gja5, Laptm5, Aqp7, Gja4, Mlec, P2ry2, and Cd97; (13) a multi-tissue adipose tissue and lymph node non-venule endothelial cell surface marker selected from the group consisting of Unc5b, Lpar6, Sema6d, Ppap2b, and Lpar4; and (14) a multi-tissue adipose tissue and skin non-venule endothelial cell surface marker selected from the group consisting of Ly86, H2-Aa, and Cd74.

In some embodiments, FACS comprises staining at least one antibody specific for an endothelial cell surface marker selected from the group consisting of: (1) a venule endothelial cell surface marker selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker selected from the group consisting of Nrp2, Htr2b, Mr1, Lifr, Anxa1, Lphn2, Vamp5, Olr1, Eps8, Slco2b1, and Slco2a1; (3) an adipose tissue venule endothelial cell surface marker selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node venule endothelial cell surface marker selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker comprising Gpr182; (6) a multi-tissue adipose tissue and lymph node venule endothelial cell surface marker selected from the group consisting of H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker selected from the group consisting of Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (8) a non-venule endothelial cell surface marker selected from the group consisting of Cxcr4, Unc5b, Flt4, Ednrb, Notch4, Prnd, Gja5, Gja4, Alpl, Kcna5, P2ry2, Efnb2, and Itm2a; (9) a skin non-venule endothelial cell surface marker selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker selected from the group consisting of Mtap2, Cxcr7, Palm, Tbxa2r, Enpp3, Pmp22, Mmd, Ptprg, Spatal3, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker selected from the group consisting of Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker selected from the group consisting of Ramp3, Olfr1396, Slc1a1, Cldn15, and Cd109; and (14) a multi-tissue adipose tissue and skin non-venule endothelial cell surface marker selected from the group consisting of Sell, Cd79b, Ly86, Chrm3, Ptger4, and Sema7a. In some embodiments, the venule endothelial cell surface marker is not Sele (also known as Elam-1. In some embodiments, the venule endothelial cell surface marker is not Selp (also known as GMP-140). In some embodiments, the skin non-venule endothelial cell surface marker is not Sell (also known as LEU-8). In some embodiments, the skin non-venule endothelial cell surface marker is not Siglech. In some embodiments, the skin non-venule endothelial cell surface marker is not Cd44. In some embodiments, the skin non-venule endothelial cell surface marker is not Sell. In some embodiments, the lymph node non-venule endothelial cell surface marker is not Pmp22. In some embodiments, the method further comprises quantifying the sorted endothelial cells. In some embodiments, the method further includes preserving the sorted endothelial cells. In some embodiments, the endothelial cells comprise human endothelial cells. In some embodiments, the method further comprises assessing the ability of the candidate agent to exhibit an anti-inflammatory effect. In some embodiments, the candidate agent is assessed for its ability to exhibit a systemic anti-inflammatory effect. In some embodiments, the candidate agent is assessed for its ability to exhibit a tissue-specific anti-inflammatory effect. In some embodiments, the candidate agent is assessed for its ability to exhibit an anti-inflammatory effect in a tissue selected from the group consisting of skin, adipose tissue, and lymph nodes. In some embodiments, the method further comprises coupling the candidate agent to an endothelial cell targeting agent that binds to a protein expressed on the surface of an endothelial cell, and assessing the ability of the endothelial cell targeting agent to target the candidate agent to a targeted tissue comprising the endothelial cell. In some embodiments, the endothelial cell targeting agent is a venule endothelial cell targeting agent that binds to a protein expressed on the surface of venule endothelial cells. In some embodiments, the protein is encoded by a gene selected from the group consisting of Sele, Selp, Il6st, Plxnb2, Lepr, Bst1, and Icam1. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the protein is not encoded by the Sele gene. In some embodiments, the protein is not encoded by the Selp gene. In some embodiments, the endothelial cell targeting agent is a non-venule endothelial cell targeting agent that binds to a protein expressed on the surface of non-venule endothelial cells. In some embodiments, the protein is encoded by a gene selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a. In some embodiments, the endothelial cell targeting agent is a skin venule endothelial cell targeting agent that binds to a protein expressed on the surface of skin venule endothelial cells. In some embodiments, the protein is encoded by a gene selected from the group consisting of Nrp2, Gpr1, C630004H02Rik, Fndc1, 2310046K01Rik, Insr, and Slco2a1. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1.

In some embodiments, the skin venule endothelial cell targeting agent is assessed for its ability to target the candidate agent to the skin. In some embodiments, the endothelial cell targeting agent is a skin non-venule endothelial cell targeting agent that binds to a protein expressed on the surface of skin non-venule endothelial cells. In some embodiments, the protein is encoded by a gene selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the protein is not encoded by the Sell gene. In some embodiments, the protein is not encoded by the Cd44 gene. In some embodiments, the protein is not encoded by the Siglech gene. In some embodiments, the skin non-venule endothelial cell targeting agent is assessed for its ability to target the candidate agent to the skin.

In some embodiments, the endothelial cell targeting agent is an adipose tissue venule endothelial cell targeting agent that binds to a protein expressed on the surface of adipose tissue venule endothelial cells. In some embodiments, the protein is encoded by a gene selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrm4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the adipose tissue venule endothelial cell targeting agent is assessed for its ability to target the candidate agent to adipose tissue. In some embodiments, the endothelial cell targeting agent is an adipose tissue non-venule endothelial cell targeting agent that binds to a protein expressed on the surface of adipose tissue non-venule endothelial cells. In some embodiments, the protein is encoded by a gene selected from the group consisting of Adora2a, H2-Ab1, Hspg2, Gpr81, Kcna5, Jam3, and Gpc4. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the adipose tissue non-venule endothelial cell targeting agent is assessed for its ability to target the candidate agent to adipose tissue.

In some embodiments, the endothelial cell targeting agent is a lymph node venule endothelial cell targeting agent that binds to a protein expressed on the surface of lymph node venule endothelial cells. In some embodiments, the protein is encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the protein is encoded by a gene selected from the group consisting of Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the lymph node venule endothelial cell targeting agent is assessed for its ability to target the candidate agent to lymph nodes. In some embodiments, the endothelial cell targeting agent is a lymph node non-venule endothelial cell targeting agent that binds to a protein expressed on the surface of lymph node non-venule endothelial cells. In some embodiments, the protein is encoded by a gene selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Pmp22 gene. In some embodiments, the lymph node non-venule endothelial cell targeting agent is assessed for its ability to target the candidate agent to lymph nodes.

In some aspects, disclosed herein is a method of modulating leukocyte trafficking and/or inflammation in a subject in need thereof, comprising: (a) administering to the subject an effective amount of an agent that modulates expression of at least one gene which is differentially expressed in venule endothelial cells compared to non-venule endothelial cells, and (b) modulating leukocyte trafficking and/or inflammation in the subject, wherein: (i) an agent that decreases expression of at least one gene which exhibits higher expression levels in venule endothelial cells compared to non-venule endothelial cells inhibits leukocyte trafficking and/or inflammation in the subject; (ii) an agent that increases expression of at least one gene which exhibits lower expression levels in venule endothelial cells compared to non-venule endothelial cells inhibits leukocyte trafficking and/or inflammation in the subject; (iii) an agent that decreases expression of at least one gene which exhibits higher expression levels in non-venule endothelial cells compared to venule endothelial cells enables leukocyte trafficking and/or inflammation to be induced in the subject; or (iv) an agent that increases expression of at least one gene which exhibits lower expression levels in non-venule endothelial cells compared to venule endothelial cells enables leukocyte trafficking and/or inflammation to be induced in the subject.

In some embodiments, the at least one gene exhibiting higher expression levels in venule endothelial cells compared to non-venule endothelial cells is selected from the group consisting of a gene or combination of genes listed in Table 1. In some embodiments, the at least one gene exhibiting lower expression levels in venule endothelial cells compared to non-venule endothelial cells is selected from the group consisting of a gene or combination of genes listed in Table 8. In some embodiments, the at least one gene exhibiting higher expression levels in non-venule endothelial cells compared to venule endothelial cells is selected from the group consisting of a gene or combination of genes listed in Table 8. In some embodiments, the at least one gene exhibiting lower expression levels in non-venule endothelial cells compared to venule endothelial cells is selected from the group consisting of a gene or combination of genes listed in Table 1.

In some embodiments, the at least one gene is differentially expressed in skin venule endothelial cells compared to skin non-venule endothelial cells. In some embodiments, the at least one gene exhibiting higher expression levels in venule endothelial cells compared to non-venule endothelial cells is selected from the group consisting of a gene or combination of genes listed in Table 2. In some embodiments, the at least one gene exhibiting lower expression levels in venule endothelial cells compared to non-venule endothelial cells is selected from the group consisting of a gene or combination of genes listed in Table 9. In some embodiments, the at least one gene exhibiting higher expression levels in non-venule endothelial cells compared to venule endothelial cells is selected from the group consisting of a gene or combination of genes listed in Table 9. In some embodiments, the at least one gene exhibiting lower expression levels in non-venule endothelial cells compared to venule endothelial cells is selected from the group consisting of a gene or combination of genes listed in Table 2.

In some embodiments, the at least one gene is differentially expressed in adipose tissue venule endothelial cells compared to adipose tissue non-venule endothelial cells. In some embodiments, at least one gene exhibiting higher expression levels in venule endothelial cells compared to non-venule endothelial cells is selected from the group consisting of a gene or combination of genes listed in Table 3. In some embodiments, the at least one gene exhibiting lower expression levels in venule endothelial cells compared to non-venule endothelial cells is selected from the group consisting of a gene or combination of genes listed in Table 10. In some embodiments, the at least one gene exhibiting higher expression levels in non-venule endothelial cells compared to venule endothelial cells is selected from the group consisting of the at least one gene exhibiting lower expression levels in non-venule endothelial cells compared to venule endothelial cells is selected from the group consisting of a gene or combination of genes listed in Table 3.

In some embodiments, the at least one gene is differentially expressed in lymph node venule endothelial cells compared to lymph node non-venule endothelial cells. In some embodiments, the at least one gene exhibiting higher expression levels in venule endothelial cells compared to non-venule endothelial cells is selected from the group consisting of a gene or combination of genes listed in Table 4. In some embodiments, the at least one gene exhibiting lower expression levels in venule endothelial cells compared to non-venule endothelial cells is selected from the group consisting of a gene or combination of genes listed in Table 11. In some embodiments, the at least one gene exhibiting higher expression levels in non-venule endothelial cells compared to venule endothelial cells is selected from the group consisting of a gene or combination of genes listed in Table 11. In some embodiments, the at least one gene exhibiting lower expression levels in non-venule endothelial cells compared to venule endothelial cells is selected from the group consisting of a gene or combination of genes listed in Table 4.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, inhibiting leukocyte trafficking and/or inflammation comprises one or more of interfering with leukocyte trafficking, interfering with leukocyte adhesion, and interfering with leukocyte extravasation. In some embodiments, inflammation is inhibited systemically. In some embodiments, inflammation is inhibited in a tissue-specific manner. In some embodiments, inflammation is inhibited in a tissue selected from the group consisting of skin, adipose tissue, and lymph nodes. In some embodiments, enabling leukocyte trafficking and/or inflammation to be induced comprises one or more of enabling leukocyte trafficking, enabling leukocyte adhesion, and enabling leukocyte extravasation. In some embodiments, inflammation is induced systemically. In some embodiments, inflammation is induced in a tissue-specific manner. In some embodiments, inflammation is induced in a tissue selected from the group consisting of skin, adipose tissue, and lymph nodes.

In some aspects, disclosed herein is a method of treating an inflammatory skin disease in a subject in need thereof, comprising administering to the subject an effective amount of an agent that inhibits the level or activity of a gene exhibiting higher expression levels in venule endothelial cells in skin compared to non-venule endothelial cells in skin. In some embodiments, inhibiting the level or activity of the gene interferes with leukocyte interactions with leukocyte interactions with the venule endothelial cells in the skin. In some embodiments, inhibiting the level or activity of the gene interferes with extravasation of leukocytes to the extravascular compartment in the skin. In some embodiments, inhibiting the level or activity of the gene decreases a local inflammatory response in the skin. In some embodiments, the gene encodes a protein selected from the group consisting of an enzyme, a protein kinase, a transcriptional regulator, and a venule endothelial cell surface protein.

In some embodiments, the agent inhibits enzymatic activity of the enzyme. In some embodiments, the agent inhibits the level or activity of phosphorylation of the protein kinase. In some embodiments, the agent inhibits activation of transcription or a signaling pathway. In some embodiments, the agent inhibits leukocyte adhesion to the venule endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the inflammatory skin disease is selected from the group consisting of acne, dermatitis, eczema, oily skin, rosacea, cutaneus lymphoma and urticaria. In some embodiments, the dermatitis is selected from the group consisting of atopic dermatitis, psoriasis and contact dermatitis.

In some embodiments, the venule endothelial cell is selected from a post-capillary venule endothelial cell and a collecting venule endothelial cell.

In some aspects, disclosed herein is a method of treating a disease characterized by visceral fat inflammation in a subject in need thereof, comprising administering to the subject an effective amount of an agent that inhibits the level or activity of a gene exhibiting higher expression levels in venule endothelial cells in adipose tissue compared to non-venule endothelial cells in adipose tissue.

In some embodiments, inhibiting the level or activity of the gene interferes with leukocyte interactions with leukocyte interactions with the venule endothelial cells in the adipose tissue. In some embodiments, inhibiting the level or activity of the gene interferes with extravasation of leukocytes to the extravascular compartment in the adipose tissue. In some embodiments, inhibiting the level or activity of the gene decreases a local inflammatory response in the adipose tissue.

In some embodiments, the gene encodes a protein selected from the group consisting of an enzyme, a protein kinase, a transcriptional regulator, and a venule endothelial cell surface protein. In some embodiments, the agent inhibits enzymatic activity of the enzyme. In some embodiments, the agent inhibits the level or activity of phosphorylation of the protein kinase. In some embodiments, the agent inhibits activation of transcription or a signaling pathway. In some embodiments, the agent inhibits leukocyte adhesion to the venule endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the disease is selected from the group consisting of cancer, CVHD, fibrosis, hypertension, lypodystrophy, obesity, metabolic syndrome, and type II diabetes.

In some aspects, disclosed herein is a method of treating a disease characterized by lymphadenitis in a subject in need thereof, comprising administering to the subject an effective amount of an agent that inhibits the level or activity of a gene exhibiting higher expression levels in venule endothelial cells in lymph nodes compared to non-venule endothelial cells in lymph nodes.

In some embodiments, inhibiting the level or activity of the gene interferes with leukocyte interactions with the venule endothelial cells in the lymph nodes. In some embodiments, inhibiting the level or activity of the gene interferes with extravasation of leukocytes to the extravascular compartment of the lymph nodes. In some embodiments, inhibiting the level or activity of the gene decreases a local inflammatory response in the lymph nodes.

In some embodiments, the gene encodes a protein selected from the group consisting of an enzyme, a protein kinase, a transcriptional regulator, and a venule endothelial cell surface protein.

In some embodiments, the agent inhibits enzymatic activity of the enzyme.

In some embodiments, the agent inhibits the level or activity of phosphorylation of the protein kinase. In some embodiments, the agent inhibits activation of transcription or a signaling pathway. In some embodiments, the agent inhibits leukocyte adhesion to the venule endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the disease is selected from the group consisting of cancer, connective tissue disorders, and infection. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome. In some embodiments, the cancer is selected from the group consisting of leukemias, lymphomas, and metastatic cancer.

In some aspects, disclosed herein is a composition comprising an agent that modulates expression of a gene that is differentially expressed in venule endothelial cells compared to non-venule endothelial cells, wherein the agent is selected from the group consisting of: (1) an agent that decreases expression of at least one gene which exhibits higher expression levels in venule endothelial cells compared to non-venule endothelial cells inhibits inflammation in the subject; (ii) an agent that increases expression of at least one gene which exhibits lower expression levels in venule endothelial cells compared to non-venule endothelial cells inhibits inflammation in the subject; (iii) an agent that decreases expression of at least one gene which exhibits higher expression levels in non-venule endothelial cells compared to venule endothelial cells induces inflammation in the subject; or (iv) an agent that increases expression of at least one gene which exhibits lower expression levels in non-venule endothelial cells compared to venule endothelial cells induces inflammation in the subject.

In some embodiments, the at least one gene exhibiting higher expression levels in venule endothelial cells compared to non-venule endothelial cells is selected from the group consisting of a gene or combination of genes listed in Table 1. In some embodiments, the at least one gene exhibiting lower expression levels in venule endothelial cells compared to non-venule endothelial cells is selected from the group consisting of a gene or combination of genes listed in Table 8. In some embodiments, the at least one gene exhibiting higher expression levels in non-venule endothelial cells compared to venule endothelial cells is selected from the group consisting of a gene or combination of genes listed in Table 8. In some embodiments, the at least one gene exhibiting lower expression levels in non-venule endothelial cells compared to venule endothelial cells is selected from the group consisting of a gene or combination of genes listed in Table 1.

In some embodiments, the at least one gene is differentially expressed in skin venule endothelial cells compared to skin non-venule endothelial cells. In some embodiments, the at least one gene exhibiting higher expression levels in venule endothelial cells compared to non-venule endothelial cells is selected from the group consisting of a gene or combination of genes listed in Table 2. In some embodiments, the at least one gene exhibiting lower expression levels in venule endothelial cells compared to non-venule endothelial cells is selected from the group consisting of a gene or combination of genes listed in Table 9. In some embodiments, the at least one gene exhibiting higher expression levels in non-venule endothelial cells compared to venule endothelial cells is selected from the group consisting of a gene or combination of genes listed in Table 9. In some embodiments, the at least one gene exhibiting lower expression levels in non-venule endothelial cells compared to venule endothelial cells is selected from the group consisting of a gene or combination of genes listed in Table 2.

In some embodiments, the at least one gene is differentially expressed in adipose tissue venule endothelial cells compared to adipose tissue non-venule endothelial cells. In some embodiments, the at least one gene exhibiting higher expression levels in venule endothelial cells compared to non-venule endothelial cells is selected from the group consisting of a gene or combination of genes listed in Table 3. In some embodiments, the at least one gene exhibiting lower expression levels in venule endothelial cells compared to non-venule endothelial cells is selected from the group consisting of a gene or combination of genes listed in Table 10. In some embodiments, the at least one gene exhibiting higher expression levels in non-venule endothelial cells compared to venule endothelial cells is selected from the group consisting of a gene or combination of genes listed in Table 10. In some embodiments, the at least one gene exhibiting lower expression levels in non-venule endothelial cells compared to venule endothelial cells is selected from the group consisting of a gene or combination of genes listed in Table 3.

In some embodiments, the at least one gene is differentially expressed in lymph node venule endothelial cells compared to lymph node non-venule endothelial cells. In some embodiments, the at least one gene exhibiting higher expression levels in venule endothelial cells compared to non-venule endothelial cells is selected from the group consisting of a gene or combination of genes listed in Table 4. In some embodiments, the at least one gene exhibiting lower expression levels in venule endothelial cells compared to non-venule endothelial cells is selected from the group consisting of a gene or combination of genes listed in Table 11. In some embodiments, the at least one gene exhibiting higher expression levels in non-venule endothelial cells compared to venule endothelial cells is selected from the group consisting of a gene or combination of genes listed in Table 11. In some embodiments, the at least one gene exhibiting lower expression levels in non-venule endothelial cells compared to venule endothelial cells is selected from the group consisting of a gene or combination of genes listed in Table 4.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, modulating expression modulates inflammation. In some embodiments, modulating inflammation comprises inhibiting inflammation. In some embodiments, inhibiting inflammation comprises one or more of interfering with leukocyte trafficking, interfering with leukocyte adhesion, and interfering with leukocyte extravasation. In some embodiments, inflammation is inhibited systemically. In some embodiments, inflammation is inhibited in a tissue-specific manner. In some embodiments, inflammation is inhibited in a tissue selected from the group consisting of skin, adipose tissue, and lymph nodes.

In some embodiments, modulating inflammation comprises inducing inflammation. In some embodiments, inducing inflammation comprises one or more of enabling leukocyte trafficking, enabling leukocyte adhesion, and enabling leukocyte extravasation. In some embodiments, inflammation is induced systemically. In some embodiments, inflammation is induced in a tissue-specific manner.

In some embodiments, inflammation is induced in a tissue selected from the group consisting of skin, adipose tissue, and lymph nodes.

In some embodiments, the agent is coupled to an endothelial cell targeting agent that binds to a protein expressed on the surface of the endothelial cell. In some embodiments, the agent is coupled to a venule endothelial cell targeting agent that binds to a protein expressed on the surface of venule endothelial cells. In some embodiments, the protein is encoded by a gene selected from the group consisting of Sele, Selp, Il6st, Plxnb2, Lepr, Bst1, and Icam1. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the protein is not encoded by the Darc gene. In some embodiments, the protein is not encoded by the Sele gene. In some embodiments, the protein is not encoded by the Selp gene. In some embodiments, the protein is encoded by the Bst1 gene.

In some embodiments, the agent is coupled to a non-venule endothelial cell targeting agent that binds to a protein expressed on the surface of non-venule endothelial cells. In some embodiments, the protein is encoded by a gene selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a.

In some embodiments, the agent is coupled to a skin venule endothelial cell targeting agent that binds to a protein expressed on the surface of skin venule endothelial cells. In some embodiments, the protein is encoded by a gene selected from the group consisting of Nrp2, Gpr1, C630004H02Rik, Fndc1, 2310046K01Rik, Insr, and Slco2a1. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1.

In some embodiments, the agent is coupled to a skin non-venule endothelial cell targeting agent that binds to a protein expressed on the surface of skin non-venule endothelial cells. In some embodiments, the protein is encoded by a gene selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the protein is not encoded by the Sell gene. In some embodiments, the protein is not encoded by the Cd44 gene. In some embodiments, the protein is not encoded by the Siglech gene.

In some embodiments, the agent is coupled to an adipose tissue venule endothelial cell targeting agent that binds to a protein expressed on the surface of adipose tissue venule endothelial cells. In some embodiments, the protein is encoded by a gene selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the protein is encoded by the Fcer1a gene.

In some embodiments, the agent is coupled to an adipose tissue non-venule endothelial cell targeting agent that binds to a protein expressed on the surface of adipose tissue non-venule endothelial cells. In some embodiments, the protein is encoded by a gene selected from the group consisting of Adora2a, H2-Ab1, Hspg2, Gpr81, Kcna5, Jam3, and Gpc4. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the agent is coupled to a lymph node venule endothelial cell targeting agent that binds to a protein expressed on the surface of lymph node venule endothelial cells. In some embodiments, the protein is encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the protein is encoded by a gene selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the agent is coupled to a lymph node non-venule endothelial cell targeting agent that binds to a protein expressed on the surface of lymph node non-venule endothelial cells. In some embodiments, the protein is encoded by a gene selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the lymph node non-venule endothelial cell targeting agent does not bind to lymph node non-venule endothelial cell marker Pmp22.

In some embodiments, the endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is encapsulated in a nanoparticle or microparticle. In some embodiments, the agent is encapsulated in a lipid nanoparticle or microparticle. In some embodiments, the agent is coupled to the endothelial cell targeting agent via a linker. In some embodiments, the agent is coupled to a detectable reporter. In some embodiments, the endothelial cell targeting agent is coupled to a detectable reporter.

In some aspects, disclosed herein is a composition comprising an agent to be targeted to microvessel endothelial cells, wherein the agent is coupled to a microvessel endothelial cell targeting agent.

In some embodiments, the microvessel endothelial cell targeting agent binds to a protein expressed on the surface of a microvessel endothelial cell. In some embodiments, the protein is encoded by a gene exhibiting higher expression levels in venule endothelial cells compared to non-venule endothelial cells. In some embodiments, the gene is selected from the group consisting of Sele, Selp, Il6st, Plxnb2, Lepr, Bst1, and Icam1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the gene is not Darc. In some embodiments, the gene is not Sele. In some embodiments, the gene is not Selp. In some embodiments, the gene is Bst1.

In some embodiments, the gene exhibits higher expression levels in venule endothelial cells in skin compared to venule endothelial cells in other tissues. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1.

In some embodiments, the gene exhibits higher expression levels in venule endothelial cells in adipose tissue compared to venule endothelial cells in other tissues. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the gene is Fcer1a.

In some embodiments, the gene exhibits higher expression levels in venule endothelial cells in lymph nodes compared to venule endothelial cells in other tissues. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the gene is selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the gene exhibits higher expression levels in venule endothelial cells in skin and lymph nodes compared to venule endothelial cells in other tissues. In some embodiments, the gene is selected from the group consisting of Gpr182 and Slco2b1. In some embodiments, the gene is Gpr182.

In some embodiments, the gene exhibits higher expression levels in venule endothelial cells in adipose tissue and lymph nodes compared to venule endothelial cells in other tissues. In some embodiments, the gene is selected from the group consisting of Cd63, Sirpa, Slc2a1, Vmn1r100, Vmn1r148, Vmn1r132, and Vmn1r125. In some embodiments, the gene is selected from the group consisting of H60b, Ppap2c, Celsr1, Glycam1, Slc37a1, Cd59a, Slc2a1, Tnfrsf9, Tes, Pglyrp1, Il27ra, and Eda2r.

In some embodiments, the gene exhibits higher expression levels in venule endothelial cells in adipose tissue and skin compared to venule endothelial cells in other tissues. In some embodiments, the gene is selected from the group consisting of Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is encoded by a gene exhibiting higher expression levels in non-venule endothelial cells compared to venule endothelial cells. In some embodiments, the gene is selected from the group consisting of Flt4, Jup, Lgals3bp, Ednrb, Ptp4a3, Gpihbp1, Notch4, Slc9a3r2, Pmd, Sdc3, Alpl, Cldn15, Kdr, Slc6a6, Podxl, Efnb2, Sema7a, and Itm2a. In some embodiments, the gene is selected from the group consisting of Cxcr4, Unc5b, Flt4, Ednrb, Notch4, Prnd, Gja5, Gja4, Alpl, Kcna5, P2ry2, Efnb2, and Itm2a.

In some embodiments, the gene exhibits higher expression levels in non-venule endothelial cells in skin compared to venule endothelial cells in skin. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the gene is not Sell. In some embodiments, the gene is not Cd44. In some embodiments, the gene is not Siglech.

In some embodiments, the gene exhibits higher expression levels in non-venule endothelial cells in adipose tissue compared to venule endothelial cells in adipose tissue. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Tttl7, Clca5, TVmn1r100, Vmn1r148, Vmn1r114, Vmn1r132, Vmn1r93, Vmn1r-ps79, Vmn1r125, Epor, and Jam3.

In some embodiments, the gene exhibits higher expression levels in non-venule endothelial cells in lymph nodes compared to venule endothelial cells lymph nodes. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the gene is not Pmp22.

In some embodiments, the gene exhibits higher expression levels in non-venule endothelial cells in skin and lymph nodes compared to venule endothelial cells in skin and lymph nodes. In some embodiments, the gene is selected from the group consisting of Tns1, Cxcr4, Atp1b1, Car4, Cd7, Itga1, Gja5, Laptm5, Aqp7, Gja4, Mlec, P2ry2, and Cd97. In some embodiments, the gene is selected from the group consisting of Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4.

In some embodiments, the gene exhibits higher expression levels in non-venule endothelial cells in adipose tissue and lymph nodes compared to venule endothelial cells in adipose tissue and lymph nodes. In some embodiments, the gene is selected from the group consisting of Unc5b, Lpar6, Sema6d, Ppap2b, and Lpar4. In some embodiments, the gene is selected from the group consisting of Ramp3, Olfr1396, Slc1a1, Cldn15, and Cd109.

In some embodiments, the gene exhibits higher expression levels in non-venule endothelial cells in adipose tissue and skin compared to venule endothelial cells in adipose tissue and skin. In some embodiments, the gene is selected from the group consisting of Ly86, H2-Aa, and Cd74. In some embodiments, the gene is selected from the group Sell, Cd79b, Ly86, Chrm3, Ptger4, and Sema7a. In some embodiments, the microvessel endothelial cell targeting agent is internalized into the endothelial cells lining the microvessel. In some embodiments, internalization of the microvessel endothelial cell targeting agent into the endothelial cells lining the microvessel causes the microvessel endothelial cell targeting agent to accumulate in the tissue in which the microvessel resides. In some embodiments, the microvessel endothelial cell targeting agent accumulates in the subject's skin. In some embodiments, the microvessel endothelial cell targeting agent accumulates in the subject's adipose tissue. In some embodiments, the microvessel endothelial cell targeting agent accumulates in the venule endothelial cells in the subject's lymph nodes. In some embodiments, the microvessel endothelial cell targeting agent does not accumulate in non-target tissues. In some embodiments, internalization of the microvessel endothelial cell targeting agent into the endothelial cells lining the microvessel causes the agent to accumulate in the tissue in which the microvessel resides. In some embodiments, the agent accumulates in the subject's skin. In some embodiments, the agent accumulates in the subject's adipose tissue. In some embodiments, the agent accumulates in the subject's lymph nodes. In some embodiments, the agent does not accumulate in non-target tissue.

In some embodiments, the microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the microvessel endothelial cell targeting agent is coupled to the agent via a linker. In some embodiments, the microvessel endothelial cell targeting agent or the agent is coupled to a detectable reporter. In some embodiments, the microvessel endothelial cell targeting agent and/or the agent is encapsulated in a nanoparticle or microparticle. In some embodiments, the nanoparticle comprises a lipid nanoparticle or microparticle.

In some embodiments, targeting an agent to microvessel endothelial cells of the subject treats, prevents, or ameliorates a symptom of, an inflammatory disease in the subject. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, targeting an agent to microvessel endothelial cells of the subject treats, prevents, or ameliorates a symptom of, an infection in the subject. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, targeting an agent to microvessel endothelial cells of the subject treats, prevents, or ameliorates a symptom of, cancer in the subject. In some embodiments, the cancer is selected from the group consisting of leukemias, lymphomas, and metastatic cancer. In some embodiments, targeting an agent to microvessel endothelial cells of the subject treats, prevents, or ameliorates a symptom of, a connective tissue disorder in the subject. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome.

In some aspects, the disclosure relates to the use of a composition disclosed herein for treating an individual for a condition characterized by inflammation in a specific organ or tissue. In some embodiments, the inflammation is associated with a disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the composition is used for treating an individual for a condition characterized by an infection. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the composition is used for treating an individual for cancer. In some embodiments, the cancer is selected from the group consisting of leukemias, lymphomas, and metastatic cancer. In some embodiments, the composition is used for treating an individual for a connective tissue disorder. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome.

In some aspects, disclosed herein is a binding partner that binds to an endothelial cell surface marker selected from the group consisting of: (1) a venule endothelial cell surface marker selected from the group consisting of Sele, Selp, Il6st, Plxnb2, Lepr, Bst1, and Icam1; (2) a skin venule endothelial cell surface marker selected from the group consisting of Nrp2, Gpr1, C630004H02Rik, Fndc1, 2310046K01Rik, Insr, and Slco2a1; (3) an adipose tissue endothelial cell surface marker selected from the group consisting of Il1rl1, Gm7609, Rgs1, Gpr126, P2rx1, Slc6a4, Itgb4, A530099J19Rik, Fcer1g, Fcer1a, Slc7a8, Nckap11, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; (4) a lymph node endothelial cell surface marker selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; (5) a multi-tissue skin and lymph node venule endothelial cell surface marker selected from the group consisting of Gpr182 and Slco2b1; (6) a multi-tissue adipose tissue and lymph node venule endothelial cell surface marker selected from the group consisting of Cd63, Sirpa, Slc2a1, Vmn1r100, Vmn1r148, Vmn1r132, and Vmn1r125; (7) a multi-tissue adipose tissue and skin venule endothelial cell surface marker selected from the group consisting of Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; (8) a non-venule endothelial cell surface marker selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; (9) a skin non-venule endothelial cell surface marker selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; (10) an adipose tissue non-venule endothelial cell surface marker selected from the group consisting of Adora2a, H2-Ab1, Hspg2, Gpr81, Kcna5, Jam3, and Gpc4; (11) a lymph node non-venule endothelial cell surface marker selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; (12) a multi-tissue skin and lymph node non-venule endothelial cell surface marker selected from the group consisting of Tns1, Cxcr4, Atp1b1, Car4, Cd7, Itga1, Gja5, Laptm5, Aqp7, Gja4, Mlec, P2ry2, and Cd97; (13) a multi-tissue adipose tissue and lymph node non-venule endothelial cell surface marker selected from the group consisting of Unc5b, Lpar6, Sema6d, Ppap2b, and Lpar4; and (14) a multi-tissue adipose tissue and skin non-venule endothelial cell surface marker selected from the group consisting of Ly86, H2-Aa, and Cd74.

In some aspects, disclosed herein is a binding partner that binds to an endothelial cell surface marker selected from the group consisting of: (1) a venule endothelial cell surface marker selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker selected from the group consisting of Nrp2, Htr2b, Mr1, Lifr, Anxa1, Lphn2, Vamp5, Olr1, Eps8, Slco2b1, and Slco2a1; (3) an adipose tissue venule endothelial cell surface marker selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node venule endothelial cell surface marker selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker comprising Gpr182; (6) a multi-tissue adipose tissue and lymph node venule endothelial cell surface marker selected from the group consisting of H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker selected from the group consisting of Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (8) a non-venule endothelial cell surface marker selected from the group consisting of Cxcr4, Unc5b, Flt4, Ednrb, Notch4, Prnd, Gja5, Gja4, Alpl, Kcna5, P2ry2, Efnb2, and Itm2a; (9) a skin non-venule endothelial cell surface marker selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker selected from the group consisting of Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker selected from the group consisting of Ramp3, Olfr1396, Slc1a1, Cldn15, and Cd109; and (14) a multi-tissue adipose tissue and skin non-venule endothelial cell surface marker selected from the group consisting of Ramp3, Olfr1396, Slc1a1, Cldn15, and Cd109.

In some embodiments, the binding partner does not bind to endothelial cell surface marker Sele. In some embodiments, the binding partner does not bind to endothelial cell surface marker Selp. In some embodiments, the binding partner does not bind to venule endothelial cell surface marker Sele. In some embodiments, the binding partner does not bind to venule endothelial cell surface marker Selp. In some embodiments, the binding partner does not bind to skin non-venule endothelial cell surface marker Sell. In some embodiments, the binding partner does not bind to skin non-venule endothelial cell surface marker Siglech. In some embodiments, the binding partner does not bind to skin non-venule endothelial cell surface marker Cd44. In some embodiments, the binding partner does not bind to lymph node non-venule endothelial cell surface marker Pmp22. In some embodiments, the binding partner is used in FACS. In some embodiments, the binding partner comprises an antibody. In some embodiments, the antibody is selected from the group consisting of polyclonal antibodies, monoclonal antibodies, chimeric antibodies, single-chain antibodies, antibody fragments, humanized antibodies, multi-specific antibodies, and modified antibodies. In some embodiments, the binding partner comprises an aptide.

In some aspects, the disclosure provides a method of modulating the venuleness of an endothelial cell, comprising contacting the endothelial cell with an effective amount of an agent that modulates expression and/or activity of Zfp521 or modulates the activity and/or function of an expression product of Zfp521. In some embodiments, modulating venuleness of the endothelial cell comprises changing the endothelial cell from a venule endothelial cell to a non-venule endothelial cell. In some embodiments, changing the endothelial cell from a venule endothelial cell to a non-venule endothelial cell interferes with leukocyte interactions with the endothelial cell. In some embodiments, changing the endothelial cell from a venule endothelial cell to a non-venule endothelial cell interferes with extravasation of leukocytes to the extravascular compartment in the tissue in which the endothelial cell resides. In some embodiments, changing the endothelial cell from a venule endothelial cell to non-venule endothelial cell decreases a local inflammatory response in the tissue in which the endothelial cell resides. In some embodiments, the endothelial cell is selected from the group consisting of a skin endothelial cell, an adipose tissue endothelial cell, and a lymph node endothelial cell. In some embodiments, the endothelial cell is not an adipose tissue endothelial cell. In some embodiments, the agent decreases expression and/or activity of Zfp521 or an expression product of Zfp521. In some embodiments, the agent decreases leukocyte adhesion to the endothelial cell. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes. In some embodiments, the endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the endothelial cell targeting agent comprises an aptide. In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating venuleness of the endothelial cell comprises changing the endothelial cell from a non-venule endothelial cell to a venule endothelial cell. In such embodiments, changing the endothelial cell from a non-venule endothelial cell to a venule endothelial cell enables leukocyte interactions with the endothelial cell. In such embodiments, changing the endothelial cell from a non-venule endothelial cell to a venule endothelial cell enables extravasation of leukocytes to the extravascular compartment in the tissue in which the endothelial cell resides. In such embodiments, changing the endothelial cell from a non-venule endothelial cell to a venule endothelial cell enables a local inflammatory response in the tissue in which the endothelial cell resides. In some embodiments, the agent increases leukocyte adhesion to the endothelial cell.

In some embodiments, the endothelial cell is selected from the group consisting of a skin endothelial cell, an adipose tissue endothelial cell, and a lymph node endothelial cell. In some embodiments, the endothelial cell is not an adipose tissue endothelial cell.

In some embodiments, the agent increases expression and/or activity of Zfp521 or an expression product of Zfp521. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the non-venule endothelial cell targeting agent comprises an aptide.

In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of modulating the venuleness of a microvessel, comprising contacting at least one endothelial cell of a microvessel with an effective amount of an agent that modulates expression and/or activity of Zfp521 or modulates the activity and/or function of an expression product of Zfp521. In some embodiments, modulating the venuleness of the microvessel comprises changing endothelial cells lining the microvessel from venule endothelial cells to non-venule endothelial cells. In some embodiments, changing the endothelial cells from venule endothelial cells to a non-venule endothelial cells interferes with leukocyte interactions with the microvessel. In some embodiments, changing the endothelial cells from venule endothelial cells to non-venule endothelial cells interferes with extravasation of leukocytes to the extravascular compartment in the tissue in which the microvessel resides. In some embodiments, changing the endothelial cells from venule endothelial cells to non-venule endothelial cells decreases a local inflammatory response in the tissue in which the microvessel resides. In some embodiments, changing the endothelial cells from venule endothelial cells to non-venule endothelial cells inhibits leukocyte adhesion to the microvessel. In some embodiments, the endothelial cells are selected from the group consisting of skin endothelial cells, adipose tissue endothelial cells, and lymph node endothelial cells. In some embodiments, the endothelial cells are not adipose tissue endothelial cells.

In some embodiments, the agent decreases expression and/or activity of Zfp521 or an expression product of Zfp521. In such embodiments, the agent decreases leukocyte adhesion to the endothelial cells lining the microvessel. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent comprises an aptide.

In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating the venuleness of the microvessel comprises changing endothelial cells lining the microvessel from non-venule endothelial cells to venule endothelial cells. In such embodiments, changing the endothelial cells from non-venule endothelial cells to venule endothelial cells enables leukocyte interactions with the microvessel. In such embodiments, changing the endothelial cells from non-venule endothelial cells to venule endothelial cells enables extravasation of leukocytes to the extravascular compartment in the tissue in which the microvessel resides. In such embodiments, changing the endothelial cells from non-venule endothelial cells to venule endothelial cells enables a local inflammatory response in the tissue in which the microvessel resides. In such embodiments, changing the endothelial cells from non-venule endothelial cells to venule endothelial cells inhibits leukocyte adhesion to the microvessel. In some embodiments, the endothelial cells are selected from the group consisting of skin endothelial cells, adipose tissue endothelial cells, and lymph node endothelial cells. In some embodiments, the endothelial cells are not adipose tissue endothelial cells.

In some embodiments, the agent increases expression and/or activity of Zfp521 or an expression product of Zfp521. In such embodiments, the agent increases leukocyte adhesion to the endothelial cells lining the microvessel.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene. In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of modulating leukocyte trafficking and/or inflammation in a subject in need thereof, comprising: (a) administering to the subject an effective amount of an agent that modulates expression and/or activity of Zfp521 or modulates the activity and/or function of an expression product of Zfp521.

In some embodiments, modulating leukocyte trafficking and/or inflammation comprises decreasing leukocyte trafficking and/or inflammation. In such embodiments, decreasing leukocyte trafficking and/or inflammation comprises one or more of interfering with leukocyte trafficking, interfering with leukocyte adhesion, and interfering with leukocyte extravasation. In some embodiments, inflammation is decreased systemically. In some embodiments, inflammation is decreased in a tissue-specific manner. In some embodiments, inflammation is decreased in a tissue selected from the group consisting of skin, adipose tissue, and lymph nodes. In some embodiments, expression and/or activity of Zfp521 or an expression product of Zfp521 is decreased.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent comprises an aptide.

In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating leukocyte trafficking and/or inflammation comprises increasing leukocyte trafficking and/or inflammation. In such embodiments, increasing leukocyte trafficking and/or inflammation to be induced comprises one or more of enabling leukocyte trafficking, enabling leukocyte adhesion, and enabling leukocyte extravasation. In some embodiments, inflammation is induced systemically. In some embodiments, inflammation is induced in a tissue-specific manner. In some embodiments, inflammation is induced in a tissue selected from the group consisting of skin, adipose tissue, and lymph nodes.

In some embodiments, expression and/or activity of Zfp521 or an expression product of Zfp521 is increased. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the non-venule endothelial cell targeting agent comprises an aptide.

In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of treating an inflammatory disease in a subject in need thereof, comprising administering to the subject an effective amount of an agent that modulates expression and/or activity of Zfp521 or modulates the activity and/or function of an expression product of Zfp521.

In some aspects, the disclosure provides a method of treating an inflammatory skin disease in a subject in need thereof, comprising administering to the subject an effective amount of an agent that inhibits expression and/or activity of Zfp521 or an expression product of Zfp521 in skin venule endothelial cells. In some embodiments, inhibiting expression and/or activity of Zfp521 or an expression product of Zfp521 decreases a local inflammatory response in the skin. In some embodiments, the agent inhibits leukocyte adhesion to the skin venule endothelial cells. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a skin venule endothelial cell targeting agent that binds to a protein expressed on the surface of skin venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1, Nrp2, Htr2b, Mr1, Lifr, Anxa1, Lphn2, Vamp5, Olr1, Eps8, Slco2b1, Slco2a1. In some embodiments, the skin venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the skin venule endothelial cell targeting agent comprises an aptide.

In some embodiments, the agent and/or skin venule endothelial cell targeting agent are conjugated to each other. In some embodiments, the agent and/or skin venule endothelial cell targeting agent are conjugated to each other via a linker. In some embodiments, the agent and/or the skin venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or skin venule endothelial cell targeting agent are conjugated to each other and encapsulated in a nanoparticle or microparticle.

In some embodiments, the inflammatory skin disease is selected from the group consisting of acne, dermatitis, eczema, oily skin, rosacea, cutaneus lymphoma and urticaria. In some embodiments, the dermatitis is selected from the group consisting of atopic dermatitis, psoriasis and contact dermatitis. In some embodiments, the venule endothelial cells are selected from a post-capillary venule endothelial cell and a collecting venule post-capillary venule endothelial cell and a collecting venule endothelial cell.

In some aspects, the disclosure provides a method of treating a disease characterized by visceral fat inflammation in a subject in need thereof, comprising administering to the subject an effective amount of an agent that inhibits expression and/or activity of Zfp521 or an expression product of Zfp521 in venule endothelial cells in adipose tissue. In some embodiments, inhibiting expression and/or activity of Zfp521 or an expression product of Zfp521 decreases a local inflammatory response in the adipose tissue. In some embodiments, the agent inhibits leukocyte adhesion to the adipose tissue venule endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to an adipose tissue venule endothelial cell targeting agent that binds to a protein expressed on the surface of adipose tissue venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Il1rl1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the adipose tissue venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the adipose tissue venule endothelial cell targeting agent comprises an aptide.

In some embodiments, the agent and/or adipose tissue venule endothelial cell targeting agent are conjugated to each other. In some embodiments, the agent and/or adipose tissue venule endothelial cell targeting agent are conjugated to each other via a linker. In some embodiments, the agent and/or the adipose tissue venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or adipose tissue venule endothelial cell targeting agent are conjugated to each other and encapsulated in a nanoparticle or microparticle.

In some embodiments, the disease is selected from the group consisting of cancer, CVHD, fibrosis, hypertension, lypodystrophy, obesity, metabolic syndrome, and type II diabetes.

In some aspects, the disclosure provides a method of treating a disease characterized by lymphadenitis in a subject in need thereof, comprising administering to the subject an effective amount of an agent that inhibits expression and/or activity of Zfp521 or an expression product of Zfp521 in venule endothelial cells in lymph nodes. In some embodiments, inhibiting the level or activity of the gene decreases a local inflammatory response in the lymph nodes.

In some embodiments, the agent inhibits leukocyte adhesion to the venule endothelial cell. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a lymph node venule endothelial cell targeting agent that binds to a protein expressed on the surface of lymph node venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the lymph node venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the lymph node venule endothelial cell targeting agent comprises an aptide.

In some embodiments, the agent and/or lymph node venule endothelial cell targeting agent are conjugated to each other. In some embodiments, the agent and/or lymph node venule endothelial cell targeting agent are conjugated to each other via a linker. In some embodiments, the agent and/or the lymph node venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or lymph node venule endothelial cell targeting agent are conjugated to each other and encapsulated in a nanoparticle or microparticle.

In some embodiments, the disease is selected from the group consisting of cancer, connective tissue disorders, and infection. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome. In some embodiments, the cancer is selected from the group consisting of leukemias, lymphomas, and metastatic cancer.

In some aspects, the disclosure provides a composition comprising an agent that inhibits expression and/or activity of Zfp521 or an expression product of Zfp521. In some embodiments, the composition includes an endothelial cell targeting agent that binds to a protein expressed on the surface of endothelial cells in microvessels. In some embodiments, the agent and/or endothelial cell targeting agent are selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent and/or endothelial cell targeting agent are conjugated to each other. In some embodiments, the agent and/or endothelial cell targeting agent are conjugated to each other via a linker. In some embodiments, the agent and/or the endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or endothelial cell targeting agent are conjugated to each other and encapsulated in a nanoparticle or microparticle.

In some embodiments, the endothelial cell targeting agent comprises a venule endothelial cell targeting agent that binds to a protein expressed on the surface of venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the endothelial cell targeting agent comprises a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some aspects, the disclosure relates to the use of an agent that inhibits expression and/or activity of Zfp521 or an expression product of Zfp521 for treating inflammation. In some embodiments, the inflammation is associated with a disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments of a method disclosed herein, the agent modulates the activity and/or function of an expression product of said at least one gene. In some embodiments of a composition disclosed herein, the agent modulates the activity and/or function of an expression product of said at least one gene.

In some aspects, the disclosure relates to the use of an agent to alter the function of a microvessel endothelial cell gene product. In some embodiments, the agent modulates leukocyte interactions with the endothelial cell in which the microvessel endothelial cell gene product is expressed. In some embodiments, the agent modulates an inflammatory response. In some embodiments, the microvessel endothelial cell gene product is encoded by a gene listed in Table 1, Table 2, Table 3, Table 4, Table 5, Table 6, Table 7, Table 8, Table 9, Table 10, Table 11, Table 12, Table 13, and/or Table 14.

In some aspects, the disclosure provides a method of modulating the venuleness of an endothelial cell or a microvessel comprising the endothelial cell, comprising contacting the endothelial cell with an effective amount of an agent that modulates the activity and/or function of an expression product of at least one gene that is differentially expressed in venule endothelial cells compared to non-venule endothelial cells. In some embodiments, modulating the venuleness of the endothelial cell comprises changing the endothelial cell from a venule endothelial cell to a non-venule endothelial cell. In some embodiments, modulating the venuleness of the endothelial cell comprises changing the endothelial cell from a non-venule endothelial cell to a venule endothelial cell. In some embodiments, the at least one gene is selected from the group consisting of a gene, or combination of genes, listed in Table 1 and/or Table 8. In some embodiments, the venuleness of the endothelial cells is modulated in a tissue-specific manner. In some embodiments, the endothelial cell is a skin endothelial cell. In some embodiments, the skin endothelial cell changes from a skin venule endothelial cell to a skin non-venule endothelial cell. In some embodiments, the skin endothelial cell changes from a skin non-venule endothelial cell to a skin venule endothelial cell. In some embodiments, the at least one gene is selected from the group consisting of a gene, or combination of genes, listed in Table 2 and/or Table 9. In some embodiments, the endothelial cell is an adipose tissue endothelial cell. In some embodiments, the adipose tissue endothelial cell changes from an adipose tissue venule endothelial cell to an adipose tissue non-venule endothelial cell. In some embodiments, the adipose tissue endothelial cell changes from an adipose tissue non-venule endothelial cell to an adipose tissue venule endothelial cell. In some embodiments, the at least one gene is selected from the group consisting of a gene, or combination of genes, listed in Table 3 and/or Table 10. In some embodiments, the endothelial cell is a lymph node endothelial cell. In some embodiments, the lymph node endothelial cell changes from a lymph node venule endothelial cell to a lymph node non-venule endothelial cell. In some embodiments, the lymph node endothelial cell changes from a lymph node non-venule endothelial cell to a lymph node venule endothelial cell. In some embodiments, the at least one gene is selected from the group consisting of a gene, or combination of genes, listed in Table 4 and/or Table 11. In some embodiments, changing the endothelial cell from a venule endothelial cell to a non-venule endothelial cell interferes with leukocyte interactions with the endothelial cell. In some embodiments, changing the endothelial cell from a venule endothelial cell to a non-venule endothelial cell interferes with extravasation of leukocytes to the extravascular compartment in the tissue in which the endothelial cell resides. In some embodiments, changing the endothelial cell from a venule endothelial cell to non-venule endothelial cell decreases a local inflammatory response in the tissue in which the endothelial cell resides. In some embodiments, changing the endothelial cell from a non-venule endothelial cell to a venule endothelial cell enables leukocyte interactions with the endothelial cell. In some embodiments, changing the endothelial cell from a non-venule endothelial cell to a venule endothelial cell enables extravasation of leukocytes to the extravascular compartment in the tissue in which the endothelial cell resides. In some embodiments, changing the endothelial cell from a non-venule endothelial cell to a venule endothelial cell enables a local inflammatory response in the tissue in which the endothelial cell resides. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide. In some embodiments, the agent is coupled to an endothelial cell targeting agent that binds to a protein expressed on the surface of the endothelial cell. In some embodiments, the endothelial cell targeting agent comprises an aptide. In some embodiments, the agent is coupled to a venule endothelial cell targeting agent that binds to a protein expressed on the surface of venule endothelial cells. In some embodiments, the venule endothelial cell targeting agent comprises an aptide. In some embodiments, the agent and/or endothelial cell targeting agent are encapsulated in a nanoparticle or microparticle. In some embodiments, the agent and/or venule endothelial cell targeting agent are encapsulated in a nanoparticle or microparticle. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the agent is coupled to a non-venule endothelial cell targeting agent that binds to a protein expressed on the surface of non-venule endothelial cells. In some embodiments, the non-venule endothelial cell targeting agent comprises an aptide. In some embodiments, the agent and/or non-venule endothelial cell targeting agent are encapsulated in a nanoparticle or microparticle. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a. In some embodiments, the agent is coupled to a skin venule endothelial cell targeting agent that binds to a protein expressed on the surface of skin venule endothelial cells. In some embodiments, the skin venule endothelial cell targeting agent comprises an aptide. In some embodiments, the agent and/or skin venule endothelial cell targeting agent are encapsulated in a nanoparticle or microparticle. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1. In some embodiments, the agent is coupled to a skin non-venule endothelial cell targeting agent that binds to a protein expressed on the surface of skin non-venule endothelial cells. In some embodiments, the skin non-venule endothelial cell targeting agent comprises an aptide. In some embodiments, the agent and/or skin non-venule endothelial cell targeting agent are encapsulated in a nanoparticle or microparticle. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the agent is coupled to an adipose tissue venule endothelial cell targeting agent that binds to a protein expressed on the surface of adipose tissue venule endothelial cells. In some embodiments, the adipose tissue venule endothelial cell targeting agent comprises an aptide. In some embodiments, the agent and/or adipose tissue venule endothelial cell targeting agent are encapsulated in a nanoparticle or microparticle. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the agent is coupled to an adipose tissue non-venule endothelial cell targeting agent that binds to a protein expressed on the surface of adipose tissue non-venule endothelial cells. In some embodiments, the adipose tissue non-venule endothelial cell targeting agent comprises an aptide. In some embodiments, the agent and/or adipose tissue non-venule endothelial cell targeting agent are encapsulated in a nanoparticle or microparticle. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the agent is coupled to a lymph node venule endothelial cell targeting agent that binds to a protein expressed on the surface of lymph node venule endothelial cells. In some embodiments, the lymph node venule endothelial cell targeting agent comprises an aptide. In some embodiments, the agent and/or lymph node venule endothelial cell targeting agent are encapsulated in a nanoparticle or microparticle. In some embodiments, the protein is encoded by a gene selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the agent is coupled to a lymph node non-venule endothelial cell targeting agent that binds to a protein expressed on the surface of lymph node non-venule endothelial cells. In some embodiments, the lymph node non-venule endothelial cell targeting agent comprises an aptide. In some embodiments, the agent and/or lymph node non-venule endothelial cell targeting agent are encapsulated in a nanoparticle or microparticle. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Darc gene, or the Sele gene, or the Selp gene, or the Sell gene, or the Cd44 gene, or the il6st gene. In some embodiments, the nanoparticle comprises a polymeric nanoparticle constructed from low molecular weight polyamines and lipids.

In some aspects, the disclosure provides a method of modulating leukocyte trafficking and/or inflammation in a subject in need thereof, comprising: (a) administering to the subject an effective amount of an agent that modulates the activity and or function of an expression product of at least one gene which is differentially expressed in venule endothelial cells compared to non-venule endothelial cells, wherein the agent modulates leukocyte trafficking and/or inflammation in the subject. In some embodiments, the at least one gene is selected from the group consisting of a gene or combination of genes listed in Table 1, Table 2, Table 3, Table 4, Table 5, Table 6, Table 7, Table 8, Table 9, Table 10, Table 11, Table 12, Table 13, and/or Table 14. In some embodiments, the at least one gene is differentially expressed in skin venule endothelial cells compared to skin non-venule endothelial cells. In some embodiments, the at least one gene is differentially expressed in adipose tissue venule endothelial cells compared to adipose tissue non-venule endothelial cells. In some embodiments, the at least one gene is differentially expressed in lymph node venule endothelial cells compared to lymph node non-venule endothelial cells. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide. In some embodiments, the agent is coupled to an endothelial cell targeting agent that binds to a protein expressed on the surface of the endothelial cell. In some embodiments, the agent and/or endothelial cell targeting agent are encapsulated in a nanoparticle or microparticle. In some embodiments, the agent is coupled to a venule endothelial cell targeting agent that binds to a protein expressed on the surface of venule endothelial cells. In some embodiments, the venule endothelial cell targeting agent comprises an aptide. In some embodiments, the agent and/or venule endothelial cell targeting agent are encapsulated in a nanoparticle or microparticle. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the agent is coupled to a non-venule endothelial cell targeting agent that binds to a protein expressed on the surface of non-venule endothelial cells. In some embodiments, the non-venule endothelial cell targeting agent comprises an aptide. In some embodiments, the agent and/or non venule endothelial cell targeting agent are encapsulated in a nanoparticle or microparticle. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a. In some embodiments, the agent is coupled to a skin venule endothelial cell targeting agent that binds to a protein expressed on the surface of skin venule endothelial cells. In some embodiments, the skin venule endothelial cell targeting agent comprises an aptide. In some embodiments, the agent and/or skin venule endothelial cell targeting agent are encapsulated in a nanoparticle or microparticle. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1. In some embodiments, the agent is coupled to a skin non-venule endothelial cell targeting agent that binds to a protein expressed on the surface of skin non-venule endothelial cells. In some embodiments, the skin non-venule endothelial cell targeting agent comprises an aptide. In some embodiments, the agent and/or skin non-venule endothelial cell targeting agent are encapsulated in a nanoparticle or microparticle. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap11, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the agent is coupled to an adipose tissue venule endothelial cell targeting agent that binds to a protein expressed on the surface of adipose tissue venule endothelial cells. In some embodiments, the adipose tissue venule endothelial cell targeting agent comprises an aptide. In some embodiments, the agent and/or adipose tissue venule endothelial cell targeting agent are encapsulated in a nanoparticle or microparticle. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the agent is coupled to an adipose tissue non-venule endothelial cell targeting agent that binds to a protein expressed on the surface of adipose tissue non-venule endothelial cells. In some embodiments, the adipose tissue non-venule endothelial cell targeting agent comprises an aptide. In some embodiments, the agent and/or adipose tissue non-venule endothelial cell targeting agent are encapsulated in a nanoparticle or microparticle. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the agent is coupled to a lymph node venule endothelial cell targeting agent that binds to a protein expressed on the surface of lymph node venule endothelial cells. In some embodiments, the lymph node venule endothelial cell targeting agent comprises an aptide. In some embodiments, the agent and/or lymph node venule endothelial cell targeting agent are encapsulated in a nanoparticle or microparticle. In some embodiments, the protein is encoded by a gene selected from the group consisting of Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the agent is coupled to a lymph node non-venule endothelial cell targeting agent that binds to a protein expressed on the surface of lymph node non-venule endothelial cells. In some embodiments, the a lymph node non-venule endothelial cell targeting agent comprises an aptide. In some embodiments, the agent and/or lymph node non-venule endothelial cell targeting agent are encapsulated in a nanoparticle or microparticle. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Darc gene, or the Sele gene, or the Selp gene, or the Sell gene, or the Cd44 gene, or the il6st gene.

In some aspects, the disclosure provides a composition comprising an agent that modulates activity and/or function of an expression product of at least one gene which is differentially expressed in venule endothelial cells compared to non-venule endothelial cells. In some embodiments, the at least one gene is selected from the group consisting of a gene or combination of genes listed in Table 1, Table 2, Table 3, Table 4, Table 5, Table 6, Table 7, Table 8, Table 9, Table 10, Table 11, Table 12, Table 13, and/or Table 14. In some embodiments, the at least one gene is differentially expressed in skin venule endothelial cells compared to skin non-venule endothelial cells. In some embodiments, the at least one gene is differentially expressed in adipose tissue venule endothelial cells compared to adipose tissue non-venule endothelial cells. In some embodiments, the at least one gene is differentially expressed in lymph node venule endothelial cells compared to lymph node non-venule endothelial cells. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is coupled to an endothelial cell targeting agent that binds to a protein expressed on the surface of the endothelial cell. In some embodiments, the agent is coupled to a venule endothelial cell targeting agent that binds to a protein expressed on the surface of venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, and Itm2a. In some embodiments, the agent is coupled to a skin venule endothelial cell targeting agent that binds to a protein expressed on the surface of skin venule endothelial cells. In some embodiments, the protein is encoded by a gene selected from the group consisting of Nrp2, Htr2b, Mr1, Lifr, Anxa1, Lphn2, Vamp5, Olr1, Eps8, Slco2b1, and Slco2a1. In some embodiments, the agent is coupled to a skin non-venule endothelial cell targeting agent that binds to a protein expressed on the surface of skin non-venule endothelial cells. In some embodiments, the protein is encoded by a gene selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the agent is coupled to an adipose tissue venule endothelial cell targeting agent that binds to a protein expressed on the surface of adipose tissue venule endothelial cells. In some embodiments, the protein is encoded by a gene selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the agent is coupled to an adipose tissue non-venule endothelial cell targeting agent that binds to a protein expressed on the surface of adipose tissue non-venule endothelial cells. In some embodiments, the protein is encoded by a gene selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3. In some embodiments, the agent is coupled to a lymph node venule endothelial cell targeting agent that binds to a protein expressed on the surface of lymph node venule endothelial cells. In some embodiments, the protein is encoded by a gene selected from the group consisting of Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1. In some embodiments, the agent is coupled to a lymph node non-venule endothelial cell targeting agent that binds to a protein expressed on the surface of lymph node non-venule endothelial cells. In some embodiments, the protein is encoded by a gene selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the protein is not encoded by the Darc gene, or the Sele gene, or the Selp gene, or the Sell gene, or the Cd44 gene, or the il6st gene. In some embodiments, the agent and/or endothelial cell targeting agent (e.g., venule-, non-venule-, skin venule-, skin non-venule, adipose tissue venule-, adipose tissue non-venule, lymph node venule-, and/or lymph node non-venule-endothelial cell targeting agents) comprise aptides. In some embodiments, the agent and/or endothelial cell targeting agent (e.g., venule-, non-venule-, skin venule-, skin non-venule, adipose tissue venule-, adipose tissue non-venule, lymph node venule-, and/or lymph node non-venule-endothelial cell targeting agents) are encapsulated in a nanoparticle or microparticle. In some embodiments, the nanoparticle comprises a polymeric nanoparticle constructed from low molecular weight polyamines and lipids.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5 is a micrograph of whole mount staining in mouse cremaster muscle showing that DARC expression is restricted to venules in murine tissue. Note that similar findings (data not shown) were observed in bladder, bone marrow, brain, colon, eye, liver, lymph nodes, muscle, pancreas, Peyer's patches, skin, small intestine, spinal cord, and thymus.

FIG. 6A shows staining of venules with anti-DARC Ab (left panel). FIG. 6B shows staining of microvasculature with anti-CD31 Ab (middle panel). FIG. 6C shows FIGS. 6A and 6B merged together. Arrows on the merged image (right panel) indicate the localization of an arteriole, capillaries and venules. Note that only postcapillay and small collecting venules stain with DARC.

FIG. 12A is a Venn Diagram depicting over-represented genes in venular ECs. FIG. 12B is a table listing the purported functions of the 143 genes over-represented in non-venular ECs in adipose tissue, 33 genes over-represented in non-venular ECs in skin, and the 186 genes over-represented in non-venular ECs in lymph nodes.

FIG. 13 also shows that venular (V) and non-venular (NV) transcriptomes in any given tissue are distinct, but more similar of each other than to corresponding segments in other tissues.

FIG. 19 shows representative confocal micrographs of whole mount adipose tissue (omentum) stained with MAbs against CD31 (yellow) and DARC (blue) (FIG. 19A) and ICAM2 (red) (FIG. 19B) after PBS, si-RNA against ICAM-2 (si-ICAM2) or si-RNA control (si-Luc) injection.

FIG. 21A shows a network analysis of over-represented genes that are shared (64 genes) in venule endothelial cells (V-ECs) compared to non-venular endothelial cells (NV-ECs) of adipose tissue, lymph node and skin. FIG. 21B shows a network analysis of over-represented genes that are uniquely expressed in V-ECs compared to NV-ECs of adipose tissue. FIG. 21C shows a network analysis of over-represented genes that are uniquely expressed in V-ECs compared to NV-ECs of lymph node. FIG. 21D shows a network analysis of over-represented genes that are uniquely expressed in V-ECs compared to NV-ECs of skin. The links displayed in the network analysis (FIGS. 21A, 21B, 21C and 21D) are provided by the software Ingenuity Pathway Analysis. A relationship is created between 2 genes based on the published literature. If the relationship has been demonstrated by the authors on the bench side, the link will be displayed as a full line.

FIG. 22 is a micrograph of whole mount staining in WT (top row) and Zfp521 ko (bottom row) mouse skin showing staining of the microvasculature with anti-CD31 Ab (first panel) and venules with anti-DARC Ab (second panel). There is no detection of DARC expression on venules from Zfp521 ko mouse as shown in the bar graph (n=3 pictures/2 animals analyzed in each condition). DARC expression is still detected on red blood cells by flow cytometry in Zfp521 ko animals.

FIG. 23 is a micrograph of whole mount staining in mouse omentum (top row) and skin (bottom row) showing staining of the microvasculature with anti-CD31 Ab (first panel) and venules with anti-DARC Ab (second panel). The third and fourth panels show the presence of anti-CD130 conjugated fluorescent beads and isotype control conjugated beads respectively, after intravenous injection. The specific binding of anti-CD130 conjugated beads to DARC+ venules has been validated in vivo by intravital microscopy as well.

DETAILED DESCRIPTION OF THE INVENTION

Figure 1:
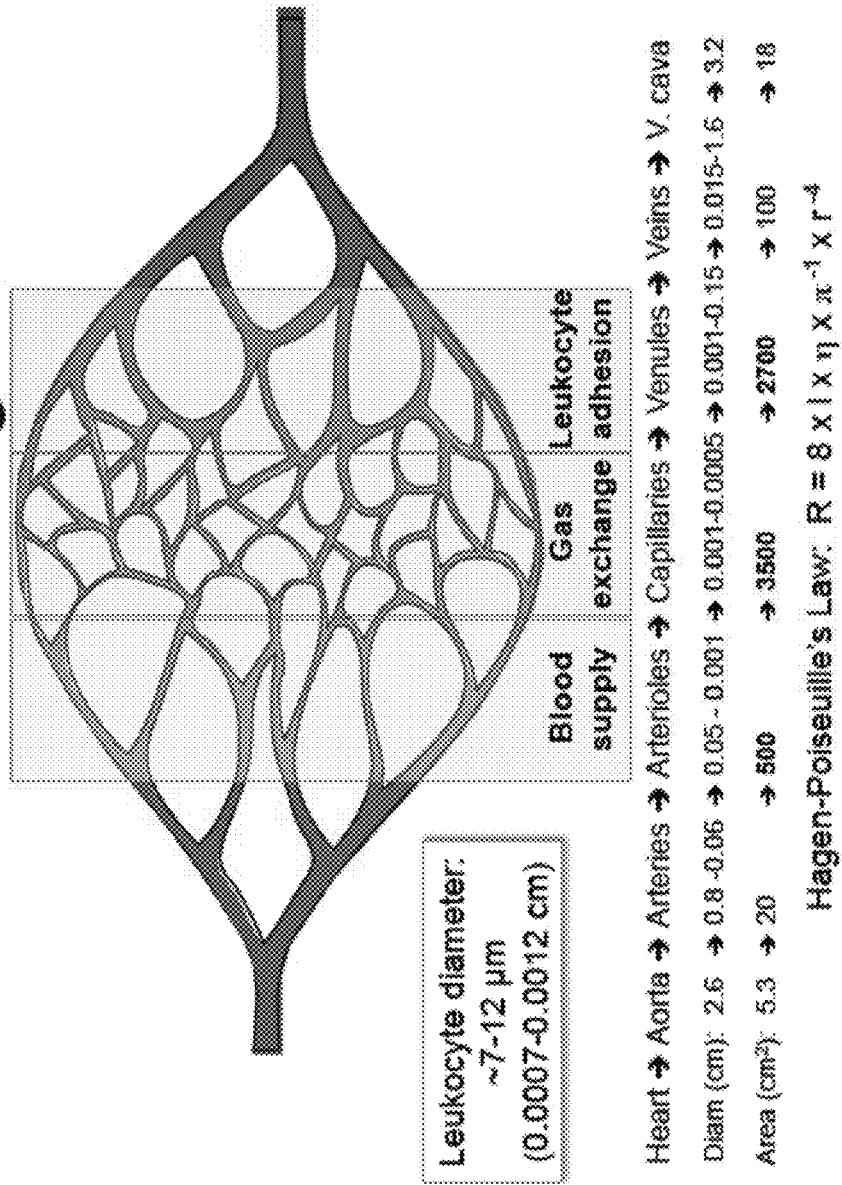
FIG. 1 is a diagrammatic illustration depicting segmentation of the microvascular.

Disclosed herein are genes which are differentially expressed in venule endothelial cells (V-ECs) compared to non-venule endothelial cells (NV-ECs) and methods and compositions relating to those genes. In particular, disclosed herein are methods of modulating the venuleness of an endothelial cell or microvessel, methods of modulating leukocyte trafficking, methods of modulating inflammation, methods of targeting agents to tissues based on their ability to bind to surface markers expressed in a microvessel (e.g., venules and non-venules), methods of identifying the venuleness of endothelial cells or microvessels, methods of identifying agents that modulate the venuleness of endothelial cells or microvessels, methods of identifying agents that target microvessels, methods for treating diseases associated with leukocyte trafficking, methods for treating inflammatory diseases, and compositions and kits for use in the methods.

Methods for Modulating Venuleness

In one aspect, disclosed herein is a method of modulating the venuleness of an endothelial cell, comprising contacting the endothelial cell with an effective amount of an agent that modulates expression of at least one gene that is differentially expressed in venule endothelial cells compared to non-venule endothelial cells. In some aspects, the disclosure provides a method of modulating the venuleness of an endothelial cell or a microvessel comprising the endothelial cell, comprising contacting the endothelial cell with an effective amount of an agent that modulates the activity and/or function of an expression product of at least one gene that is differentially expressed in venule endothelial cells compared to non-venule endothelial cells.

Venuleness of endothelial cells can be modulated both in vitro and in vivo, as well as in certain ex vivo applications, as will be appreciated by those skilled in the art. As used herein, "venuleness" refers to exhibiting one or more properties of venules. As used herein, "venule" refers to a microvessel in which the endothelium of the microvessel comprises venule endothelial cells, and in which leukocyte trafficking occurs (e.g., a post-capillary venule or a collecting venule). As used herein, "venule endothelial cells," "V-ECs" and "venular endothelial cells" are used interchangeably to refer to endothelial cells that form the endothelium of venules. It should be appreciated that a venule or venule endothelial cell may display a marker or combination of markers indicative of venuleness (e.g., a gene or combination of genes which is differentially or selectively expressed in venule endothelial cells compared to non-venule endothelial cells). In contrast to a venule, a "non-venule" refers to a microvessel in which the endothelium of the microvessel comprises non-venule endothelial cells, and in which leukocyte trafficking typically does not occur (e.g., a capillary or arteriole). As used herein, "non-venule endothelial cell", and "NV-EC" are used interchangeably to refer to endothelial cells that form the endothelium of non-venules. It should be appreciated that a non-venule or non-venule endothelial cell may display a marker or combination of markers indicative of non-venuleness (e.g., a gene or combination of genes which is differentially or selectively expressed in non-venule endothelial cells compared to venule-endothelial cells).

Figure 2:
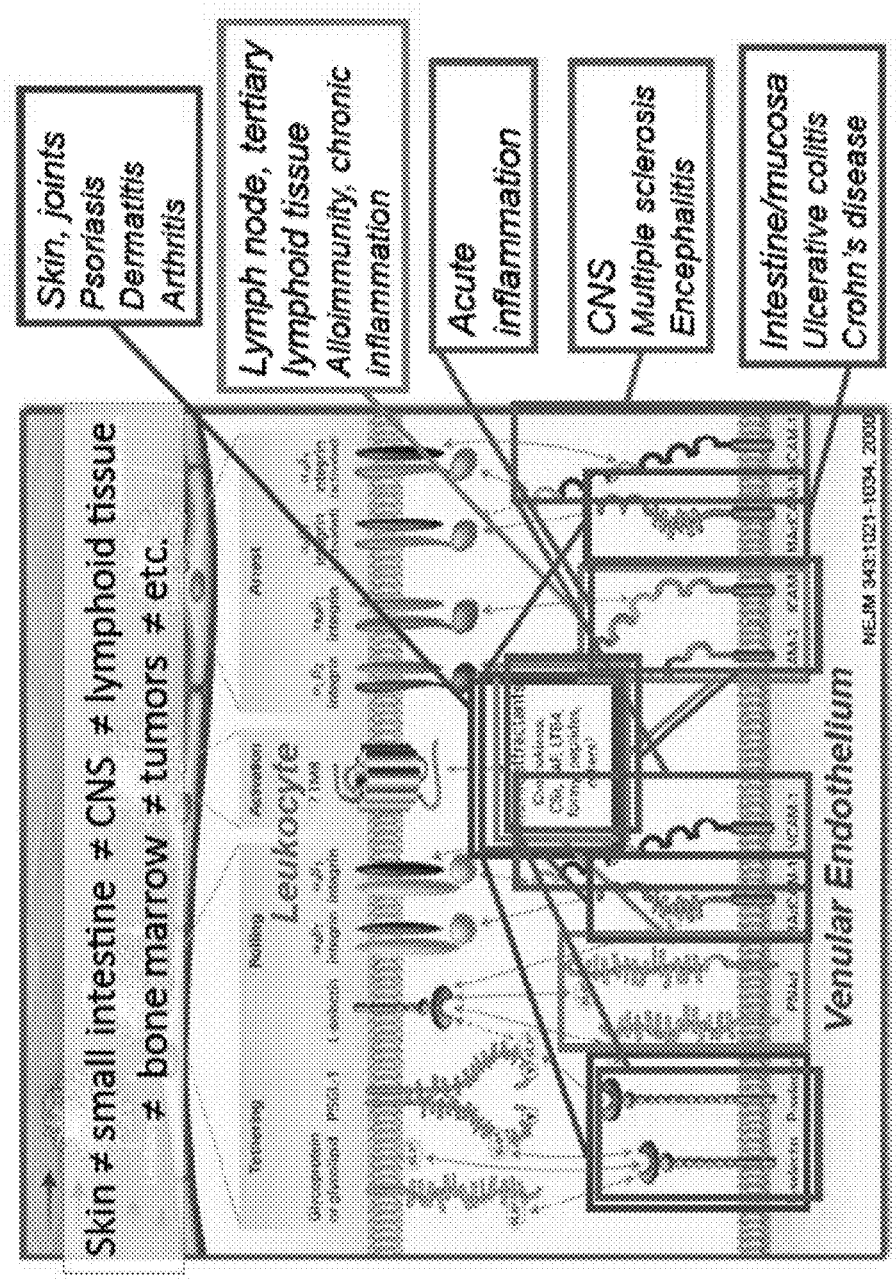
FIG. 2 is a diagrammatic illustration depicting multi-step leukocyte adhesion cascades in various tissues.
Figure 3:
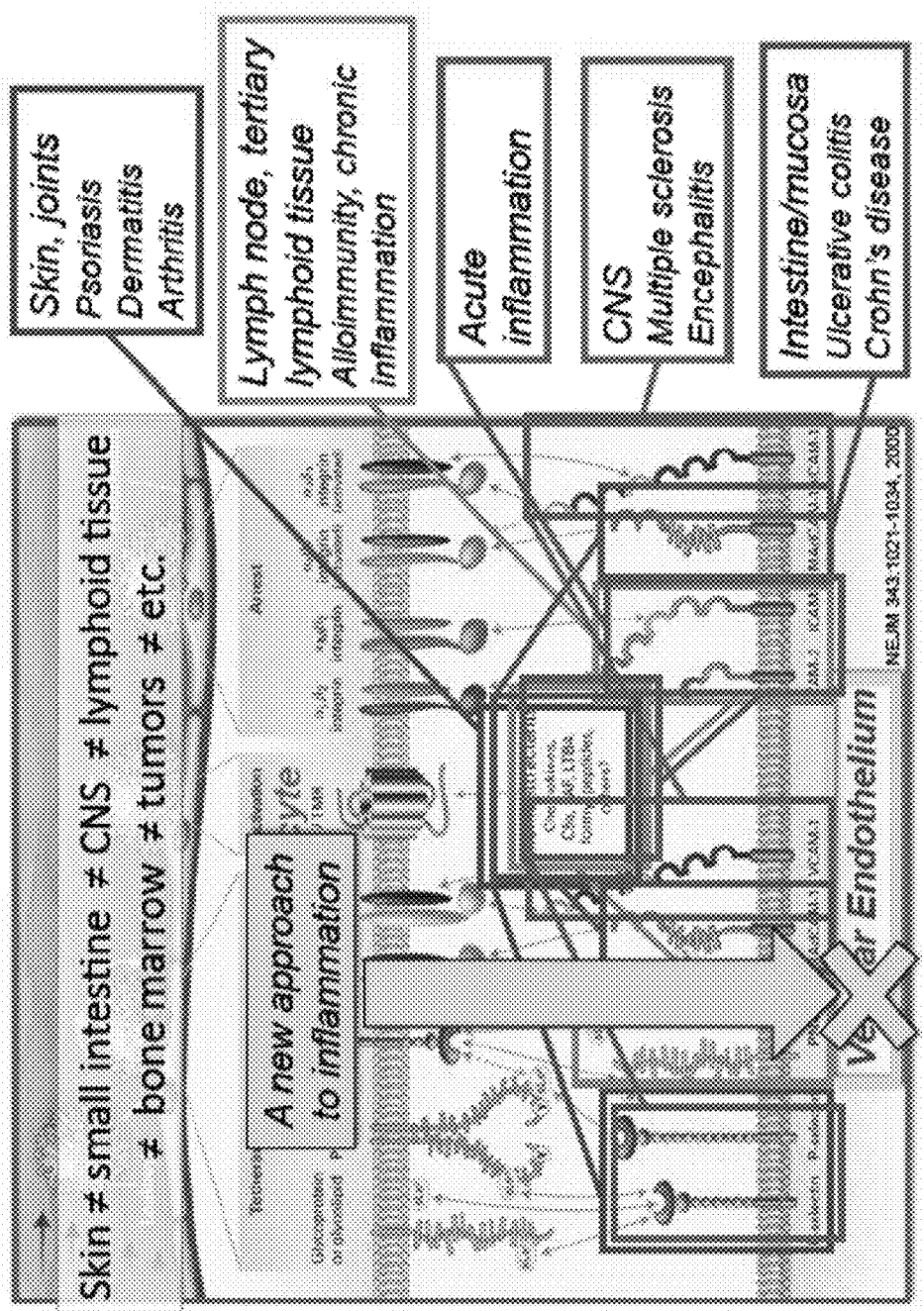
FIG. 3 is a diagrammatic illustration depicting the novel anti-inflammatory drug discovery approach disclosed herein.
Figure 4:
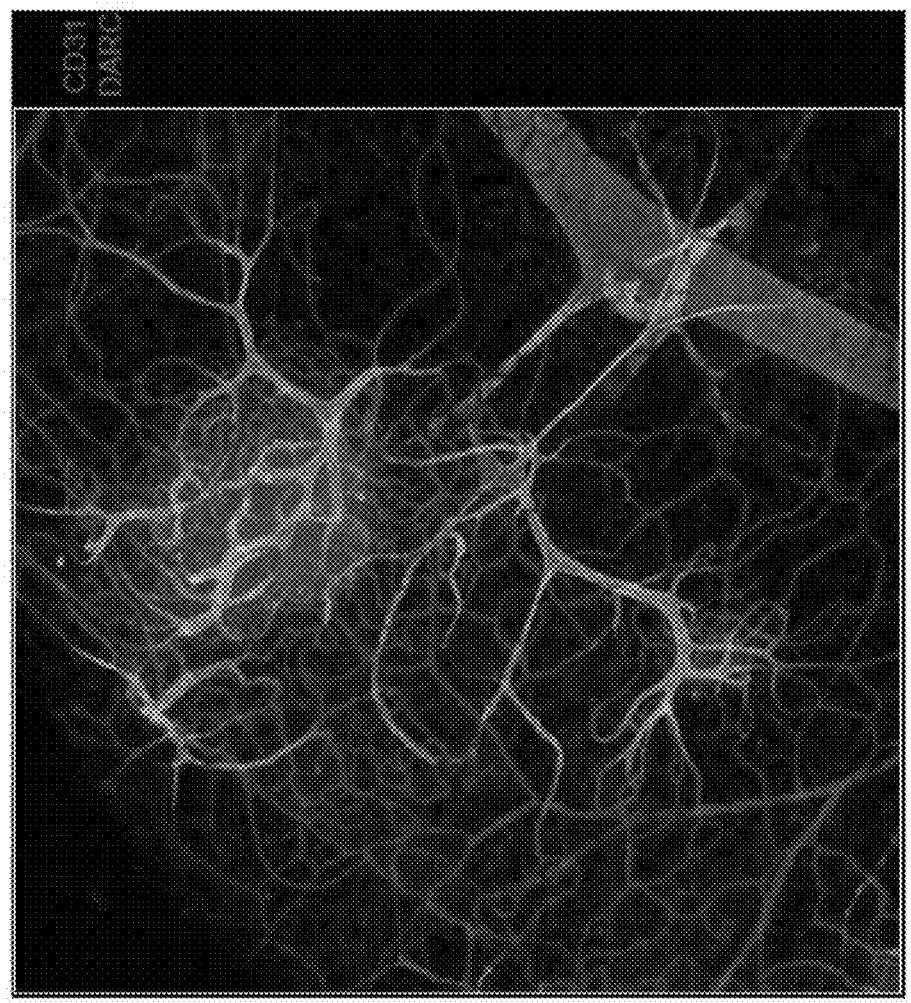
FIG. 4 is a micrograph of whole mount staining in mouse omentum showing that DARC expression is restricted to venules in murine tissues.

The disclosure contemplates changing venule endothelial cells to non-venule endothelial cells. As used herein, "changing" an endothelial cell from a venule to non-venule endothelial cell refers to altering the phenotype of an endothelial cell to the extent that the venule endothelial cell acts or behaves more like a non-venule endothelial cell than a venule endothelial cell (e.g., the resulting endothelial cell's capacity for leukocyte trafficking, adhesion, and/or extravasation is decreased, i.e., the resulting endothelial cell acts like a non-venule endothelial cell which does not enable leukocyte trafficking, adhesion, and/or extravasation). It is believed that changing an endothelial cell from a venule to a non-venule endothelial cell can decrease an inflammatory response in a tissue in which the endothelial cell resides by interfering with multi-step adhesion cascades that enable inflammation in that tissue (see, for example, FIGS. 2 and 3).

The disclosure contemplates changing an endothelial cell from a venule endothelial cell to a non-venule endothelial cell for any purpose in which doing so would be desirable. In some embodiments, changing the endothelial cell from a venule endothelial cell to a non-venule endothelial cell interferes with leukocyte interactions with the endothelial cell. In some embodiments, changing the endothelial cell from a venule endothelial cell to a non-venule endothelial cell interferes with extravasation of leukocytes to the extravascular compartment in the tissue in which the endothelial cell resides. In some embodiments, changing the endothelial cell from a venule endothelial cell to non-venule endothelial cell decreases a local inflammatory response in the tissue in which the endothelial cell resides.

Those skilled in the art will appreciate that changing venule endothelial cells to non-venule endothelial cells can be achieved via either upregulation and activation of a gene described herein (e.g., increasing expression of at least one gene exhibiting lower expression levels in venule endothelial cells compared to non-venule endothelial cells or increasing expression of at least one gene exhibiting higher expression levels in non-venule endothelial cells compared to venule endothelial cells) or via downregulation and inhibition of a gene described herein (e.g., decreasing expression of at least one gene exhibiting higher expression levels in venule endothelial cells compared to non-venule endothelial cells or decreasing expression of at least one gene exhibiting lower expression levels in non-venule endothelial cells compared to venule endothelial cells). Accordingly, in some embodiments a method of modulating the venuleness of an endothelial cell comprises a method of changing a venule endothelial cell to a non-venule endothelial cell. Exemplary methods of changing a venule endothelial cell to a non-venule endothelial cell include contacting a venule endothelial cell with an effective amount of an agent that: (a) decreases expression of at least one gene exhibiting higher expression levels in venule endothelial cells compared to non-venule endothelial cells; (b) increases expression of at least one gene exhibiting lower expression levels in venule endothelial cells compared to non-venule endothelial cells; (c) increases expression of at least one gene exhibiting higher expression levels in non-venule endothelial cells compared to venule endothelial cells; or (d) decreases expression of at least one gene exhibiting lower expression levels in non-venule endothelial cells compared to venule endothelial cells.

In some embodiments, modulating the venuleness of endothelial cells to change an endothelial cell from a venule endothelial cell to a non-venule endothelial cell occurs globally (e.g., regardless of which tissue the endothelial cells reside in). In such embodiments, the at least one gene in (a) exhibiting higher expression levels in venule endothelial cells compared to non-venule endothelial cells is selected from the group consisting of a gene, or combination of genes, listed in Table 1. In such embodiments, the at least one gene in (b) exhibiting lower expression levels in venule endothelial cells compared to non-venule endothelial cells is selected from the group consisting of a gene, or combination of genes, listed in Table 8. In such embodiments, the at least one gene in (c) exhibiting higher expression levels in non-venule endothelial cells compared to venule endothelial cells is selected from the group consisting of a gene, or combination of genes, listed in Table 8. In such embodiments, the at least one gene in (d) exhibiting lower expression levels in non-venule endothelial cells compared to venule endothelial cells is selected from the group consisting of a gene, or combination of genes, listed in Table 1.

In some embodiments, the venuleness of the endothelial cells is modulated in a tissue-specific manner. The disclosure contemplates modulating the venuleness of endothelial cells in any tissue in which genes are differentially expressed in venule endothelial cells in the tissue compared to non-venule endothelial cells in the tissue. In some embodiments, the endothelial cell is a skin endothelial cell and is modulated specifically in skin (e.g., the skin endothelial cell changes from a skin venule endothelial cell to a skin non-venule endothelial cell). Accordingly, in some embodiments a method of modulating the venuleness of an endothelial cell comprises a method of changing a skin venule endothelial cell to a skin non-venule endothelial cell. An exemplary method of changing a skin venule endothelial cell to a skin non-venule endothelial cell comprises contacting a skin venule endothelial cell with an effective amount of an agent that: (a) decreases expression of at least one gene exhibiting higher expression levels in skin venule endothelial cells compared to skin non-venule endothelial cells; (b) increases expression of at least one gene exhibiting lower expression levels in skin venule endothelial cells compared to skin non-venule endothelial cells; (c) increases expression of at least one gene exhibiting higher expression levels in skin non-venule endothelial cells compared to skin venule endothelial cells; or (d) decreases expression of at least one gene exhibiting lower expression levels in skin non-venule endothelial cells compared to skin venule endothelial cells.

In such embodiments, the at least one gene in (a) exhibiting higher expression levels in skin venule endothelial cells compared to skin non-venule endothelial cells is selected from the group consisting of a gene, or combination of genes, listed in Table 2. In such embodiments, the at least one gene in (b) exhibiting lower expression levels in skin venule endothelial cells compared to skin non-venule endothelial cells is selected from the group consisting of a gene, or combination of genes, listed in Table 9. In such embodiments, the at least one gene in (c) exhibiting higher expression levels in skin non-venule endothelial cells compared to skin venule endothelial cells is selected from the group consisting of a gene, or combination of genes, listed in Table 9. In such embodiments, the at least one gene in (d) exhibiting lower expression levels in skin non-venule endothelial cells compared to skin venule endothelial cells is selected from the group consisting of a gene, or combination of genes, listed in Table 2. In some embodiments, the endothelial cell is an adipose tissue endothelial cell and is modulated specifically in adipose tissue (e.g., the adipose tissue endothelial cell changes from an adipose tissue venule endothelial cell to an adipose tissue non-venule endothelial cell). Accordingly, in some embodiments a method of modulating the venuleness of an endothelial cell comprises a method of changing an adipose tissue venule endothelial cell to an adipose tissue non-venule endothelial cell. An exemplary method of changing an adipose tissue venule endothelial cell to an adipose tissue non-venule endothelial cell comprises contacting the adipose tissue venule endothelial cell with an effective amount of an agent that: (a) decreases expression of at least one gene exhibiting higher expression levels in adipose tissue venule endothelial cells compared to adipose tissue non-venule endothelial cells; (b) increases expression of at least one gene exhibiting lower expression levels in adipose tissue venule endothelial cells compared to adipose tissue non-venule endothelial cells; (c) increases expression of at least one gene exhibiting higher expression levels in adipose tissue non-venule endothelial cells compared to adipose tissue venule endothelial cells; or (d) decreases expression of at least one gene exhibiting lower expression levels in adipose tissue non-venule endothelial cells compared to adipose tissue venule endothelial cells.

In such embodiments, the at least one gene in (a) exhibiting higher expression levels in adipose tissue venule endothelial cells compared to adipose tissue non-venule endothelial cells is selected from the group consisting of a gene, or combination of genes, listed in Table 3. In such embodiments, the at least one gene in (b) exhibiting lower expression levels in adipose tissue venule endothelial cells compared to adipose tissue non-venule endothelial cells is selected from the group consisting of a gene, or combination of genes, listed in Table 10. In such embodiments, the at least one gene in (c) exhibiting higher expression levels in adipose tissue non-venule endothelial cells compared to adipose tissue venule endothelial cells is selected from the group consisting of a gene, or combination of genes, listed in Table 10. In such embodiments, the at least one gene in (d) exhibiting lower expression levels in adipose tissue non-venule endothelial cells compared to adipose tissue venule endothelial cells is selected from the group consisting of a gene, or combination of genes, listed in Table 3.

In some embodiments, the endothelial cell is a lymph node endothelial cell and is modulated specifically in lymph node (e.g., the lymph node endothelial cell changes from a lymph node venule endothelial cell to a lymph node non-venule endothelial cell). Accordingly, in some embodiments a method of modulating the venuleness of an endothelial cell comprises a method of changing a lymph node venule endothelial cell to a lymph node non-venule endothelial cell. An exemplary method of changing a lymph node venule endothelial cell to a lymph node non-venule endothelial cell comprises contacting the lymph node venule endothelial cell with an effective amount of an agent that: (a) decreases expression of at least one gene exhibiting higher expression levels in lymph node venule endothelial cells compared to lymph node non-venule endothelial cells; (b) increases expression of at least one gene exhibiting lower expression levels in lymph node venule endothelial cells compared to lymph node non-venule endothelial cells; (c) increases expression of at least one gene exhibiting higher expression levels in lymph node non-venule endothelial cells compared to lymph node venule endothelial cells; or (d) decreases expression of at least one gene exhibiting lower expression levels in lymph node non-venule endothelial cells compared to lymph node venule endothelial cells.

In such embodiments, the at least one gene in (a) exhibiting higher expression levels in lymph node venule endothelial cells compared to lymph node non-venule endothelial cells is selected from the group consisting of a gene, or combination of genes, listed in Table 4. In such embodiments, the at least one gene in (b) exhibiting lower expression levels in lymph node venule endothelial cells compared to lymph node non-venule endothelial cells is selected from the group consisting of a gene, or combination of genes, listed in Table 11. In such embodiments, the at least one gene in (c) exhibiting higher expression levels in lymph node non-venule endothelial cells compared to lymph node venule endothelial cells is selected from the group consisting of a gene, or combination of genes, listed in Table 11. In such embodiments, the at least one gene in (d) exhibiting lower expression levels in lymph node non-venule endothelial cells compared to lymph node venule endothelial cells is selected from the group consisting of a gene, or combination of genes, listed in Table 4.

In the context of modulating the venuleness of an endothelial cell, the disclosure also contemplates changing non-venule endothelial cells to venule endothelial cells. As used herein, "changing" an endothelial cell from a non-venule to a venule endothelial cell refers to altering the phenotype of an endothelial cell to the extent that the endothelial cell acts or behaves more like a venule endothelial cell than a non-venule endothelial cell (e.g., the resulting endothelial cell's capacity for leukocyte trafficking, adhesion, and/or extravasation is increased, i.e., the resulting endothelial cell acts like a venule endothelial cell which enables leukocyte trafficking, adhesion, and/or extravasation). It is believed that changing an endothelial cell from a non-venule to a venule endothelial cell can enable an inflammatory response to be induced in a tissue in which the endothelial cell resides by permitting multi-step adhesion cascades that enable inflammation (see, for example, FIGS. 2 and 3).

The disclosure contemplates changing an endothelial cell from a non-venule endothelial cell to a venule endothelial cell for any purpose in which doing so would be desirable. In some embodiments, changing the endothelial cell from a non-venule endothelial cell to a venule endothelial cell enables leukocyte interactions with the endothelial cell. In some embodiments, changing the endothelial cell from a non-venule endothelial cell to a venule endothelial cell enables extravasation of leukocytes to the extravascular compartment in the tissue in which the endothelial cell resides. In some embodiments, changing the endothelial cell from a non-venule endothelial cell to a venule endothelial cell enables a local inflammatory response to be induced in the tissue in which the endothelial cell resides.

Those skilled in the art will appreciate that changing non-venule endothelial cells to venule endothelial cells can be achieved via either upregulation and activation of a gene described herein (e.g., increasing expression of at least one gene exhibiting higher expression levels in venule endothelial cells compared to non-venule endothelial cells or increasing expression of at least one gene exhibiting lower expression levels in non-venule endothelial cells compared to venule endothelial cells) or via downregulation and inhibition of a gene described herein (e.g., decreasing expression of at least one gene exhibiting lower expression levels in venule endothelial cells compared to non-venule endothelial cells or decreasing expression of at least one gene exhibiting higher expression levels in non-venule endothelial cells compared to venule endothelial cells).

Accordingly, in some embodiments a method of modulating the venuleness of an endothelial cell comprises a method of changing a non-venule endothelial cell to a venule endothelial cell. Exemplary methods of changing a non-venule endothelial cell to a venule endothelial cell include contacting a non-venule endothelial cell with an effective amount of an agent that: (a) increases expression of at least one gene exhibiting higher expression levels in venule endothelial cells compared to non-venule endothelial cells; (b) decreases expression of at least one gene exhibiting lower expression levels in venule endothelial cells compared to non-venule endothelial cells; (c) decreases expression of at least one gene exhibiting higher expression levels in non-venule endothelial cells compared to venule endothelial cells; or (d) increases expression of at least one gene exhibiting lower expression levels in non-venule endothelial cells compared to venule endothelial cells.

In some embodiments, modulating the venuleness of endothelial cells to change an endothelial cell from a non-venule endothelial cell to a venule endothelial cell occurs globally (e.g., regardless of which tissue the endothelial cells reside in). In such embodiments, the at least one gene in (a) exhibiting higher expression levels in venule endothelial cells compared to non-venule endothelial cells is selected from the group consisting of a gene, or combination of genes, listed in Table 1. In such embodiments, the at least one gene in (b) exhibiting lower expression levels in venule endothelial cells compared to non-venule endothelial cells is selected from the group consisting of a gene, or combination of genes, listed in Table 8. In such embodiments, the at least one gene in (c) exhibiting higher expression levels in non-venule endothelial cells compared to venule endothelial cells is selected from the group consisting of a gene, or combination of genes, listed in Table 8. In such embodiments, the at least one gene in (d) exhibiting lower expression levels in non-venule endothelial cells compared to venule endothelial cells is selected from the group consisting of a gene, or combination of genes, listed in Table 1.

In some embodiments, the venuleness of the endothelial cells is modulated in a tissue-specific manner. The disclosure contemplates modulating the venuleness of endothelial cells in any tissue in which genes are differentially expressed in venule endothelial cells in the tissue compared to non-venule endothelial cells in the tissue. In some embodiments, the endothelial cell is a skin endothelial cell and is modulated specifically in skin (e.g., the skin endothelial cell changes from a skin non-venule endothelial cell to a skin venule endothelial cell). Accordingly, in some embodiments a method of modulating the venuleness of an endothelial cell comprises a method of changing a skin non-venule endothelial cell to a skin venule endothelial cell.

An exemplary method of changing a skin non-venule endothelial cell to a skin venule endothelial cell comprises contacting a skin non-venule endothelial cell with an effective amount of an agent that: (a) increases expression of at least one gene exhibiting higher expression levels in skin venule endothelial cells compared to skin non-venule endothelial cells; (b) decreases expression of at least one gene exhibiting lower expression levels in skin venule endothelial cells compared to skin non-venule endothelial cells; (c) decreases expression of at least one gene exhibiting higher expression levels in skin non-venule endothelial cells compared to skin venule endothelial cells; or (d) increases expression of at least one gene exhibiting lower expression levels in skin non-venule endothelial cells compared to skin venule endothelial cells.

In such embodiments, the at least one gene in (a) exhibiting higher expression levels in skin venule endothelial cells compared to skin non-venule endothelial cells is selected from the group consisting of a gene, or combination of genes, listed in Table 2. In such embodiments, the at least one gene in (b) exhibiting lower expression levels in skin venule endothelial cells compared to skin non-venule endothelial cells is selected from the group consisting of a gene, or combination of genes, listed in Table 9. In such embodiments, the at least one gene in (c) exhibiting higher expression levels in skin non-venule endothelial cells compared to skin venule endothelial cells is selected from the group consisting of a gene, or combination of genes, listed in Table 9. In such embodiments, the at least one gene in (d) exhibiting lower expression levels in skin non-venule endothelial cells compared to skin venule endothelial cells is selected from the group consisting of a gene, or combination of genes, listed in Table 2.

In some embodiments, the endothelial cell is an adipose tissue endothelial cell and is modulated specifically in adipose tissue (e.g., the adipose endothelial cell changes from an adipose tissue non-venule endothelial cell to an adipose tissue venule endothelial cell). Accordingly, in some embodiments a method of modulating the venuleness of an endothelial cell comprises a method of changing an adipose tissue non-venule endothelial cell to an adipose tissue venule endothelial cell.

An exemplary method of changing an adipose tissue non-venule endothelial cell to an adipose tissue venule endothelial cell comprises contacting an adipose tissue non-venule endothelial cell with an effective amount of an agent that: (a) increases expression of at least one gene exhibiting higher expression levels in adipose tissue venule endothelial cells compared to adipose tissue non-venule endothelial cells; (b) decreases expression of at least one gene exhibiting lower expression levels in adipose tissue venule endothelial cells compared to adipose tissue non-venule endothelial cells; (c) decreases expression of at least one gene exhibiting higher expression levels in adipose tissue non-venule endothelial cells compared to adipose tissue venule endothelial cells; or (d) increases expression of at least one gene exhibiting lower expression levels in adipose tissue non-venule endothelial cells compared to adipose tissue venule endothelial cells.

In such embodiments, the at least one gene in (a) exhibiting higher expression levels in adipose tissue venule endothelial cells compared to adipose tissue non-venule endothelial cells is selected from the group consisting of a gene, or combination of genes, listed in Table 3. In such embodiments, the at least one gene in (b) exhibiting lower expression levels in adipose tissue venule endothelial cells compared to adipose tissue non-venule endothelial cells is selected from the group consisting of a gene, or combination of genes, listed in Table 10. In such embodiments, the at least one gene in (c) exhibiting higher expression levels in adipose tissue non-venule endothelial cells compared to adipose tissue venule endothelial cells is selected from the group consisting of a gene, or combination of genes, listed in Table 10. In such embodiments, the at least one gene in (d) exhibiting lower expression levels in adipose tissue non-venule endothelial cells compared to adipose tissue venule endothelial cells is selected from the group consisting of a gene, or combination of genes, listed in Table 3.

In some embodiments, the endothelial cell is a lymph node endothelial cell and is modulated specifically in lymph node (e.g., the lymph node endothelial cell changes from a lymph node non-venule endothelial cell to a lymph node venule endothelial cell). Accordingly, in some embodiments a method of modulating the venuleness of an endothelial cell comprises a method of changing a lymph node non-venule endothelial cell to a lymph node venule endothelial cell.

An exemplary method of changing a lymph node non-venule endothelial cell to a lymph node venule endothelial cell comprises contacting a lymph node non-venule endothelial cell with an effective amount of an agent that: (a) increases expression of at least one gene exhibiting higher expression levels in lymph node venule endothelial cells compared to lymph node non-venule endothelial cells; (b) decreases expression of at least one gene exhibiting lower expression levels in lymph node venule endothelial cells compared to lymph node non-venule endothelial cells; (c) decreases expression of at least one gene exhibiting higher expression levels in lymph node non-venule endothelial cells compared to lymph node venule endothelial cells; or (d) increases expression of at least one gene exhibiting lower expression levels in lymph node non-venule endothelial cells compared to lymph node venule endothelial cells.

In such embodiments, the at least one gene in (a) exhibiting higher expression levels in lymph node venule endothelial cells compared to lymph node non-venule endothelial cells is selected from the group consisting of a gene, or combination of genes, listed in Table 4. In such embodiments, the at least one gene in (b) exhibiting lower expression levels in lymph node venule endothelial cells compared to lymph node non-venule endothelial cells is selected from the group consisting of a gene, or combination of genes, listed in Table 11. In such embodiments, the at least one gene in (c) exhibiting higher expression levels in lymph node non-venule endothelial cells compared to lymph node venule endothelial cells is selected from the group consisting of a gene, or combination of genes, listed in Table 11. In such embodiments, the at least one gene in (d) exhibiting lower expression levels in lymph node non-venule endothelial cells compared to lymph node venule endothelial cells is selected from the group consisting of a gene, or combination of genes, listed in Table 4.

In another aspect, disclosed herein is a method of modulating the venuleness of a microvessel, comprising contacting at least one endothelial cell of a microvessel with an effective amount of an agent that modulates expression of at least one gene that is differentially expressed in venule endothelial cells compared to non-venule endothelial cells. Those skilled in the art will also appreciate that changing the venule endothelial cells to non-venule endothelial cells and vice versa can be achieved via modulating the activity and/or function of an expression product of said at least one gene. In some embodiments, the at least one gene is selected from the group consisting of a gene, or combination of genes, listed in Table 1 and/or Table 8. In some embodiments, the endothelial cell is a skin endothelial cell. In some embodiments, the skin endothelial cell changes from a skin venule endothelial cell to a skin non-venule endothelial cell. In some embodiments, the skin endothelial cell changes from a skin non-venule endothelial cell to a skin venule endothelial cell. In some embodiments, the at least one gene is selected from the group consisting of a gene, or combination of genes, listed in Table 2 and/or Table 9. In some embodiments, the endothelial cell is an adipose tissue endothelial cell. In some embodiments, the adipose tissue endothelial cell changes from an adipose tissue venule endothelial cell to an adipose tissue non-venule endothelial cell. In some embodiments, the adipose tissue endothelial cell changes from an adipose tissue non-venule endothelial cell to an adipose tissue venule endothelial cell. In some embodiments, the at least one gene is selected from the group consisting of a gene, or combination of genes, listed in Table 3 and/or Table 10. In some embodiments, the endothelial cell is a lymph node endothelial cell. In some embodiments, the lymph node endothelial cell changes from a lymph node venule endothelial cell to a lymph node non-venule endothelial cell. In some embodiments, the lymph node endothelial cell changes from a lymph node non-venule endothelial cell to a lymph node venule endothelial cell. In some embodiments, the at least one gene is selected from the group consisting of a gene, or combination of genes, listed in Table 4 and/or Table 11.

In some aspects, a method of modulating the venuleness of a microvessel, comprising contacting endothelium of a microvessel with an effective amount of an agent that modulates expression of at least one gene that is differentially expressed in venule endothelial cells compared to non-venule endothelial cells.

As used herein, "microvessel", "microvascular", and "microvasculature" are used interchangeably to refer to venules and non-venules.

It should be appreciated that modulating the venuleness of a microvessel refers to altering the venular phenotype (e.g., venule or non-venule) of a microvessel to the extent that the resulting microvessel acts and behaves as if it were a microvessel of the resulting venular phenotype. In some embodiments, modulating the venuleness of a microvessel comprises changing the venular phenotype of at least about 1%, 5%, 10%, 15%, 20%, 27%, 30%, 34%, 41%, 47%, 50%, 55%, 60%, 62%, 68%, 72%, 75%, 80%, 85%, 90%, 95%, 96%, 97%, 98%, 99%, or up to 100% of the endothelial cells lining the microvessel or a portion thereof. In some embodiments, modulating the venuleness of a microvessel comprises changing the venular phenotype of a majority of the endothelial cells lining the microvessel. In some embodiments, modulating the venuleness of a microvessel comprises changing the venular phenotype of endothelial cells lining a microvessel in a diseased tissue. In some embodiments, modulating the venuleness of a microvessel comprises changing the venular phenotype of endothelial cells lining a diseased portion of a microvessel. In some embodiments, modulating the venuleness of a microvessel comprises changing the venular phenotype of endothelial cells lining an inflamed portion of a microvessel. In some embodiments, modulating the venuleness of a microvessel comprises changing the venular phenotype of endothelial cells lining a microvessel residing in inflamed tissue. In some embodiments, modulating the venuleness of a microvessel comprises changing the venular phenotype of endothelial cells lining a microvessel in which leukocyte trafficking, adhesion, or extravasation is increased. In some embodiments, modulating the venuleness of a microvessel comprises changing the venular phenotype of endothelial cells lining a microvessel in which leukocyte trafficking, adhesion, or extravasation is aberrant. In some embodiments, modulating the venuleness of a microvessel comprises changing the venular phenotype of endothelial cells lining a microvessel in which leukocyte trafficking, adhesion, or extravasation is impaired. In some embodiments, modulating the venuleness of a microvessel comprises changing the venular phenotype of endothelial cells lining a microvessel in which leukocyte trafficking, adhesion, or extravasation otherwise wouldn't occur but for modulating the venuleness of the microvessel.

In the context of modulating the venuleness of a microvessel, the disclosure contemplates changing a venule to a non-venule (e.g., endothelial cells lining the microvessel change from venule endothelial cells to non-venule endothelial cells). As used herein, "changing" endothelial cells lining a microvessel from venule to non-venule endothelial cells refers to altering the phenotype of the endothelial cells lining the microvessel to the extent that the microvessel acts or behaves more like a non-venule than a venule (e.g., the resulting microvessel's capacity for leukocyte trafficking, adhesion, and/or extravasation is decreased, i.e., the resulting microvessel acts like a non-venule which does not enable leukocyte trafficking, adhesion, and/or extravasation). It is believed that changing a microvessel from a venule to a non-venule can decrease an inflammatory response in a tissue in which the microvessel resides by interfering with multi-step adhesion cascades that enable inflammation (see, for example, FIGS. 2 and 3).

The disclosure contemplates changing a microvessel from a venule to a non-venule (e.g., changing the endothelial cells lining the microvessel from venule endothelial cells to non-venule endothelial cells) for any purpose in which doing so would be desirable. In some embodiments, changing the endothelial cells from venule endothelial cells to non-venule endothelial cells interferes with leukocyte interactions with the microvessel. In some embodiments, changing the endothelial cells from venule endothelial cells to non-venule endothelial cells interferes with extravasation of leukocytes to the extravascular compartment in the tissue in which the microvessel resides. In some embodiments, changing the endothelial cells from venule endothelial cells to non-venule endothelial cells decreases a local inflammatory response in the tissue in which the microvessel resides. In some embodiments, changing the endothelial cells from venule endothelial cells to non-venule endothelial cells inhibits leukocyte adhesion to the microvessel.

Those skilled in the art will appreciate that changing endothelial cells lining a microvessel (i.e., modulating the venuleness of a microvessel) from venule endothelial cells to non-venule endothelial cells can be achieved via either upregulation and activation of a gene described herein (e.g., increasing expression of at least one gene exhibiting lower expression levels in venule endothelial cells compared to non-venule endothelial cells or increasing expression of at least one gene exhibiting higher expression levels in non-venule endothelial cells compared to venule endothelial cells) or via downregulation and inhibition of a gene described herein (e.g., decreasing expression of at least one gene exhibiting higher expression levels in venule endothelial cells compared to non-venule endothelial cells or decreasing expression of at least one gene exhibiting lower expression levels in non-venule endothelial cells compared to venule endothelial cells).

Accordingly, in some embodiments a method of modulating the venuleness of a microvessel comprises a method of changing a venule to a non-venule. Exemplary methods of changing a venule to a non-venule include contacting a venule or venule endothelium with an effective amount of an agent that: (a) decreases expression of at least one gene exhibiting higher expression levels in venule endothelial cells compared to non-venule endothelial cells; (b) increases expression of at least one gene exhibiting lower expression levels in venule endothelial cells compared to non-venule endothelial cells; (c) increases expression of at least one gene exhibiting higher expression levels in non-venule endothelial cells compared to venule endothelial cells; or (d) decreases expression of at least one gene exhibiting lower expression levels in non-venule endothelial cells compared to venule endothelial cells.

In some embodiments, modulating the venuleness of a microvessel to change from a venule to a non-venule occurs globally (e.g., regardless of which tissue the microvessel reside in). In such embodiments, the at least one gene in (a) exhibiting higher expression levels in venule endothelial cells compared to non-venule endothelial cells is selected from the group consisting of a gene, or combination of genes, listed in Table 1. In such embodiments, the at least one gene in (b) exhibiting lower expression levels in venule endothelial cells compared to non-venule endothelial cells is selected from the group consisting of a gene, or combination of genes, listed in Table 8. In such embodiments, the at least one gene in (c) exhibiting higher expression levels in non-venule endothelial cells compared to venule endothelial cells is selected from the group consisting of a gene, or combination of genes, listed in Table 8. In such embodiments, the at least one gene in (d) exhibiting lower expression levels in non-venule endothelial cells compared to venule endothelial cells is selected from the group consisting of a gene, or combination of genes, listed in Table 1.

In some embodiments, the venuleness of a microvessel is modulated in a tissue-specific manner. The disclosure contemplates modulating the venuleness of a microvessel in any tissue in which genes are differentially expressed in venule endothelial cells in the tissue compared to non-venule endothelial cells in the tissue.

In some embodiments, the venuleness of the microvessel is modulated in skin (e.g., endothelial cells lining the microvessel in the skin change from skin venule endothelial cells to skin non-venule endothelial cells). Accordingly, in some embodiments a method of modulating the venuleness of a microvessel comprises a method of changing a skin venule to a skin non-venule. An exemplary method of changing a skin venule to a skin non-venule comprises contacting a skin venule or skin venule endothelium with an effective amount of an agent that: (a) decreases expression of at least one gene exhibiting higher expression levels in skin venule endothelial cells compared to skin non-venule endothelial cells; (b) increases expression of at least one gene exhibiting lower expression levels in skin venule endothelial cells compared to skin non-venule endothelial cells; (c) increases expression of at least one gene exhibiting higher expression levels in skin non-venule endothelial cells compared to skin venule endothelial cells; or (d) decreases expression of at least one gene exhibiting lower expression levels in skin non-venule endothelial cells compared to skin venule endothelial cells.

In such embodiments, the at least one gene in (a) exhibiting higher expression levels in skin venule endothelial cells compared to skin non-venule endothelial cells is selected from the group consisting of a gene, or combination of genes, listed in Table 2. In such embodiments, the at least one gene in (b) exhibiting lower expression levels in skin venule endothelial cells compared to skin non-venule endothelial cells is selected from the group consisting of a gene, or combination of genes, listed in Table 9. In such embodiments, the at least one gene in (c) exhibiting higher expression levels in skin non-venule endothelial cells compared to skin venule endothelial cells is selected from the group consisting of a gene, or combination of genes, listed in Table 9. In such embodiments, the at least one gene in (d) exhibiting lower expression levels in skin non-venule endothelial cells compared to skin venule endothelial cells is selected from the group consisting of a gene, or combination of genes, listed in Table 2.

In some embodiments, the venuleness of the microvessel is modulated in adipose tissue (e.g., endothelial cells lining the microvessel change from adipose tissue venule endothelial cells to adipose tissue non-venule endothelial cells). Accordingly, in some embodiments a method of modulating the venuleness of a microvessel comprises a method of changing an adipose tissue venule to an adipose tissue non-venule. An exemplary method of changing an adipose tissue venule to an adipose tissue non-venule comprises contacting an adipose tissue venule with an effective amount of an agent that: (a) decreases expression of at least one gene exhibiting higher expression levels in adipose tissue venule endothelial cells compared to adipose tissue non-venule endothelial cells; (b) increases expression of at least one gene exhibiting lower expression levels in adipose tissue venule endothelial cells compared to adipose tissue non-venule endothelial cells; (c) increases expression of at least one gene exhibiting higher expression levels in adipose tissue non-venule endothelial cells compared to adipose tissue venule endothelial cells; or (d) decreases expression of at least one gene exhibiting lower expression levels in adipose tissue non-venule endothelial cells compared to adipose tissue venule endothelial cells.

In such embodiments, the at least one gene in (a) exhibiting higher expression levels in adipose tissue venule endothelial cells compared to adipose tissue non-venule endothelial cells is selected from the group consisting of a gene, or combination of genes, listed in Table 3. In such embodiments, the at least one gene in (b) exhibiting lower expression levels in adipose tissue venule endothelial cells compared to adipose tissue non-venule endothelial cells is selected from the group consisting of a gene, or combination of genes, listed in Table 10. In such embodiments, the at least one gene in (c) exhibiting higher expression levels in adipose tissue non-venule endothelial cells compared to adipose tissue venule endothelial cells is selected from the group consisting of a gene, or combination of genes, listed in Table 10. In such embodiments, the at least one gene in (d) exhibiting lower expression levels in adipose tissue non-venule endothelial cells compared to adipose tissue venule endothelial cells is selected from the group consisting of a gene, or combination of genes, listed in Table 3.

In some embodiments, the venuleness of the microvessel is modulated in lymph nodes (e.g., endothelial cells lining the microvessel change from lymph node venule endothelial cells to lymph node non-venule endothelial cells). Accordingly, in some embodiments a method of modulating the venuleness of a microvessel comprises a method of changing a lymph node venule to a lymph node non-venule. An exemplary method of changing lymph node venule to lymph node non-venule comprises contacting a lymph node venule or lymph node venule endothelium with an effective amount of an agent that: (a) decreases expression of at least one gene exhibiting higher expression levels in lymph node venule endothelial cells compared to lymph node non-venule endothelial cells; (b) increases expression of at least one gene exhibiting lower expression levels in lymph node venule endothelial cells compared to lymph node non-venule endothelial cells; (c) increases expression of at least one gene exhibiting higher expression levels in lymph node non-venule endothelial cells compared to lymph node venule endothelial cells; or (d) decreases expression of at least one gene exhibiting lower expression levels in lymph node non-venule endothelial cells compared to lymph node venule endothelial cells.

In such embodiments, the at least one gene in (a) exhibiting higher expression levels in lymph node venule endothelial cells compared to lymph node non-venule endothelial cells is selected from the group consisting of a gene, or combination of genes, listed in Table 4. In such embodiments, the at least one gene in (b) exhibiting lower expression levels in lymph node venule endothelial cells compared to lymph node non-venule endothelial cells is selected from the group consisting of a gene, or combination of genes, listed in Table 11. In such embodiments, the at least one gene in (c) exhibiting higher expression levels in lymph node non-venule endothelial cells compared to lymph node venule endothelial cells is selected from the group consisting of a gene, or combination of genes, listed in Table 11. In such embodiments, the at least one gene in (d) exhibiting lower expression levels in lymph node non-venule endothelial cells compared to lymph node venule endothelial cells is selected from the group consisting of a gene, or combination of genes, listed in Table 4.

In the context of modulating the venuleness of a microvessel, the disclosure contemplates changing a non-venule to a venule (e.g., endothelial cells lining the microvessel change from non-venule endothelial cells to venule endothelial cells). As used herein, "changing" endothelial cells lining a microvessel from non-venule to venule endothelial cells refers to altering the phenotype of the endothelial cells lining the microvessel to the extent that the microvessel acts or behaves more like a venule than a non-venule (e.g., the resulting microvessel's capacity for leukocyte trafficking, adhesion, and/or extravasation is increased, i.e., the resulting microvessel acts like a venule which enables leukocyte trafficking, adhesion, and/or extravasation). It is believed that changing a microvessel from a non-venule to a venule can enable an inflammatory response to be induced in a tissue in which the microvessel resides by permitting multi-step adhesion cascades that enable inflammation in the tissue (see, for example, FIGS. 2 and 3).

The disclosure contemplates changing a microvessel from a non-venule to a venule (e.g., changing the endothelial cells lining the microvessel from non-venule endothelial cells to venule endothelial cells) for any purpose in which doing so would be desirable. In some embodiments, changing the endothelial cells from non-venule endothelial cells to venule endothelial cells enables leukocyte interactions with the microvessel. In some embodiments, changing the endothelial cells from non-venule endothelial cells to venule endothelial cells enables extravasation of leukocytes to the extravascular compartment in the tissue in which the microvessel resides. In some embodiments, changing the endothelial cells from non-venule endothelial cells to venule endothelial cells enables a local inflammatory response in the tissue in which the microvessel resides.

Accordingly, in some embodiments, a method of modulating the venuleness of a microvessel comprises a method of changing a non-venule to a venule. Exemplary method of changing a non-venule to a venule include contacting a non-venule or non-venule endothelium with an effective amount of an agent that (a) increases expression of at least one gene exhibiting higher expression levels in venule endothelial cells compared to non-venule endothelial cells; (b) decreases expression of at least one gene exhibiting lower expression levels in venule endothelial cells compared to non-venule endothelial cells; (c) decreases expression of at least one gene exhibiting higher expression levels in non-venule endothelial cells compared to venule endothelial cells; or (d) increases expression of at least one gene exhibiting lower expression levels in non-venule endothelial cells compared to venule endothelial cells.

In some embodiments, modulating the venuleness of a microvessel to change from a non-venule to a venule occurs globally (e.g., regardless of which tissue the microvessel resides in). In such embodiments, the at least one gene in (a) exhibiting higher expression levels in venule endothelial cells compared to non-venule endothelial cells is selected from the group consisting of a gene, or combination of genes, listed in Table 1. In such embodiments, the at least one gene in (b) exhibiting lower expression levels in venule endothelial cells compared to non-venule endothelial cells is selected from the group consisting of a gene, or combination of genes, listed in Table 8. In such embodiments, the at least one gene in (c) exhibiting higher expression levels in non-venule endothelial cells compared to venule endothelial cells is selected from the group consisting of a gene, or combination of genes, listed in Table 8. In such embodiments, the at least one gene in (d) exhibiting lower expression levels in non-venule endothelial cells compared to venule endothelial cells is selected from the group consisting of a gene, or combination of genes, listed in Table 1.

In some embodiments, the venuleness of a microvessel is modulated in a tissue-specific manner. The disclosure contemplates modulating the venuleness of a microvessel in any tissue in which genes are differentially expressed in venule endothelial cells in the tissue compared to non-venule endothelial cells in the tissue.

In some embodiments, the venuleness of the microvessel is modulated in skin (e.g., endothelial cells lining the microvessel in the skin change from skin non-venule endothelial cells to skin venule endothelial cells). Accordingly, in some embodiments a method of modulating the venuleness of a microvessel comprises a method of changing a skin non-venule to a skin venule.

An exemplary method of changing a skin non-venule to a skin venule comprises contacting a skin non-venule or skin non-venule endothelium with an effective amount of an agent that: (a) increases expression of at least one gene exhibiting higher expression levels in skin venule endothelial cells compared to skin non-venule endothelial cells; (b) decreases expression of at least one gene exhibiting lower expression levels in skin venule endothelial cells compared to skin non-venule endothelial cells; (c) decreases expression of at least one gene exhibiting higher expression levels in skin non-venule endothelial cells compared to skin venule endothelial cells; or (d) increases expression of at least one gene exhibiting lower expression levels in skin non-venule endothelial cells compared to skin venule endothelial cells.

In such embodiments, the at least one gene in (a) exhibiting higher expression levels in skin venule endothelial cells compared to skin non-venule endothelial cells is selected from the group consisting of a gene, or combination of genes, listed in Table 2. In such embodiments, the at least one gene in (b) exhibiting lower expression levels in skin venule endothelial cells compared to skin non-venule endothelial cells is selected from the group consisting of a gene, or combination of genes, listed in Table 9. In such embodiments, the at least one gene in (c) exhibiting higher expression levels in skin non-venule endothelial cells compared to skin venule endothelial cells is selected from the group consisting of a gene, or combination of genes, listed in Table 9. In such embodiments, the at least one gene in (d) exhibiting lower expression levels in skin non-venule endothelial cells compared to skin venule endothelial cells is selected from the group consisting of a gene, or combination of genes, listed in Table 2.

In some embodiments, the venuleness of the microvessel is modulated in adipose tissue (e.g., endothelial cells lining the microvessel change from adipose tissue non-venule endothelial cells to adipose tissue venule endothelial cells). Accordingly, in some embodiments a method of modulating the venuleness of a microvessel comprises a method of changing an adipose tissue non-venule to an adipose tissue venule.

An exemplary method of changing an adipose tissue non-venule to an adipose tissue venule comprises contacting an adipose tissue non-venule or adipose tissue non-venule endothelium with an effective amount of an agent that: (a) increases expression of at least one gene exhibiting higher expression levels in adipose tissue venule endothelial cells compared to adipose tissue non-venule endothelial cells; (b) decreases expression of at least one gene exhibiting lower expression levels in adipose tissue venule endothelial cells compared to adipose tissue non-venule endothelial cells; (c) decreases expression of at least one gene exhibiting higher expression levels in adipose tissue non-venule endothelial cells compared to adipose tissue venule endothelial cells; or (d) increases expression of at least one gene exhibiting lower expression levels in adipose tissue non-venule endothelial cells compared to adipose tissue venule endothelial cells.

In such embodiments, the at least one gene in (a) exhibiting higher expression levels in adipose tissue venule endothelial cells compared to adipose tissue non-venule endothelial cells is selected from the group consisting of a gene, or combination of genes, listed in Table 3. In such embodiments, the at least one gene in (b) exhibiting lower expression levels in adipose tissue venule endothelial cells compared to adipose tissue non-venule endothelial cells is selected from the group consisting of a gene, or combination of genes, listed in Table 10. In such embodiments, the at least one gene in (c) exhibiting higher expression levels in adipose tissue non-venule endothelial cells compared to adipose tissue venule endothelial cells is selected from the group consisting of a gene, or combination of genes, listed in Table 10. In such embodiments, the at least one gene in (d) exhibiting lower expression levels in adipose tissue non-venule endothelial cells compared to adipose tissue venule endothelial cells is selected from the group consisting of a gene, or combination of genes, listed in Table 3.

In some embodiments, the venuleness of the microvessel is modulated in lymph nodes (e.g., endothelial cells lining the microvessel change from lymph node non-venule endothelial cells to lymph node venule endothelial cells). Accordingly, in some embodiments a method of modulating the venuleness of a microvessel comprises a method of changing a lymph node non-venule to a lymph node venule.

An exemplary method of changing a lymph node non-venule to a lymph node venule comprises contacting a lymph node non-venule or lymph node non-venule endothelium with an effective amount of an agent that: (a) increases expression of at least one gene exhibiting higher expression levels in lymph node venule endothelial cells compared to lymph node non-venule endothelial cells; (b) decreases expression of at least one gene exhibiting lower expression levels in lymph node venule endothelial cells compared to lymph node non-venule endothelial cells; (c) decreases expression of at least one gene exhibiting higher expression levels in lymph node non-venule endothelial cells compared to lymph node venule endothelial cells; or (d) increases expression of at least one gene exhibiting lower expression levels in lymph node non-venule endothelial cells compared to lymph node venule endothelial cells.

In such embodiments, the at least one gene in (a) exhibiting higher expression levels in lymph node venule endothelial cells compared to lymph node non-venule endothelial cells is selected from the group consisting of a gene, or combination of genes, listed in Table 4. In such embodiments, the at least one gene in (b) exhibiting lower expression levels in lymph node venule endothelial cells compared to lymph node non-venule endothelial cells is selected from the group consisting of a gene, or combination of genes, listed in Table 11. In such embodiments, the at least one gene in (c) exhibiting higher expression levels in lymph node non-venule endothelial cells compared to lymph node venule endothelial cells is selected from the group consisting of a gene, or combination of genes, listed in Table 11. In such embodiments, the at least one gene in (d) exhibiting lower expression levels in lymph node non-venule endothelial cells compared to lymph node venule endothelial cells is selected from the group consisting of a gene, or combination of genes, listed in Table 4.

Methods of Modulating Leukocyte Trafficking and/or Inflammation

In some aspects, the disclosure provides a method for modulating leukocyte trafficking and/or inflammation in a subject in need thereof. An exemplary method of modulating leukocyte trafficking and/or inflammation in a subject in need thereof comprises: (a) administering to the subject an effective amount of an agent that modulates expression of at least one gene which is differentially expressed in venule endothelial cells compared to non-venule endothelial cells, and (b) modulating leukocyte trafficking and/or inflammation in the subject, wherein: (i) an agent that decreases expression of at least one gene which exhibits higher expression levels in venule endothelial cells compared to non-venule endothelial cells inhibits leukocyte trafficking and/or inflammation in the subject; (ii) an agent that increases expression of at least one gene which exhibits lower expression levels in venule endothelial cells compared to non-venule endothelial cells inhibits leukocyte trafficking and/or inflammation in the subject; (iii) an agent that decreases expression of at least one gene which exhibits higher expression levels in non-venule endothelial cells compared to venule endothelial cells enables leukocyte trafficking and/or inflammation in the subject; or (iv) an agent that increases expression of at least one gene which exhibits lower expression levels in non-venule endothelial cells compared to venule endothelial cells enables leukocyte trafficking and/or inflammation in the subject.

In some aspects, the disclosure provides a method of modulating leukocyte trafficking and/or inflammation in a subject in need thereof, comprising: (a) administering to the subject an effective amount of an agent that modulates the activity and or function of an expression product of at least one gene which is differentially expressed in venule endothelial cells compared to non-venule endothelial cells, wherein the agent modulates leukocyte trafficking and/or inflammation in the subject. The methods of modulating leukocyte trafficking and/or inflammation disclosed herein contemplate modulating expression of any gene which is differentially expressed in venule endothelial cells compared to non-venule endothelial cells. In some embodiments, the at least one gene exhibiting higher expression levels in venule endothelial cells compared to non-venule endothelial cells is selected from the group consisting of a gene or combination of genes listed in Table 1. In some embodiments, the at least one gene exhibiting lower expression levels in venule endothelial cells compared to non-venule endothelial cells is selected from the group consisting of a gene or combination of genes listed in Table 8. In some embodiments, the at least one gene exhibiting higher expression levels in non-venule endothelial cells compared to venule endothelial cells is selected from the group consisting of a gene or combination of genes listed in Table 8. In some embodiments, the at least one gene exhibiting lower expression levels in non-venule endothelial cells compared to venule endothelial cells is selected from the group consisting of a gene or combination of genes listed in Table 1.

In some embodiments, the at least one gene is differentially expressed in skin venule endothelial cells compared to skin non-venule endothelial cells. In such embodiments, the methods of modulating leukocyte trafficking and/or inflammation can be used to treat or prevent a skin inflammatory disease. In such embodiments, the at least one gene exhibiting higher expression levels in venule endothelial cells compared to non-venule endothelial cells is selected from the group consisting of a gene or combination of genes listed in Table 2. In such embodiments, the at least one gene exhibiting lower expression levels in venule endothelial cells compared to non-venule endothelial cells is selected from the group consisting of a gene or combination of genes listed in Table 9. In such embodiments, the at least one gene exhibiting higher expression levels in non-venule endothelial cells compared to venule endothelial cells is selected from the group consisting of a gene or combination of genes listed in Table 9. In such embodiments, the at least one gene exhibiting lower expression levels in non-venule endothelial cells compared to venule endothelial cells is selected from the group consisting of a gene or combination of genes listed in Table 2.

In some embodiments, the at least one gene is differentially expressed in adipose tissue venule endothelial cells compared to adipose tissue non-venule endothelial cells. In such embodiments, the methods of modulating leukocyte trafficking and/or inflammation can be used to treat or prevent a disease characterized by visceral fat inflammation. In such embodiments, the at least one gene exhibiting higher expression levels in venule endothelial cells compared to non-venule endothelial cells is selected from the group consisting of a gene or combination of genes listed in Table 3. In such embodiments, the at least one gene exhibiting lower expression levels in venule endothelial cells compared to non-venule endothelial cells is selected from the group consisting of a gene or combination of genes listed in Table 10. In such embodiments, the at least one gene exhibiting higher expression levels in non-venule endothelial cells compared to venule endothelial cells is selected from the group consisting of a gene or combination of genes listed in Table 10. In such embodiments, the at least one gene exhibiting lower expression levels in non-venule endothelial cells compared to venule endothelial cells is selected from the group consisting of a gene or combination of genes listed in Table 3.

In some embodiments, the at least one gene is differentially expressed in lymph node venule endothelial cells compared to lymph node non-venule endothelial cells. In such embodiments, the methods of modulating leukocyte trafficking and/or inflammation can be used for treating or preventing a disease characterized by lymphadenitis. In such embodiments, the at least one gene exhibiting higher expression levels in venule endothelial cells compared to non-venule endothelial cells is selected from the group consisting of a gene or combination of genes listed in Table 4. In such embodiments, the at least one gene exhibiting lower expression levels in venule endothelial cells compared to non-venule endothelial cells is selected from the group consisting of a gene or combination of genes listed in Table 11. In such embodiments, the at least one gene exhibiting higher expression levels in non-venule endothelial cells compared to venule endothelial cells is selected from the group consisting of a gene or combination of genes listed in Table 11. In such embodiments, the at least one gene exhibiting lower expression levels in non-venule endothelial cells compared to venule endothelial cells is selected from the group consisting of a gene or combination of genes listed in Table 4.

The methods of modulating leukocyte trafficking and/or inflammation disclosed herein also contemplate modulating the activity and/or function of an expression product of any gene which is differentially expressed in venule endothelial cells compared to non-venule endothelial cells. In some embodiments, the at least one gene is selected from the group consisting of a gene or combination of genes listed in Table 1, Table 2, Table 3, Table 4, Table 5, Table 6, Table 7, Table 8, Table 9, Table 10, Table 11, Table 12, Table 13, and/or Table 14. In some embodiments, the at least one gene is differentially expressed in skin venule endothelial cells compared to skin non-venule endothelial cells. In some embodiments, the at least one gene is differentially expressed in adipose tissue venule endothelial cells compared to adipose tissue non-venule endothelial cells. In some embodiments, the at least one gene is differentially expressed in lymph node venule endothelial cells compared to lymph node non-venule endothelial cells.

Inhibiting leukocyte trafficking and/or inflammation can include one or more of interfering with leukocyte trafficking, interfering with leukocyte adhesion, and interfering with leukocyte extravasation. In some embodiments, leukocyte trafficking and/or inflammation is inhibited systemically (e.g., specifically in all venules or non-venules regardless of which tissue they reside in). In some embodiments, leukocyte trafficking and/or inflammation is inhibited in a tissue-specific manner (e.g., in skin, adipose tissue, or lymph nodes).

Inducing leukocyte trafficking and/or inflammation can include one or more of enabling leukocyte trafficking, enabling leukocyte adhesion, and enabling leukocyte extravasation. In some embodiments, leukocyte trafficking and/or inflammation is enabled systemically. In some embodiments, leukocyte trafficking and/or inflammation is induced in a tissue-specific manner (e.g., in skin, adipose tissue, or lymph nodes).

Those skilled in the art will appreciate that the efficacy of the methods, compositions, and agents described herein toward inhibiting and/or enabling leukocyte trafficking and/or inflammation can be assessed by measuring one or more markers of inflammation in a subject. Exemplary markers of inflammation include, but are not limited to leukocyte count, plasma c-reactive protein, fibrinogen, interleukin-6 (IL-6), and tumor necrosis factor-alpha (TNF-alpha). Methods of measuring such markers of inflammation are apparent to the skilled artisan.

Methods of Targeting Microvessels

In yet another aspect, disclosed herein is a method of targeting an agent to microvessel endothelial cells in a subject, comprising administering to the subject a therapeutically effective amount of an agent to be targeted to microvessel endothelial cells. In some embodiments, the agent comprises a microvessel endothelial cell targeting agent. In some embodiments, the agent is coupled to a microvessel endothelial cell targeting agent.

In still another aspect, disclosed herein is a method of targeting an agent to microvessel endothelial cells in a subject, comprising administering to the subject a therapeutically effective amount of an agent to be targeted to microvessel endothelial cells, wherein the agent is coupled to a microvessel endothelial cell targeting agent.

As used herein "target" and "targeting" are used interchangeable to refer to the process of delivering a molecule (e.g., an agent described herein, including an endothelial cell targeting agent described herein) to a specific intended site in a way that minimizes delivery of the molecule to an unintended site.

As used herein a "targeting agent" refers to any molecule that recognizes, binds to, or otherwise interacts with an endothelial cell surface marker described herein or a variant thereof with sufficient affinity and specificity to target the molecule to an endothelial cell expressing such surface marker, without targeting or only negligibly targeting the molecule to other cells. It should be appreciated that the targeting agent can recognize, bind to, or otherwise interact with an endothelial cell surface marker described herein or a variant thereof and can influence the physiological function of the endothelial cell surface marker (e.g., by inhibiting or augmenting the surface marker itself or downstream activities of the surface marker). Alternatively or additionally, the targeting agent can recognize, bind to, or otherwise interact with an endothelial cell surface marker described herein or a variant thereof and bring an agent described herein into close proximity to an endothelial cell expressing the surface marker. In such instances, the agent may influence the physiological function of the endothelial cell surface marker or otherwise be internalized into the endothelial cell.

As used herein, "endothelial cell surface marker" and "microvessel endothelial cell surface marker" are used interchangeable to refer to a protein expressed on the surface of an endothelial cell of a microvessel (e.g., a venule or non-venule endothelial cell) or a variant thereof. Examples of endothelial cell surface markers include, but are not limited to: (1) pan-venular endothelial cell surface markers (e.g., Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1); (2) skin venule endothelial cell surface markers (e.g., Nrp2, Gpr1, C630004H02Rik, Fndc1, 2310046K01Rik, Insr, and Slco2a1; and/or Nrp2, Htr2b, Mr1, Lifr, Anxa1, Lphn2, Vamp5, Olr1, Eps8, Slco2b1, and Slco2a1); (3) adipose tissue venule endothelial cell surface markers (e.g., Il1r11, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrm4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam); (4) lymph node venule endothelial cell surface markers (e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1); (5) multi-tissue skin and lymph node venule endothelial cell surface markers (e.g., Gpr182 and Slco2b1); (6) multi-tissue adipose tissue and lymph node venule endothelial cell surface markers (e.g., Cd63, Sirpa, Slc2a1, Vmn1r100, Vmn1r148, Vmn1r132, and Vmn1r125; and/or H60b, Ppap2c, Celsr1, Glycam1, Slc37a1, Cd59a, Slc2a1, Tnfrsf9, Tes, Pglyrp1, Il27ra, and Eda2r); (7) multi-tissue adipose tissue and skin venule endothelial cell surface markers (e.g., Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1); (8) non-venule endothelial cell surface markers (e.g., Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Prnd, Gja5, Gja4, Alpl, Kcna5, P2ry2, Efnb2, and Itm2a); (9) skin non-venule endothelial cell surface markers (e.g., Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9); (10) adipose tissue non-venule endothelial cell surface markers (e.g., Adora2a, H2-Ab1, Hspg2, Gpr81, Kcna5, Jam3, and Gpc4; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3); (11) lymph node non-venule endothelial cell surface markers (e.g., Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3); (12) multi-tissue skin and lymph node non-venule endothelial cell surface markers (e.g., Tns1, Cxcr4, Atp1b1, Car4, Cd7, Itga1, Gja5, Laptm5, Aqp7, Gja4, Mlec, P2ry2, and Cd97; and/or Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4); (13) multi-tissue adipose tissue and lymph node non-venule endothelial cell surfaces (e.g., Unc5b, Lpar6, Sema6d, Ppap2b, and Lpar4; and/or Ramp3, Olfr1396, Slc1a1, Cldn15, Cd109); and (14) multi-tissue adipose tissue and skin non-venule endothelial cell surface markers (e.g., Ly86, H2-Aa, and Cd74; and/or Sell, Cd79b, Ly86, Chrm3, Ptger4, Sema7a). In some embodiments, the endothelial cell surface marker is not Sele. In some embodiments, the endothelial cell surface marker is not Selp. In some embodiments, the pan-venular endothelial cell surface marker is not Sele. In some embodiments, the pan-venular endothelial cell surface marker is not Selp. In some embodiments, the skin non-venule endothelial cell surface marker is not Sell. In some embodiments, the skin non-venule endothelial cell surface marker is not Siglech. In some embodiments, the skin non-venule endothelial cell surface marker is not Cd44. In some embodiments, the lymph node non-venule endothelial cell surface markers is not Pmp22. In some embodiments, the endothelial cell surface marker is not il6st.

As used herein, "microvessel endothelial cell targeting agent" refers to a targeting agent that is capable of targeting to endothelial cells lining a microvessel by binding to an endothelial cell surface marker described herein (e.g., a protein expressed on the surface of a microvessel endothelial cell (e.g., a venule endothelial cell or a non-venule endothelial cell).

As noted above, the microvessel endothelial cell targeting agents described herein are capable of recognizing, binding to, or otherwise interacting with endothelial cell surface markers lining microvessels. Accordingly, in some embodiments, the microvessel endothelial cell targeting agent binds to a protein expressed on the surface of an endothelial cell lining a microvessel. In some instances, the microvessel endothelial cell targeting agent influences a physiological function of the protein itself or downstream activities of the protein (e.g., signaling pathways).

In other instances, the microvessel endothelial cell targeting agent is internalized into the endothelial cells lining the microvessel. In some embodiments, internalization of the microvessel endothelial cell targeting agent into the endothelial cells lining the microvessel causes the microvessel endothelial cell targeting agent to accumulate in the tissue in which the microvessel resides. In some embodiments, the microvessel endothelial cell targeting agent accumulates in the subject's skin. In some embodiments, the microvessel endothelial cell targeting agent accumulates in the subject's adipose tissue. In some embodiments, the microvessel endothelial cell targeting agent accumulates in the venule endothelial cells in the subject's lymph nodes. In some embodiments, the microvessel endothelial cell targeting agent does not accumulate in non-target tissues. In some embodiments, negligible amounts of the microvessel endothelial cell targeting agent accumulate in non-target tissues.

The disclosure contemplates targeting an agent to microvessel endothelial cells for any purpose in which such targeting would be desirable. In some embodiments, targeting an agent to microvessel endothelial cells of a subject treats, prevents, or ameliorates a symptom of, an inflammatory disease. In such embodiments, the agent can comprise an anti-inflammatory agent coupled to a microvessel endothelial cell targeting agent. In some embodiments, the microvessel endothelial cell targeting agent may exhibit anti-inflammatory activity, for example, by binding to an endothelial cell surface marker in the microvessel (e.g., venules) in a way that interferes with leukocyte trafficking, adhesion, and/or extravasation into the extravascular compartment surrounding the microvessel (e.g., a target tissue). In some embodiments, the agent is an agent that modulates the venuleness of an endothelial cell or microvessel described herein, for example, coupled to a microvessel endothelial cell targeting agent.

The disclosure contemplates treating, preventing, or ameliorating a symptom of, any inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the inflammatory disease is not mediated by, or does not involve, Sele. In some embodiments, the inflammatory disease is not mediated by, or does not involve, Sell. In some embodiments, the inflammatory disease is not mediated by, or does not involve, Selp. In some embodiments, the inflammatory disease is not mediated by, or does not involve, Cd44. In some embodiments, the inflammatory disease is not mediated by, or does not involve, Cd130.

The disclosure contemplates targeting agents to any microvessel in which delivering an agent to endothelium would be desirable.

In some embodiments, the microvessel is a venule and the endothelial cell surface marker is a protein encoded by a gene exhibiting higher expression levels in venule endothelial cells compared to non-venule endothelial cells. Examples of such genes include Sele, Selp, Il6st, Plxnb2, Lepr, Bst1, and Icam1. Examples of such genes also include Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. In some embodiments, the gene is not Darc. In some embodiments, the gene is not Sele. In some embodiments, the gene is not Selp. In some embodiments, the gene is Bst1.

In some embodiments, the microvessel is a non-venule and the endothelial cell surface marker is a protein encoded by a gene exhibiting higher expression levels in non-venule endothelial cells compared to venule endothelial cells. Examples of such genes include Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. Examples of such genes also include Cxcr4, Unc5b, Flt4, Ednrb, Notch4, Prnd, Gja5, Gja4, Alpl, Kcna5, P2ry2, Efnb2, and Itm2a.

The disclosure also contemplates targeting agents to microvessels in a tissue-specific manner. In some embodiments, the agents are targeted to microvessels in skin. Accordingly, in one aspect, disclosed herein is a method of targeting an agent to microvessel endothelial cells in skin, comprising administering to a subject a therapeutically effective amount of an agent to be targeted to microvessel endothelial cells in skin. In some embodiments, the agent is a skin microvessel endothelial cell targeting agent. In some embodiments, the agent is coupled to a skin microvessel endothelial cell targeting agent.

In some aspects, a method of targeting an agent to microvessel endothelial cells in skin comprises administering to a subject a therapeutically effective amount of an agent to be targeted to microvessel endothelial cells in skin, wherein the agent is coupled to a skin microvessel endothelial cell targeting agent.

The skin microvessel endothelial cell targeting agents described herein are capable of recognizing, binding to, or otherwise interacting with skin endothelial cell surface markers lining skin microvessels. Accordingly, in some embodiments, the skin microvessel endothelial cell targeting agent binds to a protein expressed on the surface of an endothelial cell lining a microvessel in the subject's skin. In some instances, the skin microvessel endothelial cell targeting agent influences a physiological function of the protein itself or downstream activities of the protein (e.g., signaling pathways).

In other instances, the skin microvessel endothelial cell targeting agent is internalized into the endothelial cells lining a microvessel in the subject's skin. In some embodiments, internalization of the skin microvessel endothelial cell targeting agent into the endothelial cells lining the microvessel in the subject's skin causes the skin microvessel endothelial cell targeting agent to accumulate in the subject's skin. In some embodiments, the skin microvessel endothelial cell targeting agent does not accumulate in tissues other than skin. In some embodiments, the negligible amounts of the skin microvessel endothelial cell targeting agent accumulate in tissues other than skin. In some embodiments, internalization of the skin microvessel endothelial cell targeting agent into the endothelial cells lining the microvessel in the subject's skin causes the agent to be internalized into the endothelial cells lining the microvessel in the subject's skin. In some embodiments, internalization of the agent causes the agent to accumulate in the subject's skin. In some embodiments, the agent does not accumulate in tissues other than skin. In some embodiments, negligible amounts of the agent accumulate in tissues other than skin.

In some embodiments, the microvessel in the subject's skin comprises a venule (e.g., the venules to be specifically targeted are skin venules). In such embodiments, the skin microvessel endothelial cell targeting agent comprises a skin venule endothelial cell targeting agent. In such embodiments, the protein is encoded by a gene exhibiting higher expression levels in skin venule endothelial cells compared to skin non-venule endothelial cells. Examples of such genes include Nrp2, Gpr1, C630004H02Rik, Fndc1, 2310046K01Rik, Insr, and Slco2a1. Examples of such genes also include Nrp2, Htr2b, Mrl, Lifr, Anxa1, Lphn2, Vamp5, Olr1, Eps8, Slco2b1, and Slco2a1.

In some embodiments, the microvessel in the subject's skin comprises a non-venule (e.g., the non-venules to be specifically targeted are skin non-venules). In such embodiments, the skin microvessel endothelial cell targeting agent comprises a skin non-venule endothelial cell targeting agent. In such embodiments, the protein is encoded by a gene exhibiting higher expression levels in skin non-venule endothelial cells compared to skin venule endothelial cells. Examples of such genes include Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. Examples of such genes also include Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the protein is not encoded by the Sell gene. In some embodiments, the protein is not encoded by the Cd44 gene. In some embodiments, the protein is not encoded by the Siglech gene.

The disclosure contemplates targeting an agent to skin microvessel endothelial cells for any purpose in which such targeting would be desirable. In some embodiments, targeting an agent to skin microvessel endothelial cells of a subject treats, prevents, or ameliorates a symptom of, a skin inflammatory disease. The disclosure contemplates treating, preventing, or ameliorating a symptom of, any skin inflammatory disease. In some embodiments, the skin inflammatory disease is selected from the group consisting of acne, dermatitis, eczema, oily skin, rosacea, cutaneus lymphoma and urticaria. In some embodiments, the dermatitis is selected from the group consisting of atopic dermatitis, psoriasis and contact dermatitis. In some embodiments, the skin inflammatory disease is not mediated by, or does not involve, Sele. In some embodiments, the skin inflammatory disease is not mediated by, or does not involve, Sell. In some embodiments, the skin inflammatory disease is not mediated by, or does not involve, Selp. In some embodiments, the skin inflammatory disease is not mediated by, or does not involve, Cd44. In some embodiments, the skin inflammatory disease is not mediated by, or does not involve, Cd130.

In some embodiments, the agents are targeted to microvessel in adipose tissue. Accordingly, in one aspect, disclosed herein is a method of targeting an agent to microvessel endothelial cells in adipose tissue, comprising administering to a subject a therapeutically effective amount of an agent to be targeted to microvessel endothelial cells in the subject's adipose tissue. In some embodiments, the agent is an adipose tissue microvessel endothelial cell targeting agent. In some embodiments, the agent is coupled to an adipose tissue microvessel endothelial cell targeting agent.

In some aspects, a method of targeting an agent to microvessel endothelial cells in adipose tissue comprises administering to a subject a therapeutically effective amount of an agent to be targeted to microvessel endothelial cells in the subject's adipose tissue, wherein the agent is coupled to an adipose tissue microvessel targeting agent.

The adipose tissue microvessel endothelial cell targeting agents described herein are capable of recognizing, binding to, or otherwise interacting with adipose tissue endothelial cell surface markers lining adipose tissue microvessels. Accordingly, in some embodiments, the adipose tissue microvessel endothelial cell targeting agent binds to a protein expressed on the surface of an endothelial cell lining a microvessel in the subject's adipose tissue. In some instances, the adipose tissue microvessel endothelial cell targeting agent influences a physiological function of the protein itself or downstream activities of the protein (e.g., signaling pathways).

In other instances, the adipose tissue microvessel endothelial cell targeting agent is internalized into the endothelial cells lining a microvessel in the subject's adipose tissue. In some embodiments, internalization of the adipose tissue microvessel endothelial cell targeting agent into the endothelial cells lining the microvessel in the subject's adipose tissue causes the adipose tissue microvessel endothelial cell targeting agent to accumulate in the subject's adipose tissue. In some embodiments, the adipose tissue microvessel endothelial cell targeting agent does not accumulate in tissues other than adipose tissue. In some embodiments, negligible amounts of the adipose tissue microvessel endothelial cell targeting agent accumulate in tissues other than adipose tissue. In some embodiments, internalization of the adipose tissue microvessel endothelial cell targeting agent into the endothelial cells lining the microvessel in the subject's adipose tissue causes the agent to be internalized into the endothelial cells lining the microvessel in the subject's adipose tissue. In some embodiments, internalization of the agent causes the agent to accumulate in the subject's adipose tissue. In some embodiments, the agent does not accumulate in tissues other than adipose tissue. In some embodiments, negligible amounts of the agent accumulate in tissues other than adipose tissue.

In some embodiments, the microvessel in the subject's adipose tissue comprises a venule (e.g., the venules to be specifically targeted are adipose tissue venules). In such embodiments, the adipose tissue microvessel endothelial cell targeting agent comprises an adipose tissue venule endothelial cell targeting agent. In such embodiments, the protein is encoded by a gene exhibiting higher expression levels in adipose tissue venule endothelial cells compared to adipose tissue non-venule endothelial cells. Examples of such genes include Il1rl1, Gm7609, Rgs1, Gpr126, P2rx1, Slc6a4, Itgb4, A530099J19Rik, Fcer1g, Fcer1a, Slc7a8, Nckap11, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Examples of such genes also include Tnfrsf11a, Mpz, Dnm3os, Icos1, Osbp18, Itga3, Flrt2, Sla, Csf2rb2, Slc2a13, Emp2, Dll1, Entpd1, Ptprj, Lrm4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the microvessel in the subject's adipose tissue comprises a non-venule (e.g., the non-venules to be specifically targeted are adipose tissue non-venules). In such embodiments, the adipose tissue microvessel endothelial cell targeting agent comprises an adipose tissue non-venule endothelial cell targeting agent. In such embodiments, the protein is encoded by a gene exhibiting higher expression levels in adipose tissue non-venule endothelial cells compared to adipose tissue venule endothelial cells. Examples of such genes include Adora2a, H2-Ab1, Hspg2, Gpr81, Kcna5, Jam3, and Gpc4. Examples of such genes also include Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

The disclosure contemplates targeting an agent to adipose tissue microvessel endothelial cells for any purpose in which such targeting would be desirable. In some embodiments, targeting an agent to adipose tissue microvessel endothelial cells of a subject treats, prevents, or ameliorates a symptom of, a disease characterized by inflammation in the subject's visceral fat. The disclosure contemplates treating, preventing, or ameliorating a symptom of, any disease characterized by visceral fat inflammation. In some embodiments, the disease is selected from the group consisting of cancer, CVHD, fibrosis, hypertension, lypodystrophy, obesity, metabolic syndrome, and diabetes (e.g., type II diabetes). In some embodiments, the disease is characterized by visceral fat inflammation that is not mediated by, or does not involve, Sele. In some embodiments, the disease is characterized by visceral fat inflammation that is not mediated by, or does not involve, Sell. In some embodiments, the disease is characterized by visceral fat inflammation that is not mediated by, or does not involve, Selp. In some embodiments, the disease is characterized by visceral fat inflammation that is not mediated by, or does not involve, Cd44. In some embodiments, the disease is characterized by visceral fat inflammation that is not mediated by, or does not involve, Cd130.

In some embodiments, the agents are targeted to microvessels in lymph nodes. Accordingly, in one aspect, disclosed herein is a method of targeting an agent to microvessel endothelial cells in lymph nodes, comprising administering to a subject a therapeutically effective amount of an agent to be targeted to microvessel endothelial cells in the subject's lymph nodes. In some embodiments, the agent is a lymph node microvessel endothelial cell targeting agent. In some embodiments, the agent is coupled to a lymph node microvessel endothelial cell targeting agent.

In some aspects, a method of targeting an agent to microvessel endothelial cells in lymph nodes comprises administering to a subject a therapeutically effective amount of an agent to be targeted to microvessel endothelial cells in the subject's lymph nodes, wherein the agent is coupled to a lymph node microvessel endothelial cell targeting agent.

The lymph node microvessel endothelial cell targeting agents described herein are capable of recognizing, binding to, or otherwise interacting with lymph node endothelial cell surface markers lining lymph node microvessels. Accordingly, in some embodiments, the lymph node microvessel endothelial cell targeting agent binds to a protein expressed on the surface of an endothelial cell lining a microvessel in the subject's lymph nodes. In some instances, the lymph node microvessel endothelial cell targeting agent influences a physiological function of the protein itself or downstream activities of the protein (e.g., signaling pathways).

In other instances, the lymph node microvessel endothelial cell targeting agent is internalized into the endothelial cells lining a microvessel in the subject's lymph nodes. In some embodiments, internalization of the lymph node microvessel endothelial cell targeting agent into the endothelial cells lining the microvessel in the subject's lymph nodes causes the lymph node microvessel endothelial cell targeting agent to accumulate in the subject's lymph nodes. In some embodiments, the lymph node microvessel endothelial cell targeting agent does not accumulate in tissues other than lymph nodes. In some embodiments, negligible amounts of the lymph node microvessel endothelial cell targeting agent accumulate in tissues other than lymph nodes. In some embodiments, internalization of the lymph node microvessel endothelial cell targeting agent into the endothelial cells lining the microvessel in the subject's lymph nodes causes the agent to be internalized into the endothelial cells lining the microvessel in the subject's lymph nodes. In some embodiments, internalization of the agent causes the agent to accumulate in the subject's lymph nodes. In some embodiments, the agent does not accumulate in tissues other than lymph nodes. In some embodiments, negligible amounts of the agent accumulate in tissues other than lymph nodes.

In some embodiments, the microvessel in the subject's lymph node comprises a venule (e.g., the venules to be specifically targeted are lymph node venules). In such embodiments, the lymph node microvessel endothelial cell targeting agent comprises a lymph node venule endothelial cell targeting agent. In such embodiments, the protein is encoded by a gene exhibiting higher expression levels in lymph node venule endothelial cells compared to lymph node non-venule endothelial cells. Examples of such genes include Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. Examples of such genes also include Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the microvessel in the subject's lymph node comprises a non-venule (e.g., the non-venules to be specifically targeted are lymph node non-venules). In such embodiments, the lymph node microvessel endothelial cell targeting agent comprises a lymph node non-venule endothelial cell targeting agent. In such embodiments, the protein is encoded by a gene exhibiting higher expression levels in lymph node non-venule endothelial cells compared to lymph node venule endothelial cells. Examples of such genes include Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Examples of such genes also include Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the gene is not Pmp22.

The disclosure contemplates targeting an agent to lymph node microvessel endothelial cells for any purpose in which such targeting would be desirable. In some embodiments, targeting an agent to lymph node microvessel endothelial cells of a subject treats, prevents, or ameliorates a symptom of, a disease characterized by lymphadenitis. The disclosure contemplates the treatment, prevention, or amelioration of a symptom of, any disease characterized by lymphadenitis. In some embodiments, the disease is characterized lymphadenitis that is not mediated by, or does not involve, Sele. In some embodiments, the disease is characterized by lymphadenitis that is not mediated by, or does not involve, Sell. In some embodiments, the disease is characterized by lymphadenitis that is not mediated by, or does not involve, Selp. In some embodiments, the disease is characterized by lymphadenitis that is not mediated by, or does not involve, Cd44. In some embodiments, the disease is characterized by lymphadenitis that is not mediated by, or does not involve, Cd130.

In some embodiments, the disease is cancer (e.g., leukemias, lymphomas, and metastatic cancer).

In some embodiments, the disease is a connective tissue disorder (e.g., systemic lupus erythematosus (SLE), sarcoidosis, Kawasaki disease, juvenile idiopathic arthritis, Kikuchi lymphadenopathy, rheumatoid arthritis, and Sjögren syndrome).

In some embodiments, the disease is an infection (e.g., a bacterial or viral infection). Examples of such infections include, but are not limited to, upper respiratory tract infections, oropharyngeal infections, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess.

In some embodiments, the methods disclosed herein can be used to specifically target microvessels in multiple tissues (e.g., by binding specifically to proteins that are expressed on the surface of microvessel endothelial cells in two or more, but not all, tissues).

In some embodiments, the microvessels are venules and the venules to be specifically targeted in multiple tissues are skin and lymph node venules. In such embodiments, the microvessel endothelial cell targeting agent comprises a multi-tissue skin and lymph node venule endothelial cell targeting agent. In such embodiments, the gene exhibits higher expression levels in venule endothelial cells in skin and lymph nodes compared to venule endothelial cells in other tissues. Examples of such genes include Gpr182 and Slco2b1. In some embodiments, the gene is Gpr182.

In some embodiments, the microvessels are non-venules and the non-venules to be specifically targeted in multiple tissues are skin and lymph node venules. In such embodiments, the microvessel endothelial cell targeting agent comprises a multi-tissue skin and lymph node non-venule endothelial cell targeting agent. In such embodiments, the gene exhibits higher expression levels in non-venule endothelial cells in skin and lymph nodes compared to venule endothelial cells in skin and lymph nodes. Examples of such genes include Tns1, Cxcr4, Atp1b1, Car4, Cd7, Itga1, Gja5, Laptm5, Aqp7, Gja4, Mlec, P2ry2, and Cd97. Examples of such genes also include Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4.

In some embodiments, the microvessels are venules and the venules to be specifically targeted in multiple tissues are adipose tissue and lymph node venules. In such embodiments, the microvessel endothelial cell targeting agent comprises a multi-tissue adipose tissue and lymph node venule endothelial cell targeting agent. In such embodiments, the gene exhibits higher expression levels in venule endothelial cells in adipose tissue and lymph nodes compared to venule endothelial cells in other tissues. Examples of such genes include Cd63, Sirpa, Slc2a1, Vmn1r100, Vmn1r148, Vmn1r132, and Vmn1r125. Examples of such genes also include H60b, Ppap2c, Celsr1, Glycam1, Slc37a1, Cd59a, Slc2a1, Tnfrsf9, Tes, Pglyrp1, Il27ra, and Eda2r.

In some embodiments, the microvessels are non-venules and the venules to be specifically targeted in multiple tissues are adipose tissue and lymph node venules. In such embodiments, the microvessel endothelial cell targeting agent comprises a multi-tissue adipose tissue and lymph node non-venule endothelial cell targeting agent. In such embodiments, the gene exhibits higher expression levels in non-venule endothelial cells in adipose tissue and lymph nodes compared to venule endothelial cells in adipose tissue and lymph nodes. Examples of such genes include Unc5b, Lpar6, Sema6d, Ppap2b, and Lpar4. Examples of such genes also include Ramp3, Olfr1396, Slc1a1, Cldn15, and Cd109.

In some embodiments, the microvessels are venules and the venules to be specifically targeted in multiple tissues are adipose and skin venules. In such embodiments, the microvessel endothelial cell targeting agent comprises a multi-tissue adipose tissue and skin venule endothelial cell targeting agent. In such embodiments, the gene exhibits higher expression levels in venule endothelial cells in adipose tissue and skin compared to venule endothelial cells in other tissues. Examples of such genes include Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Examples of such genes also include Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the microvessels are non-venules and the non-venules to be specifically targeted in multiple tissues are adipose tissue and skin venules. In such embodiments, the microvessel endothelial cell targeting agent comprises a multi-tissue adipose tissue and skin non-venule endothelial cell targeting agent. In such embodiments, the gene exhibits higher expression levels in non-venule endothelial cells in adipose tissue and skin compared to venule endothelial cells in adipose tissue and skin. Examples of such genes include Ly86, H2-Aa, and Cd74. Examples of such genes include Sell, Cd79b, Ly86, Chrm3, Ptger4, and Sema7a.

Those skilled in the art will appreciate that any molecule that is capable of recognizing, binding to, or otherwise interacting with an endothelial cell surface marker described herein can be used as a microvessel endothelial cell targeting agent (e.g., skin microvessel endothelial cell targeting agent, adipose tissue microvessel endothelial cell targeting agent, lymph node microvessel targeting agent, etc.) to target endothelial cells or microvessels. The disclosure contemplates any suitable technique for identifying such molecules. Examples of suitable techniques are described herein. Other suitable techniques are apparent to the skilled artisan.

Identification Methods

In one aspect, disclosed herein is a method of identifying the venuleness of an endothelial cell or a population of endothelial cells. An exemplary method of identifying the venuleness of an endothelial cell or population of endothelial cells comprises: (a) obtaining an endothelial cell or a population of endothelial cells to be identified; (b) detecting an expression level in the endothelial cell or the population of endothelial cells of at least one gene which is differentially expressed in venule endothelial cells compared to non-venule endothelial cells; and (c) identifying the venuleness of the endothelial cell, wherein: (i) an elevated level of expression in the endothelial cell or the population of endothelial cells of at least one gene exhibiting higher expression levels in venule endothelial cells compared to non-venule endothelial cells indicates that the endothelial cells comprise venule endothelial cells; (ii) a reduced level of expression in the endothelial cell or the population of endothelial cells of at least one gene exhibiting lower expression levels in venule endothelial cells compared to non-venule endothelial cells indicates that the endothelial cells comprise venule endothelial cells; (iii) an elevated level of expression in the endothelial cell or the population of endothelial cells of at least one gene exhibiting higher expression levels in non-venule endothelial cells compared to venule endothelial cells indicates that the endothelial cells comprise non-venule endothelial cells; or (iv) a reduced level of expression in the endothelial cell or the population of endothelial cells of at least one gene exhibiting lower expression levels in non-venule endothelial cells compared to venule endothelial cells indicates that the endothelial cells comprise non-venule endothelial cells.

In another aspect, disclosed herein is a method of identifying the venuleness of a microvessel. An exemplary method of identifying the venuleness of a microvessel comprises: (a) obtaining an endothelial cell or a population of endothelial cells lining a microvessel to be identified; (b) detecting an expression level in the endothelial cell or the population of endothelial cells of at least one gene which is differentially expressed in venule endothelial cells compared to non-venule endothelial cells; and (c) identifying the venuleness of the microvessel, wherein: (i) an elevated level of expression in the endothelial cell or the population of endothelial cells of at least one gene exhibiting higher expression levels in venule endothelial cells compared to non-venule endothelial cells indicates that the indicates that the microvessel is a venule; (ii) a reduced level of expression in the endothelial cell or the population of endothelial cells of at least one gene exhibiting lower expression levels in venule endothelial cells compared to non-venule endothelial cells indicates that the microvessel is a venule; (iii) an elevated level of expression in the endothelial cell or the population of endothelial cells of at least one gene exhibiting higher expression levels in non-venule endothelial cells compared to venule endothelial cells indicates that the microvessel is a non-venule; or (iv) a reduced level of expression in the endothelial cell or the population of endothelial cells of at least one gene exhibiting lower expression levels in non-venule endothelial cells compared to venule endothelial cells indicates that the microvessel is a non-venule.

As used herein, a "maker of venuleness" refers to any one or a combination of a gene or combination of genes exhibiting higher expression levels in venule endothelial cells compared to non-venule endothelial cells or exhibiting lower expression levels in venule endothelial cells compared to non-venule endothelial cells, a signaling pathway or combination of signaling pathways enriched in venule endothelial cells compared to non-venule endothelial cells, and a biological process or combination of biological processes enriched in venule endothelial cells compared to non-venule endothelial cells.

In some embodiments, the at least one gene in (i) exhibiting higher expression levels in venule endothelial cells compared to non-venule endothelial cells is selected from the group consisting of a gene, or combination of genes, listed in Table 1. Those skilled in the art will appreciate any gene or combination of genes listed in Table 1 exhibiting higher expression levels in venule endothelial cells compared to non-venule endothelial cells are to be considered markers of venuleness. In some embodiments, the at least one gene in (ii) exhibiting reduced expression levels in venule endothelial cells compared to non-venule endothelial cells is selected from the group consisting of a gene, or combination of genes, listed in Table 8. Those skilled in the art will appreciate any gene or combination of genes listed in Table 8 exhibiting lower expression levels in venule endothelial cells compared to non-venule endothelial cells are to be considered markers of venuleness.

The markers of venuleness disclosed herein include skin markers of venuleness. Accordingly, in some embodiments, the at least one gene is differentially expressed in skin venule endothelial cells compared to skin non-venule endothelial cells. It is to be understood that at least one gene differentially expressed in skin venule endothelial cells compared to skin non-venule endothelial cells (e.g., exhibiting higher or lower levels of expression in the skin venule endothelial cells compared to skin non-venule endothelial cells) are to be considered skin markers of venuleness. In such embodiments, the at least one gene in (i) exhibiting higher expression levels in venule endothelial cells compared to non-venule endothelial cells is selected from the group consisting of a gene, or combination of genes, listed in Table 2. In such embodiments, the at least one gene in (ii) exhibiting lower expression levels in venule endothelial cells compared to non-venule endothelial cells is selected from the group consisting of a gene, or combination of genes, listed in Table 9.

The markers of venuleness disclosed herein further include adipose tissue markers of venuleness. Accordingly, in some embodiments, the at least one gene is differentially expressed in adipose tissue venule endothelial cells compared to adipose tissue non-venule endothelial cells. It is to be understood that at least one gene differentially expressed in adipose tissue venule endothelial cells compared to adipose tissue non-venule endothelial cells (e.g., exhibiting higher or lower levels of expression in the adipose tissue venule endothelial cells compared to adipose tissue non-venule endothelial cells) are to be considered adipose tissue markers of venuleness. In such embodiments, the at least one gene in (i) exhibiting higher expression levels in venule endothelial cells compared to non-venule endothelial cells is selected from the group consisting of a gene listed in Table 3. In such embodiments, the at least one gene in (ii) exhibiting lower expression levels in venule endothelial cells compared to non-venule endothelial cells is selected from the group consisting of a gene, or combination of genes, listed in Table 10.

The markers of venuleness disclosed herein even further include lymph node markers of venuleness. Accordingly, in some embodiments, the at least one gene is differentially expressed in lymph node venule endothelial cells compared to lymph node non-venule endothelial cells. It is to be understood that at least one gene differentially expressed in lymph node venule endothelial cells compared to lymph node non-venule endothelial cells (e.g., exhibiting higher or lower levels of expression in the lymph node venule endothelial cells compared to lymph node non-venule endothelial cells) are to be considered lymph node markers of venuleness. In such embodiments, the at least one gene in (i) exhibiting higher expression levels in venule endothelial cells compared to non-venule endothelial cells is selected from the group consisting of a gene, or combination of genes, listed in Table 4. In such embodiments, the at least one gene in (ii) exhibiting lower expression levels in venule endothelial cells compared to non-venule endothelial cells is selected from the group consisting of a gene, or combination of genes, listed in Table 11.

As used herein, a "maker of non-venuleness" refers to any one or a combination of a gene or combination of genes exhibiting higher expression levels in non-venule endothelial cells compared to venule endothelial cells or exhibiting lower expression levels in non-venule endothelial cells compared to venule endothelial cells, a signaling pathway or combination of signaling pathways enriched in non-venule endothelial cells compared to venule endothelial cells, and a biological process or combination of biological processes enriched in non-venule endothelial cells compared to venule endothelial cells. The disclosure contemplates assessing enrichment of biological processes according to any technique available to the skilled artisan. In some embodiments, assessing enrichment of biological processes comprises conducting a Gene Ontology (GO). In some embodiments, the Gene Ontology comprises DAVID's Gene Ontology. The disclosure contemplates assessing enrichment of a signaling pathway according to any technique available to the skilled artisan. In some embodiments, assessing enrichment of signaling pathways comprises conducting a Gene Set Enrichment Analysis (GSEA).

In some embodiments, the at least one gene in (iii) exhibiting higher expression levels in non-venule endothelial cells compared to venule endothelial cells is selected from the group consisting of a gene, or combination of genes, listed in Table 8. Those skilled in the art will appreciate that any gene or combination of genes listed in Table 8 exhibiting higher expression levels in non-venule endothelial cells compared to venule endothelial cells are to be considered markers of non-venuleness. In some embodiments, the at least one gene in (iv) exhibiting lower expression levels in non-venule endothelial cells compared to venule endothelial cells is selected from the group consisting of a gene, or combination of genes, listed in Table 1. Those skilled in the art will appreciate that any gene or combination of genes listed in Table 1 exhibiting lower expression levels in non-venule endothelial cells compared to venule endothelial cells are to be considered markers of non-venuleness.

The markers of non-venuleness disclosed herein include skin markers of non-venuleness. Accordingly, in some embodiments, the at least one gene is differentially expressed in skin non-venule endothelial cells compared to skin venule endothelial cells. It is to be understood that at least one gene differentially expressed in skin non-venule endothelial cells compared to skin venule endothelial cells (e.g., exhibiting higher or lower levels of expression in the skin non-venule endothelial cells compared to skin venule endothelial cells) are to be considered skin markers of non-venuleness. In such embodiments, the at least one gene in (iii) exhibiting higher expression levels in non-venule endothelial cells compared to venule endothelial cells is selected from the group consisting of a gene, or combination of genes, listed in Table 9. In such embodiments, the at least one gene in (iv) exhibiting lower expression levels in non-venule endothelial cells compared to venule endothelial cells is selected from the group consisting of a gene, or combination of genes, listed in Table 2.

The markers of non-venuleness disclosed herein include adipose tissue markers of non-venuleness. Accordingly, in some embodiments, the at least one gene is differentially expressed in adipose tissue non-venule endothelial cells compared to adipose tissue venule endothelial cells. It is to be understood that at least one gene differentially expressed in adipose tissue non-venule endothelial cells compared to adipose tissue venule endothelial cells (e.g., exhibiting higher or lower levels of expression in the adipose tissue non-venule endothelial cells compared to adipose tissue venule endothelial cells) are to be considered adipose tissue markers of non-venuleness. In such embodiments, the at least one gene in (iii) exhibiting higher expression levels in non-venule endothelial cells compared to venule endothelial cells is selected from the group consisting of a gene, or combination of genes, listed in Table 10. In such embodiments, the at least one gene in (iv) exhibiting lower expression levels in non-venule endothelial cells compared to venule endothelial cells is selected from the group consisting of a gene, or combination of genes, listed in Table 3.

The markers of non-venuleness disclosed herein include lymph node markers of non-venuleness. Accordingly, in some embodiments, the at least one gene is differentially expressed in lymph node non-venule endothelial cells compared to lymph node venule endothelial cells. It is to be understood that at least one gene differentially expressed in lymph node non-venule endothelial cells compared to lymph node venule endothelial cells (e.g., exhibiting higher or lower levels of expression in the lymph node non-venule endothelial cells compared to lymph node venule endothelial cells) are to be considered lymph node tissue markers of non-venuleness. In such embodiments, the at least one gene in (iii) exhibiting higher expression levels in non-venule endothelial cells compared to venule endothelial cells is selected from the group consisting of a gene, or combination of genes, listed in Table 11. In such embodiments, the at least one gene in (iv) exhibiting lower expression levels in non-venule endothelial cells compared to venule endothelial cells is selected from the group consisting of a gene, or combination of genes, listed in Table 4.

It is to be understood that the markers of venuleness and markers of non-venuleness described herein may be detectably expressed in the form of protein and or mRNA within an endothelial cell or population of endothelial cells (e.g., endothelial cells lining a microvessel). Accordingly, as used herein, "protein marker of venuleness" refers to a protein encoded by a gene which is a marker of venuleness. As used herein, "protein marker of non-venuleness" refers to a protein encoded by a gene which is a marker of non-venuleness. As used herein, "mRNA marker of venuleness" refers to a mRNA encoded by a gene which is a marker of venuleness. As used herein, "mRNA marker of non-venuleness" refers to a mRNA encoded by a gene which is a marker of non-venuleness.

The markers and methods described herein are capable of identifying the venuleness of any endothelial cell, population of endothelial cells (e.g., endothelium), or microvessel (e.g., distinguishing between venules and non-venules). Generally, distinguishing between venules and non-venules can be accomplished by analyzing putative venule endothelial cells (e.g., a sample comprising endothelial cells lining a microvessel modulated according to the methods described herein) for one or more markers of venuleness. On the one hand, if the putative venule endothelial cells or a population of putative endothelial cells displays one or more markers of venuleness, then the putative venule endothelial cells or population of putative venule endothelial cells are likely venule endothelial cells. On the other hand, if a putative endothelial cell or a population of putative endothelial cells displays one or more markers of non-venuleness, then the putative venule endothelial cell or population of putative venule endothelial cells are likely non-venule endothelial cells. Those skilled in the art will appreciate that confirmation of venuleness or non-venuleness can be done by detecting Darc expression as described herein (e.g., if the putative venule endothelial cell or population of putative venule endothelial cells can be confirmed as venule endothelial cells if they are Darc+).

The disclosure contemplates distinguishing venuleness and non-venuleness by detecting the level of expression of at least one gene which is differentially expressed between venule endothelial cells and non-venule endothelial cells in an endothelial cell, a putative endothelial cell, a population of endothelial cells, a putative population of endothelial cells, or a microvessel. Those skilled in the art will appreciate that any suitable method can be used to detect expression levels of the genes described herein (e.g., to detect the expression levels of the genes in a putative endothelial cell or a population of endothelial cells to determine whether at least one gene which is differentially expressed in venule endothelial cells compared to non-venule endothelial cells is elevated or reduced). In some embodiments, measuring or detecting expression comprises utilizing a technique selected from the group consisting of a microarray analysis, Nanostring technology, RNA-seq, RT-PCR, and q-RT-PCR. Other suitable methods will be apparent to those skilled in the art. In some embodiments, detecting expression comprises conducting at least one binding assay to determine the expression level of the one or more genes.

In some aspects, the disclosure provides a method of detecting the venuleness of an endothelial cell, population of endothelial cells, or a microvessel. An exemplary method of detecting the venuleness of an endothelial cell, population of endothelial cells, or a microvessel comprises conducting at least one binding assay for at least one marker of venuleness in an endothelial cell, population of endothelial cells, or a microvessel (or putative versions thereof), wherein the presence of the at least one marker of venuleness in the endothelial cell, population of endothelial cells, or the microvessel indicates that the endothelial cell, population of endothelial cells, or a microvessel are venule endothelial cells, a population of venule endothelial cells, or venules.

The disclosure contemplates detecting the venuleness of an endothelial cell, population of endothelial cells, or a microvessel by detecting the presence of any marker of venuleness in a cell, population of cells, or microvessel. The cell, population of cells, or microvessel can be a cell, population of cells, or microvessel suspected of exhibiting venuleness (e.g., a culture differentiating stem cells, or a sample comprising cells lining a microvessel contacted with an agent that modulates venuleness described herein).

In some embodiments, the at least one marker venuleness is a marker of venuleness selected from the group consisting of a skin marker of venuleness described herein, an adipose tissue marker of venuleness described herein, or a lymph node marker of venuleness described herein. In some embodiments, the at least one marker of venuleness comprises an mRNA marker of venuleness described herein (e.g., mRNA marker of skin venuleness, mRNA marker of adipose tissue venuleness, mRNA marker of lymph node venuleness, etc.). In some embodiments, the at least one marker of venuleness comprises a protein marker of venuleness described herein (e.g., a protein marker of skin venuleness, a protein marker of adipose tissue venuleness, a protein marker of lymph node venuleness, etc.).

In some aspects, the disclosure provides a method of detecting the non-venuleness of an endothelial cell, a population of endothelial cells, or a microvessel. An exemplary method of detecting the non-venuleness of an endothelial cell, a population of endothelial cells, or a microvessel comprises conducting at least one binding assay for at least one marker of non-venuleness in a cell, population of cells, or microvessel (e.g., a putative non-venule endothelial cell, a putative population of non-venule endothelial cells, or a putative non-venule), wherein the presence of the at least one marker of non-venuleness in the cell, population of cells, or microvessel indicates that the cell, population of cells, or microvessel exhibit non-venuleness.

The disclosure contemplates detecting the non-venuleness of a cell, population of cells, or microvessel by detecting the presence of any marker of non-venuleness in a cell, population of cells, or microvessel. The cell, population of cells, or microvessel can be a cell, population of cells, or microvessel suspected of exhibiting non-venuleness (e.g., a culture differentiating stem cells, or a population of cells taken from a microvessel contacted with an agent that modulates venuleness described herein, for example).

In some embodiments, the at least one marker of non-venuleness is selected from the group consisting of a marker of non-venuleness described herein, a skin marker of non-venuleness described herein, an adipose tissue marker of non-venuleness described herein, and a lymph node marker of non-venuleness described herein. In some embodiments, the at least one marker of non-venuleness comprises an mRNA marker of non-venuleness (e.g., a mRNA marker of skin non-venuleness, a mRNA marker of adipose tissue non-venuleness, a mRNA marker of lymph node non-venuleness, etc.). In some embodiments, the at least one marker of non-venuleness comprises a protein marker of non-venuleness (e.g., a protein marker of skin non-venuleness, a protein marker of adipose tissue non-venuleness, a protein marker of lymph node non-venuleness, etc.).

Generally, the presence of a protein marker of venuleness in an endothelial cell, population of endothelial cells, or microvessel is indicative that the endothelial cell, population of endothelial cells, or microvessel comprises a venule endothelial cell, a population of venule endothelial cells, or a venule, whereas the absence of the same protein marker in the endothelial cell, population of endothelial cells, or microvessel may be indicative that the endothelial cell, population of endothelial cells, or microvessel does not comprise a venule endothelial cell, population of venule endothelial cells or venule, respectively.

Conversely, the presence of a protein marker of non-venuleness in an endothelial cell, population of endothelial cell, or microvessel is indicative that the endothelial cell, population of endothelial cells, or microvessel comprises a non-venule endothelial cell, a population of non-venule endothelial cells, or a non-venule, whereas the absence of the same protein marker in the endothelial cell, population of endothelial cells, microvessel may be indicative that the endothelial cell, population of endothelial cells, or microvessel do not comprise non-venule endothelial cells, a population non-venule endothelial cells, or a non-venule, respectively.

The disclosure contemplates detecting the presence or absence of protein markers of venuleness or non-venuleness according to any technique available to the skilled artisan. In some embodiments, detecting the presence or absence of protein markers of venuleness or non-venuleness comprises immunostaining (e.g., Western blotting, immunohistochemistry, ELISA, etc). In such embodiments, antibodies targeted to a particular protein marker of venuleness or non-venuleness can be used to detect the presence or absence of the particular protein marker. For the purposes of the disclosure the immunostaining techniques described or mentioned herein are considered binding assays.

Such antibodies can include polyclonal antibodies, monoclonal antibodies, chimeric antibodies, single-chain antibodies, antibody fragments, humanized antibodies, multi-specific antibodies, and modified antibodies (e.g., fused to a protein to facilitate detection.) Suitable anti-marker protein antibodies can be generated according to routine protocols, or can be readily obtained from a variety of commercial sources (e.g., Sigma-Aldrich). Other suitable techniques for detecting the presence of proteins in endothelial cells are apparent to those skilled in the art.

Generally, the levels of mRNA markers of venuleness in an endothelial cell, population of endothelial cells, or microvessel can be indicative that the endothelial cell, population of endothelial cells, or microvessel comprises a venule endothelial cell, population of venule endothelial cells, or venules, whereas the absence of the same levels of mRNA markers in the endothelial cell, population of endothelial cells, or microvessel may be indicative that the endothelial cell, population of endothelial cells, or microvessel does not comprise a venule endothelial cell, a population of venule endothelial cells, or a venule.

Conversely, the levels of mRNA markers of non-venuleness in an endothelial cell, population of endothelial cells, or microvessel can be indicative that the endothelial cell, population of endothelial cells, or microvessel comprises a non-venule endothelial cell, population of non-venule endothelial cells, or a non-venule, whereas the absence of the same levels of mRNA markers in the endothelial cell, population of endothelial cells, or microvessel may be indicative that the an endothelial cell, population of endothelial cells, or microvessel do not comprise a non-venule endothelial cell, a population of non-venule endothelial cells, or a non-venule.

It is to be understood that the phrase "levels of mRNA" refers to levels of mRNA in a venule endothelial cell relative to a non-venule endothelial cell or levels of mRNA in a non-venule endothelial cell relative to a venule endothelial cell. Levels of mRNA may be represented as a fold-change in expression of the mRNA in the venule endothelial cell relative to the non-venule endothelial cell, and vice versa.

The disclosure contemplates detecting the levels of mRNA according to any technique available to the skilled artisan. In some embodiments, detecting the levels of mRNA markers of venuleness or non-venuleness in an endothelial cell, a population of endothelial cells, or a microvessel comprises conducting one or more hybridization assays. In some embodiments, the one or more hybridization assays comprise a microarray. In some embodiments, the one or more hybridization assay comprises RNA-seq. In some embodiments, the one or more hybridization assays comprises q-RT-PCR. For the purposes of the disclosure the hybridization assays described or mentioned herein are considered binding assays.

In some embodiments, the levels of mRNA markers of venuleness comprise at least a 2 fold increase, a 3 fold increase, a 4 fold increase, a 5 fold increase, or N-fold increase (where N is a positive integer) in the levels of the mRNA marker in a venule endothelial cell relative to the levels of the mRNA maker in non-venule endothelial cells.

In some embodiments, the levels of mRNA markers of non-venuleness comprises at least a 2 fold increase, a 3 fold increase, a 4 fold increase, a 5 fold increase, or N-fold increase (where N is a positive integer) in the levels of the mRNA marker in a non-venule endothelial cell relative to the levels of the mRNA marker in a venule endothelial cell.

The disclosure also contemplates that the methods of identifying venuleness (e.g., of an endothelial cell or microvessel) can be used to assess the efficacy of candidate agents that modulate venuleness that are identified by the methods described herein. Those skilled in the art will appreciate that such assessments can be performed both in vitro (e.g., to confirm that an agent that modulates venuleness is effective at modulating venuleness in vitro) and in vivo (e.g., to confirm that an agent is effective at modulating venuleness in vivo and is effective at modulating a disorder associated with leukocyte trafficking).

In some aspects, disclosed herein are binding partners specific for an endothelial cell surface marker described herein. Exemplary binding partners include binding partners specific for an endothelial cell surface marker selected from the group consisting of: (1) a venule endothelial cell surface marker selected from the group consisting of Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. (2) a skin venule endothelial cell surface marker selected from the group consisting of Nrp2, Gpr1, C630004H02Rik, Fndc1, 2310046K01Rik, Insr, and Slco2a1; and/or Nrp2, Htr2b, Mr1, Lifr, Anxa1, Lphn2, Vamp5, Olr1, Eps8, Slco2b1, and Slco2a1; (3) an adipose tissue endothelial cell surface marker selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node endothelial cell surface marker selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker selected from the group consisting of Gpr182 and Slco2b1; (6) a multi-tissue adipose tissue and lymph node venule endothelial cell surface marker selected from the group consisting of Cd63, Sirpa, Slc2a1, Vmn1r100, Vmn1r148, Vmn1r132, and Vmn1r125; and/or H60b, Ppap2c, Celsr1, Glycam1, Slc37a1, Cd59a, Slc2a1, Tnfrsf9, Tes, Pglyrp1, Il27ra, Eda2r; (7) a multi-tissue adipose tissue and skin venule endothelial cell surface marker selected from the group consisting of Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (8) a non-venule endothelial cell surface marker selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Pmd, Gja5, Gja4, Alpl, Kcna5, P2ry2, Efnb2, and Itm2a; (9) a skin non-venule endothelial cell surface marker selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker selected from the group consisting of Adora2a, H2-Ab1, Hspg2, Gpr81, Kcna5, Jam3, and Gpc4; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker selected from the group consisting of Tns1, Cxcr4, Atp1b1, Car4, Cd7, Itga1, Gja5, Laptm5, Aqp7, Gja4, Mlec, P2ry2, and Cd97; and/or Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker selected from the group consisting of Unc5b, Lpar6, Sema6d, Ppap2b, and Lpar4; and/or Ramp3, Olfr1396, Slc1a1, Cldn15, and Cd109; and (14) a multi-tissue adipose tissue and skin non-venule endothelial cell surface marker selected from the group consisting of Ly86, H2-Aa, and Cd74; and/or Sell, Cd79b, Ly86, Chrm3, Ptger4, and Sema7a.

In some embodiments, the binding partner is not specific for endothelial cell surface marker Sele. In some embodiments, the binding partner does not bind to Sele. In some embodiments, the binding partner is not specific for endothelial cell surface marker Selp. In some embodiments, the binding partner does not bind to Selp. In some embodiments, the binding partner is not specific for venule endothelial cell surface marker Sele. In some embodiments, the binding partner is not specific for venule endothelial cell surface marker Selp. In some embodiments, the binding partner is not specific for skin non-venule endothelial cell surface marker Sell. In some embodiments, the binding partner does not bind to Sell. In some embodiments, the binding partner is not specific for skin non-venule endothelial cell surface marker Siglech. In some embodiments, the binding partner does not bind to Siglech. In some embodiments, the binding partner is not specific for skin non-venule endothelial cell surface marker Cd44. In some embodiments, the binding partner does not bind to Cd44. In some embodiments, the binding partner is not specific for lymph node non-venule endothelial cell surface marker Pmp22. In some embodiments, the binding partner does not bind to Pmp22. In some embodiments, the binding partner is an antibody specific for an endothelial cell surface marker described herein. The skilled artisan will appreciate that the binding partners (e.g., antibodies) described herein can be used for a variety of purposes (e.g., identifying venules, for example, by conjugating a detectable label or reporter moiety to the binding partner). In some embodiments, the binding partner (e.g., antibody) is used in FACS.

Exemplary antibodies include, but are not limited to, polyclonal antibodies, monoclonal antibodies, chimeric antibodies, single-chain antibodies, antibody fragments, humanized antibodies, multi-specific antibodies, and modified antibodies. In some embodiments, the binding partner is an aptide.

Screening Methods

The disclosure contemplates various screening methods using the markers described herein. In particular, the markers described herein can be measured in endothelial cells or populations of endothelial cells to assay for agents that modulate venuleness (e.g., agents that induce endothelial cells to become venule or non-venule endothelial cells), agents that modulate leukocyte interactions with endothelial cells or microvessels (e.g., agents that increase or decrease leukocyte interactions with endothelial cells or microvessel), agents that modulate inflammation (e.g., agents that increase or decrease inflammation in tissues, for example, by increasing or decreasing leukocyte interactions with endothelial cells or microvessel residing in the tissues), and agents that target endothelial cells, microvessels, or tissues (e.g., agents that recognize, bind to, or otherwise interact with endothelial cell surface markers described herein, and in some instances are internalized into a targeted tissue and/or accumulate in the targeted tissue).

Identification of agents (or factors) that modulate venuleness can be used for administration to subjects to modulate leukocyte trafficking, inflammation, and/or to treat diseases associated with leukocyte trafficking (e.g., inflammatory diseases). For example, an agent that causes venules to become non-venules can be used to decrease leukocyte interactions with a microvessel and decrease inflammation in tissues surrounding the microvessel. As an additional example, an agent that causes non-venules to become venules can be used to increase leukocyte interactions with a microvessel and increase inflammation in tissue surrounding the microvessel.

Generally, the identification methods disclosed herein can be achieved by contacting endothelial cells, endothelium, or microvessels with test agents and assessing their ability to produce a particular result in those cells or microvessels or in tissues comprising those cells or microvessels. For example, identifying agents that modulate venuleness can be achieved by contacting endothelial cells, endothelium, or microvessels with test agents and assessing their ability to change the venular phenotype of the endothelial cells (e.g., venule endothelial cells change to non-venule endothelial cells) or microvessels (e.g., a non-venule changes to a venule). Those skilled in the art will appreciate that the genes described herein (e.g., genes which are differentially expressed in venule endothelial cells compared to non-venule endothelial cells) can be used to assess whether the venular phenotype of the endothelial cells or microvessel has changed.

Accordingly, in one aspect, the disclosure provides a method of identifying a candidate agent that modulate venuleness. In some embodiments, the disclosure provides methods of identifying a candidate agent that modulates venuleness of an endothelial cell.

An exemplary method of identifying a candidate agent that modulates venuleness of an endothelial cell comprises comprising: (a) contacting an endothelial cell or a population of endothelial cells with a test agent; (b) detecting expression levels in the endothelial cell or the population of endothelial cells, in the presence of the test agent, of at least one gene which is differentially expressed in venule endothelial cells compared to non-venule endothelial cells; and (c) identifying a candidate agent that modulates the venuleness of an endothelial cell, wherein: (i) the test agent is a candidate agent that induces endothelial cells to become venule endothelial cells if, in the presence of the test agent, the endothelial cell or the population of endothelial cells exhibit elevated levels of expression of at least one gene exhibiting higher expression levels in venule endothelial cells compared to non-venule endothelial cells; (ii) the test agent is a candidate agent that induces endothelial cells to become venule endothelial cells if, in the presence of the test agent, the endothelial cell or the population of endothelial cells exhibit reduced levels of expression of at least one gene exhibiting lower expression levels in venule endothelial cells compared to non-venule endothelial cells; (iii) the test agent is a candidate agent that induces endothelial cells to become non-venule endothelial cells if, in the presence of the test agent, the endothelial cell or the population of endothelial cells exhibit elevated levels of expression of at least one gene exhibiting higher expression levels in non-venule endothelial cells compared to venule endothelial cells; or (iv) the test agent is a candidate agent that induces endothelial cells to become non-venule endothelial cells if, in the presence of the test agent, the endothelial cell or the population of endothelial cells exhibit reduced levels of expression of at least one gene exhibiting lower expression levels in non-venule endothelial cells compared to venule endothelial cells.

In some embodiments, the disclosure provides methods of identifying a candidate agent that modulates venuleness of a microvessel. An exemplary method of identifying a candidate agent that modulates venuleness of a microvessel comprises: (a) contacting a microvessel or microvessel endothelium with a test agent; (b) detecting expression levels in endothelial cells lining the microvessel, in the presence of the test agent, of at least one gene which is differentially expressed in venule endothelial cells compared to non-venule endothelial cells; and (c) identifying a candidate agent that modulates the venuleness of a microvessel, wherein: (i) the test agent is a candidate agent that induces microvessels to become venules if, in the presence of the test agent, the endothelial cells lining the microvessel exhibit elevated levels of expression of at least one gene exhibiting higher expression levels in venule endothelial cells compared to non-venule endothelial cells; (ii) the test agent is a candidate agent that induces microvessels to become venules if, in the presence of the test agent, the endothelial cells lining the microvessel exhibit reduced levels of expression of at least one gene exhibiting lower expression levels in venule endothelial cells compared to non-venule endothelial cells; (iii) the test agent is a candidate agent that induces microvessels to become non-venules if, in the presence of the test agent, the endothelial cells lining the microvessel elevated levels of expression of at least one gene exhibiting higher expression levels in non-venule endothelial cells compared to venule endothelial cells; or (iv) the test agent is a candidate agent that induces microvessels to become non-venules if, in the presence of the test agent, the endothelial cells lining the microvessel exhibit reduced levels of expression of at least one gene exhibiting lower expression levels in non-venule endothelial cells compared to venule endothelial cells.

In some aspects, the disclosure provides a method of identifying a candidate agent that modulates leukocyte trafficking. An exemplary method of identifying a candidate agent that modulates leukocyte trafficking comprises: (a) contacting an endothelial cell or a population of endothelial cells with a test agent; (b) detecting expression levels in the endothelial cell or the population of endothelial cells, in the presence of the test agent, of at least one gene which is differentially expressed in venule endothelial cells compared to non-venule endothelial cells; and (c) identifying a candidate agent that modulates leukocyte trafficking, wherein: (i) the test agent is a candidate agent that increases leukocyte trafficking if, in the presence of the test agent, the endothelial cell or the population of endothelial cells exhibit elevated levels of expression of at least one gene exhibiting higher expression levels in venule endothelial cells compared to non-venule endothelial cells; (ii) the test agent is a candidate agent that increases leukocyte trafficking if, in the presence of the test agent, the endothelial cell or the population of endothelial cells exhibit reduced levels of expression of at least one gene exhibiting lower expression levels in venule endothelial cells compared to non-venule endothelial cells; (iii) the test agent is a candidate agent that decreases leukocyte trafficking if, in the presence of the test agent, the endothelial cell or the population of endothelial cells exhibit elevated levels of expression of at least one gene exhibiting higher expression levels in non-venule endothelial cells compared to venule endothelial cells; or (iv) the test agent is a candidate agent that decreases leukocyte trafficking if, in the presence of the test agent, the endothelial cell or the population of endothelial cells exhibit reduced levels of expression of at least one gene exhibiting lower expression levels in non-venule endothelial cells compared to venule endothelial cells.

In certain aspects, the disclosure provides a method of identifying agents that modulate inflammation. An exemplary method of identifying a candidate agent that modulates inflammation, comprises: (a) contacting an endothelial cell or a population of endothelial cells with a test agent; (b) detecting expression levels in the endothelial cell or the population of endothelial cells, in the presence of the test agent, of at least one gene which is differentially expressed in venule endothelial cells compared to non-venule endothelial cells; and (c) identifying a candidate agent that modulates inflammation, wherein: (i) the test agent is a candidate agent that increases inflammation if, in the presence of the test agent, the endothelial cell or the population of endothelial cells exhibit elevated levels of expression of at least one gene exhibiting higher expression levels in venule endothelial cells compared to non-venule endothelial cells; (ii) the test agent is a candidate agent that increases inflammation if, in the presence of the test agent, the endothelial cell or the population of endothelial cells exhibit reduced levels of expression of at least one gene exhibiting lower expression levels in venule endothelial cells compared to non-venule endothelial cells; (iii) the test agent is a candidate agent that decreases inflammation if, in the presence of the test agent, the endothelial cell or the population of endothelial cells exhibit elevated levels of expression of at least one gene exhibiting higher expression levels in non-venule endothelial cells compared to venule endothelial cells; or (iv) the test agent is a candidate agent that decreases inflammation in endothelial cells if, in the presence of the test agent, the endothelial cell or the population of endothelial cells exhibit reduced levels of expression of at least one gene exhibiting lower expression levels in non-venule endothelial cells compared to venule endothelial cells.

Those skilled in the art will appreciate how to perform the identification methods (e.g., identifying agents for modulating venuleness, identifying agents that modulate disorders associated with leukocyte trafficking, etc.) of disclosure using routine protocols available to the skilled artisan (e.g., high-throughput screening, combinatorial chemistry, in silico screening, etc.).

It should be appreciated that a wide variety of test agents can be used in the methods (e.g., small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the individual is a human or animal.

In some embodiments the endothelial cell or the population of endothelial cells are obtained from an in vitro source.

In some embodiments the in vitro source is a culture of differentiating stem cells.

As used herein, "stem cell" refers to a cell that has the ability to differentiate into a cell of any type. Examples of stem cells that can be used in the methods of the disclosure include embryonic stem cells obtained by culturing a preimplantation early embryo, embryonic stem cells obtained by culturing an early embryo prepared by somatic cell nuclear transfer, and induced pluripotent stem cells obtained by transferring appropriate transcription factors to a somatic cell to reprogram the cell. A variety of protocols for obtaining the stem cells for use in the methods of the disclosure are available to the skilled artisan.

In some embodiments, the stem cells are human embryonic stem cells (hESCs). In some embodiments, the stem cells are induced pluripotent stem cells (iPSCs). In some embodiments, the induced pluripotent stem cells are derived from reprogramming human somatic cells. The human somatic cells can be obtained from a healthy human or a human suffering from a disorder associated with leukocyte trafficking.

The disclosure contemplates any culturing protocol that is capable of differentiating stem cells into endothelial cells (e.g., venule endothelial cells or non-venule endothelial cells).

In some embodiments, the in vitro source includes a cell bank (e.g., cryopreserved endothelial cells), a cell line, a cell culture (e.g., in vitro-differentiated endothelial cells), a cell population, and combinations thereof.

In some embodiments, the in vitro source is an artificial tissue or organ.

In some embodiments, the in vitro source is an artificial tissue selected from the group consisting of skin, adipose tissue, and lymph nodes.

In some embodiments, the endothelial cell or population of endothelial cells are obtained from an in vivo source.

In some embodiments, the in vivo source is an individual that has received an administration of an agent described herein (e.g., an agent that modulates venuleness, microvessel targeting agent, a microvessel targeting agent coupled to a therapeutic agent (e.g., an agent that modulates venuleness described herein)). In such embodiments, an individual can be administrated the agent, and the methods described herein can be used to confirm the efficacy of the agent. Exemplary microvessel targeting agents include a skin microvessel targeting agent (e.g., a skin venule endothelial cell targeting agent and a skin non-venule endothelial cell targeting agent), an adipose tissue microvessel targeting agent (e.g., an adipose tissue venule endothelial cell targeting agent and an adipose tissue non-venule endothelial cell targeting agent), and a lymph node targeting agent (e.g., a lymph node venule endothelial cell targeting agent and a lymph node non-venule endothelial cell targeting agent).

In some embodiments, the in vivo source is an individual suffering from a disease selected from the group consisting of an inflammatory disease, a disease characterized by visceral fat inflammation, an infection, and cancer. In some embodiments, the in vivo source is an individual suffering from a disease involving leukocyte trafficking. In some embodiments, the in vivo source is an individual suffering from a disease involving leukocyte adhesion to endothelial cells. In some embodiments, the in vivo source is a tissue or organ obtained from a donor individual. In some embodiments, the individual is a human or animal individual. In such embodiments, a biological sample comprising endothelial cells can be obtained from the individual.

The disclosure contemplates obtaining a biological sample comprising endothelial cells (e.g., endothelial cells lining a microvessel) from the individual according to any technique available to the skilled artisan.

In some embodiments, the disclosure contemplates sorting the venule and non-venule endothelial cells identified.

Suitable methods of sorting cells are apparent to the skilled artisan. In some embodiments, sorting is achieved by fluorescence-activated cell sorting (FACS). In some embodiments, the FACS comprises staining at least one antibody specific for an endothelial cell surface marker selected from the group consisting of: (1) a venule endothelial cell surface marker selected from the group consisting of Sele, Selp, Il6st, Plxnb2, Lepr, Bst1, and Icam1; (2) a skin venule endothelial cell surface marker selected from the group consisting of Nrp2, Gpr1, C630004H02Rik, Fndc1, 2310046K01Rik, Insr, and Slco2a1; (3) an adipose tissue endothelial cell surface marker selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; (4) a lymph node endothelial cell surface marker selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; (5) a multi-tissue skin and lymph node venule endothelial cell surface marker selected from the group consisting of Gpr182 and Slco2b1; (6) a multi-tissue adipose tissue and lymph node venule endothelial cell surface marker selected from the group consisting of Cd63, Sirpa, Slc2a1, Vmn1r100, Vmn1r148, Vmn1r132, and Vmn1r125; (7) a multi-tissue adipose tissue and skin venule endothelial cell surface marker selected from the group consisting of Il1rl, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; (8) a non-venule endothelial cell surface marker selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; (9) a skin non-venule endothelial cell surface marker selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; (10) an adipose tissue non-venule endothelial cell surface marker selected from the group consisting of Adora2a, H2-Ab1, Hspg2, Gpr81, Kcna5, Jam3, and Gpc4; (11) a lymph node non-venule endothelial cell surface marker selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; (12) a multi-tissue skin and lymph node non-venule endothelial cell surface marker selected from the group consisting of Tns1, Cxcr4, Atp1b1, Car4, Cd7, Itga1, Gja5, Laptm5, Aqp7, Gja4, Mlec, P2ry2, and Cd97; (13) a multi-tissue adipose tissue and lymph node non-venule endothelial cell surface marker selected from the group consisting of Unc5b, Lpar6, Sema6d, Ppap2b, and Lpar4; and (14) a multi-tissue adipose tissue and skin non-venule endothelial cell surface marker selected from the group consisting of Ly86, H2-Aa, and Cd74. In some embodiments, FACS comprises staining at least one antibody specific for an endothelial cell surface marker selected from the group consisting of: (1) a venule endothelial cell surface marker selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker selected from the group consisting of Nrp2, Htr2b, Mr1, Lifr, Anxa1, Lphn2, Vamp5, Olr1, Eps8, Slco2b1, and Slco2a1; (3) an adipose tissue venule endothelial cell surface marker selected from the group consisting of Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node venule endothelial cell surface marker selected from the group consisting of Ly96, Faim3, Sell, Slc2a12, Ggt5, Madcam1, Cd63, Rtn4r11, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker comprising Gpr182; (6) a multi-tissue adipose tissue and lymph node venule endothelial cell surface marker selected from the group consisting of H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker selected from the group consisting of Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (8) a non-venule endothelial cell surface marker selected from the group consisting of Cxcr4, Unc5b, Flt4, Ednrb, Notch4, Prnd, Gja5, Gja4, Alpl, Kcna5, P2ry2, Efnb2, and Itm2a; (9) a skin non-venule endothelial cell surface marker selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker selected from the group consisting of Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker selected from the group consisting of Ramp3, Olfr1396, Slc1a1, Cldn15, and Cd109; and (14) a multi-tissue adipose tissue and skin non-venule endothelial cell surface marker selected from the group consisting of Sell, Cd79b, Ly86, Chrm3, Ptger4, and Sema7a.

In some embodiments, the FACS does not comprise staining for endothelial cell surface marker Sele. In some embodiments, the FACS does not comprise staining for endothelial cell surface marker Selp. In some embodiments, the FACS does not comprise staining for venule endothelial cell surface marker Sele. In some embodiments, the FACS does not comprise staining for venule endothelial cell surface marker Selp. In some embodiments, the FACS does not comprise staining for skin non-venule endothelial cell surface marker Sell. In some embodiments, the FACS does not comprise staining for skin non-venule endothelial cell surface marker Siglech. In some embodiments, the FACS does not comprise staining for skin non-venule endothelial cell surface marker Cd44. In some embodiments, the FACS does not comprise staining for lymph node non-venule endothelial cell surface marker Pmp22. It should be appreciated that FACS analysis can be performed in combination with the methods for detecting markers of the disclosure to sort endothelial cells expressing certain markers and quantify the percentage and levels of expression of those markers, as well as to analyze global gene expression patterns.

In some embodiments, the disclosure contemplates quantifying the sorted endothelial cells identified.

In some embodiments, the disclosure contemplates preserving the sorted cells (e.g., cryopreservation of the cells in appropriate reagents).

In some embodiments, the endothelial cells comprise human endothelial cells.

In some embodiments the methods further comprise assessing the ability of the candidate agent to exhibit an anti-inflammatory effect. In such embodiments, the candidate agent is assessed for its ability to exhibit a systemic anti-inflammatory effect. In some instances, the candidate agent is assessed for its ability to exhibit a tissue-specific anti-inflammatory effect. For example, the candidate agent is assessed for its ability to exhibit an anti-inflammatory effect in a tissue, such as skin, adipose tissue, and lymph nodes.

In some embodiments, the methods further comprise coupling the candidate agent to an endothelial cell targeting agent described that binds to a protein expressed on the surface of an endothelial cell, and assessing the ability of the endothelial cell targeting agent to target the candidate agent to a targeted tissue comprising the endothelial cell. Exemplary endothelial cell targeting agents include: a venule endothelial cell targeting agent that binds to a protein expressed on the surface of venule endothelial cells (e.g., a protein encoded by a gene selected from the group consisting of Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1); a non-venule endothelial cell targeting agent that binds to a protein expressed on the surface of non-venule endothelial cells (e.g., a protein encoded by a gene selected from the group consisting of Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Prnd, Gja5, Gja4, Alpl, Kcna5, P2ry2, Efnb2, and Itm2a); a skin venule endothelial cell targeting agent that binds to a protein expressed on the surface of skin venule endothelial cells (e.g., a protein encoded by a gene selected from the group consisting of Nrp2, Gpr1, C630004H02Rik, Fndc1, 2310046K01Rik, Insr, and Slco2a1; and/or Nrp2, Htr2b, Mrl, Lifr, Anxa1, Lphn2, Vamp5, Olr1, Eps8, Slco2b1, and Slco2a1); skin non-venule endothelial cell targeting agent that binds to a protein expressed on the surface of skin non-venule endothelial cells (e.g., a protein encoded by a gene selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9); adipose tissue venule endothelial cell targeting agent that binds to a protein expressed on the surface of adipose tissue venule endothelial cells (e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam); an adipose tissue non-venule endothelial cell targeting agent that binds to a protein expressed on the surface of adipose tissue non-venule endothelial cells (e.g., a protein encoded by a gene selected from the group consisting of Adora2a, H2-Ab1, Hspg2, Gpr81, Kcna5, Jam3, and Gpc4; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3); a lymph node venule endothelial cell targeting agent that binds to a protein expressed on the surface of lymph node venule endothelial cells (e.g., a protein encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1); a lymph node non-venule endothelial cell targeting agent that binds to a protein expressed on the surface of lymph node non-venule endothelial cells (e.g., a protein encoded by a gene selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and 630033H20Rik). In some embodiments, the endothelial cell targeting agent does not bind to Sele. In some embodiments, the endothelial cell targeting agent does not bind to Selp. In some embodiments, the vendule endothelial cell targeting agent does not bind to Sele. In some embodiments, the venule endothelial cell targeting agent does not bind to Selp. In some embodiments, the skin non-venule endothelial cell targeting agent does not bind to Sell. In some embodiments, the skin non-venule endothelial cell targeting agent does not bind to Siglech. In some embodiments, the skin non-venule endothelial cell targeting agent does not bind to Cd44. In some embodiments, the skin non-venule endothelial cell targeting agent does not bind to Pmp22. Generally, the endothelial cell targeting agents can be assessed for their ability to target the candidate agent to the desired location (e.g., the skin venule endothelial cell targeting agent is assessed for its ability to target the candidate agent to the skin; the skin non-venule endothelial cell targeting agent is assessed for its ability to target the candidate agent to the skin; adipose tissue venule endothelial cell targeting agent is assessed for its ability to target the candidate agent to adipose tissue; e.g., the adipose tissue non-venule endothelial cell targeting agent is assessed for its ability to target the candidate agent to adipose tissue; the lymph node venule endothelial cell targeting agent is assessed for its ability to target the candidate agent to lymph nodes; and the lymph node non-venule endothelial cell targeting agent is assessed for its ability to target the candidate agent to lymph nodes). The disclosure contemplates any suitable protocol for assessing the ability of the endothelial cell targeting agents to target a candidate agent to a desired location. For example, fluorescent immunoregents or nanoparticles conjugated to MAbs or other ligands specific for these candidate targets, such as aptides, can be used to analyze the accumulation of targeted reagents (relative to appropriate controls) in tissues after intravenous infusion. Molecular targets in which cross-linking leads to internalization are likely to be effective endothelial cell targeting agents. Multi-photon intravital microscopy technology can be used to make such determinations by direct in situ imaging.

In some aspects, the disclosure contemplates methods for screening for targeting agents (e.g., venule endothelial cell targeting agents, non-venule endothelial cell targeting agents, skin venule endothelial cell targeting agents, skin non-venule endothelial cell targeting agents, adipose tissue venule endothelial targeting agents, adipose tissue non-venule endothelial cell targeting agents, lymph node venule endothelial cell targeting agents, lymph node non-venule endothelial cell targeting agents, multi-tissue skin and lymph node venule endothelial cell targeting agents, multi-tissue skin and lymph node non-venule endothelial cell targeting agents, multi-tissue adipose tissue and lymph node venule endothelial cell targeting agents, multi-tissue adipose tissue and lymph node non-venule endothelial cell targeting agents, multi-tissue adipose tissue and skin venule endothelial cell targeting agents, multi-tissue adipose tissue and skin non-venule endothelial cell targeting agents) that recognize, bind to or otherwise interact with the endothelial cell surface markers identified herein (e.g., venule endothelial cell surface markers, non-venule endothelial cell surface markers, skin venule endothelial cell surface markers, skin non-venule endothelial cell surface markers, adipose tissue venule endothelial cell surface markers, adipose tissue non-venule endothelial cell surface markers, lymph node venule endothelial cell surface markers, lymph node non-venule endothelial cell surface markers, multi-tissue skin and lymph node venule endothelial cell surface markers, multi-tissue skin and lymph node non-venule endothelial cell surface markers, multi-tissue adipose tissue and lymph node venule endothelial cell surface markers, multi-tissue adipose tissue and lymph node non-venule endothelial cell surface markers, multi-tissue adipose tissue and skin venule endothelial cell surface markers, multi-tissue adipose tissue and skin non-venule endothelial cell surface markers).

The screened and identified targeting agents may be selected from, for example, antibodies, antibody fragment, small peptides, small molecules (organic and non-organic), oligonucleotides, aptamers selected via screens of small combinatorial libraries and fusion proteins. In some embodiments, the screened and identified targeting agents comprise aptides.

The targeting agents may influence physiological function of the surface markers by inhibiting or augmenting (partially or fully) downstream activities of the identified surface markers. That is, for example, by influencing signaling pathways that are activated, increased, decreased or inhibited by the identified surface markers. The agents may or may not work by entering the cell and directly or indirectly interacting with constituents of the downstream pathway(s). Agents that work without entering the cell may work by inducing or inhibiting (fully or partly) other competing pathways via interaction with other cell surface molecules or with agents that interact with other cell surface molecules. Agents that work by entering the cell may work by interacting with downstream elements or molecules that interact with downstream elements. Additionally, agents that affect transcription and/or translation of the identified cell surface markers, competing markers or pathway constituents may also influence the activities of the identified cell surface markers. It is noted here that the phrase "competes with" or similar, may mean working in opposition to the identified marker and associated pathway to partly or fully inhibit the activity; likewise, the phrase may mean working in conjunction with the identified marker and associated pathway to partly or fully augment the activity. Both meanings are assumed unless noted differently herein by the context in which the phrase is used.

An exemplary screening method for identifying targeting agents is a yeast two-hybrid system (commercially available from Clontech) which allows for the detection of protein-protein interactions in yeast. See generally, Ausubel, et al., Current Protocols in Molecular Biology (John Wiley & Sons) (pp. 13.14.1-13.14.14). The system can be used to screen specially constructed cDNA libraries for proteins that interact with a target protein (e.g., an endothelial cell surface marker described herein). The disclosure contemplates the use of the two-hybrid system to screen for agents that will bind to a protein (e.g., (1) a venule endothelial cell surface marker, e.g., Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker, e.g., Nrp2, Gpr1, C630004H02Rik, Fndc1, 2310046K01Rik, Insr, and Slco2a1; and/or Nrp2, Htr2b, Mr1, Lifr, Anxa1, Lphn2, Vamp5, Olr1, Eps8, Slco2b1, and Slco2a1; (3) an adipose tissue endothelial cell surface marker, e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node endothelial cell surface marker, e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker, e.g., Gpr182 and Slco2b1; (6) a multi-tissue adipose tissue and lymph node venule endothelial cell surface marker, e.g., Cd63, Sirpa, Slc2a1, Vmn1r100, Vmn1r148, Vmn1r132, and Vmn1r125; and/or H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker, e.g., Il1rl, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1; (8) a non-venule endothelial cell surface marker, e.g., Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Prnd, Gja5, Gja4, Alpl, Kcna5, P2ry2, Efnb2, and Itm2a.; (9) a skin non-venule endothelial cell surface marker, e.g., Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker, e.g., Adora2a, H2-Ab1, Hspg2, Gpr81, Kcna5, Jam3, and Gpc4; and/or Kcnj2, Abca8b, F2r, Robo2, Ms4a1, Arhgef26, Tll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker, e.g., Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker, e.g., Tns1, Cxcr4, Atp1b1, Car4, Cd7, Itga1, Gja5, Laptm5, Aqp7, Gja4, Mlec, P2ry2, and Cd97; and/or Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker, e.g., Unc5b, Lpar6, Sema6d, Ppap2b, and Lpar4; and/or Ramp3, Olfr1396, Slc1a1, Cldn15, and Cd109; and (14) a multi-tissue adipose tissue and skin non-venule endothelial cell surface marker, e.g., Ly86, H2-Aa, and Cd74; and/or Sell, Cd79b, Ly86, Chrm3, Ptger4, and Sema7a. Agents (e.g., proteins) identified in a two-hybrid screen which bind to the protein (e.g., endothelial cell surface marker) may represent agents capable of blocking or augmenting the signaling of the protein (e.g., endothelial cell surface marker). In some embodiments, the skin non-venule endothelial cell targeting agent does not bind to Sell. In some embodiments, the skin non-venule endothelial cell targeting agent does not bind to Siglech. In some embodiments, the skin non-venule endothelial cell targeting agent does not bind to Cd44. In some embodiments, the lymph node non-venule endothelial cell targeting agent does not bind to Pmp22.

The disclosure contemplates using phage display selection to identify aptides that show high affinity and selectivity for a target protein (e.g., an endothelial cell surface marker described herein). As used herein, "aptide" refers to a scaffold-based affinity molecule that demonstrates high affinity (e.g., less than 100 nM) and selectivity for a specific protein. In certain embodiments, aptides can be synthesized to include a "tweezer-like" structure comprising a unique central structure-stabilizing scaffolding region flanked by two high-affinity target-binding components. Aptides specific for a target protein (e.g., an endothelial cell surface marker described herein) can be identified by screening an aptide-based phage library for target protein-specific ligands. In certain embodiments, the aptides comprise an amino acid sequence having a length of 24 amino acid residues. In certain embodiments, the unique central structure-stabilizing scaffolding comprises 12 amino acid residues. In certain embodiments, each of the flanking high-affinity target-binding components comprises 6 amino acid residues, which may be the same or different. Preferably, aptides possessing nanomolar-range binding affinity for the target protein are identified. Additional information about aptides can be found in the literature (see e.g., Sangyong Jon, et al., "HER2-specific aptide conjugated magneto-nanoclusters for potential breast cancer imaging and therapy," *J. Materials Chemistry B*. 2013; DOI: 10.1039/C3TB20613K; Jon, et al., "Fibronectin extra domain B-specific aptide conjugated nanoparticles for targeted cancer imaging," *J. Control Release*. 2012; 163(2):111-8; Kim, et al., "VEGF-binding aptides and the inhibition of choroidal and retinal neovascularization," *Biomaterials*. 2014; 35(9):3052-9). Candidate aptides identified in this way can be assessed for their ability to accumulate in vivo in a specific tissue or organ, such as skin, adipose tissue, or lymph node, by intravenous injection of the adptide conjugated to an imaging agent or moiety, such as an immunofluorescent reagent.

The disclosure contemplates the use of the phage display selection to screen for aptides that will bind to a protein (e.g., (1) a venule endothelial cell surface marker, e.g., Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker, e.g., Nrp2, Gpr1, C630004H02Rik, Fndc1, 2310046K01Rik, Insr, and Slco2a1; and/or Nrp2, Htr2b, Mr1, Lifr, Anxa1, Lphn2, Vamp5, Olr1, Eps8, Slco2b1, and Slco2a1; (3) an adipose tissue endothelial cell surface marker, e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node endothelial cell surface marker, e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker, e.g., Gpr182 and Slco2b1; (6) a multi-tissue adipose tissue and lymph node venule endothelial cell surface marker, e.g., Cd63, Sirpa, Slc2a1, Vmn1r100, Vmn1r148, Vmn1r132, and Vmn1r125; and/or H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker, e.g., Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1; (8) a non-venule endothelial cell surface marker, e.g., Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Prnd, Gja5, Gja4, Alpl, Kcna5, P2ry2, Efnb2, and Itm2a; (9) a skin non-venule endothelial cell surface marker, e.g., Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker, e.g., Adora2a, H2-Ab1, Hspg2, Gpr81, Kcna5, Jam3, and Gpc4; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker, e.g., Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Caldl, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker, e.g., Tns1, Cxcr4, Atp1b1, Car4, Cd7, Itga1, Gja5, Laptm5, Aqp7, Gja4, Mlec, P2ry2, and Cd97; and/or Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker, e.g., Unc5b, Lpar6, Sema6d, Ppap2b, and Lpar4; and/or Ramp3, Olfr1396, Slc1a1, Cldn15, and Cd109; and (14) a multi-tissue adipose tissue and skin non-venule endothelial cell surface marker, e.g., Ly86, H2-Aa, and Cd74; and/or Sell, Cd79b, Ly86, Chrm3, Ptger4, and Sema7a.

In some aspects, the disclosure provides an aptide that specifically binds to a protein (e.g., (1) a venule endothelial cell surface marker, e.g., Sele, Selp, Il6st, Plxnb2, Lepr, Bst1, and Icam1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1; (2) a skin venule endothelial cell surface marker, e.g., Nrp2, Gpr1, C630004H02Rik, Fndc1, 2310046K01Rik, Insr, and Slco2a1; and/or Nrp2, Htr2b, Mr1, Lifr, Anxa1, Lphn2, Vamp5, Olr1, Eps8, Slco2b1, and Slco2a1; (3) an adipose tissue endothelial cell surface marker, e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3; and/or Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam; (4) a lymph node endothelial cell surface marker, e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1; (5) a multi-tissue skin and lymph node venule endothelial cell surface marker, e.g., Gpr182 and Slco2b1; (6) a multi-tissue adipose tissue and lymph node venule endothelial cell surface marker, e.g., Cd63, Sirpa, Slc2a1, Vmn1r100, Vmn1r148, Vmn1r132, and Vmn1r125; and/or H60b, Ppap2c, Celsr1, Glycam1, Slc37a1, Cd59a, Slc2a1, Tnfrsf9, Tes, Pglyrp1, Il27ra, and Eda2r; (7) a multi-tissue adipose tissue and skin venule endothelial cell surface marker, e.g., Il1rl1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Il1rl1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1; (8) a non-venule endothelial cell surface marker, e.g., Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a; and/or Cxcr4, Unc5b, Flt4, Ednrb, Notch4, Prnd, Gja5, Gja4, Alpl, Kcna5, P2ry2, Efnb2, and Itm2a; (9) a skin non-venule endothelial cell surface marker, e.g., Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (10) an adipose tissue non-venule endothelial cell surface marker, e.g., Adora2a, H2-Ab1, Hspg2, Gpr81, Kcna5, Jam3, and Gpc4; and/or Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (11) a lymph node non-venule endothelial cell surface marker, e.g., Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik; (12) a multi-tissue skin and lymph node non-venule endothelial cell surface marker, e.g., Tns1, Cxcr4, Atp1b1, Car4, Cd7, Itga1, Gja5, Laptm5, Aqp7, Gja4, Mlec, P2ry2, and Cd97; and/or Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4; (13) a multi-tissue adipose tissue and lymph node non-venule endothelial cell surface marker, e.g., Unc5b, Lpar6, Sema6d, Ppap2b, and Lpar4; and/or Ramp3, Olfr1396, Slc1a1, Cldn15, and Cd109; and (14) a multi-tissue adipose tissue and skin non-venule endothelial cell surface marker, e.g., Ly86, H2-Aa, and Cd74; and/or Sell, Cd79b, Ly86, Chrm3, Ptger4, and Sema7a.

The disclosure also contemplates in vitro screening methods. Protein interactions may also be detected using, for example, gel electrophoresis where protein interactions can be detected by changes in electrophoretic mobility (detecting, for example, changes in size due to the binding of one or more proteins with another protein). Additionally, protein interactions can be detected by Western blotting. Western blotting detects proteins by transferring proteins from an electrophoresis gel to, e.g., nitrocellulose paper. Antibodies are then used to detect proteins that may have been transferred to the paper. Co-localization of two or more antibodies indicates possible protein-protein interaction.

Similarly, protein-protein interactions can be detected using affinity column chromatography. In this procedure, a binding agent (e.g., a target protein such as P2X5, Slc36a2 or Slc7a10) is bound to the column media (usually, for example, sepharose beads treated to bind the selected target protein and then treated to block any unused binding sites). The protein (or a mixture of proteins) suspected of interacting with the selected target protein is then run over the column. Proteins capable of interacting with the selected protein will bind the target protein and non-interacting proteins will run through the column. Bound, interactive proteins can then be released by changing stringency conditions.

The screening methods contemplate employing combinatorial peptide and small molecule libraries. For example, another aspect of the In some embodiments relates to identifying agents which bind the markers identified herein by screening combinatorial polypeptide libraries which encode either a random or controlled collection of amino acids. One such method is identifying molecules which bind, for example, an endothelial cell surface marker described herein from a polypeptide array. An array of polypeptides is synthesized on a solid support (e.g., a biological chip) as described by Pirrung et al., U.S. Pat. No. 5,143,854, the contents of which are incorporated herein by reference. The polypeptides which are attached to the support are called probes. The resulting product is then processed to determine which polypeptides of the array bind a target protein (e.g., an endothelial cell surface marker described herein). The array linked support can be contacted with the target molecule under conditions appropriate for binding, and specific probe proteins which bind the target molecule are identified. Methods for detecting labeled markers on a support are provided by Trulson et al., U.S. Pat. No. 5,578,832, the contents of which are incorporated herein by reference.

Another method for identifying polypeptides from a library which bind to a specified molecule is provided by Dower et al., U.S. Pat. No. 5,432,018, the contents of which are incorporated herein by reference. In addition, libraries of non-polypeptide chemical agents can be screened for binding to and/or inhibition of an endothelial cell surface marker described herein by the method according to Zambias et al., U.S. Pat. No. 5,807,754, the contents of which are incorporated herein by reference, and also the method according to J. Ellman, U.S. Pat. No. 5,288,514, the contents of which are incorporated herein by reference.

Methods of Treatment

In still yet another aspect, disclosed herein are methods for treating or preventing disorders associated with leukocyte trafficking. The disclosure contemplates treating or preventing any disease or disorder in which leukocyte trafficking is involved (e.g., an inflammatory disease) or may be desirable (e.g., infection). It should be appreciated that any of the agents administered or employed in connection with the methods described herein can be administered or employed as part of a composition.

In one aspect, a method of treating or preventing an inflammatory disease in a subject in need thereof comprises administering to a subject an effective amount of an agent that modulates a gene which is differentially expressed in venule endothelial cells compared to non-venule endothelial cells.

In another aspect, a method of treating or preventing an inflammatory disease in a subject in need thereof comprises administering to a subject an effective amount of a venuleness modulating agent described herein.

In yet another aspect, a method of treating or preventing an inflammatory disease in a subject in need thereof comprises administering to a subject an effective amount of a leukocyte trafficking and/or inflammation modulating agent described herein.

In another aspect, a method of treating or preventing an inflammatory disease in a subject in need thereof comprises administering to a subject an effective amount of a venuleness modulating agent described herein coupled to an endothelial cell targeting agent described herein or a composition comprising the same.

In some aspects, a method of treating or preventing an inflammatory disease comprises a method of treating an inflammatory skin disease in a subject in need thereof. An exemplary method of treating or preventing an inflammatory skin disease comprises administering to the subject an effective amount of an agent that inhibits the level or activity of a gene exhibiting higher expression levels in venule endothelial cells in skin compared to non-venule endothelial cells in skin. In some embodiments, inhibiting the level or activity of the gene interferes with leukocyte interactions with the venule endothelial cells in the skin. In some embodiments, inhibiting the level or activity of the gene interferes with extravasation of leukocytes to the extravascular compartment in the skin. In some embodiments, inhibiting the level or activity of the gene decreases a local inflammatory response in the skin. In some embodiments, the agent inhibits leukocyte adhesion to the skin venule endothelial cell.

The disclosure contemplates treating or preventing any inflammatory skin disease in a subject. Exemplary inflammatory skin disease capable of being treated or prevented according to the methods described herein include, but are not limited to acne, dermatitis, eczema, oily skin, rosacea, cutaneus lymphoma and urticaria. In some embodiments, the dermatitis is selected from the group consisting of atopic dermatitis, psoriasis and contact dermatitis. In some embodiments, the inflammatory skin disease is not mediated by, or does not involve, Sele. In some embodiments, the inflammatory skin disease is not mediated by, or does not involve, Sell. In some embodiments, the inflammatory skin disease is not mediated by, or does not involve, Selp. In some embodiments, the inflammatory skin disease is not mediated by, or does not involve, Cd44. In some embodiments, the inflammatory skin disease is not mediated by, or does not involve, CD130. In some aspects, a method of treating or preventing an inflammatory disease comprises a method of treating or preventing a disease characterized by visceral fat inflammation in a subject in need thereof. An exemplary method of treating or preventing a disease characterized by visceral fat inflammation in a subject in need thereof comprises administering to the subject an effective amount of an agent that inhibits the level or activity of a gene exhibiting higher expression levels in venule endothelial cells in adipose tissue compared to non-venule endothelial cells in adipose tissue.

In some embodiments, inhibiting the level or activity of the gene interferes with leukocyte interactions with the venule endothelial cells in the adipose tissue. In some embodiments, inhibiting the level or activity of the gene interferes with extravasation of leukocytes to the extravascular compartment in the adipose tissue. In some embodiments, inhibiting the level or activity of the gene decreases a local inflammatory response in the adipose tissue. In some embodiments, the agent inhibits leukocyte adhesion to the venule endothelial cell in the adipose tissue.

The disclosure contemplates treating or preventing any disease characterized by visceral fat inflammation. Exemplary diseases which can be treated or prevented by the methods described herein include, but are not limited to, cancer, CVHD, fibrosis, hypertension, lypodystrophy, obesity, metabolic syndrome, and diabetes (e.g., type II diabetes).

In some aspects, a method of treating or preventing an inflammatory disease comprises a method of treating or preventing a disease characterized by lymphadenitis in a subject in need thereof. An exemplary method of treating or preventing a disease characterized by lymphadenitis in a subject in need thereof comprises administering to the subject an effective amount of an agent that inhibits the level or activity of a gene exhibiting higher expression levels in venule endothelial cells in lymph nodes compared to non-venule endothelial cells in lymph nodes.

In some embodiments, inhibiting the level or activity of the gene interferes with leukocyte interactions with the venule endothelial cells in the lymph nodes. In some embodiments, inhibiting the level or activity of the gene interferes with extravasation of leukocytes to the extravascular compartment of the lymph nodes. In some embodiments, inhibiting the level or activity of the gene decreases a local inflammatory response in the lymph nodes. In some embodiments, the agent inhibits leukocyte adhesion to the lymph node venule endothelial cell.

The disclosure contemplates treating or preventing any disease characterized by lymphadenitis in a subject. Exemplary such diseases include, but are not limited to, cancer, connective tissue disorders, and infection. In some embodiments, the cancer is selected from the group consisting of leukemias, lymphomas, and metastatic cancer. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome. In some embodiments, the disease is not, or does not involve, lymphadenitis mediated by, or involving, Sele. In some embodiments, the disease is not, or does not involve, lymphadenitis mediated by, or involving, Sell. In some embodiments, the disease is not, or does not involve, lymphadenitis mediated by, or involving, Selp. In some embodiments, the disease is not, or does not involve, lymphadenitis mediated by, or involving, Cd44. In some embodiments, the disease is not, or does not involve, lymphadenitis mediated by, or involving, Cd130.

By "treatment, prevention or amelioration of a disease" (e.g., an inflammatory disease, disease characterized by visceral fat inflammation, disease characterized by lymphadenitis, etc.) is meant delaying or preventing the onset of such a disorder (e.g. chronic inflammation), at reversing, alleviating, ameliorating, inhibiting, slowing down or stopping the progression, aggravation or deterioration the progression or severity of such a condition. In one embodiment, the symptom of a disease involving leukocyte trafficking is alleviated by at least 20%, at least 30%, at least 40%, or at least 50%. In one embodiment, the symptom of a disease involving leukocyte trafficking is alleviated by more that 50%. In one embodiment, the symptom of a disease involving leukocyte trafficking is alleviated by 80%, 90%, or greater. Treatment also includes improvements in immune function. In some embodiments, immune function improves by at least about 10%, 20%, 30%, 40%, 50% or more.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. In some embodiments of the invention, the subject suffers from a leukocyte trafficking based disorder.

In some embodiments, the methods described herein further comprise selecting a subject diagnosed with a disorder associated with leukocyte trafficking. A subject suffering from a disorder associated with leukocyte trafficking can be selected based on the symptoms presented. For example a subject suffering from a disorder characterized by visceral fat inflammation (e.g., metabolic syndrome) may show symptoms of fasting hyperglycemia, high blood pressure, central obesity, decreased HDL cholesterol levels, elevated triglycerides.

In some embodiments, the methods described herein further comprise selecting a subject at risk of developing a disorder associated with leukocyte trafficking. A subject at risk of developing a a disorder associated with leukocyte trafficking can be selected based on a genetic diagnostic test (e.g., for a mutation in a gene which is differentially expressed in venule endothelial cells compared to non-venule endothelial cells) or based on the symptoms presented.

In some embodiments, the methods described herein further comprise selecting a subject suspected of having a disorder involving leukocyte trafficking. A subject suspected of having a disorder involving leukocyte trafficking be selected based on a genetic diagnostic test (e.g., for a mutation in a gene associated with a marker of venuleness described herein) or based on the symptoms presented or a combination thereof.

Compositions

The disclosure contemplates compositions comprising at least one agent described. The compositions described herein can be employed in various methods of treatment, as will be appreciated by those skilled in the art.

Accordingly, in some aspects, a composition comprises an effective amount of an venuleness modulating agent described herein.

In some aspects, a composition comprises an effective amount of a leukocyte trafficking modulating agent described herein.

In some aspects, a composition comprises an effective amount of an inflammation modulating agent described herein.

In some aspects, a composition comprises an effective amount of an endothelial cell targeting agent described herein.

In some embodiments, the venuleness modulating agent, the leukocyte trafficking modulating agent, or the inflammation modulating agent can be coupled to an endothelial cell targeting agent described herein.

In some aspects, a composition comprises an agent that modulates expression of a gene that is differentially expressed in venule endothelial cells compared to non-venule endothelial cells.

In some aspects, the disclosure provides a composition comprising an agent that modulates activity and/or function of an expression product of at least one gene which is differentially expressed in venule endothelial cells compared to non-venule endothelial cells. In some embodiments, the at least one gene is selected from the group consisting of a gene or combination of genes listed in Table 1, Table 2, Table 3, Table 4, Table 5, Table 6, Table 7, Table 8, Table 9, Table 10, Table 11, Table 12, Table 13, and/or Table 14.

In some aspects, a composition comprises an agent that modulates expression of a gene that is differentially expressed in venule endothelial cells compared to non-venule endothelial cells, wherein the agent is selected from the group consisting of: (1) an agent that decreases expression of at least one gene which exhibits higher expression levels in venule endothelial cells compared to non-venule endothelial cells inhibits inflammation in the subject; (ii) an agent that increases expression of at least one gene which exhibits lower expression levels in venule endothelial cells compared to non-venule endothelial cells inhibits inflammation in the subject; (iii) an agent that decreases expression of at least one gene which exhibits higher expression levels in non-venule endothelial cells compared to venule endothelial cells induces inflammation in the subject; or (iv) an agent that increases expression of at least one gene which exhibits lower expression levels in non-venule endothelial cells compared to venule endothelial cells induces inflammation in the subject.

The disclosure contemplates any agent that is capable of modulating the expression of at least one gene which is differentially expressed in venule endothelial cells compared to non-venule endothelial cells. The disclosure contemplates any agent that is capable of modulating the activity and/or function of an expression product of at least one gene which is differentially expressed in venule endothelial cells compared to non-venule endothelial cells. In some embodiments, the at least one gene comprises a gene or combinations of genes (or their expression products) listed in Table 1, Table 2, Table 3, Table 4, Table 5, Table 6, Table 7, Table 8, Table 9, Table 10, Table 11, Table 12, Table 13, and/or Table 14. In some embodiments, the at least one gene exhibiting higher expression levels in venule endothelial cells compared to non-venule endothelial cells is selected from the group consisting of a gene or combination of genes listed in Table 1. In some embodiments, the at least one gene exhibiting lower expression levels in venule endothelial cells compared to non-venule endothelial cells is selected from the group consisting of a gene or combination of genes listed in Table 8. In some embodiments, the at least one gene exhibiting higher expression levels in non-venule endothelial cells compared to venule endothelial cells is selected from the group consisting of a gene or combination of genes listed in Table 8. In some embodiments, the at least one gene exhibiting lower expression levels in non-venule endothelial cells compared to venule endothelial cells is selected from the group consisting of a gene or combination of genes listed in Table 1.

In some embodiments, the at least one gene is differentially expressed in skin venule endothelial cells compared to skin non-venule endothelial cells. In such embodiments, the composition can be used for treating or preventing a skin inflammatory disease (e.g., a skin inflammatory disease disclosed herein). In such embodiments, the at least one gene exhibiting higher expression levels in venule endothelial cells compared to non-venule endothelial cells is selected from the group consisting of a gene or combination of genes listed in Table 2. In such embodiments, the at least one gene exhibiting lower expression levels in venule endothelial cells compared to non-venule endothelial cells is selected from the group consisting of a gene or combination of genes listed in Table 9. In such embodiments, the at least one gene exhibiting higher expression levels in non-venule endothelial cells compared to venule endothelial cells is selected from the group consisting of a gene or combination of genes listed in Table 9. In such embodiments, the at least one gene exhibiting lower expression levels in non-venule endothelial cells compared to venule endothelial cells is selected from the group consisting of a gene or combination of genes listed in Table 2.

In some embodiments, the at least one gene is differentially expressed in adipose tissue venule endothelial cells compared to adipose tissue non-venule endothelial cells. In such embodiments, the composition can be used for treating or preventing a disease characterized by visceral fat inflammation. In such embodiments, the at least one gene exhibiting higher expression levels in venule endothelial cells compared to non-venule endothelial cells is selected from the group consisting of a gene or combination of genes listed in Table 3. In such embodiments, the at least one gene exhibiting lower expression levels in venule endothelial cells compared to non-venule endothelial cells is selected from the group consisting of a gene or combination of genes listed in Table 10. In such embodiments, the at least one gene exhibiting higher expression levels in non-venule endothelial cells compared to venule endothelial cells is selected from the group consisting of a gene or combination of genes listed in Table 10. In such embodiments, the at least one gene exhibiting lower expression levels in non-venule endothelial cells compared to venule endothelial cells is selected from the group consisting of a gene or combination of genes listed in Table 3.

In some embodiments, the at least one gene is differentially expressed in lymph node venule endothelial cells compared to lymph node non-venule endothelial cells. In such embodiments, the composition can be used for treating or preventing a disease characterized by lymphadenitis. In such embodiments, the at least one gene exhibiting higher expression levels in venule endothelial cells compared to non-venule endothelial cells is selected from the group consisting of a gene or combination of genes listed in Table 4. In such embodiments, the at least one gene exhibiting lower expression levels in venule endothelial cells compared to non-venule endothelial cells is selected from the group consisting of a gene or combination of genes listed in Table 11. In such embodiments, the at least one gene exhibiting higher expression levels in non-venule endothelial cells compared to venule endothelial cells is selected from the group consisting of a gene or combination of genes listed in Table 11. In such embodiments, the at least one gene exhibiting lower expression levels in non-venule endothelial cells compared to venule endothelial cells is selected from the group consisting of a gene or combination of genes listed in Table 4.

Modulating expression by administering a composition described herein may be used to modulate inflammation. Modulating activity and/or function of a gene or expression product of a gene disclosed herein by administering an agent or composition described herein may be used to modulate inflammation, e.g., by modulating leukocyte interactions in endothelial cells (e.g., venular endothelial cells). In some contexts, modulating inflammation comprises inhibiting inflammation Inhibiting inflammation may be achieved by one or more of interfering with leukocyte trafficking, interfering with leukocyte adhesion, and interfering with leukocyte extravasation.

The compositions described herein contemplate inhibiting inflammation in all tissues comprising genes which are differentially expressed in venule endothelial cells compared to non-venule endothelial cells. In some embodiments, the compositions described herein can be used to inhibit inflammation in a specific tissue. In some embodiments, inflammation is inhibited in a tissue selected from the group consisting of skin, adipose tissue, and lymph nodes.

In some contexts, modulating inflammation comprises inducing, facilitating, or enabling inflammation. Inducing inflammation may result from one or more of enabling leukocyte trafficking, enabling leukocyte adhesion, and enabling leukocyte extravasation. In some embodiments, inflammation can be induced systemically by a composition described herein (e.g., by administering a composition comprising an agent that modulates non-venules to become venules). In some embodiments, the compositions can be used to induce inflammation in a specific tissue. In some embodiments, the compositions induce inflammation in a tissue selected from the group consisting of skin, adipose tissue, and lymph nodes.

In some embodiments, an agent of the composition is coupled to an endothelial cell targeting agent described herein that targets the agent to an endothelial cell surface marker described herein.

In some aspects, the disclosure provides a composition comprising an agent to be targeted to microvessel endothelial cells, wherein the agent is coupled to a microvessel endothelial cell targeting agent.

In some embodiments, the microvessel endothelial cell targeting agent binds to a protein expressed on the surface of a microvessel endothelial cell (e.g., an endothelial cell surface marker described herein).

In some embodiments, the microvessel endothelial cell targeting agent is internalized into the endothelial cells lining the microvessel. Internalization of the microvessel endothelial cell targeting agent into the endothelial cells lining the microvessel causes the microvessel endothelial cell targeting agent to accumulate in the tissue in which the microvessel resides. In some embodiments, the microvessel endothelial cell targeting agent accumulates in the subject's skin. In such embodiments, the composition can be used for treating or preventing a skin inflammatory disease (e.g., a skin inflammatory disease disclosed herein). In some embodiments, the microvessel endothelial cell targeting agent accumulates in the subject's adipose tissue. In such embodiments, the composition can be used for treating or preventing a disease (e.g., a characterized by visceral fat inflammation or an adipose tissue associated disorder). In some embodiments, the microvessel endothelial cell targeting agent accumulates in the venule endothelial cells in the subject's lymph nodes. In such embodiments, the composition can be used for treating or preventing a disease characterized by lymphadenitis. In certain embodiments, the microvessel endothelial cell targeting agent does not accumulate in non-target tissues.

Internalization of the microvessel endothelial cell targeting agent into the endothelial cells lining the microvessel also causes the agent to accumulate in the tissue in which the microvessel resides. In some embodiments, the agent accumulates in the subject's skin. In some embodiments, the agent accumulates in the subject's adipose tissue. In some embodiments, the agent accumulates in the subject's lymph nodes. In such embodiments, the agent induces a localized effect in the tissue. In some embodiments, the agent does not accumulate in non-target tissue.

Any of the compositions described herein can include an additional agent described herein (e.g., therapeutic agent, e.g., an anti-inflammatory agent, diagnostic agent, imaging agent, etc.).

The disclosure contemplates that targeting an agent to microvessel endothelial cells of the subject treats, prevents, or ameliorates a symptom of, an inflammatory disease in the subject. Examples of such inflammatory diseases include endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the inflammatory disease is not mediated by, or does not involve, Sele. In some embodiments, the inflammatory disease is not mediated by, or does not involve, Sell. In some embodiments, the inflammatory disease is not mediated by, or does not involve, Selp. In some embodiments, the inflammatory disease is not mediated by, or does not involve, Cd44. In some embodiments, the inflammatory disease is not mediated by, or does not involve, Cd130.

The disclosure also contemplates that a composition used for targeting an agent to microvessel endothelial cells of the subject treats, prevents, or ameliorates a symptom of, an infection in the subject. Such infections may include a bacterial infection, a viral infection, a parasitic infection, a fungal infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the infection is not mediated by, or does not involve, Sele. In some embodiments, the infection is not mediated by, or does not involve, Sell. In some embodiments, the infection is not mediated by, or does not involve, Selp. In some embodiments, the infection is not mediated by, or does not involve, Cd44. In some embodiments, the infection is not mediated by, or does not involve, Cd130.

The disclosure further contemplates that targeting an agent to microvessel endothelial cells of the subject treats, prevents, or ameliorates a symptom of, cancer in the subject. Such cancers include, but are not limited to, leukemias, lymphomas, and metastatic cancer. In some embodiments, the cancer is not mediated by, or does not involve, Sele. In some embodiments, the cancer is not mediated by, or does not involve, Sell. In some embodiments, the cancer is not mediated by, or does not involve, Selp. In some embodiments, the cancer is not mediated by, or does not involve, Cd44. In some embodiments, the cancer is not mediated by, or does not involve, Cd130.

The disclosure even further contemplates that targeting an agent to microvessel endothelial cells of the subject treats, prevents, or ameliorates a symptom of, a connective tissue disorder in the subject. Exemplary connective tissue disorder include, but are not limited to, systemic lupus erythematosus (SLE), sarcoidosis, Kawasaki disease, juvenile idiopathic arthritis, Kikuchi lymphadenopathy, rheumatoid arthritis, and Sjögren syndrome. In some embodiments, the connective tissue disorder is not mediated by, or does not involve, Sele. In some embodiments, the connective tissue disorder is not mediated by, or does not involve, Sell. In some embodiments, the connective tissue disorder is not mediated by, or does not involve, Selp. In some embodiments, the connective tissue disorder is not mediated by, or does not involve, Cd44. In some embodiments, the connective tissue disorder is not mediated by, or does not involve, Cd130.

In some aspects, the disclosure the use of a composition described herein for treating an individual for a condition characterized by inflammation in a specific organ or tissue. The inflammation is associated with a disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the disease is not mediated by, or does not involve, Sele. In some embodiments, the disease is not mediated by, or does not involve, Sell. In some embodiments, the disease is not mediated by, or does not involve, Selp. In some embodiments, the disease is not mediated by, or does not involve, Cd44. In some embodiments, the disease is not mediated by, or does not involve, Cd130.

In some embodiments, the composition is used for treating an individual for a condition characterized by an infection (e.g., a bacterial infection, a viral infection, a parasitic infection, a fungal infection, etc.). In some instances, the composition can be used for treating an infection including, but not limited to, an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. The oropharyngeal infection may be pharyngitis, stomatitis, or dental abscess.

In some embodiments, the composition is used for treating an individual for cancer (e.g., leukemias, lymphomas, and metastatic cancer).

In some embodiments, the composition is used for treating an individual for a connective tissue disorder (e.g., systemic lupus erythematosus (SLE), sarcoidosis, Kawasaki disease, juvenile idiopathic arthritis, Kikuchi lymphadenopathy, rheumatoid arthritis, and Sjögren syndrome).

Kits

An agent described herein can be provided in a kit. The kit includes (a) the agent, e.g., a composition that includes the agent, and (b) informational material. The informational material can be descriptive, instructional, marketing or other material that relates to the methods described herein and/or the use of the agent for the methods described herein. For example, the informational material describes methods for administering the agent to modulate the venuleness of an endothelial cell or microvessel, to treat or prevent a disorder involving leukocyte trafficking (e.g., an inflammatory disease), or at least one symptom of a disease associated with suboptimal leukocyte trafficking.

In one embodiment, the informational material can include instructions to administer the agent in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

In addition to the agent or the composition of the kit can include other ingredients, such as a solvent or buffer, a stabilizer or a preservative, and/or a second agent for treating a condition or disorder described herein, e.g. an inflammatory disease). Alternatively, the other ingredients can be included in the kit, but in different compositions or containers than the agent. In such embodiments, the kit can include instructions for admixing the agent and the other ingredients, or for using the modulator together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the agent (e.g., in a composition) and informational material. For example, the agent (e.g., in a composition) can be contained in a bottle, vial, or syringe, and the informational material can be contained in a plastic sleeve or packet. In other embodiments, the separate elements of the kit are contained within a single, undivided container. For example, the agent (e.g., in a composition) is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent (e.g., in a composition). For example, the kit includes a plurality of syringes, ampules, foil packets, or blister packs, each containing a single unit dose of the agent. The containers of the kits can be air tight and/or waterproof.

The agent (e.g., in a composition) can be administered to a subject, e.g., an adult subject, e.g., a subject suffering from a disorder associated with leukocyte trafficking (e.g., an inflammatory disease). The method can include evaluating a subject, e.g., to obtain a leukocyte count, and thereby identifying a subject as having a disorder associated with leukocyte trafficking or being pre-disposed to such disorder. Methods of obtaining a leukocyte count are apparent to the skilled artisan. In some embodiments, the subject can be evaluated for one or more markers of inflammation, e.g., plasma c-reactive protein, fibrinogen, interleukin-6 (IL-6), tumor necrosis factor-alpha (TNF-alpha), to identify a subject as having a disorder associated with leukocyte trafficking who may be a candidate for administration of an agent described herein.

Agents

The disclosure contemplates the use of various agents in connection with the methods and compositions described herein. Certain of the methods, compositions, and kits described herein relate to modulating the expression of genes which are differentially expressed in venule endothelial cells compared to non-venule endothelial cells. Certain of the methods, compositions, and kits described herein relate to modulating the activity and/or function of expression products of genes which are differentially expressed in venule endothelial cells compared to non-venule endothelial cells. In particular, the work described herein identified the genes listed in Tables 1-14 as being over- or under-represented in venules compared to non-venules globally, as well as in various tissues (e.g., skin, adipose tissue, and lymph node). As described herein, and as will be appreciated by those skilled in the art, the genes listed in Tables 1-14 can be used in methods, compositions, and kits for modulating the venuleness of endothelial cells or microvessels, modulating leukocyte trafficking, and/or modulating inflammation, as well as for identifying agents that modulate venuleness, leukocyte trafficking, and inflammation. The genes listed in Tables 1-14 can also be used in methods, compositions, and kits for modulating leukocyte interactions with endothelial cells in a tissue or organ specific manner, e.g., by modulating the expression and/or activity of a gene listed in Tables 1-14 and/or by modulating the expression and/or activity and/or function of an expression product of a gene listed in Tables 1-14, in the endothelial cells in a specific tissue or organ.

As used broadly herein, the term "modulate" means to cause or facilitate a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon.

The term "modulator" broadly refers to any molecule or agent that causes or facilitates a qualitative or quantitative change, alteration, or modification in a process, pathway, or phenomenon of interest. As used herein, the term "modulator" comprises both inhibitors and activators of a biological pathway or target. For example, "modulator" comprises both inhibitors and activators of expression and/or activity of a gene listed in Tables 1-14, as well as inhibitors and activators of an expression product of a gene listed in Tables 1-14.

As used herein, the phrase "modulation of a biological pathway" refers to modulation of activity of at least one component of the biological pathway. It is contemplated herein that modulator of the signaling pathway can be, for example, a receptor ligand (e.g., a small molecule, an antibody, an siRNA), a ligand sequestrant (e.g., an antibody, a binding protein), a modulator of phosphorylation of a pathway component or a combination of such modulators.

One of skill in the art can easily test an agent to determine if it modulates a signaling pathway by assessing, for example, phosphorylation status of the receptor or expression of downstream proteins controlled by the pathway in cultured cells and comparing the results to cells not treated with a modulator. A modulator is determined to be a signaling pathway modulator if the level of phosphorylation of the receptor or expression of downstream proteins in a culture of cells is reduced by at least 20% compared to the level of phosphorylation of the receptor or expression of downstream proteins in cells that are cultured in the absence of the modulator; preferably the level of phosphorylation is altered by at least 30%, at least 40%, at least 50%, at least 60%, at least 70%, at least 80%, at least 90%, at least 95%, or at least 99% in the presence of a pathway modulator.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit"

means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Certain methods, compositions, kits and agents contemplated herein modulate an inflammatory response. In the contexts of decreasing an inflammatory response or inflammation, the methods, compositions, kits and agents contemplated herein can decrease the inflammatory response or inflammation by at least about 10%, 20%, 30%, 40%, 50%, 60%, 70%, 80, 90%, or as much as 100% as compared to a reference level (e.g., an amount of inflammation before employing the method, composition, kit and/or agent). In the contexts of increasing an inflammatory response or inflammation, the methods, compositions, kits and agents contemplated herein can increase the inflammatory response or inflammation by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an amount of inflammation before employing the method, composition, kit and/ or agent).

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used more particularly herein "modulates", "modulating", and "modulation" are used interchangeably and refer to any one or combination of an increase (e.g., upregulation or activation) in the expression of a gene or gene product (e.g., mRNA or protein encoded by a gene which exhibits higher expression levels in venule endothelial cells compared to non-venule endothelial cells), a decrease (e.g., downregulation or inhibition) in the expression of a gene or gene product (e.g., mRNA or protein encoded by a gene which exhibits higher expression levels in venule endothelial cells compared to non-venule endothelial cells), and a change in the relative expression of one or more gene products (e.g., a reduction in the expression of mRNA or protein encoded by a gene which exhibits higher expression levels in venule endothelial cells relative to non-venule endothelial cells, or a reduction in the expression of a mutant gene which exhibits higher expression levels in endothelial cells relative to the expression of the wild-type gene). The term "expression" means the process by which information from a gene or nucleic acid (e.g., DNA) is used in the synthesis of gene products (e.g., mRNA, RNA and/or proteins) and includes, but is not limited to, one or more of the steps of replication, transcription and translation. The steps of expression which may be modulated by the agents contemplated herein may include, for example, transcription, splicing, translation and post-translational modification of a protein. It should be appreciated that the genes which are differentially expressed in venule endothelial cells compared to non-venule endothelial cells encode different types of proteins, including for example, enzymes, protein kinases, transcriptional regulators, and an endothelial cell surface protein or markers. Those skilled in the art will appreciate that the method of modulating any particular protein may depend on the type of protein (e.g., protein kinase, transcriptional regulator, enzyme, etc.), its function (e.g., transcriptional regulation, catalysis, phosphorylation, signal transduction, etc.), and its subcellular localization (e.g., extracellular space, cytoplasm, nucleus, membrane, etc.). Those skilled in the art will readily appreciate appropriate agents to be used for modulation depending on the particular context (e.g., type of protein, biological function, subcellular localization, composition, method of use, mode of inhibition, etc.). For example, an agent can be used to inhibit enzymatic activity of an enzyme, inhibits the level or activity of phosphorylation of a protein kinase, inhibit activation of transcription or a signaling pathway, inhibits leukocyte adhesion to endothelial cells, and to induce physiological results associated with such inhibition (e.g., modulating inflammation). It should be appreciated that modulation also encompasses modulation of expression, activity, and/or function of an expression product of a gene disclosed here, i.e., a gene listed in Tables 1-14.

Any suitable type of agent can be used as one of the agents, test agents, candidate agents, chemotherapeutic agents, cytotoxic agents, diagnostic agents, endothelial cell targeting agents (e.g., venule endothelial cell targeting agents, non-venule endothelial cell targeting agents, skin venule endothelial cell targeting agents, skin non-venule endothelial cell targeting agents, adipose tissue venule endothelial targeting agents, adipose tissue non-venule endothelial cell targeting agents, lymph node venule endothelial cell targeting agents, lymph node non-venule endothelial cell targeting agents, multi-tissue skin and lymph node venule endothelial cell targeting agents, multi-tissue skin and lymph node non-venule endothelial cell targeting agents, multi-tissue adipose tissue and lymph node venule endothelial cell targeting agents, multi-tissue adipose tissue and lymph node non-venule endothelial cell targeting agents, multi-tissue adipose tissue and skin venule endothelial cell targeting agents, multi-tissue adipose tissue and skin non-venule endothelial cell targeting agents), imaging agents, therapeutic agents, anti-inflammatory agents described herein. Exemplary types of agents that can be used for such agents in the methods, compositions, and kits described herein include small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; microcarrier or nanocarrier consisting of one or more polymers, proteins, nucleic acids, lips, or metals; and any combination thereof. Aptides are also exemplary agent that can be used in the methods, compositions, and kits described herein.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

As used herein, an "RNA interference molecule" refers to an agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (e.g. The succession of letters used as abbreviations for bases) that biochemically characterizes a specific nucleic acid. A polynucleotide sequence presented herein is presented in a 5' to 3' direction unless otherwise indicated.

The nucleic acid molecules that modulate the biological pathways or targets described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

Certain methods, compositions, and kits contemplate agents that modulate the venuleness of an endothelial cell or microvessel (e.g., by modulating expression of a gene or combination of genes which are differentially expressed in venule endothelial cells compared to non-venule endothelial cells). Certain methods, compositions, and kits contemplate agents that modulate the venuleness of an endothelial cell or microvessel (e.g., by modulating expression, activity and/or function of an expression product or combination of expression products of genes which are differentially expressed in venule endothelial cells compared to non-venule endothelial cells, and vice versa, e.g., genes listed in Tables 1-14). Venuleness modulating agents can be used to change a venule endothelial cell to a non-venule endothelial cell (e.g., by (a) decreasing expression of at least one gene exhibiting higher expression levels in venule endothelial cells compared to non-venule endothelial cells; (b) increasing expression of at least one gene exhibiting lower expression levels in venule endothelial cells compared to non-venule endothelial cells; (c) increasing expression of at least one gene exhibiting higher expression levels in non-venule endothelial cells compared to venule endothelial cells; or (d) decreasing expression of at least one gene exhibiting lower expression levels in non-venule endothelial cells compared to venule endothelial cells). The agents that change venules to non-venules can do so globally (e.g., by (a) decreasing in venules expression of a gene or combination of genes listed in Table 1; (b) increasing in venules expression of a gene or combination of genes listed in Table 8; (c) increasing in non-venules expression of a gene or combination of genes listed in Table 8; or (d) decreasing in non-venules expression of a gene or combination of genes listed in Table 1). The agents that change venules to non-venules can also do so in specific tissues, such as skin (e.g., by (a) decreasing in skin venules expression of a gene or combination of genes listed in Table 2; (b) increasing in skin venules expression of a gene or combination of genes listed in Table 9; (c) increasing in skin non-venules expression of a gene or combination of genes listed in Table 9; or (d) decreasing in skin non-venules expression of a gene or combination of genes listed in Table 2), adipose tissue (e.g., by (a) decreasing in adipose tissue venules expression of a gene or combination of genes listed in Table 3; (b) increasing in adipose tissue venules expression of a gene or combination of genes listed in Table 10; (c) increasing in adipose tissue non-venules expression of a gene or combination of genes listed in Table 10; or (d) decreasing in adipose tissue non-venules expression of a gene or combination of genes listed in Table 3), and lymph node (e.g., by (a) decreasing in lymph node venules expression of a gene or combination of genes listed in Table 4; (b) increasing in lymph node venules expression of a gene or combination of genes listed in Table 11; (c) increasing in lymph node non-venules expression of a gene or combination of genes listed in Table 11; or (d) decreasing in lymph node non-venules expression of a gene or combination of genes listed in Table 4).

Venuleness modulating agents can also be used to change a non-venule endothelial cell to a venule endothelial cell (e.g., by (a) increasing expression of at least one gene exhibiting higher expression levels in venule endothelial cells compared to non-venule endothelial cells; (b) decreasing expression of at least one gene exhibiting lower expression levels in venule endothelial cells compared to non-venule endothelial cells; (c) decreasing expression of at least one gene exhibiting higher expression levels in non-venule endothelial cells compared to venule endothelial cells; or (d) increasing expression of at least one gene exhibiting lower expression levels in non-venule endothelial cells compared to venule endothelial cells). The agents that change non-venules to venules can do so globally (e.g., by (a) increasing in non-venules expression of a gene or combination of genes listed in Table 1; (b) decreasing in non-venules expression of a gene or combination of genes listed in Table 8; (c) decreasing in venules expression of a gene or combination of genes listed in Table 8; or (d) increasing in venules expression of a gene or combination of genes listed in Table 1). The agents that change non-venules to venules can also do so in specific tissues, such as skin (e.g., by (a) increasing in skin non-venules expression of a gene or combination of genes listed in Table 2; (b) decreasing in skin non-venules expression of a gene or combination of genes listed in Table 9; (c) decreasing in skin venules expression of a gene or combination of genes listed in Table 9; or (d) increasing in skin venules expression of a gene or combination of genes listed in Table 2), adipose tissue (e.g., by (a) increasing in adipose tissue non-venules expression of a gene or combination of genes listed in Table 3; (b) decreasing in adipose tissue non-venules expression of a gene or combination of genes listed in Table 10; (c) decreasing in adipose tissue venules expression of a gene or combination of genes listed in Table 10; or (d) increasing in adipose tissue venules expression of a gene or combination of genes listed in Table 3), and lymph node (e.g., by (a) increasing in lymph node non-venules expression of a gene or combination of genes listed in Table 4; (b) decreasing in lymph node non-venules expression of a gene or combination of genes listed in Table 11; (c) decreasing in lymph node venules expression of a gene or combination of genes listed in Table 11; or (d) increasing in lymph node venules expression of a gene or combination of genes listed in Table 4).

Certain methods, compositions, and kits contemplate agents that modulate leukocyte trafficking and/or inflammation (e.g., by modulating expression of a gene or combination of genes which are differentially expressed in venule endothelial cells compared to non-venule endothelial cells). Certain methods, compositions, and kits contemplate agents that modulate leukocyte trafficking and/or inflammation (e.g., by modulating the expression, and/or activity, and/or function of an expression product of a gene or combination of genes which are differentially expressed in venule endothelial cells compared to non-venule endothelial cells, and vice versa). Leukocyte trafficking and/or inflammation modulating agents can be used to decrease leukocyte trafficking and/or inflammation (e.g., by (a) decreasing in venules expression of at least one gene exhibiting higher expression levels in venule endothelial cells compared to non-venule endothelial cells; or (b) increasing in venules expression of at least one gene exhibiting lower expression levels in venule endothelial cells compared to non-venule endothelial cells; (c) increasing in non-venules expression of at least one gene exhibiting higher expression levels in non-venule endothelial cells compared to venule endothelial cells; or (d) decreasing in non-venules expression of at least one gene exhibiting lower expression levels in non-venule endothelial cells compared to venule endothelial cells). The leukocyte and/or inflammation modulating agents can be used to decrease leukocyte trafficking and/or inflammation (e.g., by modulating the activity and/or function of an expression product of a gene or combination of genes listed in Tables 1-14). The leukocyte trafficking and/or inflammation modulating agents can do so globally (e.g., by (a) decreasing in venules expression of a gene or combination of genes listed in Table 1; (b) increasing in venules expression of a gene or combination of genes listed in Table 8; (c) increasing in non-venules expression of a gene or combination of genes listed in Table 8; or (d) decreasing in non-venules expression of a gene or combination of genes listed in Table 1). The leukocyte and/or inflammation modulating agents can do so globally (e.g., by modulating the activity and/or function of an expression product of a gene or combination of genes listed in Table 1 or Table 8). The leukocyte and/or inflammation modulating agents can also do so in specific tissues, such as skin (e.g., by (a) decreasing in venules expression of a gene or combination of genes listed in Table 2; (b) increasing in venules expression of a gene or combination of genes listed in Table 9; (c) increasing in non-venules expression of a gene or combination of genes listed in Table 9; or (d) decreasing in non-venules expression of a gene or combination of genes listed in Table 2), adipose tissue (e.g., by (a) decreasing in venules expression of a gene or combination of genes listed in Table 3; (b) increasing in venules expression of a gene or combination of genes listed in Table 10; (c) increasing in non-venules expression of a gene or combination of genes listed in Table 10; or (d) decreasing in non-venules expression of a gene or combination of genes listed in Table 3), and lymph node (e.g., by (a) decreasing in venules expression of a gene or combination of genes listed in Table 4; (b) increasing in venules expression of a gene or combination of genes listed in Table 11; (c) increasing in non-venules expression of a gene or combination of genes listed in Table 11; or (d) decreasing in non-venules expression of a gene or combination of genes listed in Table 4). The leukocyte and/or inflammation modulating agents can also do so in specific tissues, such as skin (e.g., by modulating the activity and/or function of an expression product of a gene or combination of genes listed in Table 2 or Table 9), adipose tissue (e.g., by modulating the activity and/or function of an expression product of a gene or combination of genes listed in Table 3 or Table 10), and lymph node (e.g., by modulating the activity and/or function of an expression product of a gene or combination of genes listed in Table 4 or Table 11).

Leukocyte trafficking and/or inflammation modulating agents can also be used to increase leukocyte trafficking and/or inflammation (e.g., by (a) increasing in venules expression of at least one gene exhibiting higher expression levels in venule endothelial cells compared to non-venule endothelial cells; (b) decreasing in venules expression of at least one gene exhibiting lower expression levels in venule endothelial cells compared to non-venule endothelial cells; (c) decreasing in non-venules expression of at least one gene exhibiting higher expression levels in non-venule endothelial cells compared to venule endothelial cells; or (d) increasing in non-venules expression of at least one gene exhibiting lower expression levels in non-venule endothelial cells compared to venule endothelial cells). The leukocyte and/or inflammation modulating agents can also be used to increase leukocyte trafficking and/or inflammation (e.g., by modulating the activity and/or function of an expression product of a gene or combination of genes listed in Tables 1-14).

Leukocyte trafficking and/or inflammation modulating agents can do so globally (e.g., by (a) increasing in venules expression of a gene or combination of genes listed in Table 1; (b) decreasing in venules expression of a gene or combination of genes listed in Table 8; (c) decreasing in non-venules expression of a gene or combination of genes listed in Table 8; or (d) increasing in non-venules expression of a gene or combination of genes listed in Table 1). Leukocyte trafficking and/or inflammation modulating agents can do so globally (e.g., by modulating the activity and/or function of an expression product of a gene or combination of genes listed in Table 1 or Table 8). Leukocyte trafficking and/or inflammation modulating agents can also do so in specific tissues, such as skin (e.g., by (a) increasing in venules expression of a gene or combination of genes listed in Table 2; (b) decreasing in venules expression of a gene or combination of genes listed in Table 9; (c) decreasing in non-venules expression of a gene or combination of genes listed in Table 9; or (d) increasing in non-venules expression of a gene or combination of genes listed in Table 2), adipose tissue (e.g., by (a) increasing in venules expression of a gene or combination of genes listed in Table 3; (b) decreasing in venules expression of a gene or combination of genes listed in Table 10; (c) decreasing in non-venules expression of a gene or combination of genes listed in Table 10; or (d) increasing in non-venules expression of a gene or combination of genes listed in Table 3), and lymph node (e.g., by (a) increasing in venules expression of a gene or combination of genes listed in Table 4; (b) decreasing in venules expression of a gene or combination of genes listed in Table 11; (c) decreasing in non-venules expression of a gene or combination of genes listed in Table 11; or (d) increasing in non-venules expression of a gene or combination of genes listed in Table 4). The leukocyte and/or inflammation modulating agents can do so in specific tissues, such as skin (e.g., by modulating the activity and/or function of an expression product of a gene or combination of genes listed in Table 2 or Table 9), adipose tissue (e.g., by modulating the activity and/or function of an expression product of a gene or combination of genes listed in Table 3 or Table 10), and lymph node (e.g., by modulating the activity and/or function of an expression product of a gene or combination of genes listed in Table 4 or Table 11).

Certain methods, compositions, and kits contemplate agents that target endothelial cells (e.g., endothelial cell targeting agents) by recognizing, binding to, or otherwise interacting with endothelial cell surface markers (e.g., proteins encoded by genes that are differentially expressed in venule endothelial cells compared to non-venule endothelial cells). In the context of the In some embodiments, agents that target endothelial cells are generally referred to as "endothelial cell targeting agents."

In some contexts, an endothelial cell targeting agent specifically targets all venules and is referred to as a "venule endothelial cell targeting agent." Venule endothelial cell targeting agents recognize, bind to, or otherwise interact with proteins expressed on the surface of venule endothelial cells referred to herein as "venule endothelial cell surface markers." Exemplary venule endothelial cell targeting agents can recognize, bind to, or otherwise interact with a venule endothelial cell surface marker including, but not limited to, Sele, Selp, Il6st, Plxnb2, Lepr, Bst1, and Icam1. In some embodiments, exemplary venule endothelial cell targeting agents can recognize, bind to, or otherwise interact with a venule endothelial cell surface marker including, but not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1. It should be appreciated that because Darc is expressed on red blood cells, Darc is not a suitable venule endothelial cell surface marker for which a venule endothelial cell targeting agent can be employed to selectively target venule endothelial cells. In some embodiments, the venule endothelial cell targeting agent does not recognize, bind to, or otherwise interact with venule endothelial cell surface marker Sele. In some embodiments, the venule endothelial cell surface marker is not Sele. In some embodiments, the venule endothelial cell targeting agent does not recognize, bind to, or otherwise interact with venule endothelial cell surface marker Selp. In some embodiments, the venule endothelial cell surface marker is not Selp.

In some contexts, an endothelial cell targeting agent specifically targets all non-venules and is referred to herein as a "non-venule endothelial cell targeting agent." Non-venule endothelial cell targeting agents recognize, bind to, or otherwise interact with proteins expressed on the surface of non-venule endothelial cells referred to herein as "non-venule endothelial cell surface markers." Exemplary non-venule endothelial cell targeting agents can recognize, bind to, or otherwise interact with a non-venule endothelial cell surface marker including, but not limited to, Flt4, Jup, Lgals3bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, and Itm2a. In some embodiments, exemplary non-venule endothelial cell targeting agents can recognize, bind to, or otherwise interact with a non-venule endothelial cell surface marker including, but not limited to, Cxcr4, Unc5b, Flt4, Ednrb, Notch4, Prnd, Gja5, Gja4, Alpl, Kcna5, P2ry2, Efnb2, and Itm2a.

In some contexts, an endothelial cell targeting agent specifically targets all skin venules and is referred to herein as a "skin venule endothelial cell targeting agent." Skin venule endothelial cell targeting agents recognize, bind to, or otherwise interact with proteins expressed on the surface of skin venule endothelial cells referred to herein as "skin venule endothelial cell surface markers." Exemplary skin venule endothelial cell targeting agents can recognize, bind to, or otherwise interact with a skin venule endothelial cell surface marker including, but not limited to, Nrp2, Gpr1, C630004H02Rik, Fndc1, 2310046K01Rik, Insr, and Slco2a1. Exemplary skin venule endothelial cell targeting agents can recognize, bind to, or otherwise interact with a skin venule endothelial cell surface marker including, but not limited to, Nrp2, Htr2b, Mr1, Lifr, Anxa1, Lphn2, Vamp5, Olr1, Eps8, Slco2b1, and Slco2a1.

In some contexts, an endothelial cell targeting agent specifically targets all skin non-venules and is referred to herein as a "skin non-venule endothelial cell targeting agent." Skin non-venule endothelial cell targeting agents recognize, bind to, or otherwise interact with proteins expressed on the surface of skin non-venule endothelial cells referred to herein as "skin non-venule endothelial cell surface markers." Exemplary skin non-venule endothelial cell targeting agents can recognize, bind to, or otherwise interact with a skin non-venule endothelial cell surface marker including, but not limited to, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, exemplary skin non-venule endothelial cell targeting agents can recognize, bind to, or otherwise interact with a skin non-venule endothelial cell surface marker including, but not limited to, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9. In some embodiments, the skin non-venule endothelial cell targeting agent does not recognize, bind to, or otherwise interact with skin non-venule endothelial cell surface marker Sell. In some embodiments, the skin non-venule endothelial cell targeting agent does not recognize, bind to, or otherwise interact with skin non-venule endothelial cell surface marker Siglech. In some embodiments, the skin non-venule endothelial cell targeting agent does not recognize, bind to, or otherwise interact with skin non-venule endothelial cell surface marker Cd44.

In some contexts, an endothelial cell targeting agent specifically targets all adipose tissue venules and is referred to as an "adipose tissue venule endothelial cell targeting agent." Adipose tissue venule endothelial cell targeting agents recognize, bind to, or otherwise interact with proteins expressed on the surface of adipose tissue venule endothelial cells referred to herein as "adipose tissue venule endothelial cell surface markers." Exemplary adipose tissue venule endothelial cell targeting agents can recognize, bind to, or otherwise interact with an adipose tissue venule endothelial cell surface marker including, but not limited to, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Exemplary adipose tissue venule endothelial cell targeting agents can recognize, bind to, or otherwise interact with an adipose tissue venule endothelial cell surface marker including, but not limited to, Tnfrsf11a, Mpz, Dnm3os, Icosl, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some contexts, an endothelial cell targeting agent specifically targets all adipose tissue non-venules and is referred to herein as an "adipose tissue non-venule endothelial cell targeting agent." Adipose tissue non-venule endothelial cell targeting agents recognize, bind to, or otherwise interact with proteins expressed on the surface of adipose tissue non-venule endothelial cells referred to herein as "adipose tissue non-venule endothelial cell surface markers." Exemplary adipose tissue non-venule endothelial cell targeting agents can recognize, bind to, or otherwise interact with an adipose tissue non-venule endothelial cell surface marker including, but not limited to, Adora2a, H2-Ab1, Hspg2, Gpr81, Kcna5, Jam3, and Gpc4. Exemplary adipose tissue non-venule endothelial cell targeting agents can recognize, bind to, or otherwise interact with an adipose tissue non-venule endothelial cell surface marker including, but not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some contexts, an endothelial cell targeting agent specifically targets all lymph node venules and is referred to as "lymph node venule endothelial cell targeting agent." Lymph node venule endothelial cell targeting agents recognize, bind to, or otherwise interact with proteins expressed on the surface of lymph node venule endothelial cells referred to herein as "lymph node venule endothelial cell surface markers." Exemplary lymph node venule endothelial cell targeting agents can recognize, bind to, or otherwise interact with a lymph node venule endothelial cell surface marker including, but not limited to, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. Exemplary lymph node venule endothelial cell targeting agents can recognize, bind to, or otherwise interact with a lymph node venule endothelial cell surface marker including, but not limited to, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some contexts, an endothelial cell targeting agent specifically targets all lymph node non-venules and is referred to herein as a "lymph node non-venule endothelial cell targeting agent." Lymph node non-venule endothelial cell targeting agents recognize, bind to, or otherwise interact with proteins expressed on the surface of lymph node non-venule endothelial cells referred to herein as "lymph node non-venule endothelial cell surface markers." Exemplary lymph node non-venule endothelial cell targeting agents can recognize, bind to, or otherwise interact with a lymph node non-venule endothelial cell surface marker including, but not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Exemplary lymph node non-venule endothelial cell targeting agents can recognize, bind to, or otherwise interact with a lymph node non-venule endothelial cell surface marker including, but not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik. In some embodiments, the lymph node non-venule endothelial cell targeting agent does not recognize, bind to, or otherwise interact with lymph node non-venule endothelial cell surface marker Pmp22.

In some contexts, an endothelial cell targeting agent specifically targets all skin and lymph node venules and is referred to as "multi-tissue skin and lymph node venule endothelial cell targeting agent." Multi-tissue skin and lymph node venule endothelial cell targeting agents recognize, bind to, or otherwise interact with proteins expressed on the surface of skin and lymph node venule endothelial cells referred to herein as "multi-tissue skin and lymph node venule endothelial cell surface markers." Exemplary multi-tissue skin and lymph node venule endothelial cell targeting agents can recognize, bind to, or otherwise interact with a multi-tissue skin and lymph node venule endothelial cell surface marker including, but not limited to, Gpr182 and Slco2b1. In some embodiments, the multi-tissue skin and lymph node venule endothelial cell targeting agents can recognize, bind to, or otherwise interact with a multi-tissue skin and lymph node venule endothelial cell surface marker Gpr182.

In some contexts, an endothelial cell targeting agent specifically targets all skin and lymph node non-venules and is referred to herein as a "multi-tissue skin and lymph node non-venule endothelial cell targeting agent." Multi-tissue skin and lymph node non-venule endothelial cell targeting agents recognize, bind to, or otherwise interact with proteins expressed on the surface of skin and lymph node non-venule endothelial cells referred to herein as "multi-tissue skin and lymph node non-venule endothelial cell surface markers." Exemplary multi-tissue skin and lymph node non-venule endothelial cell targeting agents can recognize, bind to, or otherwise interact with a multi-tissue skin and lymph node non-venule endothelial cell surface marker including, but not limited to, Tns1, Cxcr4, Atp1b1, Car4, Cd7, Itga1, Gja5, Laptm5, Aqp7, Gja4, Mlec, P2ry2, and Cd97. Exemplary multi-tissue skin and lymph node non-venule endothelial cell targeting agents can recognize, bind to, or otherwise interact with a multi-tissue skin and lymph node non-venule endothelial cell surface marker including, but not limited to, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, and Gpc4.

In some contexts, an endothelial cell targeting agent specifically targets all adipose tissue and lymph node venules and is referred to as "multi-tissue adipose tissue and lymph node venule endothelial cell targeting agent." Multi-tissue adipose tissue and lymph node venule endothelial cell targeting agents recognize, bind to, or otherwise interact with proteins expressed on the surface of adipose tissue and lymph node venule endothelial cells referred to herein as "multi-tissue adipose tissue and lymph node venule endothelial cell surface markers." Exemplary multi-tissue adipose tissue and lymph node venule endothelial cell targeting agents can recognize, bind to, or otherwise interact with a multi-tissue adipose tissue and lymph node venule endothelial cell surface marker including, but not limited to, Cd63, Sirpa, Slc2a1, Vmn1r100, Vmn1r148, Vmn1r132, and Vmn1r125. Exemplary multi-tissue adipose tissue and lymph node venule endothelial cell targeting agents can recognize, bind to, or otherwise interact with a multi-tissue adipose tissue and lymph node venule endothelial cell surface marker including, but not limited to, H60b, Ppap2c, Celsr1, Glycam1, Slc37a1, Cd59a, Slc2a1, Tnfrsf9, Tes, Pglyrp1, Il27ra, and Eda2r.

In some contexts, an endothelial cell targeting agent specifically targets all adipose tissue and lymph node non-venules and is referred to as a "multi-tissue adipose tissue and lymph node non-venule endothelial cell targeting agent." Multi-tissue adipose tissue and lymph node non-venule endothelial cell targeting agents recognize, bind to, or otherwise interact with proteins expressed on the surface of adipose tissue and lymph node non-venule endothelial cells referred to herein as "multi-tissue adipose tissue and lymph node non-venule endothelial cell surface markers." Exemplary multi-tissue adipose tissue and lymph node non-venule endothelial cell targeting agents can recognize, bind to, or otherwise interact with a multi-tissue adipose tissue and lymph node non-venule endothelial cell surface marker including, but not limited to, Unc5b, Lpar6, Sema6d, Ppap2b, and Lpar4. Exemplary multi-tissue adipose tissue and lymph node non-venule endothelial cell targeting agents can recognize, bind to, or otherwise interact with a multi-tissue adipose tissue and lymph node non-venule endothelial cell surface marker including, but not limited to, Ramp3, Olfr1396, Slc1a1, Cldn15, and Cd109.

In some contexts, an endothelial cell targeting agent specifically targets all adipose tissue and skin venules and is referred to as "multi-tissue adipose tissue and skin venule endothelial cell targeting agent." Multi-tissue adipose tissue and skin venule endothelial cell targeting agents recognize, bind to, or otherwise interact with proteins expressed on the surface of adipose tissue and skin venule endothelial cells referred to herein as "multi-tissue adipose tissue and skin venule endothelial cell surface markers." Exemplary multi-tissue adipose tissue and skin venule endothelial cell targeting agents can recognize, bind to, or otherwise interact with a multi-tissue adipose tissue and skin venule endothelial cell surface marker including, but not limited to, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Exemplary multi-tissue adipose tissue and skin venule endothelial cell targeting agents can recognize, bind to, or otherwise interact with a multi-tissue adipose tissue and skin venule endothelial cell surface marker including, but not limited to, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some contexts, an endothelial cell targeting agent specifically targets all adipose tissue and skin non-venules and is referred to herein as a "multi-tissue adipose tissue and skin non-venule endothelial cell targeting agent." Multi-tissue adipose tissue and skin non-venule endothelial cell targeting agents recognize, bind to, or otherwise interact with proteins expressed on the surface of adipose tissue and skin non-venule endothelial cells referred to herein as "multi-tissue adipose tissue and skin non-venule endothelial cell surface markers." Exemplary multi-tissue adipose tissue and skin non-venule endothelial cell targeting agents can recognize, bind to, or otherwise interact with a multi-tissue adipose tissue and skin non-venule endothelial cell surface marker including, but not limited to, Ly86, H2-Aa, and Cd74. Exemplary multi-tissue adipose tissue and skin non-venule endothelial cell targeting agents can recognize, bind to, or otherwise interact with a multi-tissue adipose tissue and skin non-venule endothelial cell surface marker including, but not limited to, Sell, Cd79b, Ly86, Chrm3, Ptger4, and Sema7a.

It should be appreciated that the disclosure contemplates employing any agent described herein in combination with any other agent which would be desirable for the skilled artisan to combine. By way of illustration, and not of limitation, any of the endothelial cell targeting agents described herein can be used to target any of the agents described herein (e.g., venuleness modulating agents, leukocyte trafficking modulating agents, inflammation modulating agents, anti-inflammatory agents, diagnostic agents, imaging agents, therapeutic agents, cytotoxic agents, chemotherapeutic agents, etc.) specifically to endothelial cells (e.g., endothelial cells lining a microvessel in an inflamed tissue). In such contexts, the endothelial cell targeting agent can be coupled to the agent to be targeted to the endothelial cell targeting agent. The endothelial cell targeting agent can be coupled directly to the agent. Alternatively, the endothelial cell targeting agent can be coupled to the agent via a linker Any suitable linker can be used.

It may also be desirable to couple the endothelial cell targeting agent to a detectable report (e.g., a fluorescent reagent, e.g., GFP). Alternatively, the agent can be coupled to a detectable reporter. In some instances, a detectable reporter can be coupled to the endothelial cell targeting agent and the agent. Any technique available to the skilled artisan can be used to couple the endothelial cell targeting agent to the agent to be targeted. It should be appreciated, however, that in some contexts, the endothelial cell targeting agent itself may exhibit a desired biological effect (e.g., by recognizing, binding to, or otherwise interacting with the endothelial cell surface marker in a way that interferes with leukocyte interactions with the endothelial cell expressing the endothelial cell surface marker).

Generally, an agent described herein can be used in combination with a therapeutic agent (e.g., a pharmaceutically active agent, e.g., a drug approved by a regulatory agency). The therapeutic agent may act synergistically with the agent described herein, or they may independently exert their intended effects. The disclosure contemplates any therapeutic agent which a skilled artisan would use in connection with a method, composition, or kit described herein. Those skilled in the art will also appreciate that that the endothelial cell targeting agents described herein can be used to target a therapeutic agent to an endothelial cell, a microvessel or a tissue. In some contexts, it may be desirable to employ a cytotoxic agent in combination with an agent described herein (e.g., to treat, prevent, or ameliorate a symptom of, a disorder or disease characterized by lymphadenitis (e.g., cancer or infection). Exemplary cytotoxic agents include but are not limited to taxol; a nitrogen mustard selected from the group consisting of mechlorethamine, cyclophosphamide, melphalan, uracil mustard and chlorambucil; thiotepa; busulfan; a nitrosourea selected from the group consisting of carmustine, lomustine, semustine and streptozocin; dacarbazine; methotrexate; fluorouracil, cytarabine, azaribine; a purine analogs selected from the group consisting of mercaptopurine and thioguanine; a vinca alkaloids selected from the group consisting of vinblastine and vincristine; an antibiotic selected from the group consisting of dactinomycin, daunorubicin, doxorubicin, bleomycin, mithramycin and mitomycin; L-asparaginase; cisplatin; hydroxyurea; procarbazine; anti-virals; vaccines; and photodynamic dyes. In some contexts, it may be desirable to employ a chemotherapeutic agent in combination with an agent described herein (e.g., to treat, prevent, or ameliorate a symptom of, a disorder or disease characterized by lymphadenitis (e.g., cancer). Exemplary chemotherapeutic agents include, but are not limited to, vinblastine, doxorubicin, bleomycin, methotrexate, 5-fluorouracil, 6-thioguanine, cytarabine, cyclophosphamide and cisplatinum. In some contexts, it may be desirable to employ an anti-inflammatory agent in combination with an agent described herein (e.g., to treat, prevent, or ameliorate a symptom of, a disorder involving leukocyte trafficking, e.g., inflammatory disease). Exemplary anti-inflammatory agents include, but are not limited to effective amounts of non-steroidal anti-inflammatory drugs (NSAIDs), including but not limited to: diclofenac potassium, diclofenac sodium, etodolac, indomethicin, ketorolac tromethamine, sulindac, tometin sodium, celecoxib, meloxicam, valdecoxib, floctafenine, mefenamic acid, nabumetone, meloxicam, piroxicam, tenoxicam, fenoprofen calcium, flubiprofen, ibuprofen, ketoprofen, naproxen, naproxen sodium, oxaprozin, tiaprofenic acid, acetylsalicylic acid, diflunisal, choline magnesium trisalicylate, choline salicylate, triethanolamine salicylate, COX1 inhibitors, COX2 inhibitors (e.g., Vioxx™, and Celebrex™). A variety of herbs and natural health products may also be used to provide anti-flammatory treatment, including but not limited to: green tea, fish oil, vitamin D, antioxidant vitamins and minerals (e.g., B carotene, vitamin A, vitamin C, vitamin D, vitamin E, co-enzyme Q10, selenium, etc.), resveratrol, turmeric, bromelain, boswellia, feverfew, quercetin, ginger, rosemary, oregano, cayenne, clove, nutmeg, willowbark.

In some contexts, an agent described herein can be administered with an antigen (e.g., to induce an immune response). In some embodiments, an adjuvant can be used in combination with the antigen.

An agent described herein can also be used in combination with an imaging agent. An agent (e.g., an endothelial cell targeting agent described herein) can be attached to imaging agents for imaging and diagnosis of various diseased organs, tissues or cell types. The agent can be labeled or conjugated a fluorophore or radiotracer for use as an imaging agent. Many appropriate imaging agents are known in the art, as are methods for their attachment to agents (e.g., attaching an imaging agent to a proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase)). An agent may also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection. The methods, compositions, and kits described herein can be used alone or in combination with other techniques, to diagnose access and monitor and direct therapy of leukocyte trafficking associated disorders. In some contexts, the imaging agent can be used for detecting and/or monitoring tumors or sites of metastasis in a subject. For example, an agent (e.g., endothelial cell targeting agent) can be administered in vivo and monitored using an appropriate label. Exemplary methods for detecting and/or monitoring an agent labeled with an imaging agent in vivo include Gamma Scintigraphy, Positron Emission Tomography (PET), Single Photon Emission Computer Tomography (SPECT), Magnetic Resonance Imaging (MRI), X-ray, Computer Assisted X-ray Tomography (CT), Near Infrared Spectroscopy, and Ultrasound. These techniques provide information regarding detection of neoplastic involvement, particularly of inaccessible nodes in subjects with malignant diseases. Knowledge on the size of the node and the filling of nodes can also be instructive. For example, agents or compositions targeted to the lymph nodes in detection applications will contain suitable contrast or imaging agents such as ferromagnetic materials such as iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels such as Fluorine-18, or those produced by neutron activation such as Samarium-153.

Imaging agents of use in the present disclosure include radioisotopes and dyes. Any conventional method according to radiolabeling which is suitable for labeling isotopes for in vivo use will be generally suitable for labeling detection agents according to the disclosure. Internal detection procedures include intraoperative, intravascular or endoscopic, including laproscopic, techniques, both surgically invasive and noninvasive.

For example, when detecting a lymph node, a high signal-to-background ratio should to be achieved. Therapy also requires a high absolute accretion of the therapeutic agent in the lymph node, as well as a reasonably long duration of uptake and binding.

Suitable radioisotopes for the methods of the disclosure include: Actinium-225, Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. The most preferred radioisotope for use in the current invention is Technetium-99m. Preferably the radioisotope will emit a particle or ray in the 10-7,000 keV range, more preferably in the 50-1,500 keV range, and most preferably in the 80-250 keV range.

Isotopes preferred for external imaging include: Iodine-123, Iodine-131, Indium-111, Gallium-67, Ruthenium-97, Technetium-99m, Cobalt-57, Cobalt-58, Chromium-51, Iron-59, Selenium-75, Thallium-201, and Ytterbium-169. Technetium-99m is the most preferred radioisotope for external imaging in the disclosure.

Isotopes most preferred for internal detection include: Iodine-125, Iodine-123, Iodine-131, Indium-111, Technetium-99m and Gallium-67. Technetium-99m is the most preferred isotope for internal detection.

In some contexts, an agent described herein can be employed in combination with a diagnostic agent.

Formulations and Administration

For administration to a subject, the inhibitors, modulators, or other agents described herein can be administered orally, parenterally, for example, subcutaneously, intravenously, intramuscularly, intraperitoneally, by intranasal instillation, or by application to mucous membranes, such as, that of the nose, throat, and bronchial tubes. For a comprehensive review on drug delivery strategies, see Ho et al., Curr. Opin. Mol. Ther. (1999), 1:336-3443; Groothuis et al., J. Neuro Virol. (1997), 3:387-400; and January, Drug Delivery Systems: Technologies and Commercial Opportunities, Decision Resources, 1998, content of all which is incorporate herein by reference.

They can be administered alone or with suitable pharmaceutical carriers, and can be in solid or liquid form such as, tablets, capsules, powders, solutions, suspensions, or emulsions.

As used herein, the term "administered" refers to the placement of an agent described herein, into a subject by a method or route which results in at least partial localization of the agent at a desired site. An agent described herein can be administered by any appropriate route which results in effective treatment in the subject, i.e. administration results in delivery to a desired location in the subject where at least a portion of the composition delivered. Exemplary modes of administration include, but are not limited to, injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The agents can be formulated in pharmaceutically acceptable compositions which comprise a therapeutically-effective amount of the agent, formulated together with one or more pharmaceutically acceptable carriers (additives) and/or diluents. The agents can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, agents can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the pharmaceutically acceptable carrier, diluent, or excipient does not comprise any of the above mentioned carriers, diluents, or excipients in their naturally occurring form. In some embodiments, the pharmaceutically acceptable carrier, diluent, or excipient comprise synthetic derivatives of any of the above mentioned carriers, diluents, or excipients which comprise at least one modification (e.g., addition of a methyl group) as compared to their naturally occurring counterpart. Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

"PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The agents can be formulated in a gelatin capsule, in tablet form, dragee, syrup, suspension, topical cream, suppository, injectable solution, or kits for the preparation of syrups, suspension, topical cream, suppository or injectable solution just prior to use. Also, agents can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J. Pharm. Sci. Tech.* 1997 51:166-171. Methods to make invention formulations include the step of bringing into association or contacting an agent with one or more excipients or carriers. In general, the formulations are prepared by uniformly and intimately bringing into association one or more agents with liquid excipients or finely divided solid excipients or both, and then, if appropriate, shaping the product.

The preparative procedure may include the sterilization of the pharmaceutical preparations. The agents may be mixed with auxiliary agents such as lubricants, preservatives, stabilizers, salts for influencing osmotic pressure, etc., which do not react deleteriously with the agents.

Examples of injectable form include solutions, suspensions and emulsions. Injectable forms also include sterile powders for extemporaneous preparation of injectible solutions, suspensions or emulsions. The agents of the disclosure can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatinA suitable carrier is 5% dextrose in saline. Frequently, it is desirable to include additives in the carrier such as buffers and preservatives or other substances to enhance isotonicity and chemical stability.

In some embodiments, agents described herein can be administrated encapsulated within a nanoparticle or microparticle (e.g., a lipid nanoparticle or microparticle). The present disclosure contemplates the use of any suitable nanoparticle or microparticle, as will be appreciated by the skilled artisan. For example, in the context of vascular delivery, a nanoparticle or microparticle of between about 1 µm and about 10 µm can be used. In some embodiments, the microparticle comprises a microparticle that is approved by a regulatory agency (e.g., Food and Drug Administration). In some embodiments, agents described herein can be administered encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., endothelial cells) can also be used as pharmaceutically acceptable carriers. In some embodiments, the agent is administered using polymeric nanoparticles, e.g., nanoparticles constructed from low molecular weight polyamines and lipids (see Dahlman and Barnes et al., "In vivo endothelial siRNA delivery using polymeric nanoparticles with low molecular weight," *Nature Nanotechnology* DOI: 10.1038/NNANO.2014.84 (2014), which is incorporated by reference herein). In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and PRIMOGEL™, and the like.

The agents can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, agents may be incorporated with excipients and used in the form of tablets, capsules, elixirs, suspensions, syrups, and the like. Such compositions and preparations should contain at least 0.1% of agent. The percentage of the agent in these compositions may, of course, be varied and may conveniently be between about 2% to about 60% of the weight of the unit. The amount of agent in such therapeutically useful compositions is such that a suitable dosage will be obtained. Preferred compositions according to the disclosure are prepared so that an oral dosage unit contains between about 100 and 2000 mg of agent.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The agents can also be administered directly to the airways in the form of an aerosol. For administration by inhalation, the agents in solution or suspension can be delivered in the form of an aerosol spray from pressured container or dispenser which contains a suitable propellant, e.g., a gas such as carbon dioxide, or hydrocarbon propellant like propane, butane or isobutene. The agents can also be administrated in a no-pressurized form such as in an atomizer or nebulizer.

The agents can also be administered parenterally. Solutions or suspensions of these agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of agent calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the agents are formulated into ointments, salves, gels, or creams as generally known in the art.

The agents can be administered to a subject in combination with other pharmaceutically active agents. Exemplary pharmaceutically active agents include, but are not limited to, those found in *Harrison's Principles of Internal Medicine,* 13$^{th}$ Edition, Eds. T. R. Harrison et al. McGraw-Hill N.Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference. In some embodiments, the pharmaceutically active agent is selected from the group consisting of butyrates, valproic acid, hydroxyuirae and Riluzole.

The agents and the other pharmaceutically active agent can be administered to the subject in the same pharmaceutical composition or in different pharmaceutical compositions (at the same time or at different times). For example, a venuleness modulating agent and an additional active agent (e.g., anti-inflammatory agent) can be administered to the subject in the same pharmaceutical composition or in different pharmaceutical compositions (at the same time or at different times). As an additional example, an endothelial cell targeting agent coupled to an anti-inflammatory agent and an additional agent described herein can be administered to the subject in the same pharmaceutical composition or in different pharmaceutical compositions (at the same or at different times).

The amount of agent which can be combined with a carrier material to produce a single dosage form will generally be that amount of the agent which produces a therapeutic effect. Generally out of one hundred percent, this amount will range from about 0.1% to 99% of agent, preferably from about 5% to about 70%, most preferably from 10% to about 30%.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

The pharmaceutical compositions can be included in a container, pack, or dispenser together with instructions for administration.

As used herein, the term "therapeutically effective amount" means an amount of the agent which is effective to modulate leukocyte interactions with endothelial cells or to modulate inflammation in a tissue comprising the endothelial cells. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in leukocyte trafficking based disorder (e.g., inflammatory diseases, e.g., autoimmune diseases, etc.).

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, GDF-8 binding assays, and immunological assays.

The dosage may be determined by a physician and adjusted, as necessary, to suit observed effects of the treatment. Generally, the compositions are administered so that the agent is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody agents, one preferred dosage is 0.1 mg/kg of body weight (generally 10 mg/kg to 20 mg/kg). If the antibody is to act in the brain, a dosage of 50 mg/kg to 100 mg/kg is usually appropriate.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

In some aspects, the disclosure provides a method of modulating the venuleness of an endothelial cell, comprising contacting the endothelial cell with an effective amount of an agent that modulates expression and/or activity of Zfp521 or modulates the activity and/or function of an expression product of Zfp521. In some embodiments, modulating venuleness of the endothelial cell comprises changing the endothelial cell from a venule endothelial cell to a non-venule endothelial cell. In some embodiments, changing the endothelial cell from a venule endothelial cell to a non-venule endothelial cell interferes with leukocyte interactions with the endothelial cell. In some embodiments, changing the endothelial cell from a venule endothelial cell to a non-venule endothelial cell interferes with extravasation of leukocytes to the extravascular compartment in the tissue in which the endothelial cell resides. In some embodiments, changing the endothelial cell from a venule endothelial cell to non-venule endothelial cell decreases a local inflammatory response in the tissue in which the endothelial cell resides. In some embodiments, the endothelial cell is selected from the group consisting of a skin endothelial cell, an adipose tissue endothelial cell, and a lymph node endothelial cell. In some embodiments, the endothelial cell is not an adipose tissue endothelial cell. In some embodiments, the agent decreases expression and/or activity of Zfp521 or an expression product of Zfp521. In some embodiments, the agent decreases leukocyte adhesion to the endothelial cell. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes. In some embodiments, the endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the endothelial cell targeting agent comprises an aptide. In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating venuleness of the endothelial cell comprises changing the endothelial cell from a non-venule endothelial cell to a venule endothelial cell. In such embodiments, changing the endothelial cell from a non-venule endothelial cell to a venule endothelial cell enables leukocyte interactions with the endothelial cell. In such embodiments, changing the endothelial cell from a non-venule endothelial cell to a venule endothelial cell enables extravasation of leukocytes to the extravascular compartment in the tissue in which the endothelial cell resides. In such embodiments, changing the endothelial cell from a non-venule endothelial cell to a venule endothelial cell enables a local inflammatory response in the tissue in which the endothelial cell resides. In some embodiments, the agent increases leukocyte adhesion to the endothelial cell.

In some embodiments, the endothelial cell is selected from the group consisting of a skin endothelial cell, an adipose tissue endothelial cell, and a lymph node endothelial cell. In some embodiments, the endothelial cell is not an adipose tissue endothelial cell.

In some embodiments, the agent increases expression and/or activity of Zfp521 or an expression product of Zfp521. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the non-venule endothelial cell targeting agent comprises an aptide.

In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of modulating the venuleness of a microvessel, comprising contacting at least one endothelial cell of a microvessel with an effective amount of an agent that modulates expression and/or activity of Zfp521 or modulates the activity and/or function of an expression product of Zfp521. In some embodiments, modulating the venuleness of the microvessel comprises changing endothelial cells lining the microvessel from venule endothelial cells to non-venule endothelial cells. In some embodiments, changing the endothelial cells from venule endothelial cells to a non-venule endothelial cells interferes with leukocyte interactions with the microvessel. In some embodiments, changing the endothelial cells from venule endothelial cells to non-venule endothelial cells interferes with extravasation of leukocytes to the extravascular compartment in the tissue in which the microvessel resides. In some embodiments, changing the endothelial cells from venule endothelial cells to non-venule endothelial cells decreases a local inflammatory response in the tissue in which the microvessel resides. In some embodiments, changing the endothelial cells from venule endothelial cells to non-venule endothelial cells inhibits leukocyte adhesion to the microvessel. In some embodiments, the endothelial cells are selected from the group consisting of skin endothelial cells, adipose tissue endothelial cells, and lymph node endothelial cells. In some embodiments, the endothelial cells are not adipose tissue endothelial cells.

In some embodiments, the agent decreases expression and/or activity of Zfp521 or an expression product of Zfp521. In such embodiments, the agent decreases leukocyte adhesion to the endothelial cells lining the microvessel. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent comprises an aptide.

In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating the venuleness of the microvessel comprises changing endothelial cells lining the microvessel from non-venule endothelial cells to venule endothelial cells. In such embodiments, changing the endothelial cells from non-venule endothelial cells to venule endothelial cells enables leukocyte interactions with the microvessel. In such embodiments, changing the endothelial cells from non-venule endothelial cells to venule endothelial cells enables extravasation of leukocytes to the extravascular compartment in the tissue in which the microvessel resides. In such embodiments, changing the endothelial cells from non-venule endothelial cells to venule endothelial cells enables a local inflammatory response in the tissue in which the microvessel resides. In such embodiments, changing the endothelial cells from non-venule endothelial cells to venule endothelial cells inhibits leukocyte adhesion to the microvessel. In some embodiments, the endothelial cells are selected from the group consisting of skin endothelial cells, adipose tissue endothelial cells, and lymph node endothelial cells. In some embodiments, the endothelial cells are not adipose tissue endothelial cells.

In some embodiments, the agent increases expression and/or activity of Zfp521 or an expression product of Zfp521. In such embodiments, the agent increases leukocyte adhesion to the endothelial cells lining the microvessel.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene. In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of modulating leukocyte trafficking and/or inflammation in a subject in need thereof, comprising: (a) administering to the subject an effective amount of an agent that modulates expression and/or activity of Zfp521 or modulates the activity and/or function of an expression product of Zfp521.

In some embodiments, modulating leukocyte trafficking and/or inflammation comprises decreasing leukocyte trafficking and/or inflammation. In such embodiments, decreasing leukocyte trafficking and/or inflammation comprises one or more of interfering with leukocyte trafficking, interfering with leukocyte adhesion, and interfering with leukocyte extravasation. In some embodiments, inflammation is decreased systemically. In some embodiments, inflammation is decreased in a tissue-specific manner. In some embodiments, inflammation is decreased in a tissue selected from the group consisting of skin, adipose tissue, and lymph nodes. In some embodiments, expression and/or activity of Zfp521 or an expression product of Zfp521 is decreased.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a venule endothelial cell targeting agent that binds to a protein expressed on the surface of the venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the protein is not encoded by the Darc, Sele, Sell, or Selp genes.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent comprises an aptide.

In some embodiments, the agent and/or venule endothelial cell targeting agent are conjugated to each other. In some embodiments, the agent and/or venule endothelial cell targeting agent are conjugated to each other via a linker. In some embodiments, the agent and/or the venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or venule endothelial cell targeting agent are conjugated to each other and encapsulated in a nanoparticle or microparticle.

In some embodiments, modulating leukocyte trafficking and/or inflammation comprises increasing leukocyte trafficking and/or inflammation. In such embodiments, increasing leukocyte trafficking and/or inflammation to be induced comprises one or more of enabling leukocyte trafficking, enabling leukocyte adhesion, and enabling leukocyte extravasation. In some embodiments, inflammation is induced systemically. In some embodiments, inflammation is induced in a tissue-specific manner. In some embodiments, inflammation is induced in a tissue selected from the group consisting of skin, adipose tissue, and lymph nodes.

In some embodiments, expression and/or activity of Zfp521 or an expression product of Zfp521 is increased. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agm, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some embodiments, the protein is not encoded by the Cd44 gene.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the non-venule endothelial cell targeting agent comprises an aptide.

In some embodiments, the agent and/or non-venule endothelial cell targeting agent are conjugated to each other. In some embodiments, the agent and/or non-venule endothelial cell targeting agent are conjugated to each other via a linker. In some embodiments, the agent and/or the non-venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or non-venule endothelial cell targeting agent are conjugated to each other and encapsulated in a nanoparticle or microparticle.

In some aspects, the disclosure provides a method of treating an inflammatory disease in a subject in need thereof, comprising administering to the subject an effective amount of an agent that modulates expression and/or activity of Zfp521 or modulates the activity and/or function of an expression product of Zfp521.

In some aspects, the disclosure provides a method of treating an inflammatory skin disease in a subject in need thereof, comprising administering to the subject an effective amount of an agent that inhibits expression and/or activity of Zfp521 or an expression product of Zfp521 in skin venule endothelial cells. In some embodiments, inhibiting expression and/or activity of Zfp521 or an expression product of Zfp521 decreases a local inflammatory response in the skin. In some embodiments, the agent inhibits leukocyte adhesion to the skin venule endothelial cells. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a skin venule endothelial cell targeting agent that binds to a protein expressed on the surface of skin venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, and Cysltr1, Nrp2, Htr2b, Mr1, Lifr, Anxa1, Lphn2, Vamp5, Olr1, Eps8, Slco2b1, Slco2a1. In some embodiments, the skin venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the skin venule endothelial cell targeting agent comprises an aptide.

In some embodiments, the agent and/or skin venule endothelial cell targeting agent are conjugated to each other. In some embodiments, the agent and/or skin venule endothelial cell targeting agent are conjugated to each other via a linker. In some embodiments, the agent and/or the skin venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or skin venule endothelial cell targeting agent are conjugated to each other and encapsulated in a nanoparticle or microparticle.

In some embodiments, the inflammatory skin disease is selected from the group consisting of acne, dermatitis, eczema, oily skin, rosacea, cutaneus lymphoma and urticaria. In some embodiments, the dermatitis is selected from the group consisting of atopic dermatitis, psoriasis and contact dermatitis. In some embodiments, the venule endothelial cells are selected from a post-capillary venule endothelial cell and a collecting venule post-capillary venule endothelial cell and a collecting venule endothelial cell.

In some aspects, the disclosure provides a method of treating a disease characterized by visceral fat inflammation in a subject in need thereof, comprising administering to the subject an effective amount of an agent that inhibits expression and/or activity of Zfp521 or an expression product of Zfp521 in venule endothelial cells in adipose tissue. In some embodiments, inhibiting expression and/or activity of Zfp521 or an expression product of Zfp521 decreases a local inflammatory response in the adipose tissue. In some embodiments, the agent inhibits leukocyte adhesion to the adipose tissue venule endothelial cell.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to an adipose tissue venule endothelial cell targeting agent that binds to a protein expressed on the surface of adipose tissue venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Il1r1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some embodiments, the adipose tissue venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the adipose tissue venule endothelial cell targeting agent comprises an aptide.

In some embodiments, the agent and/or adipose tissue venule endothelial cell targeting agent are conjugated to each other. In some embodiments, the agent and/or adipose tissue venule endothelial cell targeting agent are conjugated to each other via a linker. In some embodiments, the agent and/or the adipose tissue venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or adipose tissue venule endothelial cell targeting agent are conjugated to each other and encapsulated in a nanoparticle or microparticle.

In some embodiments, the disease is selected from the group consisting of cancer, CVHD, fibrosis, hypertension, lypodystrophy, obesity, metabolic syndrome, and type II diabetes.

In some aspects, the disclosure provides a method of treating a disease characterized by lymphadenitis in a subject in need thereof, comprising administering to the subject an effective amount of an agent that inhibits expression and/or activity of Zfp521 or an expression product of Zfp521 in venule endothelial cells in lymph nodes. In some embodiments, inhibiting the level or activity of the gene decreases a local inflammatory response in the lymph nodes.

In some embodiments, the agent inhibits leukocyte adhesion to the venule endothelial cell. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises an aptide.

In some embodiments, the agent is coupled to a lymph node venule endothelial cell targeting agent that binds to a protein expressed on the surface of lymph node venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the lymph node venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the lymph node venule endothelial cell targeting agent comprises an aptide.

In some embodiments, the agent and/or lymph node venule endothelial cell targeting agent are conjugated to each other. In some embodiments, the agent and/or lymph node venule endothelial cell targeting agent are conjugated to each other via a linker. In some embodiments, the agent and/or the lymph node venule endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or lymph node venule endothelial cell targeting agent are conjugated to each other and encapsulated in a nanoparticle or microparticle.

In some embodiments, the disease is selected from the group consisting of cancer, connective tissue disorders, and infection. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome. In some embodiments, the cancer is selected from the group consisting of leukemias, lymphomas, and metastatic cancer.

In some aspects, the disclosure provides a composition comprising an agent that inhibits expression and/or activity of Zfp521 or an expression product of Zfp521. In some embodiments, the composition includes an endothelial cell targeting agent that binds to a protein expressed on the surface of endothelial cells in microvessels. In some embodiments, the agent and/or endothelial cell targeting agent are selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent and/or endothelial cell targeting agent are conjugated to each other. In some embodiments, the agent and/or endothelial cell targeting agent are conjugated to each other via a linker. In some embodiments, the agent and/or the endothelial cell targeting agent are encapsulated in a nanoparticle or microparticle. In some embodiments, the nanoparticle comprises a polymeric nanoparticle. In some embodiments, the nanoparticle comprises a polymeric nanoparticle constructed from low molecular weight polyamines and lipids. In some embodiments, the agent and/or endothelial cell targeting agent are conjugated to each other and encapsulated in a nanoparticle or microparticle.

In some embodiments, the endothelial cell targeting agent comprises a venule endothelial cell targeting agent that binds to a protein expressed on the surface of venule endothelial cells. In some embodiments, the protein is encoded by a gene selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbpl8, Itga3, Flrt2, Sla, Csf2rb2, Slc2a13, Emp2, Dll1, Entpd1, Ptprj, Lrm4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the endothelial cell targeting agent comprises a non-venule endothelial cell targeting agent that binds to a protein expressed on the surface of non-venule endothelial cells. In some embodiments, the protein is encoded by a gene selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap11, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some aspects, the disclosure relates to the use of an agent that inhibits expression and/or activity of Zfp521 or an expression product of Zfp521 for treating inflammation. In some embodiments, the inflammation is associated with a disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some aspects, the disclosure relates to the use of an agent to alter the function of a microvessel endothelial cell gene product. In some embodiments, the agent modulates leukocyte interactions with the endothelial cell in which the microvessel endothelial cell gene product is expressed. In some embodiments, the agent modulates an inflammatory response. In some embodiments, altering the function of the microvessel endothelial cell gene product modulates leukocyte interactions with the endothelial cell in which the microvessel endothelial cell gene product is expressed. In some embodiments, altering the function of the microvessel endothelial cell gene product modulates inflammation in the microvessel or microvessel endothelial cell gene product is expressed. It should be appreciated that such modulation can be used to increase or decrease leukocyte interactions, depending on the tissue and type of endothelial cell in which the microvessel endothelial cell gene product is expressed. For example, in some embodiments altering the function of a venular endothelial cell gene product decreases leukocyte interactions in the venular endothelial cell and/or modulates inflammation mediated by leukocyte interactions with the venular endothelial cell. In some embodiments, the microvessel endothelial cell gene product is encoded by a gene listed in Table 1, Table 2, Table 3, Table 4, Table 5, Table 6, Table 7, Table 8, Table 9, Table 10, Table 11, Table 12, Table 13, and/or Table 14.

Some Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, kits and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, kits and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this In some embodiments, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1: Identification of Differentially Expressed Genes in Venular Endothelial Cells as Novel Targets for Anti-Inflammatory Introduction Inflammation is a complex biological response to a variety of noxious stimuli. It is absolutely critical to the pathogenesis of inflammation that venular endothelial cells (ECs) possess the ability to support tissue-specific multi-step adhesion cascades to recruit blood-borne leukocytes to the extravascular compartment[3]. Indeed, leukocyte migration is thought to be essential for autoimmune and inflammatory diseases that can target virtually any tissue, such as psoriasis in the skin, inflammatory bowel diseases in the small intestine and colon, multiple sclerosis in the brain and spinal cord, various forms of arthritis in joints and synovium and juvenile diabetes in the pancreas, to name a few[4]. Understanding the molecular mechanisms regulating leukocyte trafficking in health and disease may provide opportunities for the development of novel treatments for immunologically mediated diseases. Numerous intravital microscopy (IVM) studies have shown that leukocyte interactions with microvessels are restricted to postcapillary and collecting venules, whereas capillaries and arterioles usually do not support significant leukocyte adhesion. There is strong evidence indicating that this microvascular specialization is due to segmental EC differentiation and not to hemodynamic differences[2]. The mechanisms that enable venular ECs to recruit leukocytes, but prohibit capillary and arteriolar endothelium to do so are entirely unknown. We hypothesized that the as yet unknown differentiation program(s) that enable(s) leukocyte recruitment exclusively by venular ECs will be reflected at the transcriptome level. Identifying gene products that specify endothelial "venuleness" represent a novel class of attractive targets for anti-inflammatory therapy.

Current anti-inflammatory drugs, such as corticoids, non-steroidal drugs and biologics like anti-TNF or anti-alpha 4 integrin antibodies act systemically and thus affect healthy and damaged tissues alike. Adverse side effects comprise gastrointestinal and renal effects as well as in some cases, an increased susceptibility to infection linked to impaired leukocyte trafficking in healthy tissue. There is no FDA-approved anti-inflammatory drug that targets selectively the endothelium, not to mention tissue-specific vascular beds that are promoting inflammation. The present disclosure outlines a novel strategy to develop and exploit a proprietary discovery platform that will lead to a new generation of anti-inflammatory drugs that specifically target venular endothelium, either globally or exclusively in a selected tissue.

Figures 6A, 6B, 6C:
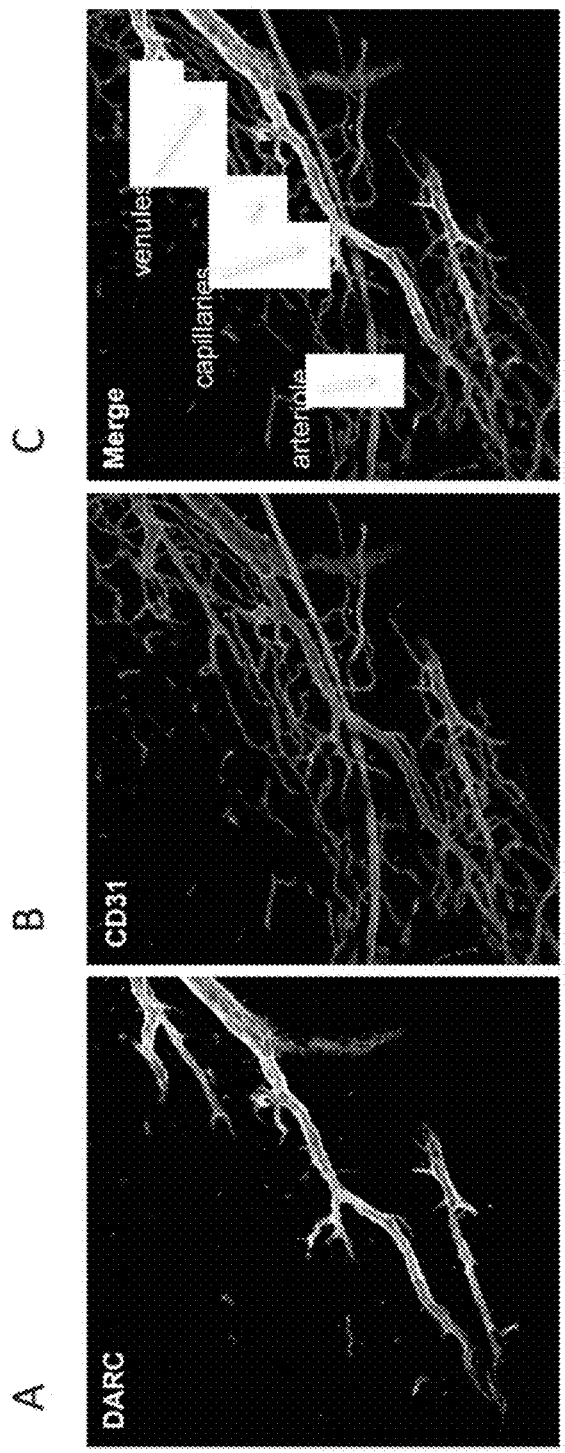
FIGS. 6A-C show micrographs of whole mount staining in mouse omentum.
Figures 7A, 7B, 7C:
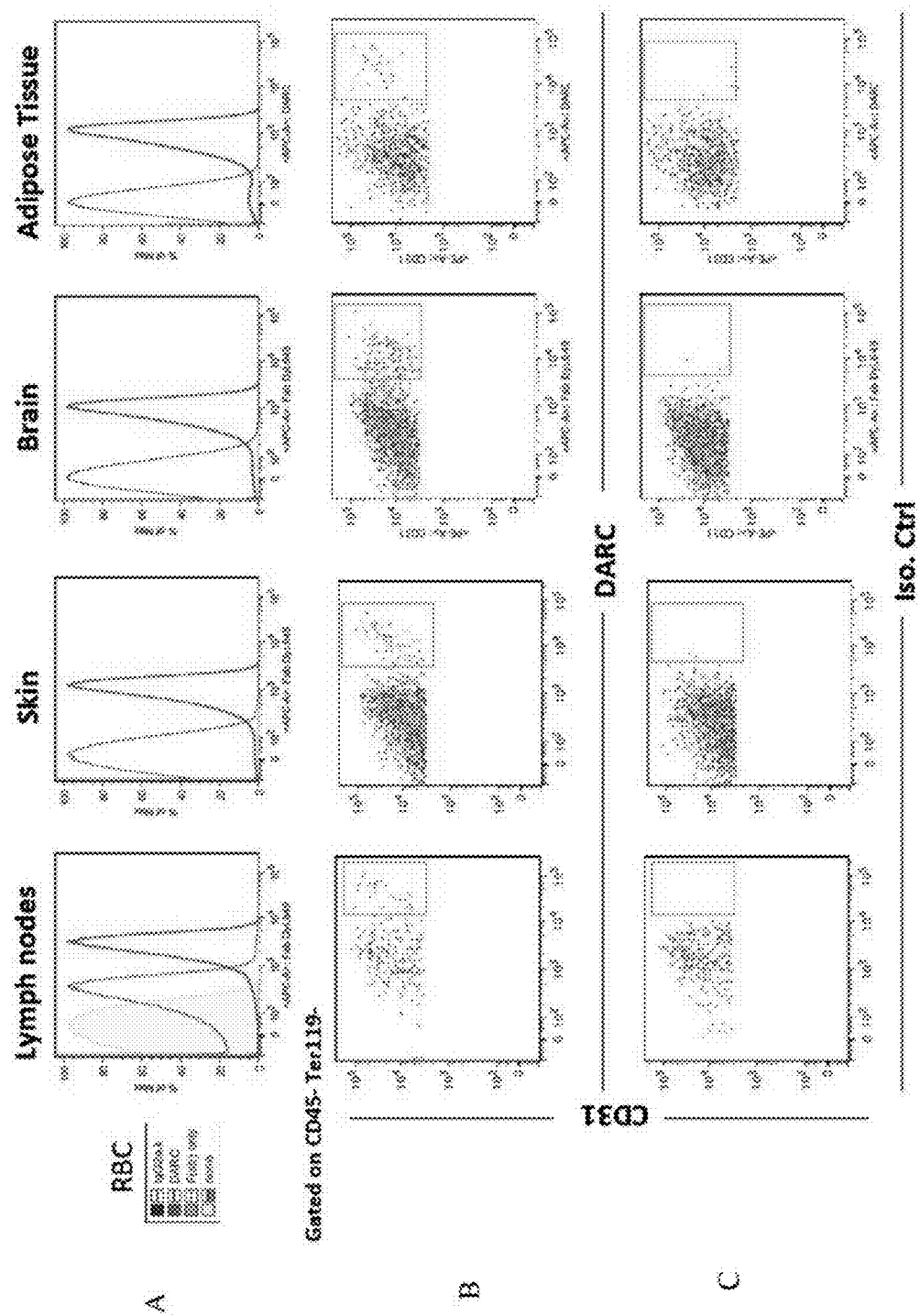
FIGS. 7A-7C illustrate DARC expression on mouse erythrocytes and endothelial cells. FACS analysis of DARC expression (FIG. 7A) on red blood cells from lymph node, skin, brain, adipose tissue. FACS dot plots are gated on Ter119+ population for all tissues displayed. FACS analysis of DARC expression (FIG. 7B) or isotype control (FIG. 7C) on endothelial cells from lymph node, skin, brain, adipose tissue. FACS dot plots are gated on CD45-CD11b-Ter119-gp38-population for all tissues displayed.
Figures 8A, 8B, 8C, 8D, 8E, 8F:
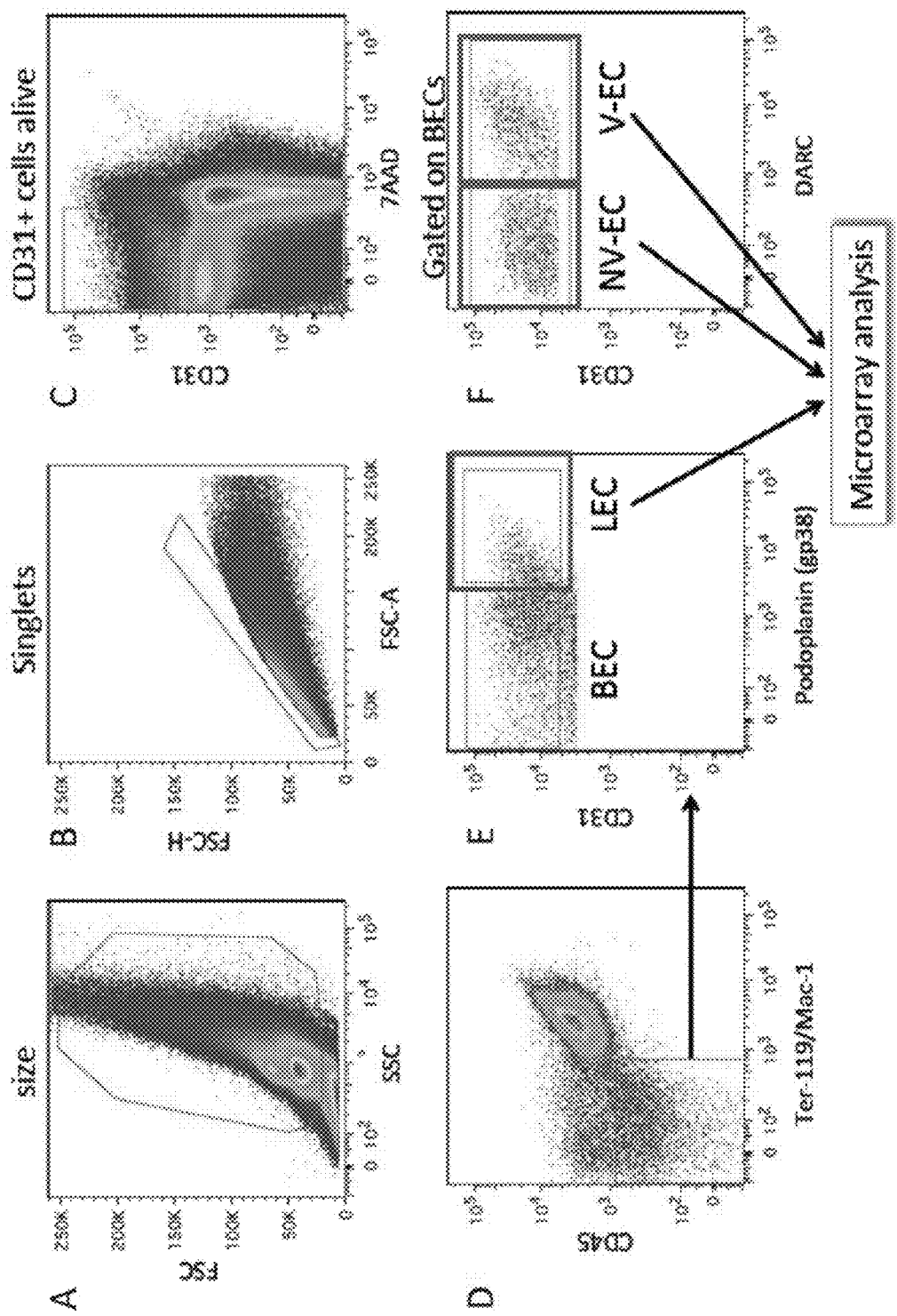
FIGS. 8A-8F show the gating strategy for sorting endothelial cell subsets. Our cell sorting strategy is the following: we gate on large population (size) (FIG. 8A) of singlet (FIG. 8B) and alive (7AAD-) cells (FIG. 8C), we exclude CD45$^+$CD11b$^+$ hematopoietic cells (FIG. 8D) and Ter119$^+$ RBCs and gate on blood ECs (BEC) as gp38$^-$CD31$^+$ and lymphatic ECs (LEC) (FIG. 8E) as gp38$^+$CD31$^+$. BEC are further differentiated into a non-venular (NV-EC) gp38$^-$CD31$^+$DARC$^-$ and a venular gp38$^-$CD31$^+$DARC$^+$ (V-EC) subset (FIG. 8F). Our sorting gates are highlighted in red.
Figures 9A, 9B, 9C:
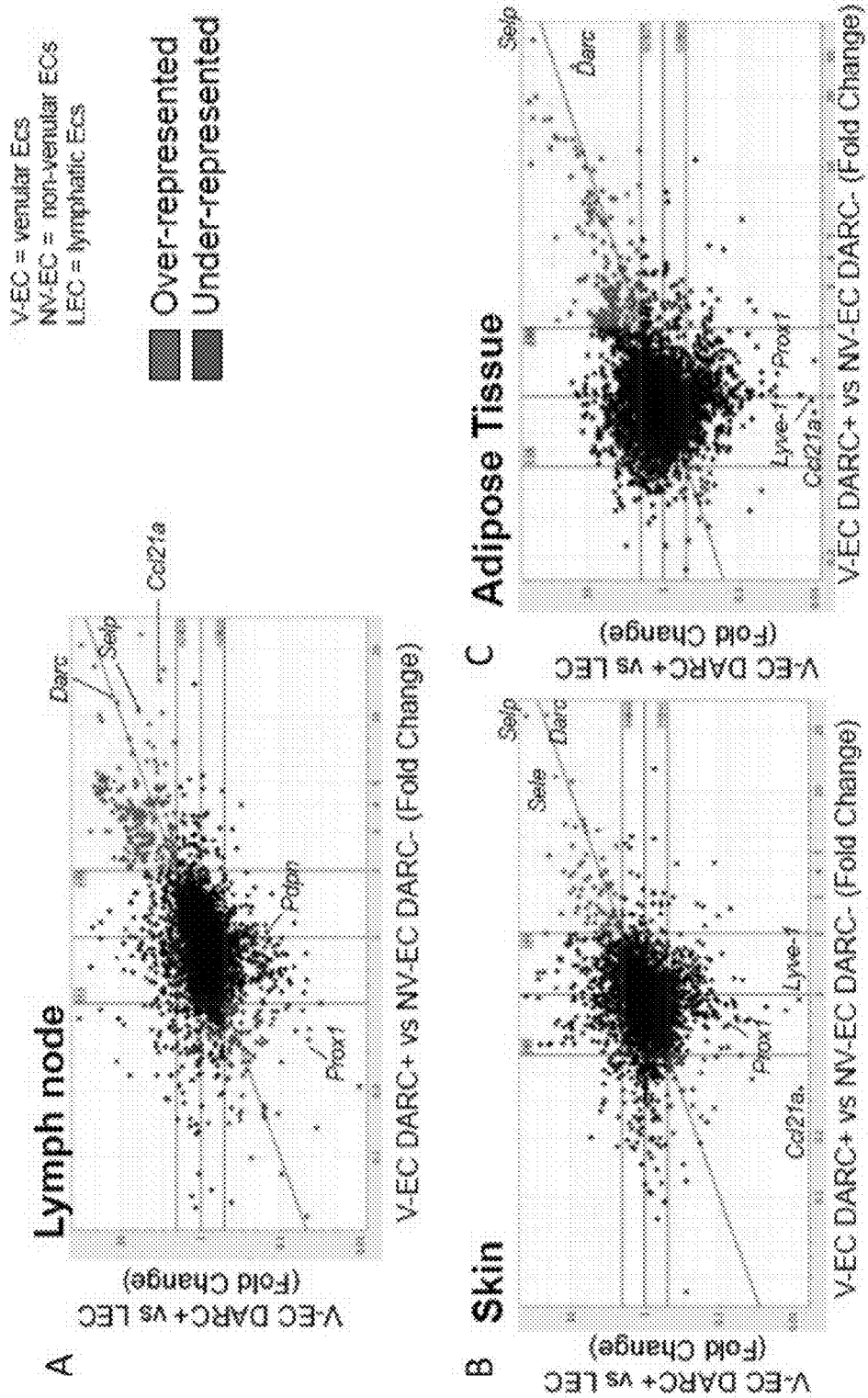
FIGS. 9A-9C show the fold change of DARC+ V-EC vs LEC/Fold Change of DARC+ V-EC vs DARC-NV-EC plots from lymph node (FIG. 9A), skin (FIG. 9B) and Adipose Tissue (FIG. 9C). Fold change/Fold change plot depicting the venular DARC+ (V-ECs) vs non-venular DARC-ECs (NV-ECs) ratio of expression on x-axis and venular DARC+ (V-ECs) vs lymphatic ECs (LECs) ratio of expression on y-axis. Red color indicates genes that are over-represented in V-ECs compared to both NV-ECs and LECs. Blue indicates genes that are under-represented in V-ECs compared to both NV-ECs and LECs. We highlighted genes that are already known to be enriched in V-ECs, such as P- and E-Selectin, von Willebrand factor (Vwf), Darc or LECs specific such as Prox1, Lyve1 and Podoplanin (Pdpn).
Figures 10A, 10B:
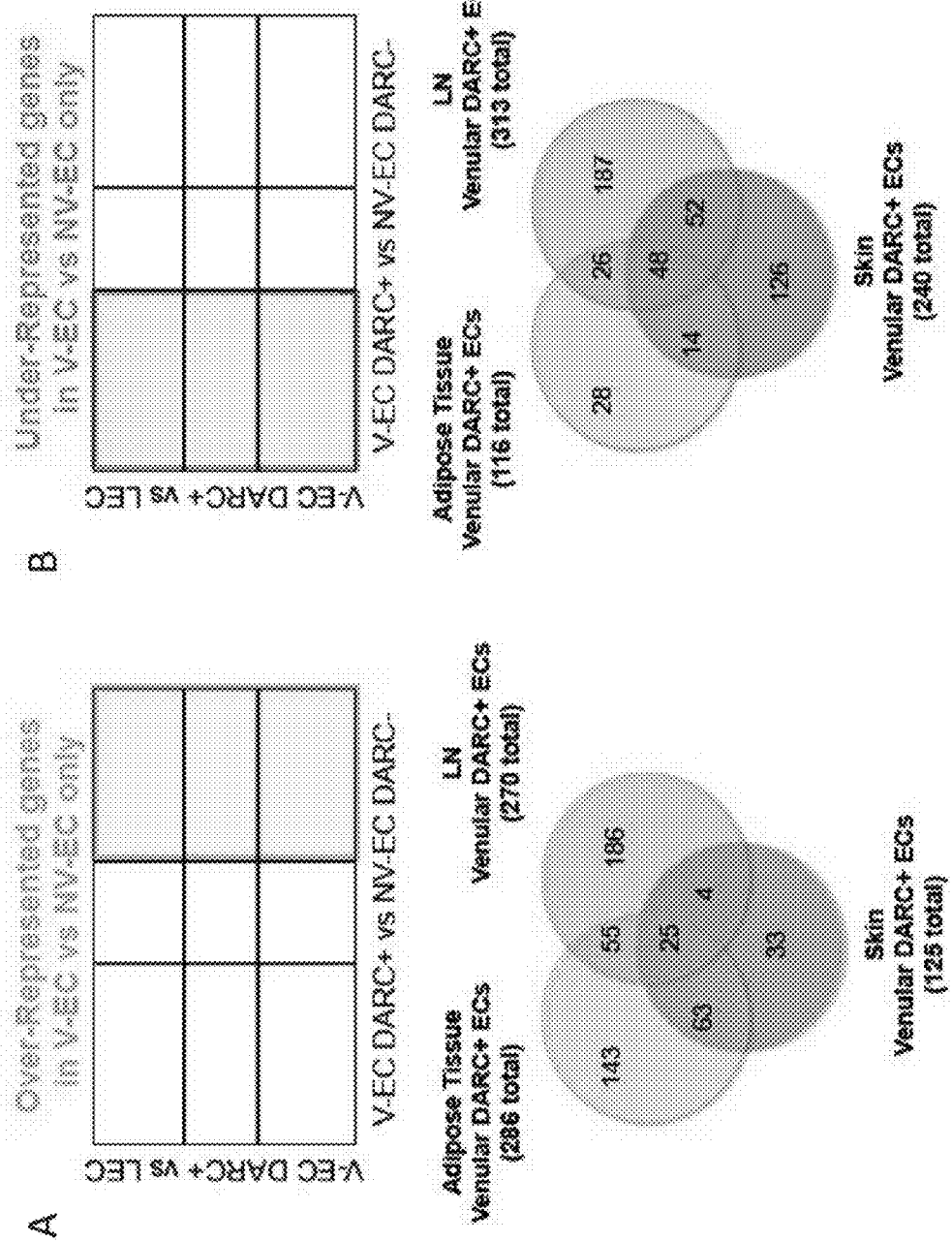
FIGS. 10A-10B are Venn Diagrams showing over-represented (FIG. 10A, left side) and under-represented genes (FIG. 10B, right side) in venular DARC+ ECs from adipose tissue, skin and lymph node.
Figures 11A, 11B:
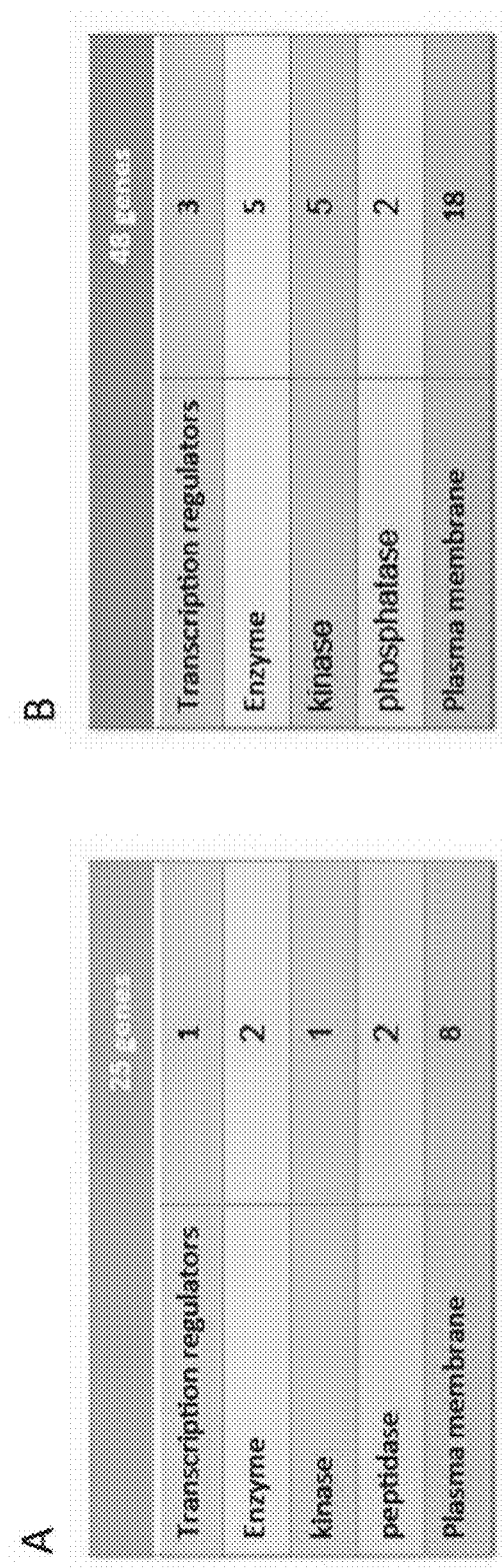
FIGS. 11A-11B are tables listing the purported functions of the 25 genes which are commonly over-represented in V-ECs of skin, adipose tissue, and lymph nodes (FIG. 11A), and the 48 genes which are commonly under-represented in V-ECs of skin, adipose tissue, and lymph nodes (FIG. 11B), as determined by the Venn Diagrams depicted in FIGS. 10A and 10B, respectively.
Figures 12A, 12B:
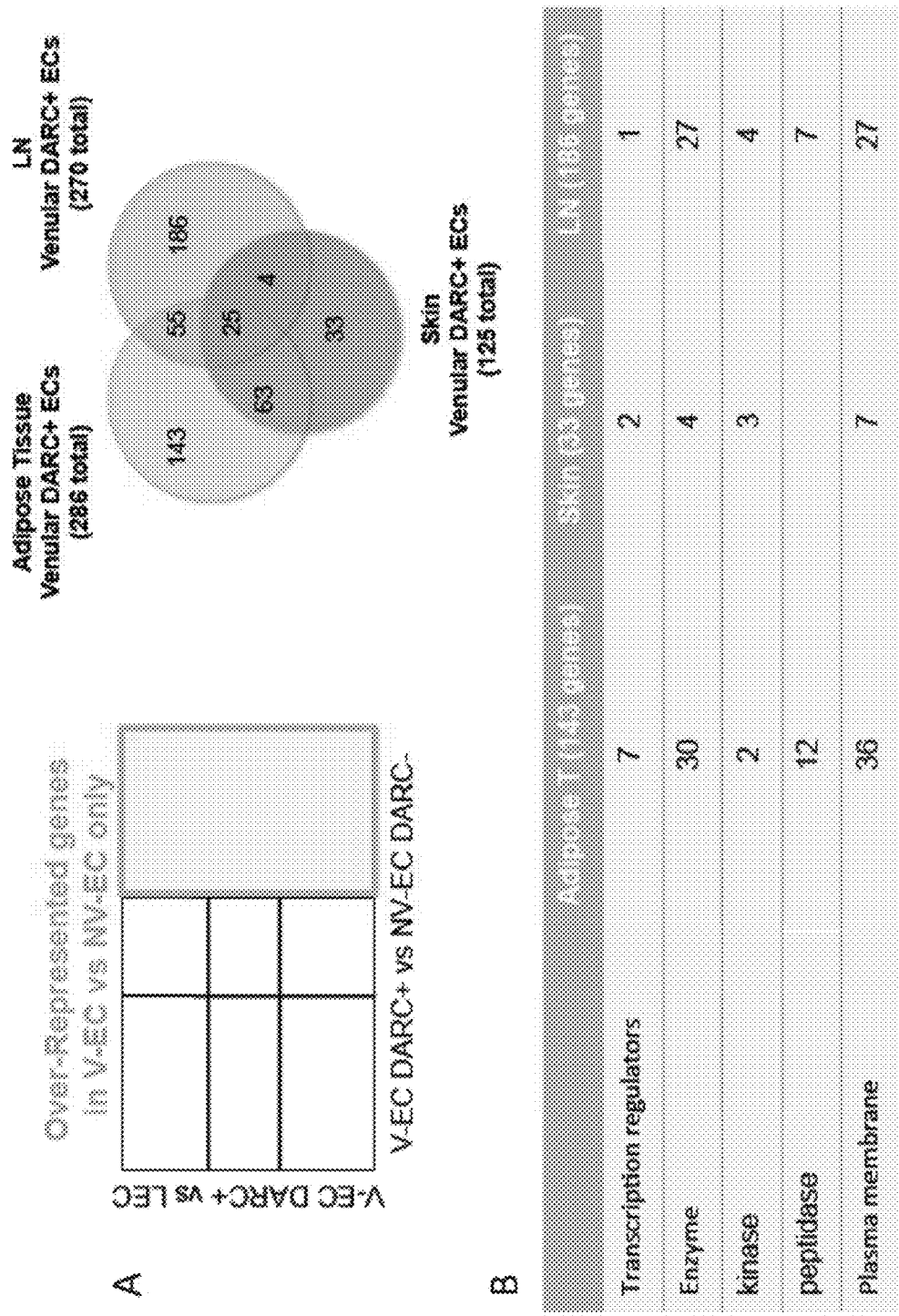
FIGS. 12A-12B show over-represented genes in venular DARC+ ECs from adipose tissue, skin or lymph node.
Figure 13:
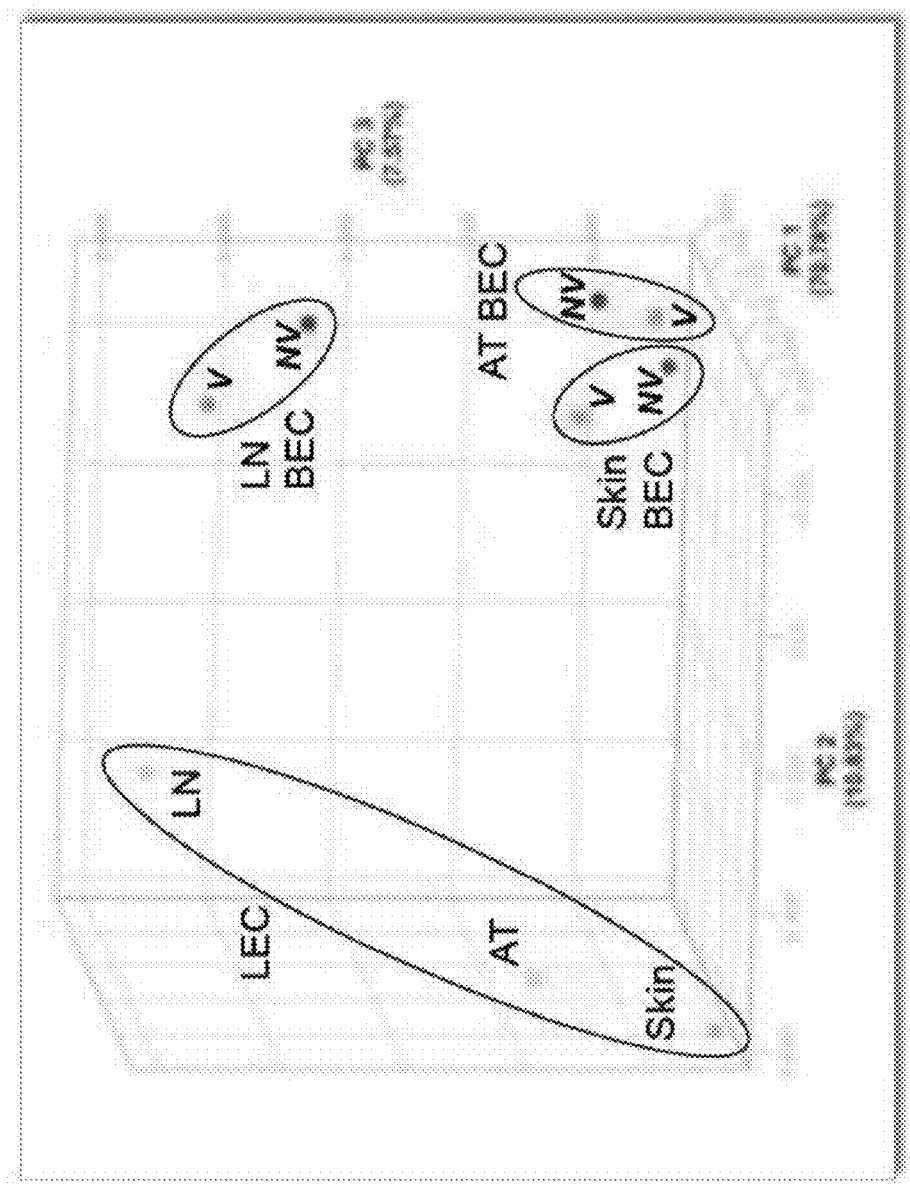
FIG. 13 is a plot of the results of a Principal Component Analysis showing that blood vessel endothelial cells (BEC) are more different from lymphatic endothelial cells (LEC) than from each other.
Figure 14:
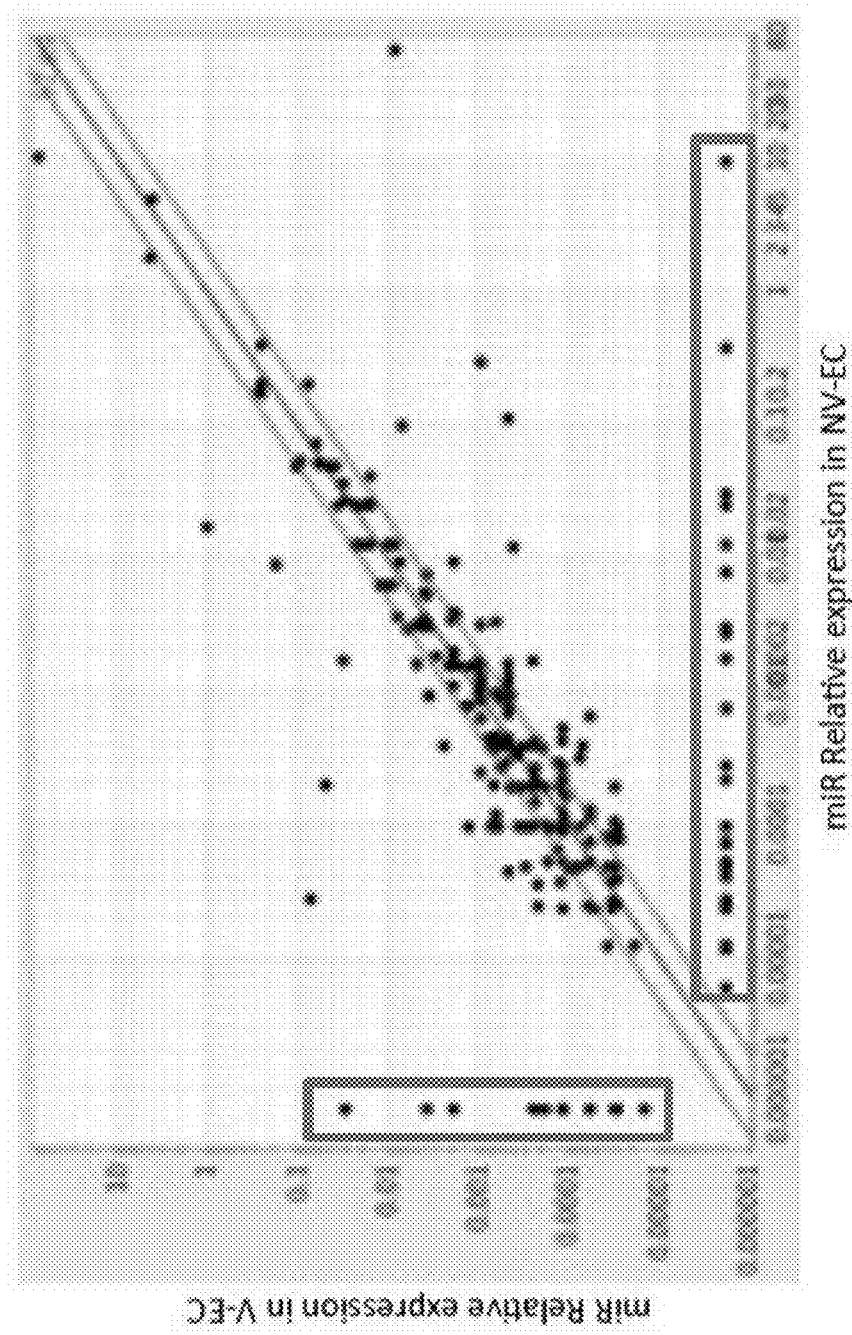
FIG. 14 is graph showing the microRNA profiling of venular and non-venular ECs in lymph nodes. From among the 263 mIRs analyzed, 52 miR are over-represented in V-EC (15 unique to V-EC) and 89 are over-represented in NV-EC (53 are unique to NV-EC).
Figure 15:
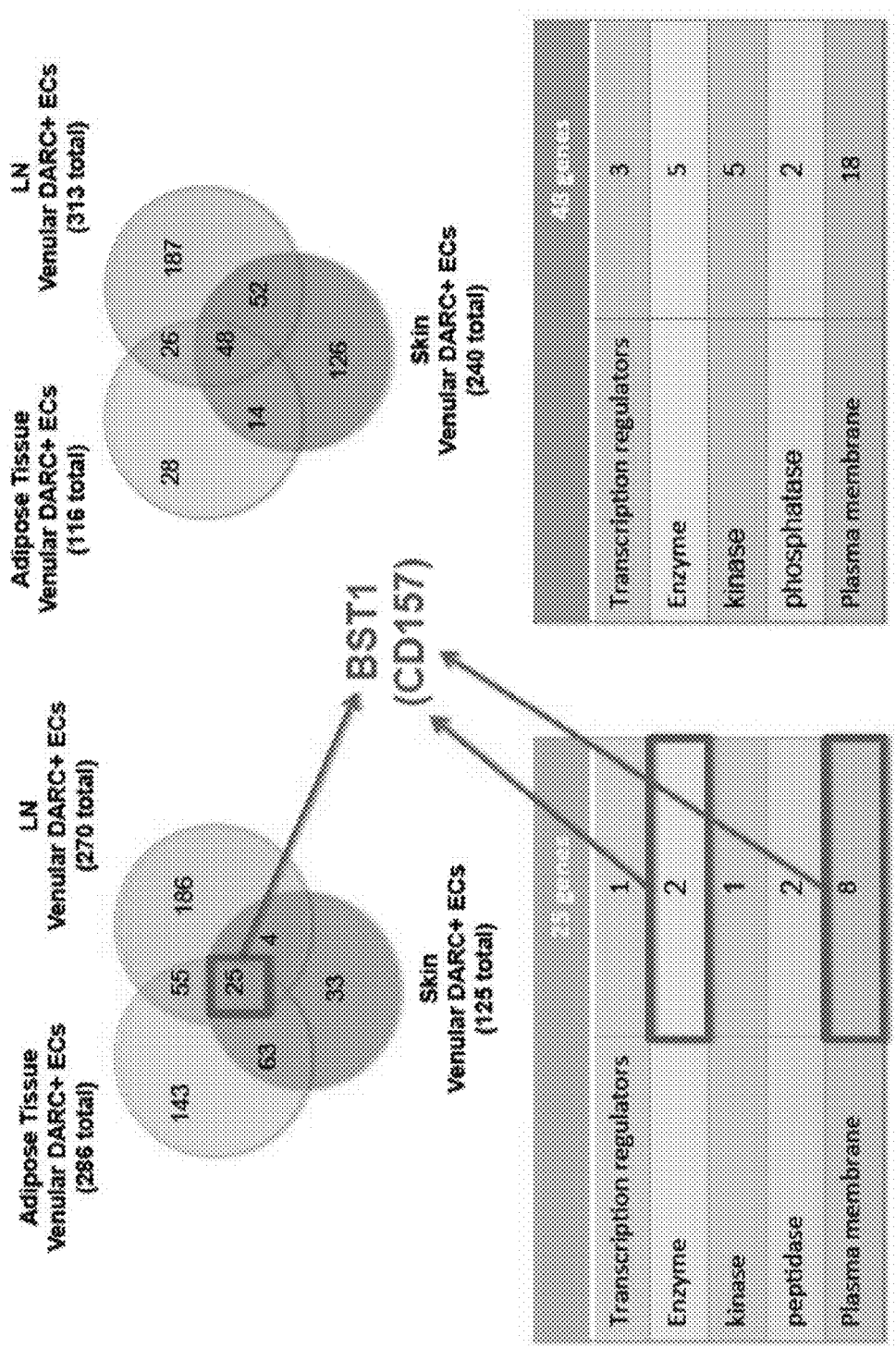
FIG. 15 shows Venn Diagrams of over- and under-represented shared genes in venular DARC+ ECs from adipose tissue, skin and lymph node indicating that BST1 (CD157) emerges as a potential venular surface molecule suitable for site-specific drug targeting of therapeutic agents (e.g., anti-inflammatory agents) to venular endothelium.
Figures 16A, 16B:
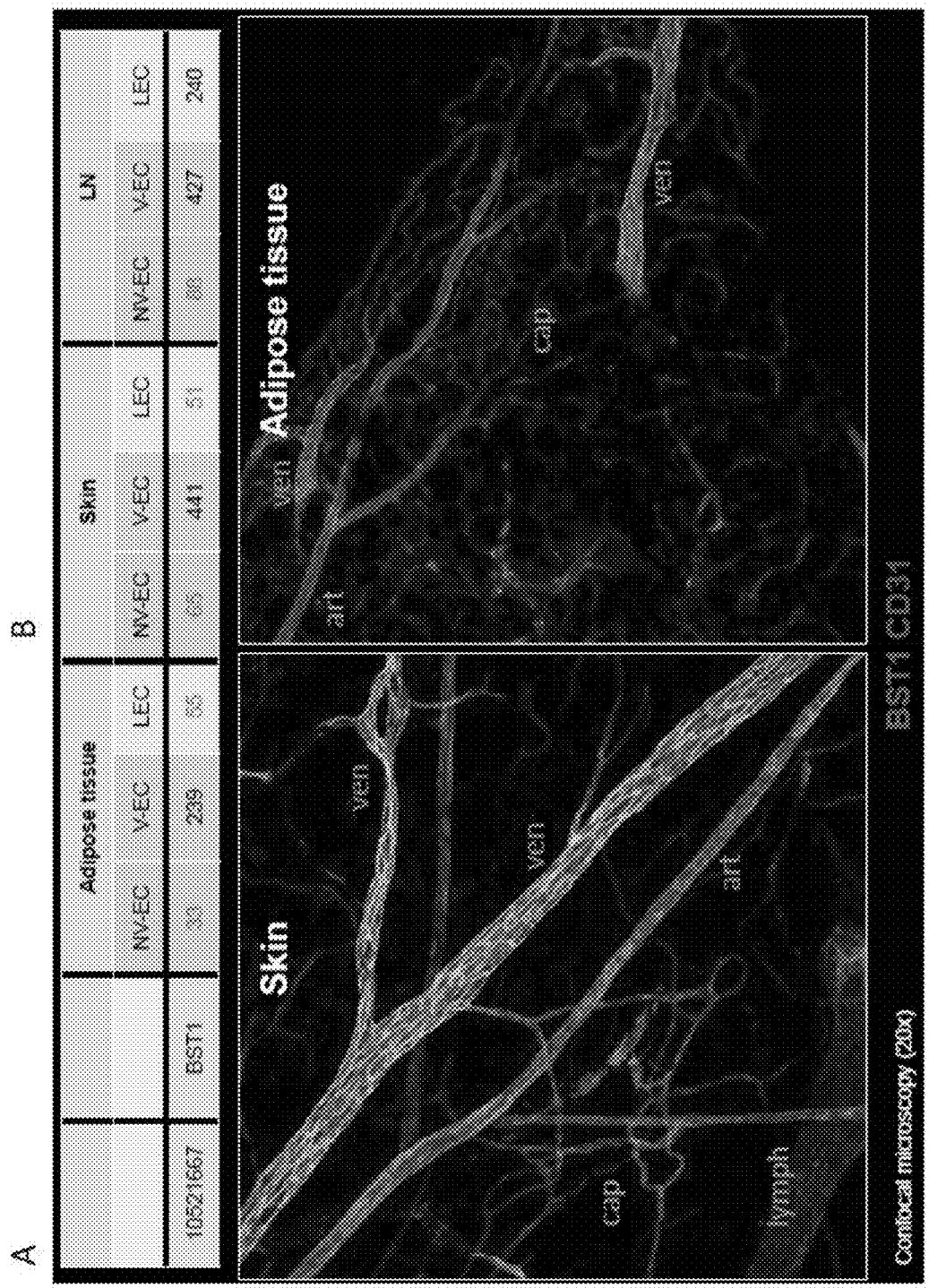
FIG. 16A-16B are Confocal microscopy images of whole mount staining in mouse skin (FIG. 16A, left panel) and adipose tissue (FIG. 16B, right panel), showing that BST1 expression (red) is restricted to venules.
Figure 17:
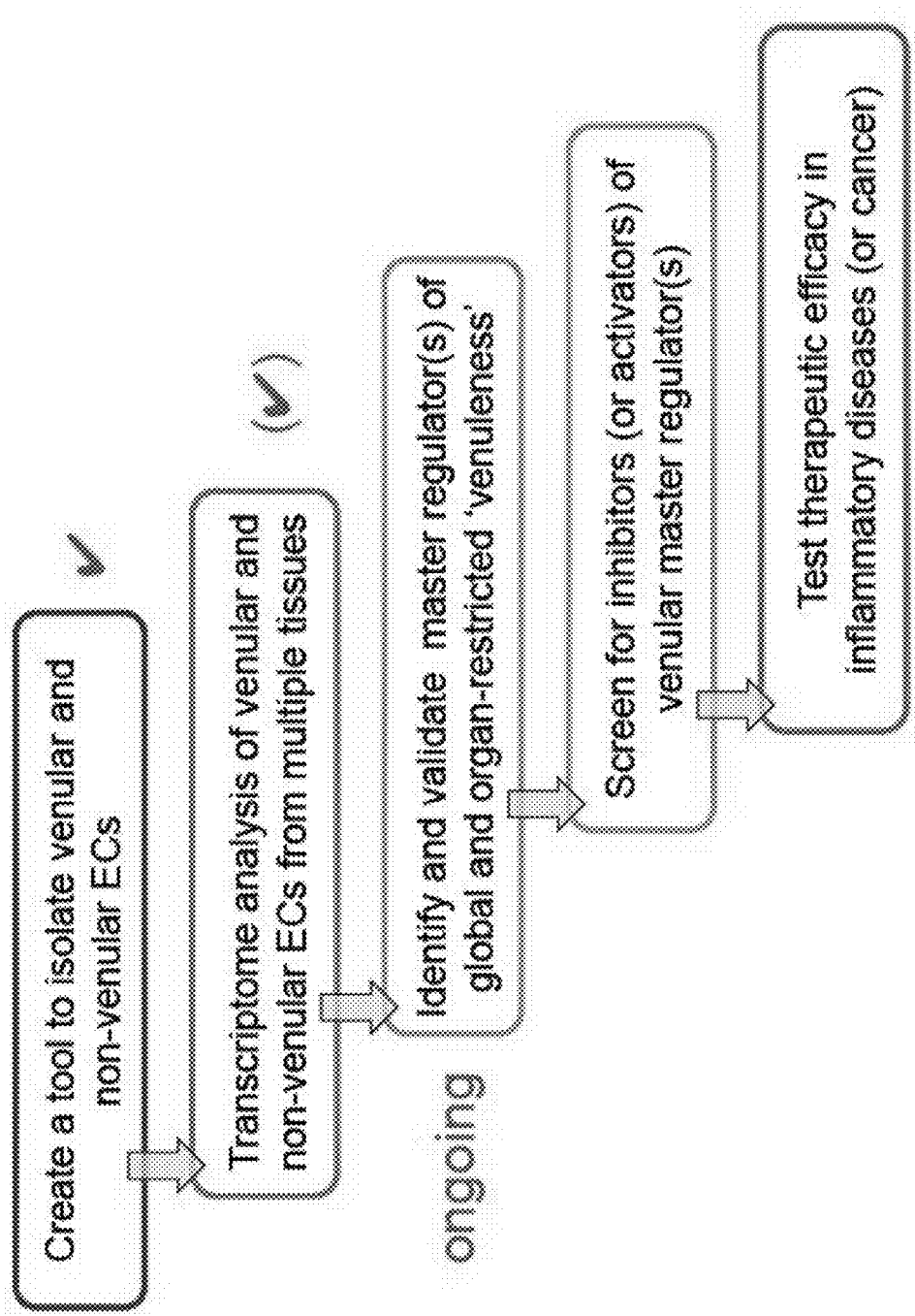
FIG. 17 is a flow chart illustrating the development strategy for the novel anti-inflammatory drug discovery approach disclosed herein.
Figure 18:
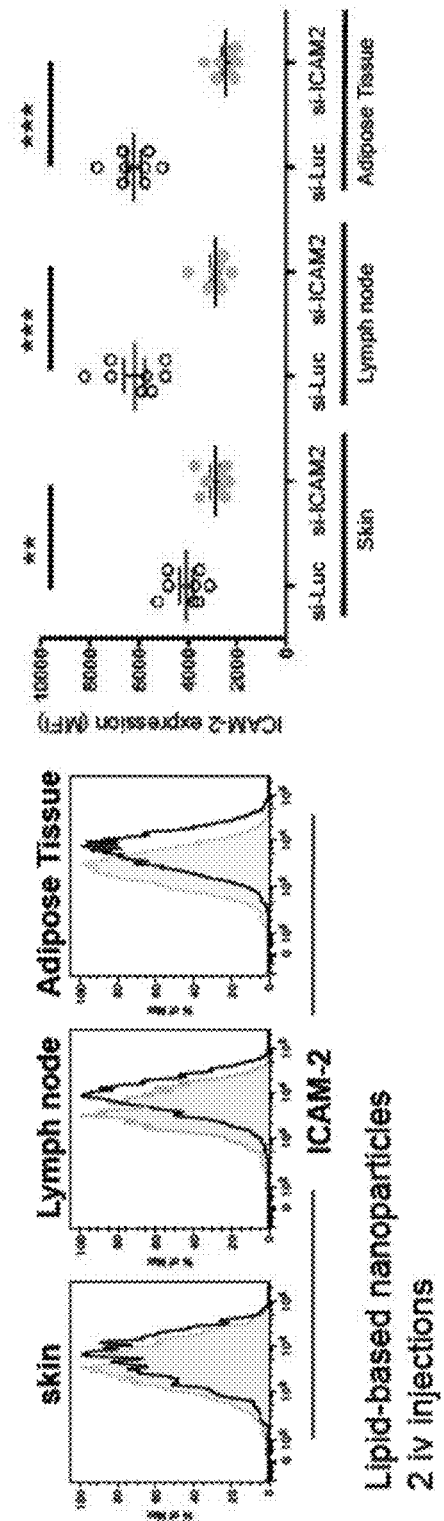
FIG. 18 depicts an exemplary validation strategy for candidate genes disclosed herein, including an example of ICAM2 knock-down using formulated siRNA.
Figures 19A, 19B:
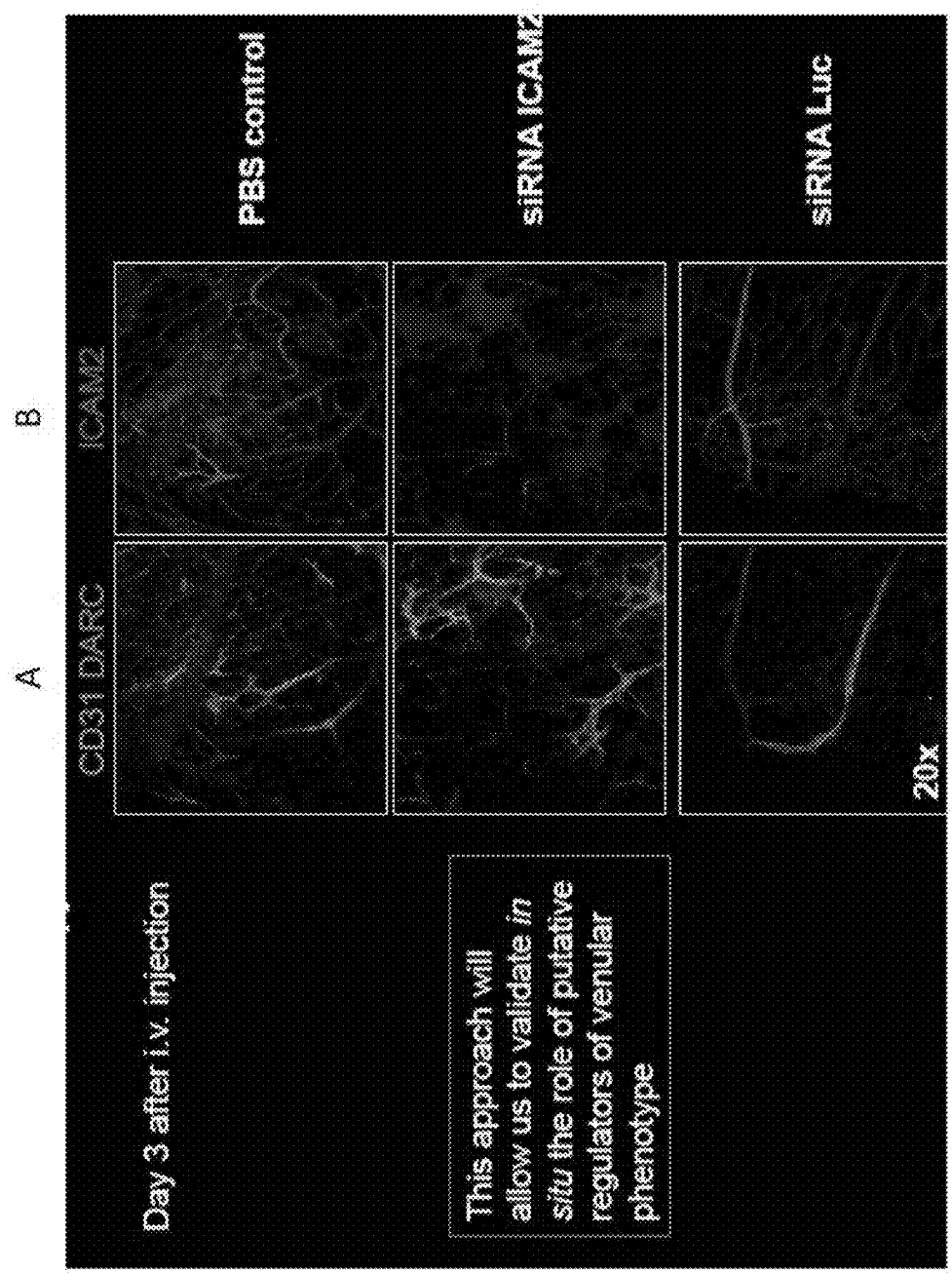
FIGS. 19A-19B are Confocal microscopy images of omentum 3 days after intravenous injection depicting the results of in vivo knockdown of ICAM2 with shRNA in cationic lipid nanoparticle or microparticles, and illustrating an approach for validating in situ the roles of putative regulators of venular phenotype.
Figure 20:
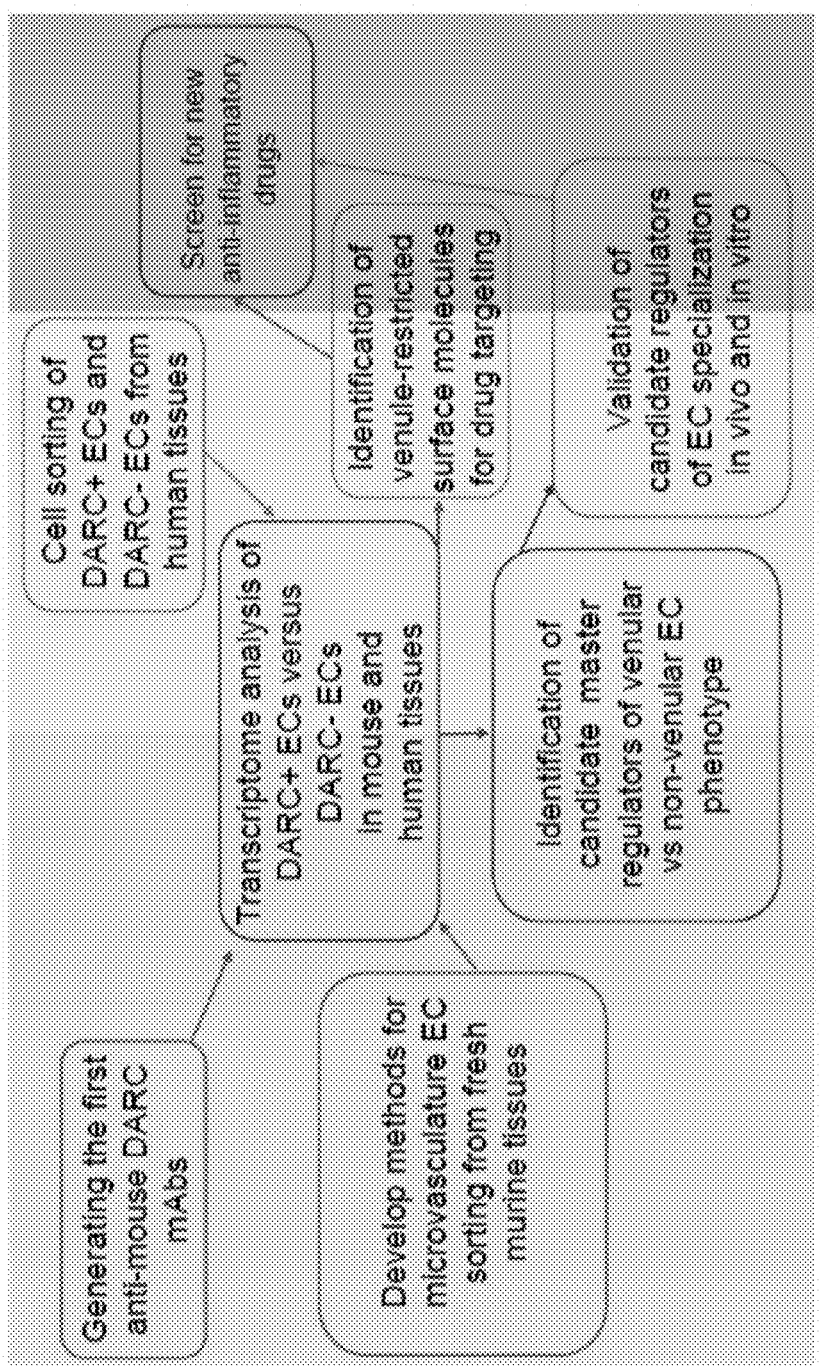
FIG. 20 is a diagrammatic illustration depicting a timeline for the novel anti-inflammatory drug discovery platform disclosed herein.

In particular, the work described herein provides lists of genes expressed by venular endothelial cells in three different murine tissues (skin, lymph nodes and adipose tissue) that can be used to identify potential targets for anti-inflammatory therapy. The inventors devised a discovery strategy that allows the skilled artisan to reliably and reproducibly conduct comprehensive transcriptome analyses of freshly purified venular and non-venular ECs from virtually any vascularized tissue. To this end, the inventors made use of a non-signaling chemokine binding receptor, DARC (Duffy Antigen/Receptor for Chemokines), which had been suggested to be a specific marker for venular ECs in humans[5,6]. The inventors generated the first monoclonal antibody (mAb) that recognizes the erythroid and endothelial forms of murine DARC. The novel mAb can be used for both FACS and immunohistochemistry (IHC) detection of DARC expression in murine tissues. An IHC micrograph demonstrating venule-restricted DARC expression in a whole-mount preparation of mouse omentum is shown in FIGS. 6A-6C. Using this approach, the inventors determined that DARC expression is highly restricted to venules in every tissue in the body. Taking advantage of this new tool, the inventors FACS sorted venular (CD31+DARC+) ECs (V-ECs), non-venular (CD31+DARC−) ECs (NV-ECs) and lymphatic ECs (LECs) from single-cell suspensions of multiple murine tissues and determined their transcriptomes by microarray analysis (Affymetrix Mouse Gene 1.0 ST Array). Disclosed herein are datasets for normal skin, lymph nodes and adipose tissue. The information gleaned from this analysis allows for the identification of genes that are selectively expressed in venules, either globally or in an organ-restricted fashion.

Results

The results of our analysis of over- and under-represented genes in V-EC data sets compared to NV-ECs from adipose tissue, lymph node and skin are shown in Tables 1-14 below. Genes that are surface expressed are italicized. These genes represent candidates for tissue-selective targeting strategies aimed to deliver therapeutic payloads to venules or non-venules either globally or in distinct organs. Genes that have been further validated at the transcript or protein level are shown in bold.

Table 1 lists genes over-represented in V-EC shared by skin, adipose tissue and lymph node. As used herein "Table 1" includes Table 1A and Table 1B below.

Table 1A—Genes over-represented in V-EC shared by skin, adipose tissue and lymph node (25 genes)

Sele, Selp, Darc, Timp2, Cmah, Tgfbi, Mctp1, Il6st, Mustn1, Plxnb2, Ehd3, Cfb, Lrg1, Zfp521, Lepr, Bst1, Prkag2, Rasgef1a, Vwf, Arrb1, 2010110P09Rik, Spint2, Tll1, Icam1, Tagln.

| Gene Symbol | Gene Name | Gene Accession Number |
|---|---|---|
| Sele | selectin, endothelial cell | NM_011345 |
| Selp | selectin, platelet | NM_011347 |
| Darc | Duffy blood group, chemokine receptor | NM_010045 |
| Timp2 | tissue inhibitor of metalloproteinase 2 | NM_011594 |
| Cmah | cytidine monophospho-N-acetylneuraminic acid hydroxylase | NM_007717, NM_001111110 |
| Tgfbi | transforming growth factor, beta induced | NM_009369 |
| Mctp1 | multiple C2 domains, transmembrane 1 | NM_030174 |
| Il6st | interleukin 6 signal transducer | NM_010560 |
| Mustn1 | musculoskeletal, embryonic nuclear protein 1 | NM_181390 |
| Plxnb2 | plexin B2 | NM_138749, NM_001159521 |
| Ehd3 | EH-domain containing 3 | NM_020578 |
| Cfb | complement factor B | NM_008198, NM_001142706 |
| Lrg1 | leucine-rich alpha-2-glycoprotein 1 | NM_029796 |
| Zfp521 | zinc finger protein 521 | NM_145492 |
| Lepr | leptin receptor | NM_146146, NM_001122899, NM_010704 |
| Bst1 | bone marrow stromal cell antigen 1 | NM_009763 |
| Prkag2 | protein kinase, AMP-activated, gamma 2 non-catalytic subunit | NM_001170555, NM_145401, NM_001170556 |
| Rasgef1a | RasGEF domain family, member 1A | NM_027526 |
| Vwf | Von Willebrand factor homolog | NM_011708 |
| Arrb1 | arrestin, beta 1 | NM_177231, NM_178220 |
| 2010110P09Rik | RIKEN cDNA 2010110P09 gene | NM_027363 |
| Spint2 | serine protease inhibitor, Kunitz type 2 | NM_011464, NM_001082548 |
| Tll1 | tolloid-like | NM_009390 |
| Icam1 | intercellular adhesion molecule 1 | NM_010493 |
| Tagln | transgelin | NM_011526 |

Table 1B—Genes over-represented in V-EC shared by skin, adipose tissue and lymph node (63 genes)

Sele, Selp, Kcnh1, Ogfrl1, Tbc1d8, Cd55, Darc, Csrp2, Gpr126, C630004H02Rik, Timp2, Odc1, Tc2n, Cmah, Tgfbi, Mctp1, Net1, Golm1, Bmp4, Gramd4, Plxnb2, Bace2, AU021092, Pdia5, Pde9a, Ehd3, Cfb, Lrg1, Zfp521, Rab3il1, Ch25h, Ptgs1, Sirpa, Dennd2d, Ecm1, Vcam1, Clca2, Lepr, Cda, Fgl2, Bst1, Pcdh7, Prkag2, Fam69a, Met, Rasgef1a, Vwf, Pdk4, Thsd7a, Dnahc6, Ret, Ctsc, Arrb1, 2010110P09Rik, Spint2, Nr2f2, Acer3, Plekha7, Tll1, Nt5e, Tagln, Lrrc1, Timp1, and Cysltr1.

| Gene Symbol | Gene Name | Gene Accession Number |
|---|---|---|
| Sele | selectin, endothelial cell | NM_011345 |
| Selp | selectin, platelet | NM_011347 |
| Kcnh1 | potassium voltage-gated channel, subfamily H (eag-related), member 1 | NM_001038607, NM_010600 |
| Ogfrl1 | opioid growth factor receptor-like 1 | NM_001081079 |
| Tbc1d8 | TBC1 domain family, member 8 | NM_018775 |
| Cd55 | CD55 antigen | NM_010016 |
| Darc | Duffy blood group, chemokine receptor | NM_010045 |
| Csrp2 | cysteine and glycine-rich protein 2 | NM_007792 |
| Gpr126 | G protein-coupled receptor 126 | NM_001002268 |
| C630004H02Rik | RIKEN cDNA C630004H02 gene | NM_175454 |
| Timp2 | tissue inhibitor of metalloproteinase 2 | NM_011594 |
| Odc1 | ornithine decarboxylase, structural 1 | NM_013614 |
| Tc2n | tandem C2 domains, nuclear | NM_028924, NM_001082976 |
| Cmah | cytidine monophospho-N-acetylneuraminic acid hydroxylase | NM_007717, NM_001111110 |
| Tgfbi | transforming growth factor, beta induced | NM_009369 |
| Mctp1 | multiple C2 domains, transmembrane 1 | NM_030174 |
| Net1 | neuroepithelial cell transforming gene 1 | NM_001047159, NM_019671 |
| Golm1 | golgi membrane protein 1 | NM_001035122, NM_027307 |
| Bmp4 | bone morphogenetic protein 4 | NM_007554 |
| Gramd4 | GRAM domain containing 4 | NM_001205353/ NM_172611 |
| Plxnb2 | plexin B2 | NM_001159521, NM_138749 |
| Bace2 | beta-site APP-cleaving enzyme 2 | NM_019517 |
| AU021092 | expressed sequence AU021092 | NM_001033220 |
| Pdia5 | protein disulfide isomerase associated 5 | NM_028295 |
| Pde9a | phosphodiesterase 9A | NM_001163748, NM_008804 |
| Ehd3 | EH-domain containing 3 | NM_020578 |
| Cfb | complement factor B | NM_001142706, NM_008198 |
| Lrg1 | leucine-rich alpha-2-glycoprotein 1 | NM_029796 |
| Zfp521 | zinc finger protein 521 | NM_145492 |
| Rab3il1 | RAB3A interacting protein (rabin3)-like 1 | NM_144538 |
| Ch25h | cholesterol 25-hydroxylase | NM_009890 |
| Ptgs1 | prostaglandin-endoperoxide synthase 1 | NM_008969 |

-continued

| Gene Symbol | Gene Name | Gene Accession Number |
| --- | --- | --- |
| Sirpa | signal-regulatory protein alpha | NM_007547, NM_001177646, NM_001177647 |
| Dennd2d | DENN/MADD domain containing 2D | NM_028110, NM_001093754 |
| Ecm1 | extracellular matrix protein 1 | NM_007899, NM_001252653 |
| Vcam1 | vascular cell adhesion molecule 1 | NM_011693 |
| Clca2 | chloride channel calcium activated 2 | NM_030601 |
| Lepr | leptin receptor | NM_010704, NM_001122899, NM_146146 |
| Cda | cytidine deaminase | NM_028176 |
| Fgl2 | fibrinogen-like protein 2 | NM_008013 |
| Bst1 | bone marrow stromal cell antigen 1 | NM_009763 |
| Pcdh7 | protocadherin 7 | NM_018764, NM_001122758 |
| Prkag2 | protein kinase, AMP-activated, gamma 2 non-catalytic subunit | NM_001170556, NM_145401, NM_001170555 |
| Fam69a | family with sequence similarity 69, member A | NM_026062 |
| Met | met proto-oncogene | NM_008591 |
| Rasgef1a | RasGEF domain family, member 1A | NM_027526 |
| Vwf | Von Willebrand factor homolog | NM_011708 |
| Pdk4 | pyruvate dehydrogenase kinase, isoenzyme 4 | NM_013743 |
| Thsd7a | thrombospondin, type I, domain containing 7A | NM_001164805 |
| Dnahc6 | dynein, axonemal, heavy chain 6 | NM_001164669 |
| Ret | ret proto-oncogene | NM_001080780, NM_009050 |
| Ctsc | cathepsin C | NM_009982 |
| Arrb1 | arrestin, beta 1 | NM_178220, NM_177231 |
| 2010110P09Rik | RIKEN cDNA 2010110P09 gene | NM_027363 |
| Spint2 | serine protease inhibitor, Kunitz type 2 | NM_001082548, NM_011464 |
| Nr2f2 | nuclear receptor subfamily 2, group F, member 2 | NM_009697, NM_183261 |
| Acer3 | alkaline ceramidase 3 | NM_025408 |
| Plekha7 | pleckstrin homology domain containing, family A member 7 | NM_172743 |
| Tll1 | tolloid-like | NM_009390 |
| Nt5e | 5' nucleotidase, ecto | NM_011851 |
| Tagln | transgelin | NM_011526 |
| Lrrc1 | leucine rich repeat containing 1 | NM_001146048, NM_172528 |
| Timp1 | tissue inhibitor of metalloproteinase 1 | NM_001044384, NM_011593 |
| Cysltr1 | cysteinyl leukotriene receptor 1 | NM_021476 |

Figure 21A:
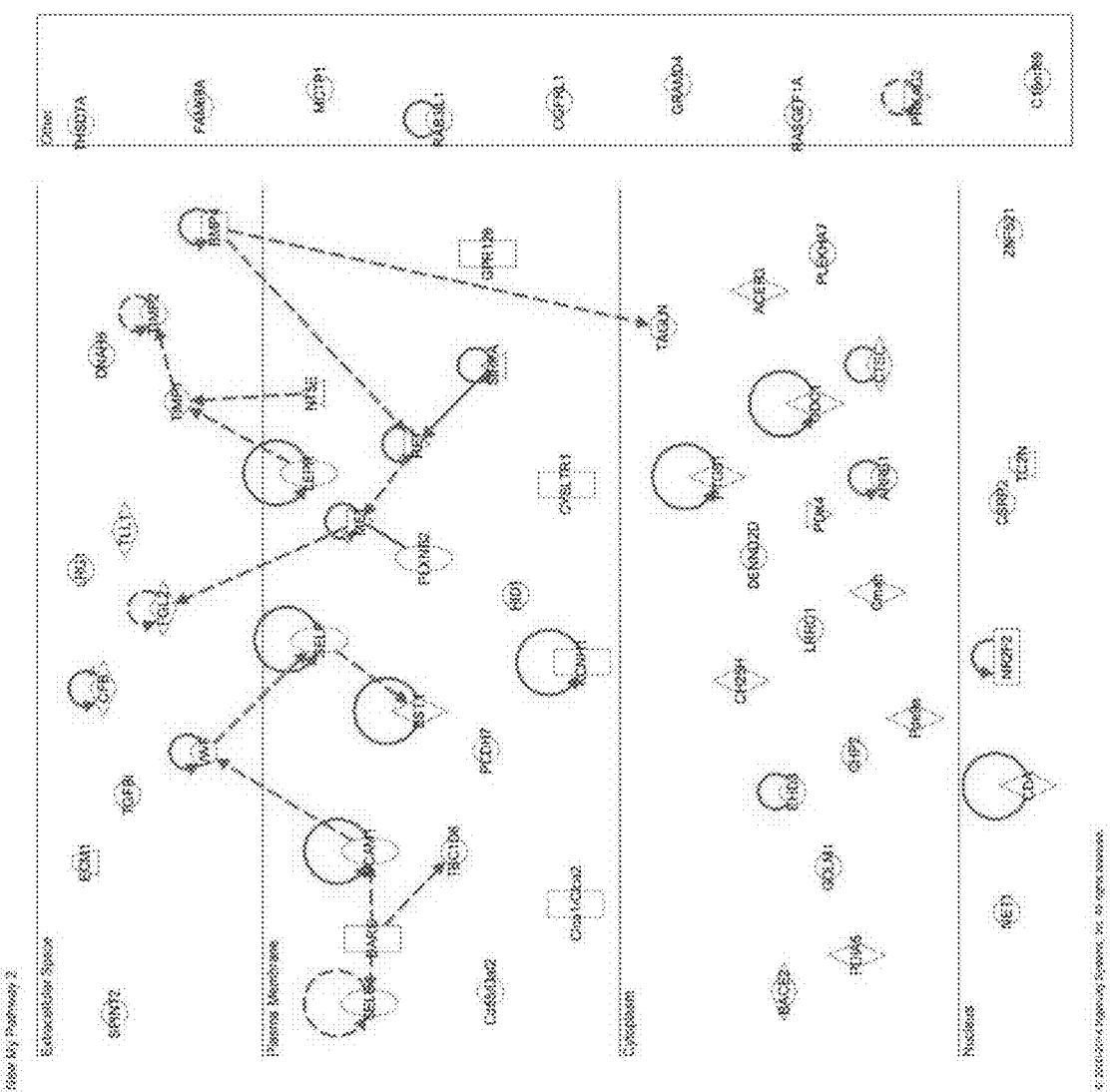
FIGS. 21A, 21B, 21C, and 21D illustrate the results of network analyses performed with Ingenuity software, showing links known in the literature btween genes over-represented in venule endothelial cells.

In some embodiments, Sele is excluded from Table 1. In some embodiments, Selp is excluded from Table 1. FIG. 21A shows a network analysis of over-represented genes that are shared in venule endothelial cells (V-ECs) compared to non-venular endothelial cells (NV-ECs) of adipose tissue, lymph node and skin, indicating potential relationships among these genes.

Table 2 below lists genes over-represented in V-EC unique to skin tissue. As used herein, "Table 2" includes Table 2A and Table 2B below.

Table 2A—Genes over-represented in V-EC unique to skin tissue (34 genes)

Nrp2, Gpr1, Steap3, Upp1, Slfn4, Slfn3, C630004H02Rik, Sectm1b, Sectm1a, Actn1, Klhl3, Golm1, Sncg, Myc, Grina, Leprel1, Fndc1, Rab3il1, Ccdc3, 2310046K01Rik, Lhx6, Serping1, Asap3, Mxra8, Cytl1, Fam69a, Ica1, Peg3, Nr2f2, Plekha7, Insr, Slco2a1, LOC100503984.

| Gene Symbol | Gene Name | Gene Accession Number |
| --- | --- | --- |
| Nrp2 | neuropilin 2 | NM_001077403, NM_001077404, NM_010939, NM_001077405 NM_001077406, NM_001077407 |
| Gpr1 | G protein-coupled receptor 1 | NM_146250 |
| Steap1, | six transmembrane epithelial antigen of the | NM_027399; |

| Gene Symbol | Gene Name | Gene Accession Number |
| --- | --- | --- |
| Steap3 | prostate 1, STEAP family member 3 | NM_133186, NM_001085409 |
| Upp1 | uridine phosphorylase 1 | NM_009477, NM_001159401, NM_001159402 |
| Slfn4 | schlafen 4 | NM_011410 |
| Slfn3 | schlafen 3 | NM_011409 |
| C630004H02Rik | RIKEN cDNA C630004H02 gene | NM_175454 |
| Sectm1b | secreted and transmembrane 1B | NM_026907 |
| Sectm1a | secreted and transmembrane 1A | NM_145373 |
| Actn1 | actinin, alpha 1 | NM_134156 |
| Klhl3 | kelch-like 3 (*Drosophila*) | NM_001195075 |
| Golm1 | golgi membrane protein 1 | NM_027307, NM_001035122 |
| Sncg | synuclein, gamma | NM_011430 |
| Myc | myelocytomatosis oncogene | NM_010849, NM_001177352 NM_001177353, NM_001177354 |
| Grina | glutamate receptor, ionotropic, N-methyl D-aspartate-associated protein 1 (glutamate binding) | NM_023168 |
| Leprel1 | leprecan-like 1 | NM_173379 |
| Fndc1 | fibronectin type III domain containing 1 | NM_001081416 |
| Rab3il1 | RAB3A interacting protein (rabin3)-like 1 | NM_144538 |
| Ccdc3 | coiled-coil domain containing 3 | NM_028804 |
| Slc52a3 | solute carrier protein family 52, member 3 | NM_027172, NM_001164819 NM_001164820 |
| Lhx6 | LIM homeobox protein 6 | NM_001083125, NM_001083126, NM_008500 NM_001083127 |
| Serping1 | serine (or cysteine) peptidase inhibitor, clade G, member 1 | NM_009776 |
| Asap3 | ArfGAP with SH3 domain, ankyrin repeat and PH domain 3 | NM_001008232 |
| Mxra8 | matrix-remodelling associated 8 | NM_024263 |
| Cytl1 | cytokine-like 1 | NM_001081106 |
| Fam69a | family with sequence similarity 69, member A | NM_026062 |
| Ica1 | islet cell autoantigen 1 | NM_001252266, NM_010492 |
| Peg3 | paternally expressed 3 | NM_008817 |
| Nr2f2 | nuclear receptor subfamily 2, group F, member 2 | NM_183261, NM_009697 |
| Plekha7 | pleckstrin homology domain containing, family A member 7 | NM_172743 |
| Insr | insulin receptor | NM_010568 |
| Slco2a1 | solute carrier organic anion transporter family, member 2a1 | NM_033314 |
| LOC100503984 | | NC_005089 |
| 2310046K01Rik | RIKEN cDNA 2310046K01 gene | BC016127 |

Table 2B—Genes over-represented in V-EC unique to skin tissue (44 genes)

Nrp2, Htr2b, Mr1, Stc2, Bod1, Sectm1a, Socs2, Plekhg3, Aspn, Rsl1, Ssbp2, Lifr, Grina, Nrbp2, Cpne8, Cebpd, St6gal1, Arhgap26, Prelid2, Anxa1, Gda, Phyh, Gm13194, Ccdc3, 3300002I08Rik///Zfp937///Zfp442, Mafb, Postn, Tiparp, Pdgfc, Lphn2, Sgip1, Mxra8, Ndufb6, Mgst1, Ica1, Gm1524, Vamp5, Olr1, Eps8, Ndn, Peg3, Slco2b1, Cpe, and Slco2a1.

| Gene Symbol | Gene Name | Gene Accession Number |
| --- | --- | --- |
| Nrp2 | neuropilin 2 | NM_001077403 |
| Htr2b | 5-hydroxytryptamine (serotonin) receptor 2B | NM_008311 |
| Mr1 | major histocompatibility complex, class I-related | NM_008209 |
| Stc2 | stanniocalcin 2 | NM_011491 |
| Bod1 | biorientation of chromosomes in cell division 1 | NM_001024919 |
| Sectm1a | secreted and transmembrane 1A | NM_145373 |
| Socs2 | suppressor of cytokine signaling 2 | NM_001168656, NM_001168657, NM_007706, NM_001168655 |

| Gene Symbol | Gene Name | Gene Accession Number |
| --- | --- | --- |
| Plekhg3 | pleckstrin homology domain containing, family G (with RhoGef domain) member 3 | NM_153804 |
| Aspn | asporin | NM_001172481, NM_025711 |
| Rsl1 | regulator of sex limited protein 1 | NM_001013769 |
| Ssbp2 | single-stranded DNA binding protein 2 | NM_024272, NM_024186 |
| Lifr | leukemia inhibitory factor receptor | NM_001113386, NM_013584 |
| Grina | glutamate receptor, ionotropic, N-methyl D-aspartate-associated protein 1 (glutamate binding) | NM_023168 |
| Nrbp2 | nuclear receptor binding protein 2 | NM_144847 |
| Cpne8 | copine VIII | NM_025815 |
| Cebpd | CCAAT/enhancer binding protein (C/EBP), delta | NM_007679 |
| St6gal1 | beta galactoside alpha 2,6 sialyltransferase 1 | NM_001252506, NM_001252505, NM_145933 |
| Arhgap26 | Rho GTPase activating protein 26 | NM_175164 |
| Prelid2 | PRELI domain containing 2 | NM_029942 |
| Anxa1 | annexin A1 | NM_010730 |
| Gda | guanine deaminase | NM_010266 |
| Phyh | phytanoyl-CoA hydroxylase | NM_010726 |
| Gm13194 | predicted gene 13194 | ENSMUST00000142299 |
| Ccdc3 | coiled-coil domain containing 3 | NM_028804 |
| 3300002I08Rik /// Zfp937 /// Zfp442 | RIKEN cDNA 3300002I08 gene /// zinc finger protein 937 /// zinc finger protein 442 | NM_001177550, NM_001142411 |
| Mafb | v-maf musculoaponeurotic fibrosarcoma oncogene family, protein B (avian) | NM_010658 |
| Postn | periostin, osteoblast specific factor | NM_001198766, NM_001198765, NM_015784 |
| Tiparp | TCDD-inducible poly(ADP-ribose) polymerase | NM_178892 |
| Pdgfc | platelet-derived growth factor, C polypeptide | NM_019971 |
| Lphn2 | latrophilin 2 | NM_001081298 |
| Sgip1 | SH3-domain GRB2-like (endophilin) interacting protein 1 | NM_144906 |
| Mxra8 | matrix-remodelling associated 8 | NM_024263 |
| Ndufb6 | NADH dehydrogenase (ubiquinone) 1 beta subcomplex, 6 | NM_001033305 |
| Mgst1 | microsomal glutathione S-transferase 1 | NM_019946 |
| Ica1 | islet cell autoantigen 1 | NM_010492, NM_001252266 |
| Gm1524 | — | ENSMUST00000103359 |
| Vamp5 | vesicle-associated membrane protein 5 | NM_001080742, NM_016872 |
| Olr1 | oxidized low density lipoprotein (lectin-like) receptor 1 | NM_138648 |
| Eps8 | epidermal growth factor receptor pathway substrate 8 | NM_007945 |
| Ndn | necdin | NM_010882 |
| Peg3 | paternally expressed 3 | NM_008817 |
| Slco2b1 | solute carrier organic anion transporter family, member 2b1 | NM_175316, NM_001252531, NM_001252530 |
| Cpe | carboxypeptidase E | NM_013494 |
| Slco2a1 | solute carrier organic anion transporter family, member 2a1 | NM_033314 |

Figure 21B:
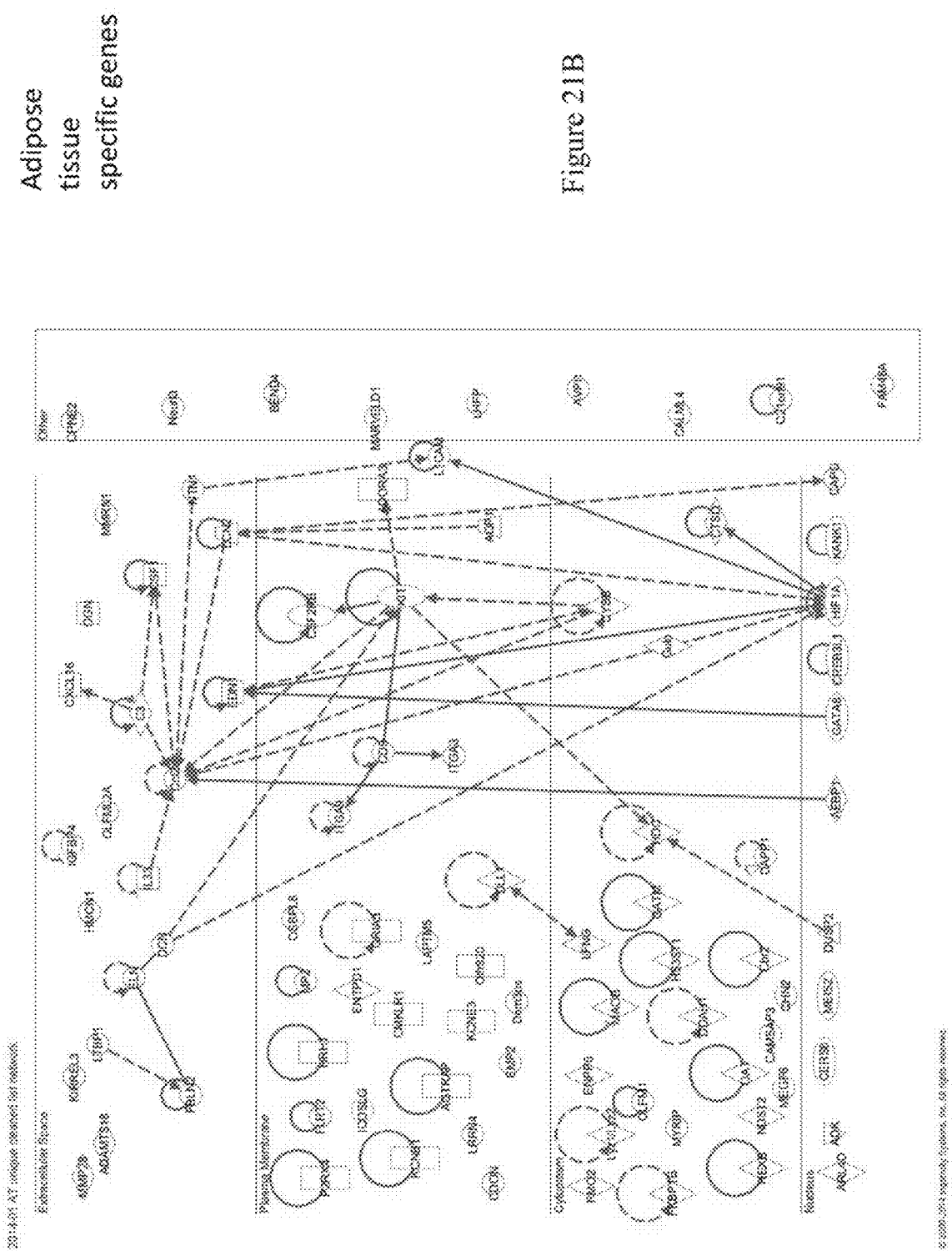
Figure 21C:
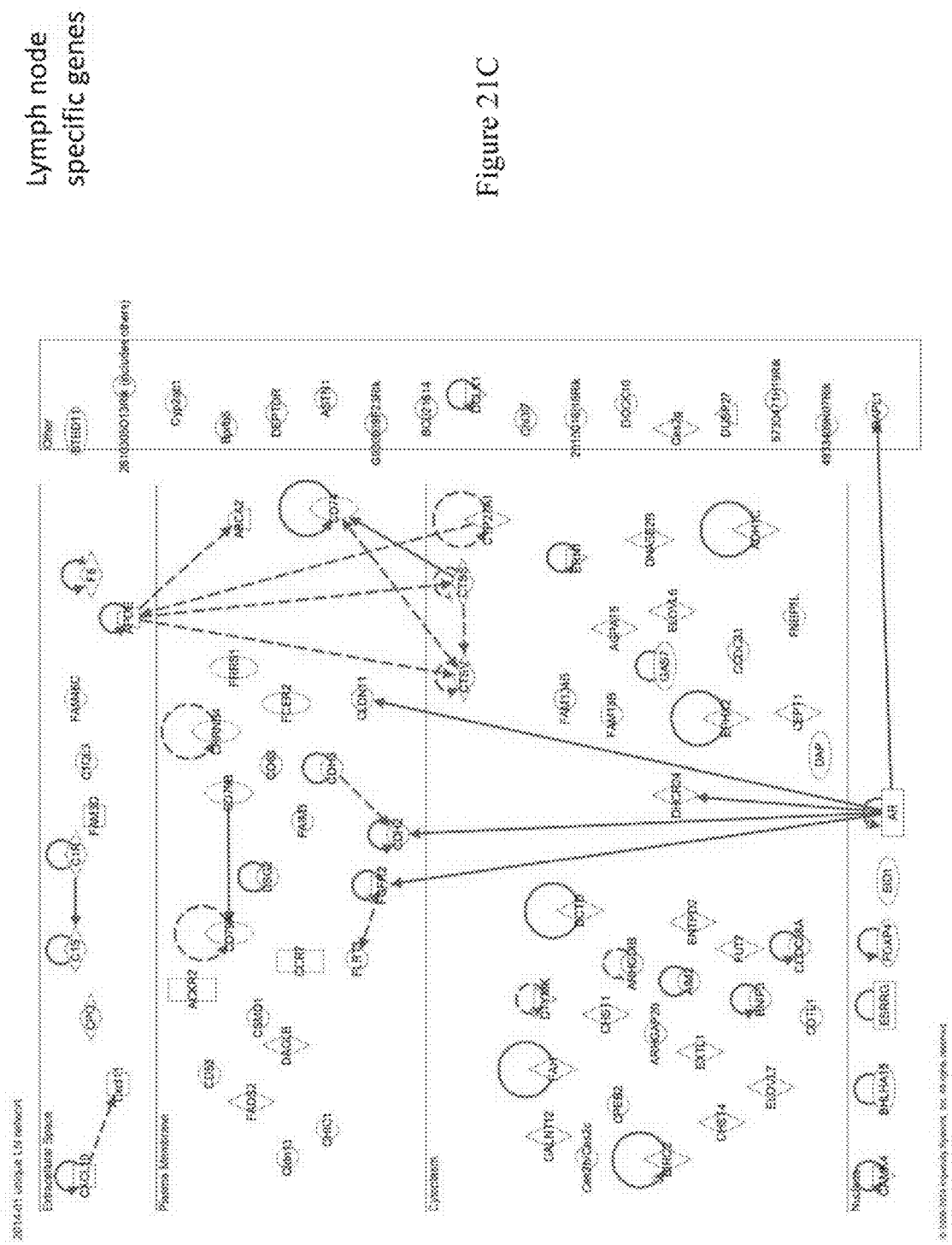
Figure 21D:
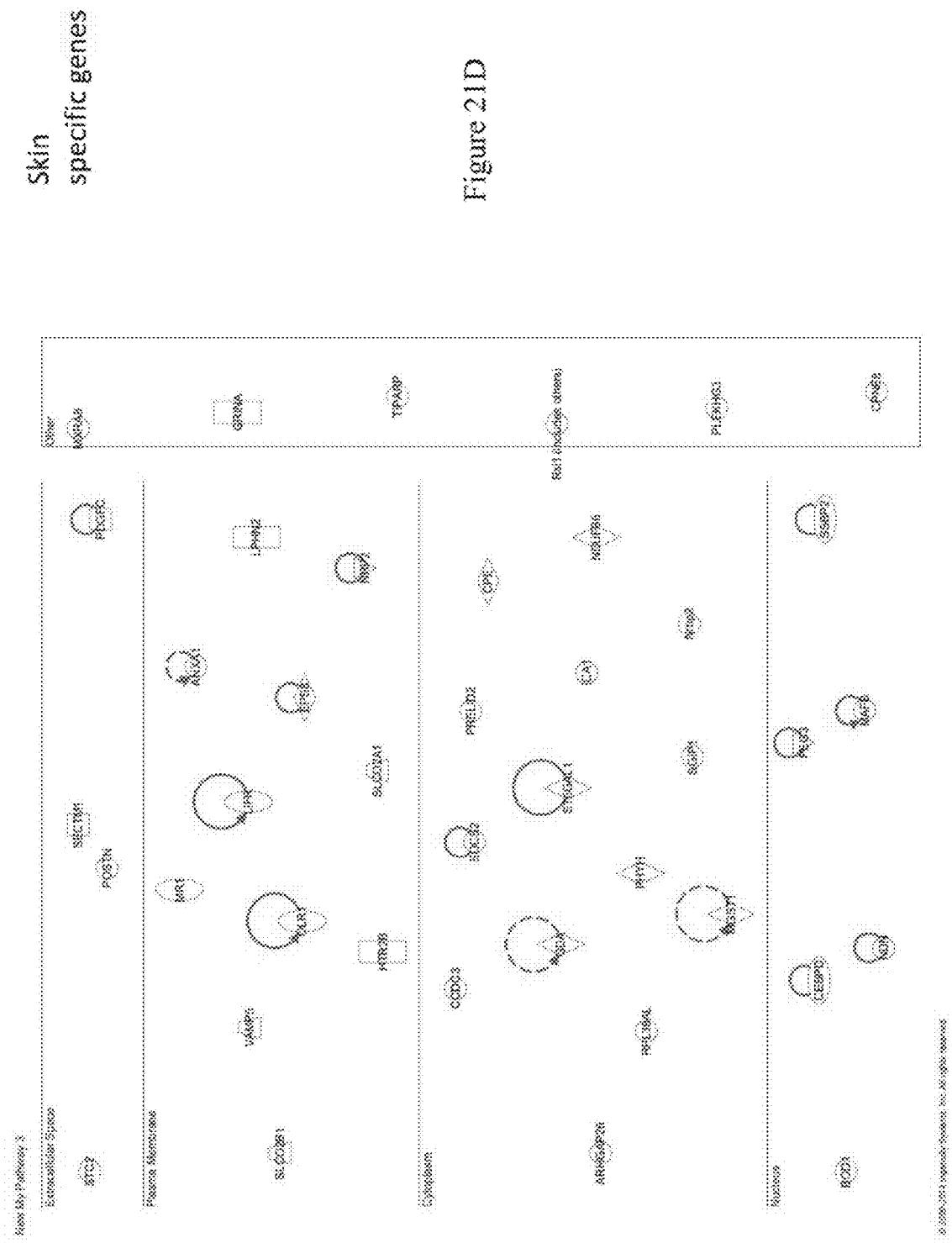
Figure 23:
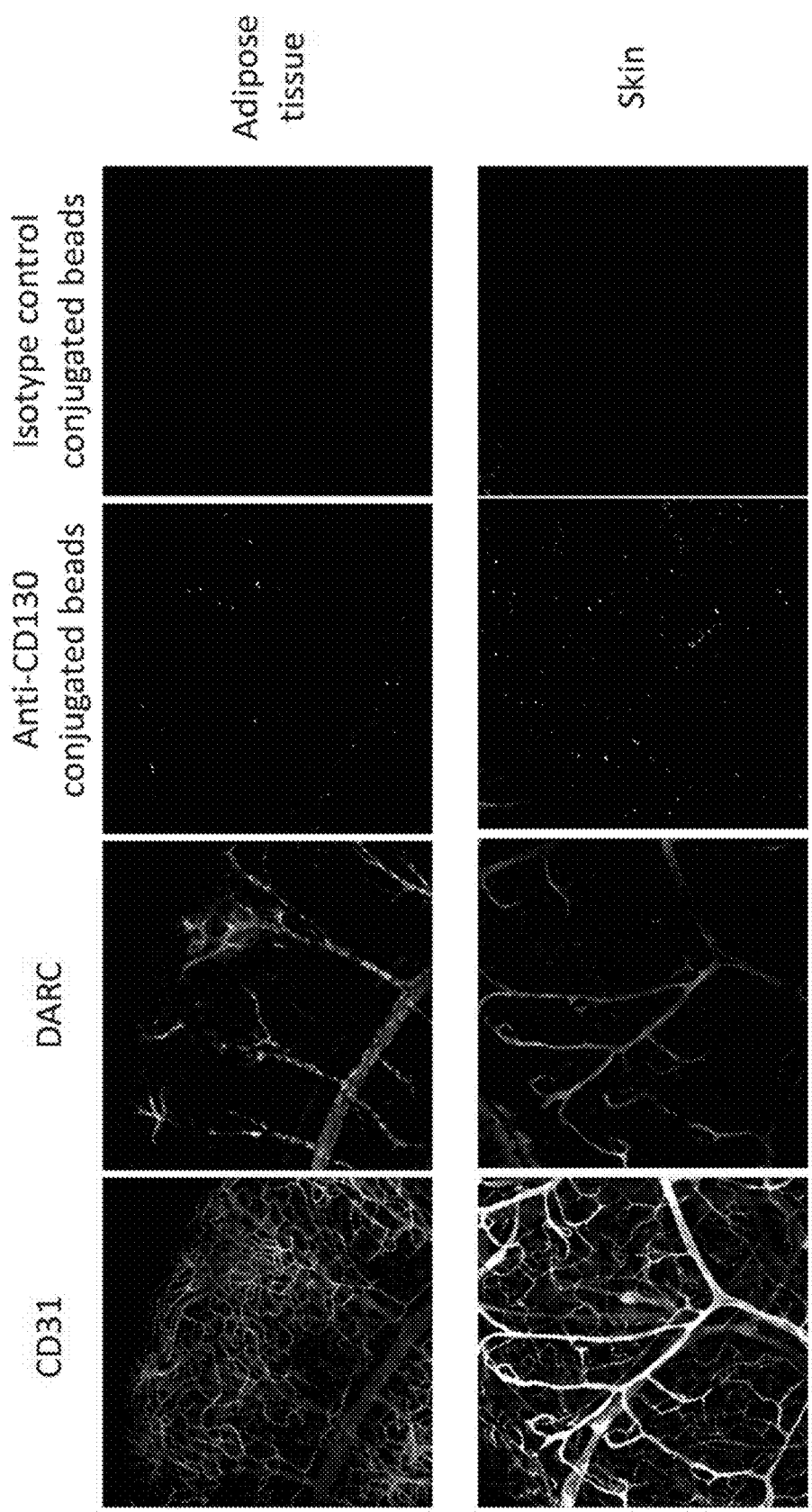
FIG. 23 demonstrates targeting agents to tissues (e.g., adipose tissue and skin) based on their ability to bind surface markers (e.g., CD130, also known as GP130) expressed in a microvessel (e.g., venules).

FIG. 21D shows a network analysis of over-represented genes that are uniquely expressed in V-ECs compared to NV-ECs of skin, indicating potential relationships among these genes.

Table 3 lists genes over-represented in V-EC unique to adipose tissue. As used herein, "Table 3" includes Table 3A and Table 3B below.

Table 3A—Genes over-represented in V-EC unique to adipose tissue (122 genes)

Il1rl1, Gm7609, Slc45a3, Neurl3, Rgs13, Rgs1, Rgs18, Hmcn1, Fmo2, Psen2, Gp49a, Lilrb4, Osbpl8, 5830405N20Rik, Gpr126, Myb, P2rx1, Slc6a4, Ccl2, Slfn2, Itgb4, Plek, Epx, Cbr2, Pqlc3, BC005685, Ahnak2, Lhfpl2, A530099J19Rik, Lrrc16a, Hexb, Fcer1g, Fcer1a, Plau, Ear2, Cma2, Ndst2, Ear1, Ear10, Slc7a8, Cma1, Mcpt4, Nckap1l, Basp1, Ube2v2, Sla, Rac2, Rnd1, Gcet2, Retnla, Emp2, Samsn1, D16Ertd472e, Prss34, Tpsb2, Pla2g7, Tpsab1, Gata6, Entpd1, Slc18a2, Ms4a2, Lass6, Prg2, Cd59a, Thbs1, Snrpb2, Creb3l1, Meis2, Hdc, Tiparp, Adora3, Ddah1, Cpa3, I830077J02Rik, Vcam1, Dapp1, Dhcr24, Laptm5, Asph, Kit, Ppbp, P2rx4, Hs3st1, Cxcl10, Cmklr1, Lat2, Eln, Pilra, Aqp1, Gp9, Fbln2, Mitf, Slc6a12, Emp1, Dnahc6, Alox5, Prss23, Prkcb, Cd33, Tph1, Mrgprb1, Mrgprb2, Capn5, Rgs10, 4930467E23Rik, Mt2, Slc7a5, Casp4, Vwa5a, Cyp11a1, Rab27a, Fam46a, Mras, Cmtm7, Tarm1, Atp1b3, Maob, Sly, LOC665406, LOC380994.

| Gene Symbol | Gene Name | Gene Accession Number |
| --- | --- | --- |
| Il1rl1 | interleukin 1 receptor-like 1 | NM_001025602, NM_010743 |
| Csprs, Gm7609 | component of Sp100-rs, predicted pseudogene 7609 | NM_033616, NM_001081746 |
| Slc45a3 | solute carrier family 45, member 3 | NM_145977, NM_001177628 |
| Neurl3 | neuralized homolog 3 homolog (Drosophila) | NM_153408 |
| Rgs13 | regulator of G-protein signaling 13 | NM_153171 |
| Rgs1 | regulator of G-protein signaling 1 | NM_015811 |
| Rgs18 | regulator of G-protein signaling 18 | NM_022881 |
| Hmcn1 | hemicentin 1 | ENSMUST00000074783 |
| Fmo2 | flavin containing monooxygenase 2 | NM_018881 |
| Fcer1g | Fc receptor, IgE, high affinity I, gamma polypeptide | NM_010185 |
| Fcer1a | Fc receptor, IgE, high affinity I, alpha polypeptide | NM_010184 |
| Psen2 | presenilin 2 | NM_011183, NM_001128605 |
| Gp49a | glycoprotein 49 A | NM_008147 |
| Lilrb4 | leukocyte immunoglobulin-like receptor, subfamily B, member 4 | NM_013532 |
| Osbpl8 | oxysterol binding protein-like 8 | NM_175489, NM_001003717 |
| Tespa1 | thymocyte expressed, positive selection associated 1 | NM_183264 |
| Gpr126 | G protein-coupled receptor 126 | NM_001002268 |
| Myb | myeloblastosis oncogene | NM_001198914, NM_010848 |
| P2rx1 | purinergic receptor P2X, ligand-gated ion channel, 1 | NM_008771 |
| Slc6a4 | solute carrier family 6 (neurotransmitter transporter, serotonin), member 4 | NM_010484 |
| Ccl2 | chemokine (C-C motif) ligand 2 | NM_011333 |
| Slfn2 | schlafen 2 | NM_011408 |
| Itgb4 | integrin beta 4 | NM_001005608, NM_133663 |
| Plek, Cnrip1 | pleckstrin, cannabinoid receptor interacting protein 1 | NM_019549, NM_029861 |
| Epx | eosinophil peroxidase | NM_007946 |
| Cbr2 | carbonyl reductase 2 | NM_007621 |
| Pqlc3 | PQ loop repeat containing | NM_172574, NM_001161111 |
| BC005685 | cDNA sequence BC005685 | BC005685 |
| Ahnak2 | AHNAK nucleoprotein 2 | BC138468 |
| Lhfpl2 | lipoma HMGIC fusion partner-like 2 | NM_172589 |
| A530099J19Rik | RIKEN cDNA A530099J19 gene | NM_175688 |
| Lrrc16a | leucine rich repeat containing 16A | NM_026825 |
| Hexb | hexosaminidase B | NM_010422 |
| Plau | plasminogen activator, urokinase | NM_008873 |
| Ear2 | eosinophil-associated, ribonuclease A family, member 2, | NM_007895 |
| Cma2 | chymase 2, mast cell | NM_001024714 |
| Ndst2 | N-deacetylase/N-sulfotransferase (heparan glucosaminyl) 2 | NM_010811 |
| Ear1 | eosinophil-associated, ribonuclease A family, member 1 | NM_007894 |
| Ear10 | eosinophil-associated, ribonuclease A family, member 10 | NM_053112 |
| Slc7a8 | solute carrier family 7 (cationic amino acid transporter, y+ system), member 8 | NM_016972 |
| Cma1 | chymase 1, mast cell | NM_010780 |
| Mcpt4 | mast cell protease 4 | NM_010779 |
| Nckap1l | NCK associated protein 1 like | NM_153505 |
| Basp1 | brain abundant, membrane attached signal protein 1 | NM_027395 |
| Ube2v2 | ubiquitin-conjugating enzyme E2 variant 2 | NM_023585, NM_001159351 |
| Sla | src-like adaptor | NM_001029841, NM_009192 |
| Rac2 | RAS-related C3 botulinum substrate 2 | NM_009008 |
| Rnd1 | Rho family GTPase 1 | NM_172612 |
| Gcet2 | germinal center expressed transcript 2 | NM_008099, NM_001159297 |
| Retnla | resistin like alpha | NM_020509 |
| Emp2 | epithelial membrane protein 2 | NM_007929 |

-continued

| Gene Symbol | Gene Name | Gene Accession Number |
| --- | --- | --- |
| Samsn1 | SAM domain, SH3 domain and nuclear localization signals, 1 | NM_023380 |
| D16Ertd472e | DNA segment, Chr 16, ERATO Doi 472, expressed | NM_001252438, NM_001252439, NM_001252440, NM_025967 |
| Prss34 | protease, serine, 34 | NM_178372 |
| Tpsb2 | tryptase beta 2 | NM_010781 |
| Pla2g7 | phospholipase A2, group VII (platelet-activating factor acetylhydrolase, plasma) | NM_013737 |
| Tpsab1 | tryptase alpha/beta 1 | NM_031187 |
| Gata6 | GATA binding protein 6 | NM_010258 |
| Entpd1 | ectonucleoside triphosphate diphosphohydrolase 1 | NM_009848 |
| Slc18a2 | solute carrier family 18 (vesicular monoamine), member 2 | NM_172523 |
| Ms4a2 | membrane-spanning 4-domains, subfamily A, member 2 | NM_013516 |
| Lass6 | LAG1 homolog, ceramide synthase 6 | NM_172856 |
| Prg2 | proteoglycan 2, bone marrow | NM_008920 |
| Cd59a, Cd59b | CD59a antigen, CD59b antigen | NM_007652, NM_001111060; NM_181858 |
| Thbs1 | thrombospondin 1 | NM_011580 |
| Snrpb2 | U2 small nuclear ribonucleoprotein B | NM_021335 |
| Creb3l1 | cAMP responsive element binding protein 3-like 1 | NM_011957 |
| Meis2 | Meis homeobox 2 | NM_010825, NM_001159567 NM_001159570, NM_001136072, NM_001159568, NM_001159569 |
| Hdc | histidine decarboxylase | NM_008230 |
| Tiparp | TCDD-inducible poly(ADP-ribose) polymerase | NM_178892 |
| Adora3 | adenosine A3 receptor | NM_001174169, NM_009631 |
| Ddah1 | dimethylarginine dimethylaminohydrolase 1 | NM_026993 |
| Cpa3 | carboxypeptidase A3, mast cell | NM_007753 |
| I830077J02Rik | RIKEN cDNA I830077J02 gene | NM_001033780 |
| Vcam1 | vascular cell adhesion molecule 1 | NM_011693 |
| Dapp1 | dual adaptor for phosphotyrosine and 3-phosphoinositides 1 | NM_011932 |
| Dhcr24 | 24-dehydrocholesterol reductase | NM_053272 |
| Laptm5 | lysosomal-associated protein transmembrane 5 | NM_010686 |
| Asph | aspartate-beta-hydroxylase | NM_001177849, NM_001177850, NM_001177852, NM_023066 NM_001177853, NM_001177854 |
| Kit | kit oncogene | NM_021099, NM_001122733 |
| Ppbp | pro-platelet basic protein | NM_023785 |
| P2rx4 | purinergic receptor P2X, ligand-gated ion channel 4 | NM_011026 |
| Hs3st1 | heparan sulfate (glucosamine) 3-O-sulfotransferase 1 | NM_010474 |
| Cxcl10 | chemokine (C—X—C motif) ligand 10 | NM_021274 |
| Cmklr1 | chemokine-like receptor 1 | NM_008153 |
| Lat2 | linker for activation of T cells family, member 2 | NM_022964, NM_020044 |
| Eln | elastin | NM_007925 |
| Pilra | paired immunoglobin-like type 2 receptor alpha | NM_153510 |
| Aqp1 | aquaporin 1 | NM_007472 |
| BC005685 | cDNA sequence BC005685 | BC005685 |
| Gp9 | glycoprotein 9 (platelet) | NM_018762 |
| Fbln2 | fibulin 2 | NM_007992, NM_001081437 |
| Mitf | microphthalmia-associated transcription factor | NM_001178049, NM_008601, NM_001113198 |

| Gene Symbol | Gene Name | Gene Accession Number |
| --- | --- | --- |
| Slc6a12 | solute carrier family 6 (neurotransmitter transporter, betaine/GABA), member 12 | NM_133661 |
| Emp1 | epithelial membrane protein 1 | NM_010128 |
| Dnahc6 | dynein, axonemal, heavy chain 6 | NM_001164669 |
| Alox5 | arachidonate 5-lipoxygenase | NM_009662 |
| Prss23 | protease, serine, 23 | NM_029614 |
| Prkcb | protein kinase C, beta | NM_008855 |
| Cd33 | CD33 antigen | NM_001111058, NM_021293 |
| Tph1 | tryptophan hydroxylase 1 | NM_009414, NM_001136084 |
| Mrgprb1 | MAS-related GPR, member B1 | NM_205810 |
| Mrgprb2 | MAS-related GPR, member B2 | NM_175531 |
| Capn5 | calpain 5 | NM_007602 |
| Rgs10 | regulator of G-protein signalling 10 | NM_026418 |
| 4930467E23Rik | RIKEN cDNA 4930467E23 gene | NM_001039553, NM_001177408 |
| Mt2 | metallothionein 2 | NM_008630 |
| 4930467E23Rik | | NM_001039553.2 |
| Slc7a5 | solute carrier family 7 (cationic amino acid transporter, y+ system), member 5 | NM_011404 |
| Casp4 | caspase 4, apoptosis-related cysteine peptidase | NM_007609 |
| Vwa5a | von Willebrand factor A domain containing 5A | NM_172767, NM_001145957 |
| Cyp11a1 | cytochrome P450, family 11, subfamily a, polypeptide 1 | NM_019779 |
| Rab27a | RAB27A, member RAS oncogene family | NM_023635 |
| Fam46a | family with sequence similarity 46, member A | NM_001160378, NM_001160379 |
| Mras | muscle and microspikes RAS | NM_008624 |
| Cmtm7 | CKLF-like MARVEL transmembrane domain containing 7 | NM_133978, NM_001252479 |
| Tarm1 | T cell-interacting, activating receptor on myeloid cells 1 | NM_177363 |
| Atp1b3 | ATPase, Na+/K+ transporting, beta 3 polypeptide | NM_007502 |
| Maob | monoamine oxidase B | NM_172778 |
| Sly | Sycp3 like Y-linked | NM_201530.2 |
| 5830405N20Rik | RIKEN cDNA for 5830405N20 gene | BC064065 |

Table 3B—Genes over-represented in V-EC unique to adipose tissue (134 genes)

Tnfrsf11a, Slc45a3, Mpz, Neurl3, Hmcn1, Dnm3os, Fmo2, Psen2, Icosl, Dcn, Osbpl8, Samd5, Lyz2, Tbc1d30, Aebp1, Tmem98, Ccl2, Slfn2, Igfbp4, Arl4d, Plek, Ntn1, Cxcl16, Mmp28, Itga3, Cbr2, Hif1a, Flrt2, Fkbp1b, Pqlc3, Edn1, Ogn, Hexb, Plau, Adk, Syt15, Ndst2, Gulo, Pkhd1l1, Sla, Csf2rb2, Slc2a13, Rnd1, Emp2, D16Ertd472e, Ltbp1, Dll1, Tpsab1, C3, Gata6, Snx24, Rnf165, Setbp1, Kank1, Il33, Entpd1, Marveld1, Avpi1, Olfm1, Olfml2a, Lass6, Thbs1, Dusp2, Lcn2, Ptprj, Ptprj, Creb3l1, Meis2, Gatm, Hdc, Lrrn4, Sulf2, Kcnb1, Zfp931, Tbl1xr1, Tbl1xr1, Lhfp, Them5, Adora3, Ddah1, Csf1, Dapp1, Lphn2, Runx1t1, Laptm5, Ptafr, Megf6, Ptpn3, Agtrap, Kit, P2rx4, Upk3b, Lfng, Hs3st1, Bend4, Cmklr1, Trpv4, Eln, Chn2, Aqp1, Mmrn1, Capg, Fbln2, Hrh1, Cd9, Kcne3, Slco3a1, Prss23, Oat, Ctsd, Camsap3, Enpp6, Tm6sf2, Cpne2, Stox2, Stox2, Adamts18, Kirrel3, Cdon, Vwa5a, Olfr920, Calml4, Sh3bgrl2, Itga9, Myrip, St3gal4, Snx33, Tln2, Fam46a, Gria3, Cybb, Maob, and L1cam.

| Gene Symbol | Gene Name | Gene Accession Number |
| --- | --- | --- |
| Tnfrsf11a | tumor necrosis factor receptor superfamily, member 11a | NM_009399 |
| Slc45a3 | solute carrier family 45, member 3 | NM_001177628, NM_145977 |
| Mpz | myelin protein zero | NM_008623 |
| Neurl3 | neuralized homolog 3 homolog (*Drosophila*) | NM_153408 |
| Hmcn1 | hemicentin 1 | NM_001024720 |
| Dnm3os | dynamin 3, opposite strand | NR_002870 |
| Fmo2 | flavin containing monooxygenase 2 | NM_018881 |
| Psen2 | presenilin 2 | NM_011183, NM_001128605 |
| Icosl | icos ligand | NM_015790 |
| Dcn | decorin | NM_001190451, NM_007833 |

-continued

| Gene Symbol | Gene Name | Gene Accession Number |
|---|---|---|
| Osbpl8 | oxysterol binding protein-like 8 | NM_001003717, NM_175489 |
| Samd5 | sterile alpha motif domain containing 5 | NM_177271 |
| Lyz2 | lysozyme 2 | NM_017372 |
| Tbc1d30 | TBC1 domain family, member 30 | NM_029057 |
| Aebp1 | AE binding protein 1 | NM_009636 |
| Tmem98 | transmembrane protein 98 | NM_029537 |
| Ccl2 | chemokine (C-C motif) ligand 2 | NM_011333 |
| Slfn2 | schlafen 2 | NM_011408 |
| Igfbp4 | insulin-like growth factor binding protein 4 | NM_010517 |
| Arl4d | ADP-ribosylation factor-like 4D | NM_025404 |
| Plek | pleckstrin | NM_019549 |
| Ntn1 | netrin 1 | NM_008744 |
| Cxcl16 | chemokine (C—X—C motif) ligand 16 | NM_023158 |
| Mmp28 | matrix metallopeptidase 28 (epilysin) | NM_080453, NM_172797 |
| Itga3 | integrin alpha 3 | NM_013565 |
| Cbr2 | carbonyl reductase 2 | NM_007621 |
| Hif1a | hypoxia inducible factor 1, alpha subunit | NM_010431 |
| Flrt2 | fibronectin leucine rich transmembrane protein 2 | NM_201518 |
| Fkbp1b | FK506 binding protein 1b | NM_016863 |
| Pqlc3 | PQ loop repeat containing | NM_172574, NM_001161111 |
| Edn1 | endothelin 1 | NM_010104 |
| Ogn | osteoglycin | NM_008760 |
| Hexb | hexosaminidase B | NM_010422 |
| Plau | plasminogen activator, urokinase | NM_008873 |
| Adk | adenosine kinase | NM_001243041, NM_134079 |
| Syt15 | synaptotagmin XV | NM_176931, NM_181529 |
| Ndst2 | N-deacetylase/N-sulfotransferase (heparan glucosaminyl) 2 | NM_010811 |
| Gulo | gulonolactone (L-) oxidase | NM_178747 |
| Pkhd1l1 | polycystic kidney and hepatic disease 1-like 1 | NM_138674 |
| Sla | src-like adaptor | NM_009192, NM_001029841 |
| Csf2rb2 | colony stimulating factor 2 receptor, beta 2, low-affinity (granulocyte-macrophage) | NM_007781 |
| Slc2a13 | solute carrier family 2 (facilitated glucose transporter), member 13 | NM_001033633 |
| Rnd1 | Rho family GTPase 1 | NM_172612 |
| Emp2 | epithelial membrane protein 2 | NM_007929 |
| D16Ertd472e | DNA segment, Chr 16, ERATO Doi 472, expressed | NM_001252438, NM_001252439, NM_001252440, NM_025967 |
| Ltbp1 | latent transforming growth factor beta binding protein 1 | NM_019919, NM_206958 |
| Dll1 | delta-like 1 (*Drosophila*) | NM_007865 |
| Tpsab1 | tryptase alpha/beta 1 | NM_031187 |
| C3 | complement component 3 | NM_009778 |
| Gata6 | GATA binding protein 6 | NM_010258 |
| Snx24 | sorting nexing 24 | NM_029394 |
| Rnf165 | ring finger protein 165 | NM_001164504 |
| Setbp1 | SET binding protein 1 | NM_053099 |
| Kank1 | KN motif and ankyrin repeat domains 1 | NM_181404 |
| Il33 | interleukin 33 | NM_001164724, NM_133775 |
| Entpd1 | ectonucleoside triphosphate diphosphohydrolase 1 | NM_009848 |
| Marveld1 | MARVEL (membrane-associating) domain containing 1 | NM_183195 |
| Avpi1 | arginine vasopressin-induced 1 | NM_027106 |
| Olfm1 | olfactomedin 1 | NM_019498, NM_001038613 |
| Olfml2a | olfactomedin-like 2A | NM_172854 |
| Lass6 | LAG1 homolog, ceramide synthase 6 | NM_172856 |
| Thbs1 | thrombospondin 1 | NM_011580 |
| Dusp2 | dual specificity phosphatase 2 | NM_010090 |
| Lcn2 | lipocalin 2 | NM_008491 |
| Ptprj | protein tyrosine phosphatase, receptor type, J | NM_001135657, NM_008982 |
| Ptprj | protein tyrosine phosphatase, receptor type, J | NM_008982, NM_001135657 |
| Creb3l1 | cAMP responsive element binding protein 3-like 1 | NM_011957 |
| Meis2 | Meis homeobox 2 | NM_010825, NM_001159570, NM_001159567, |

-continued

| Gene Symbol | Gene Name | Gene Accession Number |
| --- | --- | --- |
| | | NM_001159569, NM_001159568, NM_001136072 |
| Gatm | glycine amidinotransferase (L-arginine:glycine amidinotransferase) | NM_025961 |
| Hdc | histidine decarboxylase | NM_008230 |
| Lrrn4 | leucine rich repeat neuronal 4 | NM_177303 |
| Sulf2 | sulfatase 2 | NM_001252579, NM_001252578, NM_028072 |
| Kcnb1 | potassium voltage gated channel, Shab-related subfamily, member 1 | NM_008420 |
| Zfp931 | zinc finger protein 931 | NM_001162922 |
| Tbl1xr1 | transducin (beta)-like 1X-linked receptor 1 | NM_030732 |
| Tbl1xr1 | transducin (beta)-like 1X-linked receptor 1 | NM_030732 |
| Lhfp | lipoma HMGIC fusion partner | NM_175386 |
| Them5 | thioesterase superfamily member 5 | NM_025416 |
| Adora3 | adenosine A3 receptor | NM_009631 |
| Ddah1 | dimethylarginine dimethylaminohydrolase 1 | NM_026993 |
| Csf1 | colony stimulating factor 1 (macrophage) | NM_001113530, NM_001113529, NM_007778 |
| Dapp1 | dual adaptor for phosphotyrosine and 3-phosphoinositides 1 | NM_011932 |
| Lphn2 | latrophilin 2 | NM_001081298 |
| Runx1t1 | runt-related transcription factor 1; translocated to, 1 (cyclin D-related) | NM_009822, NM_001111027, NM_001111026 |
| Laptm5 | lysosomal-associated protein transmembrane 5 | NM_010686 |
| Ptafr | platelet-activating factor receptor | NM_001081211 |
| Megf6 | multiple EGF-like-domains 6 | NM_001162977 |
| Ptpn3 | protein tyrosine phosphatase, non-receptor type 3 | NM_011207 |
| Agtrap | angiotensin II, type I receptor-associated protein | NM_009642 |
| Kit | kit oncogene | NM_001122733, NM_021099 |
| P2rx4 | purinergic receptor P2X, ligand-gated ion channel 4 | NM_011026 |
| Upk3b | uroplakin 3B | NM_175309 |
| Lfng | LFNG O-fucosylpeptide 3-beta-N-acetylglucosaminyltransferase | NM_008494 |
| Hs3st1 | heparan sulfate (glucosamine) 3-O-sulfotransferase 1 | NM_010474 |
| Bend4 | BEN domain containing 4 | NM_001164806 |
| Cmklr1 | chemokine-like receptor 1 | NM_008153 |
| Trpv4 | transient receptor potential cation channel, subfamily V, member 4 | NM_022017 |
| Eln | elastin | NM_007925 |
| Chn2 | chimerin (chimaerin) 2 | NM_023543, NM_001163640 |
| Aqp1 | aquaporin 1 | NM_007472 |
| Mmrn1 | multimerin 1 | NM_001163507, NM_027613 |
| Capg | capping protein (actin filament), gelsolin-like | NM_007599, NM_001042534 |
| Fbln2 | fibulin 2 | NM_007992, NM_001081437 |
| Hrh1 | histamine receptor H1 | NM_001252642, NM_001252643, NM_008285 |
| Cd9 | CD9 antigen | NM_007657 |
| Kcne3 | potassium voltage-gated channel, Isk-related subfamily, gene 3 | NM_001190871, NM_001190869, NM_001190950, NM_020574, NM_001190870 |
| Slco3a1 | solute carrier organic anion transporter family, member 3a1 | NM_023908, NM_001038643 |
| Prss23 | protease, serine, 23 | NM_029614 |
| Oat | ornithine aminotransferase | NM_016978 |
| Ctsd | cathepsin D | NM_009983 |
| Camsap3 | calmodulin regulated spectrin-associated protein family, member 3 | NM_001163749, NM_027171 |
| Enpp6 | ectonucleotide pyrophosphatase/phosphodiesterase 6 | NM_177304 |
| Tm6sf2 | transmembrane 6 superfamily member 2 | NM_181540 |
| Cpne2 | copine II | NM_153507 |

| Gene Symbol | Gene Name | Gene Accession Number |
| --- | --- | --- |
| Stox2 | storkhead box 2 | NM_175162, NM_001114311 |
| Stox2 | storkhead box 2 | NM_001114311, NM_175162 |
| Adamts18 | a disintegrin-like and metallopeptidase (reprolysin type) with thrombospondin type 1 motif, 18 | NM_172466 |
| Kirrel3 | kin of IRRE like 3 (Drosophila) | NM_001190911, NM_001190912, NM_026324, NM_001190914, NM_001190913 |
| Cdon | cell adhesion molecule-related/down-regulated by oncogenes | NM_021339 |
| Vwa5a | von Willebrand factor A domain containing 5A | NM_001145957, NM_172767 |
| Olfr920 | olfactory receptor 920 | NM_146787 |
| Calml4 | calmodulin-like 4 | NM_001102468, NM_138304 |
| Sh3bgrl2 | SH3 domain binding glutamic acid-rich protein like 2 | NM_172507 |
| Itga9 | integrin alpha 9 | NM_133721 |
| Myrip | myosin VIIA and Rab interacting protein | NM_144557 |
| St3gal4 | ST3 beta-galactoside alpha-2,3-sialyltransferase 4 | NM_009178 |
| Snx33 | sorting nexin 33 | NM_175483 |
| Tln2 | talin 2 | NM_001081242 |
| Fam46a | family with sequence similarity 46, member A | NM_001160379, NM_001160378 |
| Gria3 | glutamate receptor, ionotropic, AMPA3 (alpha 3) | NM_016886 |
| Cybb | cytochrome b-245, beta polypeptide | NM_007807 |
| Maob | monoamine oxidase B | NM_172778 |
| L1cam | L1 cell adhesion molecule | NM_008478 |

FIG. 21B shows a network analysis of over-represented genes that are uniquely expressed in V-ECs compared to NV-ECs of adipose tissue, indicating potential relationships among these genes.

Table 4 below lists genes over-represented in V-EC unique to lymph node. As used herein, "Table 4" includes Table 4A and Table 4B below.

Table 4A—Genes over-represented in V-EC unique to lymph node (157 genes)

Rdh10, Ly96, Cyp27a1, Ogfrl1, Ddr2, Trdn, Slc16a9, Madcam1, Man1a, Syt1, Xbp1, Gm2a, Nefh, Ccng1, Doc2b, Serpina3n, Klhl29, Ltbp2, Serpina1b, Serpina1a, Serpina1e, Serpinb9, Ctla2a, Cts1, Gm3002, Gm8635, Trav13d-4, Clu, ENSMUSG00000068790, Gm10406, Gm3696, 4930555G01Rik, Gm5458, Oit1, 1700054O19Rik, Itih3, Gm8165, Sema5a, Pgcp, Laptm4b, Pde1b, Enpp2, Ly6i, Celsr1, Glycam1, Robo1, Krtap20-2, Gm7735, Bace2, AU021092, Ubd, Pisd-ps2, Kcng3, Dsg2, Camk4, Tmx3, Cdh2, B4galt6, Tmem173, Ms4a6b, Gcnt1, Gm10851, Plxdc2, Fut7, Abca2, Dapl1, Chst1, Lpcat4, Snap23, Psp, BC018465, Tfpi, Gm13051, Dclk1, Hmgcs2, Dennd2d, Dram2, Adh1, Fam46c, Cept1, Fnbpl1, Ndst3, Gm3893, Ccl21a, 4933409K07Rik, Ugcg, Gm3579, Rex2, Extl1, 1700029I01Rik, Speer4d, Speer8-ps1, Cpeb2, Pcdh7, Wbscr27, Speer4e, 5031410I06Rik, Rbm47, A430089I19Rik, Naaa, Sh2b2, Nxph1, Met, C1rb, Mir680-1, Timp4, C1s, Vmn2r43, Gm3994, Slc1a5, Pglyrp1, Sh3gl3, Prcp, Nucb2, Olfr538, Apoe, Vmn1r118, Snord115, Snord116, Mfge8, Lyve1, Sult1a1, Ccnd1, Man2b1, Ces2g, Zfp612, Angpt2, Il15, Il27ra, Chst4, Pvrl1, Ubl7, Stra6, Birc2, Sc5d, Fam55b, Tspan3, Tspan7, Ar, Uprt, Sh3bgrl, Mir680-2, F8, Il2rg, Srsy, LOC100504530, Ssty1, LOC665698, LOC665746, LOC665128, LOC100039753, LOC100040235.

| Gene Symbol | Gene Name | Gene Accession Number |
| --- | --- | --- |
| Rdh10 | retinol dehydrogenase 10 (all-trans) | NM_133832 |
| Ly96 | lymphocyte antigen 96 | NM_016923, NM_001159711 |
| Cyp27a1 | cytochrome P450, family 27, subfamily a, polypeptide 1 | NM_024264 |
| Ogfrl1 | opioid growth factor receptor-like 1 | NM_001081079 |
| Ddr2 | discoidin domain receptor family, member 2 | NM_022563 |
| Trdn | Triadin | NM_029726.2 |
| Slc16a9 | solute carrier family 16 (monocarboxylic acid transporters), member 9 | NM_025807 |
| Madcam1 | mucosal vascular addressin cell adhesion molecule 1 | NM_013591 |
| Man1a | mannosidase 1, alpha | NM_008548 |
| Syt1 | synaptotagmin I | NM_001252342, NM_001252341, NM_009306 |

| Gene Symbol | Gene Name | Gene Accession Number |
|---|---|---|
| Xbp1 | X-box binding protein 1 | NM_013842 |
| Gm2a | GM2 ganglioside activator protein | NM_010299 |
| Nefh | neurofilament, heavy polypeptide | NM_001243043, NM_010904 |
| Ccng1 | cyclin G1 | NM_009831 |
| Doc2b | double C2, beta | NM_007873 |
| Serpina3n | serine (or cysteine) peptidase inhibitor, clade A, member 3N | NM_009252 |
| Klhl29 | kelch-like 29 (*Drosophila*) | NM_001164493 |
| Ltbp2 | latent transforming growth factor beta binding protein 2 | NM_013589 |
| Serpina1b | serine (or cysteine) preptidase inhibitor, clade A, member 1B | NM_009244 |
| Serpina1a | serine (or cysteine) peptidase inhibitor, clade A, member 1A | NM_001252569, NM_009243 |
| Serpina1e | serine (or cysteine) peptidase inhibitor, clade A, member 1E | NM_009247 |
| Serpinb9 | serine (or cysteine) peptidase inhibitor, clade B, member 9 | NM_009256 |
| Ctla2a | cytotoxic T lymphocyte-associated protein 2 alpha | NM_007796, NM_001145799 |
| Ctsl | cathepsin L | NM_009984 |
| Gm3002 | predicted gene 3002, alpha-takusan pseudogene | NR_033388.1 |
| Gm10406, Gm10409,, Gm3373, Gm8635 Trav13d-4 | predicted gene 10406, predicted gene 10409, predicted gene 3373 | NM_001164727; NR_033121; XR_105595, XR_142386 ENSMUST00000103569 AY029362 |
| Clu | clusterin | NM_013492 |
| Gm3500, LOC100861646, Gm3685, Gm5458 | predicted gene 3500, uncharacterized LOC100861646, predicted gene 3685, predicted gene 5458 | NM_001256886, XM_003688920, XM_003688921, XM_001477746, XM_001477780; ENSMUST00000096121, NM_001024706 |
| Gm3696,, | predicted gene 3696, | NM_001024712, ENSMUST00000166509 |
| Gm10340, Gm5796, Gm2897 | predicted gene 10340, predicted gene 5796, predicted gene 2897 | XM_003945525, XM_003688913, XM_003688911, XM_003688910;, NM_001029930; NM_001177715, NM_001177714 |
| , 4930555G01Rik, , LOC100861615, Oit1 1700054O19Rik | RIKEN cDNA 4930555G01 gene, uncharacterized LOC100861615 oncoprotein induced transcript 1 | , NM_175393; NM_001270812, NM_146050 XR_106491.1 |
| Itih3 | inter-alpha trypsin inhibitor, heavy chain 3 | NM_008407 |
| Gm8165 | Predicted gene 8165 | XM_984613.2 |
| Sema5a | sema domain, seven thrombospondin repeats (type 1 and type 1-like), transmembrane domain (TM) and short cytoplasmic domain, (semaphorin) 5A | NM_009154 |
| Pgcp | plasma glutamate carboxypeptidase | NM_018755, NM_176073 |
| Laptm4b | lysosomal-associated protein transmembrane 4B | NM_033521 |
| Pde1b | phosphodiesterase 1B, Ca2+-calmodulin dependent | NM_008800 |
| Enpp2 | ectonucleotide pyrophosphatase/phosphodiesterase 2 | NM_015744, NM_001136077 |
| Ly6i | lymphocyte antigen 6 complex, locus I | NM_020498 |
| Celsr1 | cadherin, EGF LAG seven-pass G-type receptor 1 (flamingo homolog, *Drosophila*) | NM_009886 |
| Glycam1 | glycosylation dependent cell adhesion molecule 1 | NM_008134 |
| Robo1 | roundabout homolog 1 (*Drosophila*) | NM_019413 |
| Krtap20-2 | keratin associated protein 20-2 | NM_001163615.1 |
| Gm7735 | Predicted gene 7735 | ENSMUST00000062524, ENSMUST00000089098 |

-continued

| Gene Symbol | Gene Name | Gene Accession Number |
|---|---|---|
| Bace2 | beta-site APP-cleaving enzyme 2 | NM_019517 |
| AU021092 | expressed sequence AU021092 | NM_001033220 |
| Ubd | ubiquitin D | NM_023137 |
| Pisd-ps2 | phosphatidylserine decarboxylase, pseudogene 2 | NR_003519 |
| Kcng3 | potassium voltage-gated channel, subfamily G, member 3 | NM_153512 |
| Dsg2 | desmoglein 2 | NM_007883 |
| Camk4 | calcium/calmodulin-dependent protein kinase IV | NM_009793 |
| Tmx3 | thioredoxin-related transmembrane protein 3 | NM_198295 |
| Cdh2 | cadherin 2 | NM_007664 |
| B4galt6 | UDP-Gal:betaGlcNAc beta 1,4-galactosyltransferase, polypeptide 6 | NM_019737 |
| Tmem173 | transmembrane protein 173 | NM_028261 |
| Ms4a6b | membrane-spanning 4-domains, subfamily A, member 6B | NM_027209 |
| Gcnt1 | glucosaminyl (N-acetyl) transferase 1, core 2 | NM_010265, NM_173442, NM_001136484 |
| Gm10851 | predicted gene 10851 | XR_107337 |
| Plxdc2 | plexin domain containing 2 | NM_026162 |
| Fut7 | fucosyltransferase 7 | NM_013524, NM_001177366 NM_001177367 |
| Abca2 | ATP-binding cassette, sub-family A (ABC1), member 2 | NM_007379 |
| Dapl1 | death associated protein-like 1 | NM_029723 |
| Chst1 | carbohydrate (keratan sulfate Gal-6) sulfotransferase 1 | NM_023850 |
| Lpcat4 | lysophosphatidylcholine acyltransferase 4 | NM_207206 |
| Snap23 | synaptosomal-associated protein 23 | NM_009222, NM_001177792 NM_001177793 |
| Bpifa2 | BPI fold containing family A, member 2 | NM_008953 |
| Bpifb5 | BPI fold containing family B, member 5 | NM_144890 |
| Tfpi | tissue factor pathway inhibitor | NM_001177319, NM_011576 NM_001177320 |
| Gm13051, Zfp534 (plus variants 1-5) | predicted gene 13051, zinc finger protein 534 | NM_001037926; NM_001127188, XM_003945683, XM_003945682, XM_003945681, XM_003945680, XM_003945679, XM_003946409 |
| Dclk1 | doublecortin-like kinase 1 | NM_001111052, NM_019978, NM_001111051 NM_001111053, NM_001195538, NM_001195539 |
| Hmgcs2 | 3-hydroxy-3-methylglutaryl-Coenzyme A synthase 2 | NM_008256 |
| Dennd2d | DENN/MADD domain containing 2D | NM_001093754, NM_028110 |
| Dram2 | DNA-damage regulated autophagy modulator 2 | NM_026013 NM_001025582 |
| Adh1 | alcohol dehydrogenase 1 (class I) | NM_007409 |
| Fam46c | family with sequence similarity 46, member C | NM_001142952 |
| Fnbp1l | formin binding protein 1-like | NM_153118, NM_001114665 |
| Ndst3 | N-deacetylase/N-sulfotransferase (heparan glucosaminyl) 3 | NM_031186 |
| Gm3893 | predicted gene 3893 | NR_033506 |
| Ccl21a | chemokine (C-C motif) ligand 21A (serine) | NM_011124 |
| 4933409K07Rik | RIKEN cDNA 4933409K07 gene | NR_033123 |
| Ugcg | UDP-glucose ceramide glucosyltransferase | NM_011673 |
| Gm3579 | predicted gene 3579 | FJ654104 |
| Rex2, Gm13242, Gm13247, LOC100862458 (withdrawn), LOC673430 (withdrawn), Zfp600 | reduced expression 2, predicted gene 13242, predicted gene 13247, zinc finger protein 600 | NM_001177767; NM_001103158; NM_001243138, NM_001243139; NM_001177545,, NM_001177546 |

-continued

| Gene Symbol | Gene Name | Gene Accession Number |
| --- | --- | --- |
| Extl1 | exostoses (multiple)-like 1 | NM_019578 |
| 1700029I01Rik, Gm13251, Gm13139 | RIKEN cDNA 1700029I01 gene (pseudogene Znf41-ps), predicted gene 13251, predicted gene 13139 | NR_040355; NM_001085522; NM_001083918, |
| Speer4e, Gm17019, Speer4d, LOC100861621 (plus variants), Speer4c, Gm10471, Gm9758, 4930572O03Rik | spermatogenesis associated glutamate (E)-rich protein 4e, predicted gene 17019, spermatogenesis associated glutamate (E)-rich protein 4d, disks large homolog 5-like, spermatogenesis associated glutamate (E)-rich protein 4c, predicted gene 10471, predicted gene 9758, spermatogenesis associated glutamate (E)-rich protein pseudogene | NM_001122661; NM_182957; NM_025759; XM_003946463, XM_003946462, XM_003688811, XM_003688810; NM_198666; NR_073011 NM_001177579; |
| Speer8-ps1, Speer7-ps1 | spermatogenesis associated glutamate (E)-rich protein 8, pseudogene 1, spermatogenesis associated glutamate (E)-rich protein 7, pseudogene 1 | , NR_001584; NR_001585 |
| Cpeb2 | cytoplasmic polyadenylation element binding protein 2 | NM_001177379, NM_175937 |
| Pcdh7 | protocadherin 7 | NM_001122758, NM_018764 |
| Wbscr27 | Williams Beuren syndrome chromosome region 27 (human) | NM_024479 |
| , LOC100862368 LOC100862359, Gm1979, Speer4a, Speer4b, Gm10220, 5031410I06Rik | disks large homolog 5-like, disks large homolog 5-like, predicted gene 1979, spermatogenesis associated glutamate (E)-rich protein 4a, spermatogenesis associated glutamate (E)-rich protein 4b, predicted gene 10220, RIKEN cDNA 5031410I06 gene | XM_003688808; XM_003688807; XM_003946425, XM_001471959; NM_029376; NM_028561; NM_001134299; NM_207657;, |
| Rbm47 | RNA binding motif protein 47 | NM_178446, NM_139065, NM_001127382 |
| BC080696, A430089I19Rik | cDNA sequence BC080696, RIKEN cDNA A430089I19 gene | NM_177913 |
| Naaa | N-acylethanolamine acid amidase | NM_025972, NM_001163687 |
| Sh2b2 | SH2B adaptor protein 2 | NM_018825 |
| Nxph1 | neurexophilin 1 | NM_008751 |
| Nxph1 | neurexophilin 1 | ENSMUST00000162942 |
| Met | met proto-oncogene | NM_008591 |
| C1ra, C1rb | complement component 1, r subcomponent A, complement component 1, r subcomponent B | NM_023143, NM_001113356 |
| Mir680-1 | microRNA 680-1 | NR_030447 |
| Timp4 | tissue inhibitor of metalloproteinase 4 | NM_080639 |
| C1s, Gm5077 | complement component 1, s subcomponent, predicted gene 5077 | NM_144938, NM_001097617; NM173864 |
| Vmn2r43, Vmn2r31, Vmn2r35, Vmn2r39, Vmn2r50, Vmn2r44 | vomeronasal 2, receptor 43, vomeronasal 2, receptor 31, vomeronasal 2, receptor 35, vomeronasal 2, receptor 39, vomeronasal 2, receptor 50, vomeronasal 2, receptor 44 | NM_198961; NM_001105062; NM_001105067; NM_001105071; NM_001105178; NM_001105074 |
| Gm3994 | predicted gene 3994 | NC_000073.6 |
| Slc1a5 | solute carrier family 1 (neutral amino acid transporter), member 5 | NM_009201 |
| Pglyrp1 | peptidoglycan recognition protein 1 | NM_009402 |
| Sh3gl3 | SH3-domain GRB2-like 3 | NM_017400 |
| Prcp | prolylcarboxypeptidase (angiotensinase C) | NM_028243 |
| Nucb2 | nucleobindin 2 | NM_016773, NM_001130479 |
| Olfr46, Olfr538 | olfactory receptor 46, olfactory receptor 538 | NM_146934; NM_001011867 |
| Apoe | apolipoprotein E | NM_009696 |
| Vmn1r118 | predicted vomeronasal 1 receptor 118 | NM_001166742 |

-continued

| Gene Symbol | Gene Name | Gene Accession Number |
|---|---|---|
| Snord115 | Small nucleolar RNA, C/D Box 115 cluster | MGI: 3510326 |
| Snord116 | small nucleolar RNA, C/D box 116 | AF241256 |
| Mfge8 | milk fat globule-EGF factor 8 protein | NM_008594, NM_001045489 |
| Lyve1 | lymphatic vessel endothelial hyaluronan receptor 1 | NM_053247 |
| Sult1a1 | sulfotransferase family 1A, phenol-preferring, member 1 | NM_133670 |
| Ccnd1 | cyclin D1 | NM_007631 |
| Man2b1 | mannosidase 2, alpha B1 | NM_010764 |
| Ces2g | carboxylesterase 2G | NM_197999 |
| Zfp612 | zinc finger protein 612 | NM_175480 |
| Angpt2 | angiopoietin 2 | NM_007426 |
| Il15 | interleukin 15 | NM_008357, NM_001254747 |
| Il27ra | interleukin 27 receptor, alpha | NM_016671 |
| Chst4 | carbohydrate (chondroitin 6/keratan) sulfotransferase 4 | NM_011998 |
| Pvrl1 | poliovirus receptor-related 1 | NM_021424 |
| Ubl7 | ubiquitin-like 7 (bone marrow stromal cell-derived) | NM_027086, NM_001122873 |
| Stra6 | stimulated by retinoic acid gene 6 | NM_001162476, NM_009291 NM_001162475, NM_001162479 |
| Birc2 | baculoviral IAP repeat-containing 2 | NM_007465 |
| Sc5d | sterol-C5-desaturase (fungal ERG3, delta-5-desaturase) homolog (S. cerevisae) | NM_172769 |
| Fam55b | family with sequence similarity 55, member B | NM_030069 |
| Tspan3 | tetraspanin 3 | NM_019793 |
| Tspan7 | tetraspanin 7 | NM_019634 |
| Ar | androgen receptor | NM_013476 |
| Uprt | uracil phosphoribosyltransferase (FUR1) homolog (S. cerevisiae) | NM_001081189 |
| Sh3bgrl | SH3-binding domain glutamic acid-rich protein like | NM_019989 |
| Mir680-2 | microRNA 680-2 | NR_030448 |
| F8 | coagulation factor VIII | NM_007977, NM_001161373 NM_001161374 |
| Il2rg | interleukin 2 receptor, gamma chain | NM_013563 |
| ENSMUSG00000068790 | Predicted ENSMUSG00000068790 gene | BC093494 |
| PSP | Paratoid secretory protein mRNA fragment | X01697 |
| BC018465 | cDNA sequence | |
| Cept1 | | |

Table 4B—Genes over-represented in V-EC unique to lymph node (259 genes)

Rdh10, Ly96, Xrcc5, Cyp27a1, Tfcp2l1, Faim3, Ptgs2, Astn1, Sell, Aim2, Esrrg, Stau2, march4, Dock10, Dtymk, Rgs2, Dusp27, Slamf8, Slc2a12, Slc16a9, Ggt5, Madcam1, Btbd11, Mettl1, Rdh1, Rdh9, Cd63, Syt1, Ccdc88a, Gm2a, Gas7, Rtn4rl1, Gm11428, Naglu, Sphk1, Nefh, Olfr1372-ps1, Ccr7, Cd79b, Ern1, Meox2, Tshr, Serpina3f, Serpina3h, Serpina3n, Klhl29, Ltbp2, Serpina1b, Serpina1d, Serpina1a///Serpina1c, Serpina1a///Serpina1e, Serpina3c, Idi1, Ly86, Elovl7, Ctsl, Itih4, Bnip3, Nfatc4, Oit1, Itih3, Ephx2, Fam134b, Dap, Sema5a, Pgcp, Laptm4b, Deptor, Sqle, Kdelr3, Pde1b, G930009F23Rik, Sntb1, Lypd2, Lynx1, Ly6i, Robo1, Cyp2ab1, Robo2, Tagap, Gm9943, H2-DMa, Ubd, Pkdcc, H2-Aa, H2-M2, Foxp4, Kcng3, Dsg2, Camk4, Cd74, Tmx3, Cdh2, Stard4, Fam13b, Tmem173, Hdac3, Slc26a2, Ms4a6b, Vldlr, Tmem180, BC021614, Fads2, Ms4a1, Loxl4, Scd1, Gm10851, Pter, Plxdc2, Entpd2, Fut7, Abca2, Lrrc8a///Phyhd1, Lhx2, Dapl1, Chst1, Lpcat4, Gchfr, Eid1, Bpifb5, C1ql3, Ptgds, Vav2, Prr5l, Rasgrp1, Flrt3, 5730471H19Rik, Cldn11, Dclk1, Mme, Tmem154, Ctss, Hmgcs2, Frrs1, Elovl6, Adh1, Pgrmc2, Slc33a1, Fam46c, Chi3l7, Gm10673, 2010016I18Rik, Cept1, Cd53, Fnbp11, Ndst3, Dnase2b, Gm13305///Gm2002///Il11ra2///Il11ra1, 4933409K07Rik, Glipr2, Galnt12, Ugcg, Dhcr24, Lao1, Rnf19b, Gm3579, Rap1gap, Gm3579, Tox, 1810030N24Rik, 4933409K07Rik///Gm3893, Gm13305///Gm2002///Il11ra2///Il11ra1, Skint10, Extl1, 2610305D13Rik, Cpeb2, N4bp2, Pf4, Pole, Rasal1, Hvcn1, Wbscr27, Daglb, Bhlha15, Rbm47, Rassf6, Naaa, Cxcl10, Cxcl11, Pxmp2, P2rx2, Ddx54, Cldn13, Nxph1, Prr15, Gfpt1, C1rl, C1ra, C1rb///C1ra, Tfpi2, Igkj1, Reg3g, Srgap3, Timp4, Zfp9, C1s, Gm5077, Arhgdib, Slc1a5, Cd79a, Nup62-il4i1///Il4i1, Sh3gl3, Prcp, Nucb2, Apoe, Hamp, Spib, Grin2d, Mfge8, Fah, Relt, Lyve1, Sult1a1, Fgfr2, Tcergl1, Bnip3, Osbpl5, Agpat5, Zdhhc2, Dctd, Man2b1, Ces2b, Ces2d-ps///Ces2c, Ces2g, Cdh3, Tat, Zfp612, Fcer2a, Csmd1, Ifi30, Neto2, Marveld3, Chst4, Cotl1, Odc1, Ldlr, Pvrl1, Pcsk7, Pou2af1, Arhgap20, Stra6, Glb1, Ccbp2, Birc2, Sc5d, Chrnb4, Tspan3, Ccdc33, Tmed3, Srprb///Trf, BY080835, Tspan7, Ssr4, Ar, Chic1, Sh3kbp1, Klhl13, F8, and Morc4.

| Gene Symbol | Gene Name | Gene Accession Number |
|---|---|---|
| Rdh10 | retinol dehydrogenase 10 (all-trans) | NM_133832 |
| Ly96 | lymphocyte antigen 96 | NM_001159711, NM_016923 |
| Xrcc5 | X-ray repair complementing defective repair in Chinese hamster cells 5 | NM_009533 |
| Cyp27a1 | cytochrome P450, family 27, subfamily a, polypeptide 1 | NM_024264 |
| Tfcp2l1 | transcription factor CP2-like 1 | NM_023755 |
| Faim3 | Fas apoptotic inhibitory molecule 3 | NM_026976 |
| Ptgs2 | prostaglandin-endoperoxide synthase 2 | NM_011198 |
| Astn1 | astrotactin 1 | NM_001205204, NM_007495 |
| Sell | selectin, lymphocyte | NM_001164059, NM_011346 |
| Aim2 | absent in melanoma 2 | NM_001013779 |
| Esrrg | estrogen-related receptor gamma | NM_001243792, NM_011935 |
| Stau2 | staufen (RNA binding protein) homolog 2 (*Drosophila*) | NM_025303, NM_001111272 |
| march4 | membrane-associated ring finger (C3HC4) 4 | NM_001045533 |
| Dock10 | dedicator of cytokinesis 10 | NM_175291 |
| Dtymk | deoxythymidylate kinase | NM_001105667, NM_023136 |
| Rgs2 | regulator of G-protein signaling 2 | NM_009061 |
| Dusp27 | dual specificity phosphatase 27 (putative) | NM_001033344, NM_001160049 |
| Slamf8 | SLAM family member 8 | NM_029084 |
| Slc2a12 | solute carrier family 2 (facilitated glucose transporter), member 12 | NM_178934 |
| Slc16a9 | solute carrier family 16 (monocarboxylic acid transporters), member 9 | NM_025807 |
| Ggt5 | gamma-glutamyltransferase 5 | NM_011820 |
| Madcam1 | mucosal vascular addressin cell adhesion molecule 1 | NM_013591 |
| Btbd11 | BTB (POZ) domain containing 11 | NM_001017525, NM_028709 |
| Mettl1 | methyltransferase like 1 | NM_010792 |
| Rdh1 | retinol dehydrogenase 1 (all trans) | NM_080436 |
| Rdh9 | retinol dehydrogenase 9 | NM_153133 |
| Cd63 | CD63 antigen | NM_001042580, NM_007653 |
| Syt1 | synaptotagmin I | NM_009306, NM_001252341, NM_001252342 |
| Ccdc88a | coiled coil domain containing 88A | NM_176841 |
| Gm2a | GM2 ganglioside activator protein | NM_010299 |
| Gas7 | growth arrest specific 7 | NM_008088, NM_001109657 |
| Rtn4rl1 | reticulon 4 receptor-like 1 | NM_177708 |
| Gm11428 | predicted gene 11428 | NM_001081957 |
| Naglu | alpha-N-acetylglucosaminidase (Sanfilippo disease IIIB) | NM_013792 |
| Sphk1 | sphingosine kinase 1 | NM_011451, NM_001172475, NM_025367, NM_001172472, NM_001172473 |
| Nefh | neurofilament, heavy polypeptide | NM_010904 |
| Olfr1372-ps1 | olfactory receptor 1372, pseudogene 1 | NR_034155 |
| Ccr7 | chemokine (C-C motif) receptor 7 | NM_007719 |
| Cd79b | CD79B antigen | NM_008339 |
| Ern1 | endoplasmic reticulum (ER) to nucleus signalling 1 | NM_023913 |
| Meox2 | mesenchyme homeobox 2 | NM_008584 |
| Tshr | thyroid stimulating hormone receptor | NM_001113404, NM_011648 |
| Serpina3f | serine (or cysteine) peptidase inhibitor, clade A, member 3F | NM_001033335, NM_001168294, NM_001168295 |
| Serpina3h | serine (or cysteine) peptidase inhibitor, clade A, member 3H | NR_033450 |
| Serpina3n | serine (or cysteine) peptidase inhibitor, clade A, member 3N | NM_009252 |
| Klhl29 | kelch-like 29 (*Drosophila*) | NM_001164493 |
| Ltbp2 | latent transforming growth factor beta binding protein 2 | NM_013589 |
| Serpina1b | serine (or cysteine) preptidase inhibitor, clade A, member 1B | NM_009244 |
| Serpina1d | serine (or cysteine) peptidase inhibitor, clade A, member 1D | NM_009246 |
| Serpina1a /// Serpina1c | serine (or cysteine) peptidase inhibitor, clade A, member 1A /// serine (or cysteine) peptidase inhibitor, clade A, member 1C | NM_009245, NM_009243, NM_001252569 |
| Serpina1a /// Serpina1e | serine (or cysteine) peptidase inhibitor, clade A, member 1A /// serine (or cysteine) peptidase inhibitor, clade A, member 1E | NM_009247, NM_009243 |
| Serpina3c | serine (or cysteine) peptidase inhibitor, clade A, member 3C | NM_008458 |
| Idi1 | isopentenyl-diphosphate delta isomerase | NM_145360 |

-continued

| Gene Symbol | Gene Name | Gene Accession Number |
|---|---|---|
| Ly86 | lymphocyte antigen 86 | NM_010745 |
| Elovl7 | ELOVL family member 7, elongation of long chain fatty acids (yeast) | NM_029001 |
| Ctsl | cathepsin L | NM_009984 |
| Itih4 | inter alpha-trypsin inhibitor, heavy chain 4 | NM_001159299, NM_018746 |
| Bnip3 | BCL2/adenovirus E1B interacting protein 3 | NM_009760 |
| Nfatc4 | nuclear factor of activated T cells, cytoplasmic, calcineurin dependent 4 | NM_001168346, NM_023699 |
| Oit1 | oncoprotein induced transcript 1 | NM_146050 |
| Itih3 | inter-alpha trypsin inhibitor, heavy chain 3 | NM_008407 |
| Ephx2 | epoxide hydrolase 2, cytoplasmic | NM_007940 |
| Fam134b | family with sequence similarity 134, member B | NM_001034851, NM_025459 |
| Dap | death-associated protein | NM_146057 |
| Sema5a | sema domain, seven thrombospondin repeats (type 1 and type 1-like), transmembrane domain (TM) and short cytoplasmic domain, (semaphorin) 5A | NM_009154 |
| Pgcp | plasma glutamate carboxypeptidase | NM_176073, NM_018755 |
| Laptm4b | lysosomal-associated protein transmembrane 4B | NM_033521 |
| Deptor | DEP domain containing MTOR-interacting protein | NM_001037937, NM_145470 |
| Sqle | squalene epoxidase | NM_009270 |
| Kdelr3 | KDEL (Lys-Asp-Glu-Leu) endoplasmic reticulum protein retention receptor 3 | NM_134090 |
| Pde1b | phosphodiesterase 1B, Ca2+-calmodulin dependent | NM_008800 |
| G930009F23Rik | RIKEN cDNA G930009F23 gene | AK145170 |
| Sntb1 | syntrophin, basic 1 | NM_016667 |
| Lypd2 | Ly6/Plaur domain containing 2 | NM_026671 |
| Lynx1 | Ly6/neurotoxin 1 | NM_011838 |
| Ly6i | lymphocyte antigen 6 complex, locus I | NM_020498 |
| Robo1 | roundabout homolog 1 (Drosophila) | NM_019413 |
| Cyp2ab1 | cytochrome P450, family 2, subfamily ab, polypeptide 1 | NM_183158 |
| Robo2 | roundabout homolog 2 (Drosophila) | NM_175549 |
| Tagap | T cell activation Rho GTPase activating protein | NM_145968 |
| Gm9943 | — | GENSCAN00000008667 |
| H2-DMa | histocompatibility 2, class II, locus DMa | NM_010386 |
| Ubd | ubiquitin D | NM_023137 |
| Pkdcc | protein kinase domain containing, cytoplasmic | NM_134117 |
| H2-Aa | histocompatibility 2, class II antigen A, alpha | NM_010378 |
| H2-M2 | histocompatibility 2, M region locus 2 | NM_008204 |
| Foxp4 | forkhead box P4 | NM_001110825, NM_001110824, NM_028767 |
| Kcng3 | potassium voltage-gated channel, subfamily G, member 3 | NM_153512 |
| Dsg2 | desmoglein 2 | NM_007883 |
| Camk4 | calcium/calmodulin-dependent protein kinase IV | NM_009793 |
| Cd74 | CD74 antigen (invariant polypeptide of major histocompatibility complex, class II antigen-associated) | NM_001042605, NM_010545 |
| Tmx3 | thioredoxin-related transmembrane protein 3 | NM_198295 |
| Cdh2 | cadherin 2 | NM_007664 |
| Stard4 | StAR-related lipid transfer (START) domain containing 4 | NM_133774 |
| Fam13b | family with sequence similarity 13, member B | NM_146084 |
| Tmem173 | transmembrane protein 173 | NM_028261 |
| Hdac3 | histone deacetylase 3 | NM_010411 |
| Slc26a2 | solute carrier family 26 (sulfate transporter), member 2 | NM_007885 |
| Ms4a6b | membrane-spanning 4-domains, subfamily A, member 6B | NM_027209 |
| Vldlr | very low density lipoprotein receptor | NM_001161420, NM_013703 |
| Tmem180 | transmembrane protein 180 | NM_029186 |
| BC021614 | cDNA sequence BC021614 | NM_144869 |
| Fads2 | fatty acid desaturase 2 | NM_019699 |
| Ms4a1 | membrane-spanning 4-domains, subfamily A, member 1 | NM_007641 |
| Loxl4 | lysyl oxidase-like 4 | NM_053083, NM_001164311 |
| Scd1 | stearoyl-Coenzyme A desaturase 1 | NM_009127 |
| Gm10851 | predicted gene 10851 | AK153745 /// XR_107337 |
| Pter | phosphotriesterase related | NM_008961 |
| Plxdc2 | plexin domain containing 2 | NM_026162 |

| Gene Symbol | Gene Name | Gene Accession Number |
|---|---|---|
| Entpd2 | ectonucleoside triphosphate diphosphohydrolase 2 | NM_009849 |
| Fut7 | fucosyltransferase 7 | NM_013524, NM_001177367 |
| Abca2 | ATP-binding cassette, sub-family A (ABC1), member 2 | NM_007379 |
| Lrrc8a /// Phyhd1 | leucine rich repeat containing 8A /// phytanoyl-CoA dioxygenase domain containing 1 | NM_172267, NM_001252570, NM_001252568, NM_001252571 |
| Lhx2 | LIM homeobox protein 2 | NM_010710 |
| Dapl1 | death associated protein-like 1 | NM_029723 |
| Chst1 | carbohydrate (keratan sulfate Gal-6) sulfotransferase 1 | NM_023850 |
| Lpcat4 | lysophosphatidylcholine acyltransferase 4 | NM_207206 |
| Gchfr | GTP cyclohydrolase I feedback regulator | NM_177157 |
| Eid1 | EP300 interacting inhibitor of differentiation 1 | NM_025613 |
| Bpifb5 | BPI fold containing family B, member 5 | NM_144890 |
| C1ql3 | C1q-like 3 | NM_153155 |
| Ptgds | prostaglandin D2 synthase (brain) | NM_008963 |
| Vav2 | vav 2 oncogene | NM_009500 |
| Prr5l | proline rich 5 like | NM_001083810, NM_175181, NM_001110849 |
| Rasgrp1 | RAS guanyl releasing protein 1 | NM_011246 |
| Flrt3 | fibronectin leucine rich transmembrane protein 3 | NM_178382, NM_001172160 |
| 5730471H19Rik | RIKEN cDNA 5730471H19 gene | AK133873 |
| Cldn11 | claudin 11 | NM_008770 |
| Dclk1 | doublecortin-like kinase 1 | NM_001111051, NM_001111052, NM_001111053, NM_001195538, NM_001195539, NM_001195540, NM_019978 |
| Mme | membrane metallo endopeptidase | NM_008604 |
| Tmem154 | transmembrane protein 154 | NM_177260 |
| Ctss | cathepsin S | NM_001267695, NM_021281 |
| Hmgcs2 | 3-hydroxy-3-methylglutaryl-Coenzyme A synthase 2 | NM_008256 |
| Frrs1 | ferric-chelate reductase 1 | NM_001113478, NM_009146 |
| Elovl6 | ELOVL family member 6, elongation of long chain fatty acids (yeast) | NM_130450 |
| Adh1 | alcohol dehydrogenase 1 (class I) | NM_007409 |
| Pgrmc2 | progesterone receptor membrane component 2 | NM_027558 |
| Slc33a1 | solute carrier family 33 (acetyl-CoA transporter), member 1 | NM_015728 |
| Fam46c | family with sequence similarity 46, member C | NM_001142952 |
| Chi3l7 | chitinase 3-like 7 | NC_000069 |
| Gm10673 | predicted gene 10673 | AK137946 |
| 2010016I18Rik | RIKEN cDNA 2010016I18 gene | ENSMUST00000164330 /// NR_033207 |
| Cept1 | choline/ethanolaminephosphotransferase 1 | NM_133869 |
| Cd53 | CD53 antigen | NM_007651 |
| Fnbp1l | formin binding protein 1-like | NM_001114665, NM_153118 |
| Ndst3 | N-deacetylase/N-sulfotransferase (heparan glucosaminyl) 3 | NM_031186 |
| Dnase2b | deoxyribonuclease II beta | NM_019957 |
| Gm13305 /// Gm2002 /// Il11ra2 /// Il11ra1 | predicted gene 13305 /// predicted gene 2002 /// interleukin 11 receptor, alpha chain 2 /// interleukin 11 receptor, alpha chain 1 | NM_001099348, NM_010549, NM_010550, NM_001163401, NM_001172054 |
| 4933409K07Rik | RIKEN cDNA 4933409K07 gene | NR_033123 |
| Glipr2 | GLI pathogenesis-related 2 | NM_027450 |
| Galnt12 | UDP-N-acetyl-alpha-D-galactosamine:polypeptide N-acetylgalactosaminyltransferase 12 | NM_172693 |
| Ugcg | UDP-glucose ceramide glucosyltransferase | NM_011673 |
| Dhcr24 | 24-dehydrocholesterol reductase | NM_053272 |
| Lao1 | L-amino acid oxidase 1 | NM_133892 |
| Rnf19b | ring finger protein 19B | NM_029219 |
| Gm3579 | predicted gene 3579 | BC066867 |
| Rap1gap | Rap1 GTPase-activating protein | NM_029563, NM_001256218, NM_001081155 |
| Gm3579 | — | AY140895 |
| Tox | thymocyte selection-associated high mobility group box | NM_145711 |
| 1810030N24Rik | RIKEN cDNA 1810030N24 gene | NM_025471 |

| Gene Symbol | Gene Name | Gene Accession Number |
|---|---|---|
| 4933409K07Rik /// Gm3893 | RIKEN cDNA 4933409K07 gene /// predicted gene 3893 | NR_033123, NR_033506 |
| Gm13305 /// Gm2002 /// Il11ra2 /// Il11ra1 | predicted gene 13305 /// predicted gene 2002 /// interleukin 11 receptor, alpha chain 2 /// interleukin 11 receptor, alpha chain 1 | NM_001099348, NM_010549, NM_010550, NM_001163401, NM_001172054 |
| Skint10 | selection and upkeep of intraepithelial T cells 10 | NM_177668 |
| Extl1 | exostoses (multiple)-like 1 | NM_019578 |
| 2610305D13Rik | RIKEN cDNA 2610305D13 gene | NM_145078 |
| Cpeb2 | cytoplasmic polyadenylation element binding protein 2 | NM_175937, NM_001177379 |
| N4bp2 | NEDD4 binding protein 2 | NM_001024917 |
| Pf4 | platelet factor 4 | NM_019932 |
| Pole | polymerase (DNA directed), epsilon | NM_011132 |
| Rasal1 | RAS protein activator like 1 (GAP1 like) | NM_013832 |
| Hvcn1 | hydrogen voltage-gated channel 1 | NM_001042489, NM_028752 |
| Wbscr27 | Williams Beuren syndrome chromosome region 27 (human) | NM_024479 |
| Daglb | diacylglycerol lipase, beta | NM_144915 |
| Bhlha15 | basic helix-loop-helix family, member a15 | NM_010800 |
| Rbm47 | RNA binding motif protein 47 | NM_001127382, NM_139065 NM_178446 |
| Rassf6 | Ras association (RalGDS/AF-6) domain family member 6 | NM_028478 |
| Naaa | N-acylethanolamine acid amidase | NM_025972, NM_001163687 |
| Cxcl10 | chemokine (C-X-C motif) ligand 10 | NM_021274 |
| Cxcl11 | chemokine (C-X-C motif) ligand 11 | NM_019494 |
| Pxmp2 | peroxisomal membrane protein 2 | NM_008993 |
| P2rx2 | purinergic receptor P2X, ligand-gated ion channel, 2 | NM_001164834, NM_001164833, NM_153400 |
| Ddx54 | DEAD (Asp-Glu-Ala-Asp) box polypeptide 54 | NM_028041 |
| Cldn13 | claudin 13 | NM_020504 |
| Nxph1 | neurexophilin 1 | NM_008751 |
| Prr15 | proline rich 15 | NM_030024 |
| Gfpt1 | glutamine fructose-6-phosphate transaminase 1 | NM_013528 |
| C1rl | complement component 1, r subcomponent-like | NM_181344 |
| C1ra | complement component 1, r subcomponent A | NM_023143 |
| C1rb /// C1ra | complement component 1, r subcomponent B /// complement component 1, r subcomponent A | NM_001113356, NM_023143 |
| Tfpi2 | tissue factor pathway inhibitor 2 | NM_009364 |
| Igkj1 | immunoglobulin kappa joining 1 | NG_005612 |
| Reg3g | regenerating islet-derived 3 gamma | NM_011260 |
| Srgap3 | SLIT-ROBO Rho GTPase activating protein 3 | NM_080448 |
| Timp4 | tissue inhibitor of metalloproteinase 4 | NM_080639 |
| Zfp9 | zinc finger protein 9 | NM_011763 |
| C1s | complement component 1, s subcomponent | NM_001097617, NM_144938 |
| Gm5077 | predicted gene 5077 | NM_173864 |
| Arhgdib | Rho, GDP dissociation inhibitor (GDI) beta | NM_007486 |
| Slc1a5 | solute carrier family 1 (neutral amino acid transporter), member 5 | NM_009201 |
| Cd79a | CD79A antigen (immunoglobulin-associated alpha) | NM_007655 |
| Nup62-il4i1 /// Il4i1 | Nup62-Il4i1 protein /// interleukin 4 induced 1 | NM_001171024, NM_010215 |
| Sh3gl3 | SH3-domain GRB2-like 3 | NM_017400 |
| Prcp | prolylcarboxypeptidase (angiotensinase C) | NM_028243 |
| Nucb2 | nucleobindin 2 | NM_001130479, NM_016773 |
| Apoe | apolipoprotein E | NM_009696 |
| Hamp | hepcidin antimicrobial peptide | NM_032541 |
| Spib | Spi-B transcription factor (Spi-1/PU.1 related) | NM_019866 |
| Grin2d | glutamate receptor, ionotropic, NMDA2D (epsilon 4) | NM_008172 |
| Mfge8 | milk fat globule-EGF factor 8 protein | NM_001045489, NM_008594 |
| Fah | fumarylacetoacetate hydrolase | NM_010176 |
| Relt | RELT tumor necrosis factor receptor | NM_177073 |
| Lyve1 | lymphatic vessel endothelial hyaluronan receptor 1 | NM_053247 |
| Sult1a1 | sulfotransferase family 1A, phenol-preferring, member 1 | NM_133670 |
| Fgfr2 | fibroblast growth factor receptor 2 | NM_010207, NM_201601 |
| Tcerg1l | transcription elongation regulator 1-like | NM_183289 |

| Gene Symbol | Gene Name | Gene Accession Number |
|---|---|---|
| Bnip3 | BCL2/adenovirus E1B interacting protein 3 | NM_009760 |
| Osbpl5 | oxysterol binding protein-like 5 | NM_024289, NM_001199227 |
| Agpat5 | 1-acylglycerol-3-phosphate O-acyltransferase 5 (lysophosphatidic acid acyltransferase, epsilon) | NM_026792 |
| Zdhhc2 | zinc finger, DHHC domain containing 2 | NM_178395 |
| Dctd | dCMP deaminase | NM_001161516, NM_001161515, NM_178788 |
| Man2b1 | mannosidase 2, alpha B1 | NM_010764 |
| Ces2b | carboxyesterase 2B | NM_198171 |
| Ces2d-ps /// Ces2c | carboxylesterase 2D, pseudogene /// carboxylesterase 2C | NM_145603 |
| Ces2g | carboxylesterase 2G | NM_197999 |
| Cdh3 | cadherin 3 | NM_001037809, NM_007665 |
| Tat | tyrosine aminotransferase | NM_146214 |
| Zfp612 | zinc finger protein 612 | NM_175480 |
| Fcer2a | Fc receptor, IgE, low affinity II, alpha polypeptide | NM_001253743 |
| Csmd1 | CUB and Sushi multiple domains 1 | NM_053171 |
| Ifi30 | interferon gamma inducible protein 30 | NM_023065 |
| Neto2 | neuropilin (NRP) and tolloid (TLL)-like 2 | NM_001081324 |
| Marveld3 | MARVEL (membrane-associating) domain containing 3 | NM_212447, NM_028584 |
| Chst4 | carbohydrate (chondroitin 6/keratan) sulfotransferase 4 | NM_011998 |
| Cotl1 | coactosin-like 1 (*Dictyostelium*) | NM_028071 |
| Odc1 | ornithine decarboxylase, structural 1 | NM_013614 |
| Ldlr | low density lipoprotein receptor | NM_001252658, NM_010700, NM_001252659 |
| Pvrl1 | poliovirus receptor-related 1 | NM_021424 |
| Pcsk7 | proprotein convertase subtilisin/kexin type 7 | NM_008794 |
| Pou2af1 | POU domain, class 2, associating factor 1 | NM_011136 |
| Arhgap20 | Rho GTPase activating protein 20 | NM_175535 |
| Stra6 | stimulated by retinoic acid gene 6 | NM_001162479, NM_001162475, NM_009291, NM_001162476 |
| Glb1 | galactosidase, beta 1 | NM_009752 |
| Ccbp2 | chemokine binding protein 2 | NM_021609 |
| Birc2 | baculoviral IAP repeat-containing 2 | NM_007465 |
| Sc5d | sterol-C5-desaturase (fungal ERG3, delta-5-desaturase) homolog (*S. cerevisae*) | NM_172769 |
| Chrnb4 | cholinergic receptor, nicotinic, beta polypeptide 4 | NM_148944 |
| Tspan3 | tetraspanin 3 | NM_019793 |
| Ccdc33 | coiled-coil domain containing 33 | NM_029212, NM_001166282 |
| Tmed3 | transmembrane emp24 domain containing 3 | NM_025360 |
| Srprb /// Trf | signal recognition particle receptor, B subunit /// transferrin | NM_133977 |
| BY080835 | — | ENSMUST00000093784 |
| Tspan7 | tetraspanin 7 | NM_019634 |
| Ssr4 | signal sequence receptor, delta | NM_009279, NM_001166480 |
| Ar | androgen receptor | NM_013476 |
| Chic1 | cysteine-rich hydrophobic domain 1 | NM_009767 |
| Sh3kbp1 | SH3-domain kinase binding protein 1 | NM_021389, NM_001135728, NM_001135727 |
| Klhl13 | kelch-like 13 (*Drosophila*) | NM_026167 |
| F8 | coagulation factor VIII | NM_001161374, NM_007977, NM_001161373 |
| Morc4 | microrchidia 4 | NM_029413, NM_001193309 |

In some embodiments, Table 4 excludes Sell.

FIG. 21C shows a network analysis of over-represented genes that are uniquely expressed in V-ECs compared to NV-ECs of lymph node, indicating potential relationships among these genes.

Table 5 lists genes over-represented in V-EC shared between skin and lymph node. As used herein, "Table 5" includes Table 5A and Table 5B below.

Table 5A—Genes over-represented in V-EC shared between skin and lymph node (4 genes)

Gpr182, Pde9a, Pdk4, Slco2b1

| Gene Symbol | Gene Name | Gene Accession Number |
| --- | --- | --- |
| Gpr182 | G protein-coupled receptor 182 | NM_007412 |
| Pde9a | phosphodiesterase 9A | NM_008804, NM_001163748 |
| Pdk4 | pyruvate dehydrogenase kinase, isoenzyme 4 | NM_013743 |
| Slco2b1 | solute carrier organic anion transporter family, member 2b1 | NM_001252530, NM_001252531, NM_175316 |

Table 5B—Genes over-represented in V-EC shared between skin and lymph node (6 genes)

Man1a, Gpr182, Sncg, BC023105, Hsd3b7, and Uprt.

| Gene Symbol | Gene Name | Gene Accession Number |
| --- | --- | --- |
| Man1a | mannosidase 1, alpha | NM_008548 |
| Gpr182 | G protein-coupled receptor 182 | NM_007412 |
| Sncg | synuclein, gamma | NM_011430 |
| BC023105 | — | ENSMUST00000073997 |
| Hsd3b7 | hydroxy-delta-5-steroid dehydrogenase, 3 beta- and steroid delta-isomerase 7 | NM_001040684, NM_133943 |
| Uprt | uracil phosphoribosyltransferase (FUR1) homolog (S. cerevisiae) | NM_001081189 |

Table 6 lists genes over-represented in V-EC shared between adipose tissue and lymph node. As used herein, "Table 6" includes Table 6A and Table 6B below.

Table 6A—Genes over-represented in V-EC shared between adipose tissue and lymph node (25 genes)

Sulf1, Cd63, Susd2, Tc2n, Net1, Serpinb1a, Syt15, Rfk, Ch25h, Sirpa, Slc2a1, 5031410I06Rik, Thsd7a, Vmn1r100, Vmn1r148, Vmn1r114, Vmn1r132, Vmn1r158, Vmn1r93, Vmn1r-ps79, Gm10670, Vmn1r117, Vmn1r125, Vmn1r101, Snord116, LOC100042196, Ssty2, LOC100039753, LOC100040031, LOC100041704, LOC100039552, LOC100042359, LOC100041256, LOC100039147.

| Gene Symbol | Gene Name | Gene Accession Number |
| --- | --- | --- |
| Sulf1 | sulfatase 1 | NM_172294, NM_001198565, NM_001198566 |
| Cd63 | CD63 antigen | NM_007653, NM_001042580 |
| Susd2 | sushi domain containing 2 | NM_027890, NM_001162913 |
| Tc2n | tandem C2 domains, nuclear | NM_028924, NM_001082976 |
| Net1 | neuroepithelial cell transforming gene 1 | NM_001047159, NM_019671 |
| Serpinb1a | serine (or cysteine) peptidase inhibitor, clade B, member 1a | NM_025429 |
| Syt15 | synaptotagmin XV | NM_176931, NM_181529 |
| Rfk | riboflavin kinase | NM_019437 |
| Ch25h | cholesterol 25-hydroxylase | NM_009890 |
| Sirpa | signal-regulatory protein alpha | NM_007547, NM_001177646, NM_001177647 |
| Slc2a1 | solute carrier family 2 (facilitated glucose transporter), member 1 | NM_011400 |
| 5031410I06Rik | RIKEN cDNA 5031410I06 gene | NM_207657 |
| Thsd7a | thrombospondin, type I, domain containing 7A | NM_001164805 |
| Vmn1r100 | vomeronasal 1 receptor 100 | NM_001166844 |
| Vmn1r148 | vomeronasal 1 receptor 148 | NM_030736 |
| Vmn1r114 | vomeronasal 1 receptor 114 | NM_001166837 |
| Vmn1r132 | vomeronasal 1 receptor 132 | NM_001122682 |
| Vmn1r158 | vomeronasal 1 receptor 158 | NM_001166841 |
| Vmn1r93 | vomernasal 1 receptor Vmn1r93 | NM_207547 |
| Vmn1r-ps79 | vomeronasal 1 receptor, pseudogene 79 | NR_030707 |
| Vmn1r117 | vomeronasal 1 receptor 117 | NM_001166743 |
| Vmn1r125 | vomeronasal 1 receptor 125 | NM_001166740 |
| Vmn1r101 | vomeronasal 1 receptor 101 | NM_001166836 |
| Snord116 | small nucleolar RNA, C/D box 116 | MGI:1891407 |
| Gm10670 | Predicted gene 10670 | NM_001167161 |

Table 6B—Genes over-represented in V-EC shared between adipose tissue and lymph node (37 genes)

Sulf1, Raet1d, H60b, Susd2, Ppap2c, Doc2b, 9030617O03Rik, Lrrc16a, Serpinb1a, Mustn1, Clu, Fam107a, Celsr1, Dhh, Glycam1, Slc37a1, B4galt6, Rfk, Gcnt1, Cd59a, Traf1, Ralgapa2, Rorc, Tifa, LOC100862177///Gm13304///Gm10591///Ccl21b///LOC100041593///Ccl21c///Gm1987///Ccl21a, Slc2a1, Tnfrsf9, Ptpn3, Sh2b2, Tes, Pglyrp1, Rasd2, Mt2, Il27ra, Rab27a, Ctsh, and Eda2r.

| Gene Symbol | Gene Name | Gene Accession Number |
| --- | --- | --- |
| Sulf1 | sulfatase 1 | NM_001198566, NM_001198565, NM_172294 |
| Raet1d | retinoic acid early transcript delta | NM_020030 |
| H60b | histocompatibility 60b | NM_001177775 |
| Susd2 | sushi domain containing 2 | NM_027890, NM_001162913 |
| Ppap2c | phosphatidic acid phosphatase type 2C | NM_015817 |
| Doc2b | double C2, beta | NM_007873 |
| 9030617O03Rik | RIKEN cDNA 9030617O03 gene | NM_145448 |
| Lrrc16a | leucine rich repeat containing 16A | NM_026825 |

-continued

| Gene Symbol | Gene Name | Gene Accession Number |
|---|---|---|
| Serpinb1a | serine (or cysteine) peptidase inhibitor, clade B, member 1a | NM_025429 |
| Mustn1 | musculoskeletal, embryonic nuclear protein 1 | NM_181390 |
| Clu | clusterin | NM_013492 |
| Fam107a | family with sequence similarity 107, member A | NM_183187 |
| Celsr1 | cadherin, EGF LAG seven-pass G-type receptor 1 (flamingo homolog, Drosophila) | NM_009886 |
| Dhh | desert hedgehog | NM_007857 |
| Glycam1 | glycosylation dependent cell adhesion molecule 1 | NM_008134 |
| Slc37a1 | solute carrier family 37 (glycerol-3-phosphate transporter), member 1 | NM_001242427, NM_153062 |
| B4galt6 | UDP-Gal:betaGlcNAc beta 1,4-galactosyltransferase, polypeptide 6 | NM_019737 |
| Rfk | riboflavin kinase | NM_019437 |
| Gcnt1 | glucosaminyl (N-acetyl) transferase 1, core 2 | NM_001136484, NM_173442, NM_010265 |
| Cd59a | CD59a antigen | NM_007652, NM_001111060 |
| Traf1 | TNF receptor-associated factor 1 | NM_009421 |
| Ralgapa2 | Ral GTPase activating protein, alpha subunit 2 (catalytic) | NM_001033348 |
| Rorc | RAR-related orphan receptor gamma | NM_011281 |
| Tifa | TRAF-interacting protein with forkhead-associated domain | NM_145133 |
| LOC100862177 /// Gm13304 /// Gm10591 /// Ccl21b /// LOC100041593 /// Ccl21c /// Gm1987 /// Ccl21a | c-C motif chemokine 21c-like /// predicted gene 13304 /// predicted gene 10591 /// chemokine (C-C motif) ligand 21B (leucine) /// c-C motif chemokine 21c-like /// chemokine (C-C motif) ligand 21C (leucine) /// predicted gene 1987 /// chemokine (C-C motif) ligand 21A (serine) | NM_001193668, NM_001193666, NM_011335, NM_023052, NM_001270360, NM_011124, NM_001193667 |
| Slc2a1 | solute carrier family 2 (facilitated glucose transporter), member 1 | NM_011400 |
| Tnfrsf9 | tumor necrosis factor receptor superfamily, member 9 | NM_001077509, NM_001077508, NM_011612 |
| Ptpn3 | protein tyrosine phosphatase, non-receptor type 3 | NM_011207 |
| Sh2b2 | SH2B adaptor protein 2 | NM_018825 |
| Tes | testis derived transcript | NM_207176 |
| Pglyrp1 | peptidoglycan recognition protein 1 | NM_009402 |
| Rasd2 | RASD family, member 2 | NM_029182 |
| Mt2 | metallothionein 2 | NM_008630 |
| Il27ra | interleukin 27 receptor, alpha | NM_016671 |
| Rab27a | RAB27A, member RAS oncogene family | NM_023635 |
| Ctsh | cathepsin H | NM_007801 |
| Eda2r | ectodysplasin A2 receptor | NM_001161433, NM_001161432, NM_175540 |

Table 7 lists genes over-represented in V-EC shared between adipose tissue and skin. As used herein, "Table 7" includes Table 7A and Table 7B below.

Table 7A—Genes over-represented in V-EC shared between adipose tissue and skin (63 genes)

Il1r1, Tbc1d8, Cd55, Prelp, Hmcn1, Dnm3, Cadm3, Igf1, Csrp2, Nuak1, Socs2, Hif1a, Lgmn, Vcan, Lgals3, Htr2a, Bmp4, Ptk2b, Nov, Csf2rb2, Amigo2, Abi3 bp, Pdia5, Rcan1, Adrb2, Tmem252, Pgm5, Myof, Olfm1, Ptgs1, Procr, Lbp, Ehd4, Fbn1, Kcnb1, Tspan5, Ecm1, Clca1, Clca2, Gem, Ctnnal1, Fgl2, Il6, Rasa4, Tacr1, Ret, Ntf3, Fam174b, Ctsc, Anpep, Acer3, Gpm6a, Mmp2, Lpcat2, Insr, Nqo1, Nt5e, Lrrc1, Mras, Dock11, Il13ra1, Bgn, and Cysltr1.

| Gene Symbol | Gene Name | Gene Accession Number |
|---|---|---|
| Il1r1 | interleukin 1 receptor, type I | NM_008362, NM_001123382 |
| Tbc1d8 | TBC1 domain family, member 8 | NM_018775 |
| Cd55 | CD55 antigen | NM_010016 |
| Prelp | proline arginine-rich end leucine-rich repeat | NM_054077 |
| Hmcn1 | Hemicentin 1 | NM_001024720.3 |
| Dnm3 | dynamin 3 | NM_172646, NM_001038619 |
| Cadm3 | cell adhesion molecule 3 | NM_053199 |
| Igf1 | insulin-like growth factor 1 | NM_001111274, NM_184052, NM_010512, NM_001111275, NM_001111276 |

| Gene Symbol | Gene Name | Gene Accession Number |
|---|---|---|
| Csrp2 | cysteine and glycine-rich protein 2 | NM_007792 |
| Nuak1 | NUAK family, SNF1-like kinase, 1 | NM_001004363 |
| Socs2 | suppressor of cytokine signaling 2 | NM_001168656, NM_001168657, NM_007706, NM_001168655 |
| Hif1a | hypoxia inducible factor 1, alpha subunit | NM_010431 |
| Lgmn | legumain | NM_011175 |
| Vcan | versican | NM_001134474, NM_172955, NM_001134475, NM_001081249, NM_019389 |
| Lgals3 | lectin, galactose binding, soluble 3 | NM_001145953, NM_010705 |
| Htr2a | 5-hydroxytryptamine (serotonin) receptor 2A | NM_172812 |
| Bmp4 | bone morphogenetic protein 4 | NM_007554 |
| Ptk2b | PTK2 protein tyrosine kinase 2 beta | NM_001162365, NM_001162366, NM_172498 |
| Nov | nephroblastoma overexpressed gene | NM_010930 |
| Csf2rb2 | colony stimulating factor 2 receptor, beta 2, low-affinity (granulocyte-macrophage) | NM_007781 |
| Amigo2 | adhesion molecule with Ig like domain 2 | NM_178114, NM_001164602, NM_001164563 |
| Abi3bp | ABI gene family, member 3 (NESH) binding protein | NM_001014423, NM_001014424, NM_178790, NM_001014399, NM_001014422 |
| Pdia5 | protein disulfide isomerase associated 5 | NM_028295 |
| Rcan1 | regulator of calcineurin 1 | NM_019466, NM_001081549 |
| Adrb2 | adrenergic receptor, beta 2 | NM_007420 |
| Tmem252 | transmembrane protein 252 | NM_183160 |
| Pgm5 | phosphoglucomutase 5 | NM_175013 |
| Myof | myoferlin | NM_001099634 |
| Olfm1 | olfactomedin 1 | NM_001038612, NM_019498, NM_001038613, NM_001038614 |
| Ptgs1 | prostaglandin-endoperoxide synthase 1 | NM_008969 |
| Procr | protein C receptor, endothelial | NM_011171 |
| Lbp | lipopolysaccharide binding protein | NM_008489 |
| Ehd4 | EH-domain containing 4 | NM_133838 |
| Fbn1 | fibrillin 1 | NM_007993 |
| Kcnb1 | potassium voltage gated channel, Shab-related subfamily, member 1 | NM_008420 |
| Tspan5 | tetraspanin 5 | NM_019571 |
| Ecm1 | extracellular matrix protein 1 | NM_001252653, NM_007899 |
| Clca1 | chloride channel calcium activated 1 | NM_009899 |
| Clca2 | chloride channel calcium activated 2 | NM_030601 |
| Gem | GTP binding protein (gene over-expressed in skeletal muscle) | NM_010276 |
| Ctnnal1 | catenin (cadherin associated protein), alpha-like 1 | NM_018761 |
| Fgl2 | fibrinogen-like protein 2 | NM_008013 |
| Il6 | interleukin 6 | NM_031168 |
| Rasa4 | RAS p21 protein activator 4 | NM_001039103, NM_133914 |
| Tacr1 | tachykinin receptor 1 | NM_009313 |
| Ret | ret proto-oncogene | NM_009050, NM_001080780 |
| Ntf3 | neurotrophin 3 | NM_001164034, NM_001164035, NM_008742 |
| Fam174b | family with sequence similarity 174, member B | NM_001162532 |
| Ctsc | cathepsin C | NM_009982 |
| Anpep | alanyl (membrane) aminopeptidase | NM_008486 |
| Acer3 | alkaline ceramidase 3 | NM_025408 |
| Gpm6a | glycoprotein m6a | NM_001253754, NM_153581, NM_001253756 |
| Mmp2 | matrix metallopeptidase 2 | NM_008610 |
| Lpcat2 | lysophosphatidylcholine acyltransferase 2 | NM_173014 |
| Insr | insulin receptor | NM_010568 |
| Nqo1 | NAD(P)H dehydrogenase, quinone 1 | NM_008706 |
| Nt5e | 5' nucleotidase, ecto | NM_011851 |
| Lrrc1 | leucine rich repeat containing 1 | NM_172528, NM_001146048 |
| Mras | muscle and microspikes RAS | NM_008624 |
| Dock11 | dedicator of cytokinesis 11 | NM_001009947 |
| Il13ra1 | interleukin 13 receptor, alpha 1 | NM_133990 |
| Bgn | biglycan | NM_007542 |
| Cysltr1 | cysteinyl leukotriene receptor 1 | NM_021476 |

Table 7B—Genes over-represented in V-EC shared between adipose tissue and skin (84 genes)

Il1r1, Serpinb8, Gpr1, Steap3, Prelp, Hmcn1, Dnm3, Cadm3, Igf1, Rassf9, Nuak1, Tmtc2, Upp1, EfEmp1, Slfn4, Slfn3, Itgb4, Sectm1b, Actn1, Lgmn, Foxc1, Lhfpl2, Il6st, Klhl3, Vcan, Lgals3, Htr2a, Stab1, Ptk2b, Nov, Myc, Amigo2, Abi3bp, Hunk, Masp1, Leprel1, Rcan1, Zfp57, Fndc1, Cd14, Adrb2, Atp8b1, E030010A14Rik, Pgm5, Myof, Nmt2, Slc52a3, Procr, Lbp, Lhx6, Serping1, Ehd4, Fbn1, Car13, Tspan5, Ccdc109b, Clca1, Gem, Tlr4, Asap3, Ctnnal1, Ctps, Il6, Cytl1, Rasa4, Baiap2l1, Tacr1, Ntf3, Fam174b, Prss23, Fut2, Anpep, Capn5, Gpm6a, Mmp2, Lpcat2, Insr, Nqo1, Icam1, Mras, Mras, Dock11, Il13ra1, and Bgn.

| Gene Symbol | Gene Name | Gene Accession Number |
|---|---|---|
| Il1r1 | interleukin 1 receptor, type I | NM_001123382, NM_008362 |
| Serpinb8 | serine (or cysteine) peptidase inhibitor, clade B, member 8 | NM_011459, NM_001159748 |
| Gpr1 | G protein-coupled receptor 1 | NM_146250 |
| Steap3 | STEAP family member 3 | NM_001085409, NM_133186 |
| Prelp | proline arginine-rich end leucine-rich repeat | NM_054077 |
| Hmcn1 | hemicentin 1 | NM_001024720 |
| Dnm3 | dynamin 3 | NM_001038619, NM_172646 |
| Cadm3 | cell adhesion molecule 3 | NM_053199 |

-continued

| Gene Symbol | Gene Name | Gene Accession Number |
|---|---|---|
| Igf1 | insulin-like growth factor 1 | NM_001111276, NM_001111275, NM_001111274, NM_010512 |
| Rassf9 | Ras association (RalGDS/AF-6) domain family (N-terminal) member 9 | NM_146240 |
| Nuak1 | NUAK family, SNF1-like kinase, 1 | NM_001004363 |
| Tmtc2 | transmembrane and tetratricopeptide repeat containing 2 | NM_177368 |
| Upp1 | uridine phosphorylase 1 | NM_001159402, NM_001159401, NM_009477 |
| Efemp1 | epidermal growth factor-containing fibulin-like extracellular matrix protein 1 | NM_146015 |
| Slfn4 | schlafen 4 | NM_011410 |
| Slfn3 | schlafen 3 | NM_011409 |
| Itgb4 | integrin beta 4 | NM_001005608, NM_133663 |
| Sectm1b | secreted and transmembrane 1B | NM_026907 |
| Actn1 | actinin, alpha 1 | NM_134156 |
| Lgmn | legumain | NM_011175 |
| Foxc1 | forkhead box C1 | NM_008592 |
| Lhfpl2 | lipoma HMGIC fusion partner-like 2 | NM_172589 |
| Il6st | interleukin 6 signal transducer | NM_010560 |
| Klhl3 | kelch-like 3 (*Drosophila*) | NM_001195075 |
| Vcan | versican | NM_001134474, NM_001134475, NM_001081249, NM_019389 |
| Lgals3 | lectin, galactose binding, soluble 3 | NM_001145953, NM_010705 |
| Htr2a | 5-hydroxytryptamine (serotonin) receptor 2A | NM_172812 |
| Stab1 | stabilin 1 | NM_138672 |
| Ptk2b | PTK2 protein tyrosine kinase 2 beta | NM_001162365, NM_001162366, NM_172498 |
| Nov | nephroblastoma overexpressed gene | NM_010930 |
| Myc | myelocytomatosis oncogene | NM_001177354, NM_001177353, NM_001177352, NM_010849 |
| Amigo2 | adhesion molecule with Ig like domain 2 | NM_001164563, NM_001164602, NM_178114 |
| Abi3bp | ABI gene family, member 3 (NESH) binding protein | NM_001014422, NM_001014399, NM_178790, NM_001014424, NM_001014423 |
| Hunk | hormonally upregulated Neu-associated kinase | NM_015755 |
| Masp1 | mannan-binding lectin serine peptidase 1 | NM_008555 |
| Leprel1 | leprecan-like 1 | NM_173379 |
| Rcan1 | regulator of calcineurin 1 | NM_001081549 |
| Zfp57 | zinc finger protein 57 | NM_001168501, NM_001013745, NM_001168502 |
| Fndc1 | fibronectin type III domain containing 1 | NM_001081416 |
| Cd14 | CD14 antigen | NM_009841 |
| Adrb2 | adrenergic receptor, beta 2 | NM_007420 |
| Atp8b1 | ATPase, class I, type 8B, member 1 | NM_001001488 |
| E030010A14Rik | RIKEN cDNA E030010A14 gene | NM_183160 |
| Pgm5 | phosphoglucomutase 5 | NM_175013 |
| Myof | myoferlin | NM_001099634 |
| Nmt2 | N-myristoyltransferase 2 | NM_008708 |
| Slc52a3 | solute carrier protein family 52, member 3 | NM_027172, NM_001164820, NM_001164819 |
| Procr | protein C receptor, endothelial | NM_011171 |
| Lbp | lipopolysaccharide binding protein | NM_008489 |
| Lhx6 | LIM homeobox protein 6 | NM_001083125, NM_001083126, NM_001083127, NM_008500 |
| Serping1 | serine (or cysteine) peptidase inhibitor, clade G, member 1 | NM_009776 |

-continued

| Gene Symbol | Gene Name | Gene Accession Number |
|---|---|---|
| Ehd4 | EH-domain containing 4 | NM_133838 |
| Fbn1 | fibrillin 1 | NM_007993 |
| Car13 | carbonic anhydrase 13 | NM_024495 |
| Tspan5 | tetraspanin 5 | NM_019571 |
| Ccdc109b | coiled-coil domain containing 109B | NM_025779 |
| Clca1 | chloride channel calcium activated 1 | NM_009899 |
| Gem | GTP binding protein (gene overexpressed in skeletal muscle) | NM_010276 |
| Tlr4 | toll-like receptor 4 | NM_021297 |
| Asap3 | ArfGAP with SH3 domain, ankyrin repeat and PH domain 3 | NM_001008232 |
| Ctnnal1 | catenin (cadherin associated protein), alpha-like 1 | NM_018761 |
| Ctps | cytidine 5'-triphosphate synthase | NM_016748 |
| Il6 | interleukin 6 | NM_031168 |
| Cytl1 | cytokine-like 1 | NM_001081106 |
| Rasa4 | RAS p21 protein activator 4 | NM_133914, NM_001039103 |
| Baiap2l1 | BAI1-associated protein 2-like 1 | NM_025833 |
| Tacr1 | tachykinin receptor 1 | NM_009313 |
| Ntf3 | neurotrophin 3 | NM_008742, NM_001164035, NM_001164034 |
| Fam174b | family with sequence similarity 174, member B | NM_001162532 |
| Prss23 | protease, serine, 23 | NM_029614 |
| Fut2 | fucosyltransferase 2 | NM_018876 |
| Anpep | alanyl (membrane) aminopeptidase | NM_008486 |
| Capn5 | calpain 5 | NM_007602 |
| Gpm6a | glycoprotein m6a | NM_001253756, NM_001253754, NM_153581 |
| Mmp2 | matrix metallopeptidase 2 | NM_008610 |
| Lpcat2 | lysophosphatidylcholine acyltransferase 2 | NM_173014 |
| Insr | insulin receptor | NM_010568 |
| Nqo1 | NAD(P)H dehydrogenase, quinone 1 | NM_008706 |
| Icam1 | intercellular adhesion molecule 1 | NM_010493 |
| Mras | muscle and microspikes RAS | NM_008624 |
| Mras | muscle and microspikes RAS | NM_008624 |
| Dock11 | dedicator of cytokinesis 11 | NM_001009947 |
| Il13ra1 | interleukin 13 receptor, alpha 1 | NM_133990 |
| Bgn | biglycan | NM_007542 |

Table 8 lists genes under-represented in V-EC shared by skin, adipose tissue and lymph node. As used herein, "Table 8" includes Table 8A and Table 8B below.

Table 8A—Genes over-represented in V-EC shared by skin, adipose tissue and lymph node (48 genes)

Efhd1, Fn1, Lama4, Flt4, Igfbp3, Btnl9, Rasd1, Jup, Lgals3bp, Efr3b, Sema3g, 1190002H23Rik, Ednrb, Ptp4a3, Gpihbp1, Cdc42ep1, Pdgfb, Notch4, Clic5, Rasgrp3, Slc9a3r2, Map4k3, Ablim3, Map4k2, Dll4, Prnd, Id1, Hey1, Pik3r3, Sdc3, Penk, Alpl, Rbp7, Cldn15, Fscn1, Kdr, Oas2, Slc6a6, Cxcl12, Podxl, 1200009O22Rik, Mcf2l, Carl, Efnb2, Sema7a, Coro2b, Itm2a, Kctd12b.

| Gene Symbol | Gene Name | Gene Accession Number |
|---|---|---|
| Efhd1 | EF hand domain containing 1 | NM_028889 |
| Fn1 | fibronectin 1 | NM_010233 |
| Lama4 | laminin, alpha 4 | NM_010681 |
| Flt4 | FMS-like tyrosine kinase 4 | NM_008029 |
| Igfbp3 | insulin-like growth factor binding protein 3 | NM_008343 |
| Btnl9 | butyrophilin-like 9 | NM_172793 |
| Rasd1 | RAS, dexamethasone-induced 1 | NM_009026 |
| Jup | junction plakoglobin | NM_010593 |
| Lgals3bp | lectin, galactoside-binding, soluble, 3 binding protein | NM_011150 |
| Efr3b | EFR3 homolog B (S. cerevisiae) | NM_001082483 |
| Sema3g | sema domain, immunoglobulin domain (Ig), short basic domain, secreted, (semaphorin) 3G | NM_001025379 |
| 1190002H23Rik | RIKEN cDNA 1190002H23 gene | NM_025427 |
| Ednrb | endothelin receptor type B | NM_001136061, NM_007904 |

-continued

| Gene Symbol | Gene Name | Gene Accession Number |
|---|---|---|
| Ptp4a3 | protein tyrosine phosphatase 4a3 | NM_001166390, NM_001166388, NM_008975, NM_001166389 |
| Gpihbp1 | GPI-anchored HDL-binding protein 1 | NM_026730 |
| Cdc42ep1 | CDC42 effector protein (Rho GTPase binding) 1 | NM_027219 |
| Pdgfb | platelet derived growth factor, B polypeptide | NM_011057 |
| Notch4 | notch 4 | NM_010929 |
| Clic5 | chloride intracellular channel 5 | NM_172621 |
| Rasgrp3 | RAS, guanyl releasing protein 3 | NM_207246, NM_001166493 |
| Slc9a3r2 | solute carrier family 9 (sodium/hydrogen exchanger), member 3 regulator 2 | NM_023449, NM_023055 |
| Map4k3 | mitogen-activated protein kinase kinase kinase kinase 3 | NM_001081357 |
| Ablim3 | actin binding LIM protein family, member 3 | NM_198649, NM_001164491 |
| Map4k2 | mitogen-activated protein kinase kinase kinase kinase 2 | NM_009006 |
| Dll4 | delta-like 4 (Drosophila) | NM_019454 |
| Prnd | prion protein dublet | NM_023043, NM_001126338 |
| Id1 | inhibitor of DNA binding 1 | NM_010495 |
| Hey1 | hairy/enhancer-of-split related with YRPW motif 1 | NM_010423 |
| Pik3r3 | phosphatidylinositol 3 kinase, regulatory subunit, polypeptide 3 (p55) | NM_181585 |
| Sdc3 | syndecan 3 | NM_011520 |
| Penk | preproenkephalin | NM_001002927 |
| Alpl | alkaline phosphatase, liver/bone/kidney | NM_007431 |
| Rbp7 | retinol binding protein 7, cellular | NM_022020 |
| Cldn15 | claudin 15 | NM_021719 |
| Fscn1 | fascin homolog 1, actin bundling protein (Strongylocentrorus purpuratus) | NM_007984 |
| Kdr | kinase insert domain protein receptor | NM_010612 |
| Oas2 | 2'-5' oligoadenylate synthetase 2 | NM_145227 |
| Slc6a6 | solute carrier family 6 (neurotransmitter transporter, taurine), member 6 | NM_009320 |
| Cxcl12 | chemokine (C-X-C motif) ligand 12 | NM_013655, NM_001012477, NM_021704 |
| Podxl | podocalyxin-like | NM_013723 |
| Tril | TLR4 interactor with leucine-rich repeats | NM_025817 |
| Mcf2l | mcf.2 transforming sequence-like | NM_178076, NM_001159486, NM_001159485 |
| Car7 | carbonic anhydrase 7 | NM_053070 |
| Efnb2 | ephrin B2 | NM_010111 |
| Sema7a | sema domain, immunoglobulin domain (Ig), and GPI membrane anchor, (semaphorin) 7A | NM_011352 |
| Coro2b | coronin, actin binding protein, 2B | NM_175484 |
| Itm2a | integral membrane protein 2A | NM_008409 |
| Kctd12b | potassium channel tetramerisation domain containing 12b | NM_175429 |

Table 8B—Genes over-represented in V-EC shared by skin, adipose tissue and lymph node (46 genes)

Efhd1, Fn1, Cxcr4, Unc5b, Slc26a10, Flt4, Nos2, Igfbp3, Btnl9, Rasd1, Cmpk2, Efr3b, Rsad2, Akr1c14, Esm1, Sema3g, 1190002H23Rik, Ednrb, Notch4, Clic5, Map4k3, Map4k2, Ifit2, Prnd, Nebl, Gja5, Hey1, Pik3r3, Penk, Gja4, Alpl, Rbp7, Unc119b, Oas2, Cxcl12, Tril, Kcna5, Vwa3a, Eps8l2, P2ry2, Mcf2l, Carl, Efnb2, Coro2b, Itm2a, and Kctd12b.

| Gene Symbol | Gene Name | Gene Accession Number |
|---|---|---|
| Efhd1 | EF hand domain containing 1 | NM_028889 |
| Fn1 | fibronectin 1 | NM_010233 |
| Cxcr4 | chemokine (C—X—C motif) receptor 4 | NM_009911 |
| Unc5b | unc-5 homolog B (C. elegans) | NM_029770 |
| Slc26a10 | solute carrier family 26, member 10 | NM_177615 |
| Flt4 | FMS-like tyrosine kinase 4 | NM_008029 |

-continued

| Gene Symbol | Gene Name | Gene Accession Number |
|---|---|---|
| Nos2 | nitric oxide synthase 2, inducible | NM_010927 |
| Igfbp3 | insulin-like growth factor binding protein 3 | NM_008343 |
| Btnl9 | butyrophilin-like 9 | NM_172793 |
| Rasd1 | RAS, dexamethasone-induced 1 | NM_009026 |
| Cmpk2 | cytidine monophosphate (UMP-CMP) kinase 2, mitochondrial | NM_020557 |
| Efr3b | EFR3 homolog B (S. cerevisiae) | NM_001082483 |
| Rsad2 | radical S-adenosyl methionine domain containing 2 | NM_021384 |
| Akr1c14 | aldo-keto reductase family 1, member C14 | NM_134072 |
| Esm1 | endothelial cell-specific molecule 1 | NM_023612 |
| Sema3g | sema domain, immunoglobulin domain (Ig), short basic domain, secreted, (semaphorin) 3G | NM_001025379 |
| 1190002H23Rik | RIKEN cDNA 1190002H23 gene | NM_025427 |
| Ednrb | endothelin receptor type B | NM_007904, NM_001136061 |
| Notch4 | notch 4 | NM_010929 |
| Clic5 | chloride intracellular channel 5 | NM_172621 |
| Map4k3 | mitogen-activated protein kinase kinase kinase kinase 3 | NM_001081357 |
| Map4k2 | mitogen-activated protein kinase kinase kinase kinase 2 | NM_009006 |
| Ifit2 | interferon-induced protein with tetratricopeptide repeats 2 | NM_008332 |
| Prnd | prion protein dublet | NM_001126338, NM_023043 |
| Nebl | nebulette | NM_028757 |
| Gja5 | gap junction protein, alpha 5 | NM_008121 |
| Hey1 | hairy/enhancer-of-split related with YRPW motif 1 | NM_010423 |
| Pik3r3 | phosphatidylinositol 3 kinase, regulatory subunit, polypeptide 3 (p55) | NM_181585 |
| Penk | preproenkephalin | NM_001002927 |
| Gja4 | gap junction protein, alpha 4 | NM_008120 |
| Alpl | alkaline phosphatase, liver/bone/kidney | NM_007431 |
| Rbp7 | retinol binding protein 7, cellular | NM_022020 |
| Unc119b | unc-119 homolog B (C. elegans) | NM_175352 |
| Oas2 | 2'-5' oligoadenylate synthetase 2 | NM_145227 |
| Cxcl12 | chemokine (C—X—C motif) ligand 12 | NM_001012477 |
| Tril | TLR4 interactor with leucine-rich repeats | NM_025817 |
| Kcna5 | potassium voltage-gated channel, shaker-related subfamily, member 5 | NM_145983 |
| Vwa3a | von Willebrand factor A domain containing 3A | NM_177697 |
| Eps8l2 | EPS8-like 2 | NM_133191 |
| P2ry2 | purinergic receptor P2Y, G-protein coupled 2 | NM_008773 |
| Mcf2l | mcf.2 transforming sequence-like | NM_001159486 |
| Car7 | carbonic anhydrase 7 | NM_053070 |
| Efnb2 | ephrin B2 | NM_010111 |
| Coro2b | coronin, actin binding protein, 2B | NM_175484 |
| Itm2a | integral membrane protein 2A | NM_008409 |
| Kctd12b | potassium channel tetramerisation domain containing 12b | NM_175429 |

Table 9 lists genes under-represented in V-EC unique to skin. As used herein, "Table 9" includes Table 9A and Table 9B below.

Table 9A—Genes over-represented in V-EC unique to skin (94 genes)

Sell, Stk17b, St8sia4, Ptprc, Rgs2, Rgs1, Fcer1g, Tgfb2, Cdk19, Gp49a, Lilrb4, Tmem229b, B4galnt1, Amd1, Slc26a10, Ikzf1, Bcl11a, Lcp2, Atp2a3, Coro6, Plek, Ccdc85a, Cyfip2, Cd68, Bcl6b, Abr, Ccl6, Cd79b, Pld4, Stxbp6, Bmp6, Cd180, Mast4, Gm3002, Rnase6, Lcp1, Cyth4, Lgals1, Azin1, Mtss1, Ly6d, Rac2, Cldn5, B4galt4, Atp13a3, Cd200, Tagap, H2-DMa, H2-Eb1, Runx2, Ehd1, Cybasc3, Mpeg1, Papss2, Ifit3, Fads2, Dapl1, Nebl, Cd44, Car3, Terc, Cd53, Fam102b, Ccl21a, Coro2a, Cyth3, Alox5ap, Selplg, Irak2, Cd69, Tyrobp, Nkg7, Klk1, Siglech, Ucp2, Lsp1, Spib, Cd37, Snord116, Hbb-b1, Gprc5b, Cox6a2, Irf7, Igf2, Lpl, Herpud1, Irf8, Cd209a, Cd209d, Ifi30, Cyba, Dennd4a, Ccr9, Cybb, LOC100042196, LOC100040223, Ssty2, LOC100039753, LOC100040031, LOC100039552, LOC100041256, LOC665406, LOC665746, LOC100041704.

| Gene Symbol | Gene Name | Gene Accession Number |
|---|---|---|
| Sell | selectin, lymphocyte | NM_011346, NM_001164059 |
| Stk17b | serine/threonine kinase 17b (apoptosis-inducing) | NM_133810 |
| St8sia4 | ST8 alpha-N-acetyl-neuraminide alpha-2,8-sialyltransferase 4 | NM_001159745, NM_009183 |

-continued

| Gene Symbol | Gene Name | Gene Accession Number |
|---|---|---|
| Ptprc | protein tyrosine phosphatase, receptor type, C | NM_001111316, NM_011210, NM_001268286 |
| Rgs2 | regulator of G-protein signaling 2 | NM_009061 |
| Rgs1 | regulator of G-protein signaling 1 | NM_015811 |
| Fcer1g | Fc receptor, IgE, high affinity I, gamma polypeptide | NM_010185 |
| Tgfb2 | transforming growth factor, beta 2 | NM_009367 |
| Cdk19 | cyclin-dependent kinase 19 | NM_198164, NM_001168304 |
| Gp49a | glycoprotein 49 A | NM_008147 |
| Lilrb4 | leukocyte immunoglobulin-like receptor, subfamily B, member 4 | NM_013532 |
| Tmem229b | transmembrane protein 229B | NM_178745, NM_001170401 |
| B4galnt1 | beta-1,4-N-acetyl-galactosaminyl transferase 1 | NM_001244617, NM_027739 NM_001244618, NM_008080 |
| Amd1 | S-adenosylmethionine decarboxylase 1 | NM_009665 |
| Slc26a10 | solute carrier family 26, member 10 | NM_177615 |
| Ikzf1 | IKAROS family zinc finger 1 | NM_009578, NM_001025597 |
| Bcl11a | B cell CLL/lymphoma 11A (zinc finger protein) | NM_001159289, NM_001159290, NM_001242934, NM_016707 |
| Lcp2 | lymphocyte cytosolic protein 2 | NM_010696 |
| Atp2a3 | ATPase, Ca++ transporting, ubiquitous | NM_001163337, NM_016745 NM_001163336 |
| Coro6 | coronin 6 | NM_139130, NM_139128, NM_139129 |
| Plek | pleckstrin | NM_019549 |
| Ccdc85a | coiled-coil domain containing 85A | NM_001166661, NM_001166662, NM_181577 |
| Cyfip2 | cytoplasmic FMR1 interacting protein 2 | NM_133769, NM_001252459 NM_001252460 |
| Cd68 | CD68 antigen | NM_009853 |
| Bcl6b | B cell CLL/lymphoma 6, member B | NM_007528 |
| Abr | active BCR-related gene | NM_198895, NM_198018, NM_198894 |
| Ccl6 | chemokine (C-C motif) ligand 6 | NM_009139 |
| Cd79b | CD79B antigen | NM_008339 |
| Pld4 | phospholipase D family, member 4 | NM_178911 |
| Stxbp6 | syntaxin binding protein 6 (amisyn) | NM_144552 |
| Bmp6 | bone morphogenetic protein 6 | NM_007556 |
| Cd180 | CD180 antigen | NM_008533 |
| Mast4 | microtubule associated serine/threonine kinase family member 4 | NM_175171 |
| Gm3002 | predicted gene 3002 | NR_033388.1 |
| Rnase6 | ribonuclease, RNase A family, 6 | NM_030098 |
| Lcp1 | lymphocyte cytosolic protein 1 | NM_008879, NM_001247984 |
| Cyth4 | cytohesin 4 | NM_028195 |
| Lgals1 | lectin, galactose binding, soluble 1 | NM_008495 |
| Azin1 | antizyme inhibitor 1 | NM_001102458, NM_018745 |
| Mtss1 | metastasis suppressor 1 | NM_144800, NM_001146180 |
| Ly6d | lymphocyte antigen 6 complex, locus D | NM_010742 |
| Rac2 | RAS-related C3 botulinum substrate 2 | NM_009008 |
| Cldn5 | claudin 5 | NM_013805 |
| B4galt4 | UDP-Gal:betaGlcNAc beta 1,4-galactosyltransferase, polypeptide 4 | NM_019804 |
| Atp13a3 | ATPase type 13A3 | NM_001128096, NM_001128094 |
| Cd200 | CD200 antigen | NM_010818 |
| Tagap | T cell activation Rho GTPase activating protein | NM_145968 |
| H2-DMa | histocompatibility 2, class II, locus DMa | NM_010386 |
| H2-Eb1 | histocompatibility 2, class II antigen E beta | NM_010382 |

| Gene Symbol | Gene Name | Gene Accession Number |
|---|---|---|
| Runx2 | runt related transcription factor 2 | NM_001145920, NM_001146038, NM_009820 |
| Ehd1 | EH-domain containing 1 | NM_010119 |
| Cybasc3 | cytochrome b, ascorbate dependent 3 | NM_201351 |
| Mpeg1 | macrophage expressed gene 1 | NM_010821 |
| Papss2 | 3'-phosphoadenosine 5'-phosphosulfate synthase 2 | NM_011864, NM_001201470 |
| Ifit3 | interferon-induced protein with tetratricopeptide repeats 3 | NM_010501 |
| Fads2 | fatty acid desaturase 2 | NM_019699 |
| Dapl1 | death associated protein-like 1 | NM_029723 |
| Nebl | nebulette | NM_028757 |
| Cd44 | CD44 antigen | NM_001177787, NM_009851, NM_001177785, NM_001039150, NM_001039151, NM_001177786 |
| Car3 | carbonic anhydrase 3 | NM_007606 |
| Terc | telomerase RNA component | NR_001579 |
| Cd53 | CD53 antigen | NM_007651 |
| Fam102b | family with sequence similarity 102, member B | NM_001163567 |
| Ccl21a | chemokine (C-C motif) ligand 21A (serine) | NM_011124 |
| Coro2a | coronin, actin binding protein 2A | NM_001164804, NM_178893 |
| Cyth3 | cytohesin 3 | NM_011182, NM_001163548 |
| Alox5ap | arachidonate 5-lipoxygenase activating protein | NM_009663 |
| Selplg | selectin, platelet (p-selectin) ligand | NM_009151 |
| Irak2 | interleukin-1 receptor-associated kinase 2 | NM_172161, NM_001113553 |
| Cd69 | CD69 antigen | NM_001033122 |
| Tyrobp | TYRO protein tyrosine kinase binding protein | NM_011662 |
| Nkg7 | natural killer cell group 7 sequence | NM_024253 |
| Klk1 | kallikrein 1 | NM_010639 |
| Siglech | sialic acid binding Ig-like lectin H | NM_178706 |
| Ucp2 | uncoupling protein 2 (mitochondrial, proton carrier) | NM_011671 |
| Lsp1 | lymphocyte specific 1 | NM_019391, NM_001136071 |
| Spib | Spi-B transcription factor (Spi-1/PU.1 related) | NM_019866 |
| Cd37 | CD37 antigen | NM_007645 |
| Snord116 | small nucleolar RNA, C/D box 116 | AF241256 |
| Hbb-b1, Hbb-b2, Beta-s | hemoglobin, beta adult major chain, hemoglobin, beta adult minor chain, hemoglobin subunit beta-1-like | NM_016956, NM_008220, NM_001201391 |
| Gprc5b | G protein-coupled receptor, family C, group 5, member B | NM_022420, NM_001195774 |
| Cox6a2 | cytochrome c oxidase, subunit VI a, polypeptide 2 | NM_009943 |
| Irf7 | interferon regulatory factor 7 | NM_016850, NM_001252600, NM_001252601 |
| Igf2 | insulin-like growth factor 2 | NM_001122737, NM_010514, NM_001122736 |
| Lpl | lipoprotein lipase | NM_008509 |
| Herpud1 | homocysteine-inducible, endoplasmic reticulum stress-inducible, ubiquitin-like domain member 1 | NM_022331 |
| Irf8 | interferon regulatory factor 8 | NM_008320 |
| Cd209a | CD209a antigen | NM_133238 |
| Cd209d | CD209d antigen | NM_130904 |
| Ifi30 | interferon gamma inducible protein 30 | NM_023065 |
| Cyba | cytochrome b-245, alpha polypeptide | NM_007806 |
| Dennd4a | DENN/MADD domain containing 4A | NM_001162917 |
| Ccr9 | chemokine (C-C motif) receptor 9 | NM_009913, NM_001166625 |
| Cybb | cytochrome b-245, beta polypeptide | NM_007807 |

In some embodiments, Table 9 excludes Sell. In some embodiments, Table 9 excludes Siglech. In some embodiments, Table 9 excludes Cd44.

Table 9B—Genes over-represented in V-EC unique to skin (197 genes)

Gm7609, Csprs, Glul, Itpkb, Stk17b, Ankrd44, Tns1, Fam124b, Dock10, Ptprc, Rgs2, Rgs1, Fcer1g, Trdn, Cdk19, Gp49a, Lilrb4, Tmem229b, Smpdl3a, Itgb2, Hmha1, B4galnt1, Amd2///Amd1, Amd2///Amd1, Slc41a2, Glipr1, Ikzf1, Glul, Spred2, Bcl11a, Lcp2, Atp2a3, Tmem100, Chad, Fmnl1, Plek, Dock2, Cyfip2, Cd68, Bcl6b, Abr, Evi2a, Ccl9, Ccl6, Cd300c, Cd7, Pld4, Stxbp6, Ifi2712a, Hist1h2bn, Hist1h2bk, Hist1h2ac///Hist1h2ae///Hist1h2ag///Hist1h2ah///Hist1h2an///Hist1h2ab///Hist1h2ai///Hist1h2af///Hist1h2ad///Hist1h2ao///Hist1h2ap, Hist1h2bb, Bmp6, Cd180, Gpr137b-ps, Hist1h2ak, Hist1h2ac///Hist1h2ae///Hist1h2an///Hist1h2ab///Hist1h2ai///Hist1h2ad///Hist1h2ao///Hist1h2ap///Hist1h2ag, Hist1h2bf///Hist1h2bj///Hist1h2b1///Hist1h2bn, Mast4, Gapt, Gm3002, Rnase6, Lcp1, Gzmb, Rb1, Gpr183, Fyb, Myo10, Ptp4a3, Cyth4, Lgals1, Nckap1l, Il7r, Azin1, Mtss1, Sla, Ly6d, Il2rb, Rac2, Slc38a1, Cldn5, B4galt4, Tigit, Cd200, Tagap, H2-DMa, H2-Ab1, H2-Eb1, Amd2///Amd1, H2-Aa, Hspa1a, Runx2, Rftn1, 9430020K01Rik, Cd74, Lox, Amd2///Amd1, Ehd1, Cybasc3, Mpeg1, Papss2, Ifit3, Kif11, Ctsw, Fads2, AW112010, Blnk, Rapgef1, Dapl1, Itga4, Sfpi1, Slc28a2, Id1, Rnd3, Cytip, Cd44, Bcl2l1, Stmn2, Adh1, Cpa3, F630111L10Rik, Lrat, Terc, Cd53, Fam102b, 6330407A03Rik, LOC100862177///Gm13304///Gm10591///Ccl21b///LOC100041593///Ccl21c///Gm1987///Ccl21a, Laptm5, Runx3, Coro2a, Amd2///Amd1, BC013712, Cd52, Pion, Kit, EG665031, LOC620551, Hvcn1, Gpr30, Cyth3, Alox5ap, Rheb, Prom1, Lnx1, Plac8, Selplg, Amd1, Cd8b1, Gata2, Gkn3, Nup210, Timp4, Cd4, Cd69, Dusp16, Cd79a, Tyrobp, Nkg7, Klk1///Klk1b5, Siglech, Fchsd2, Itgal, Ifitm1, Lsp1, Lair1, Spib, Cd37, Mctp2, Hbb-b1///Hbb-b2///Beta-s, Hbb-b1///Hbb-b2///Beta-s, Gprc5b, Igsf6, Coro1a, Cox6a2, Igf2, Ifitm1, Gm10674, Lpl, Herpud1, Lrrc36, Plcg2, Irf8, Cd209a, Cd209d, Plekha2, Ifi30, Cyba, Dennd4a, Dennd4a, Tlr9, Ccr9, Filip1, Sh3kbp1, Cybb, Pls3, LOC665406, and LOC100041704.

| Gene Symbol | Gene Name | Gene Accession Number |
| --- | --- | --- |
| Gm7609, Csprs | predicted pseudogene 7609 /// component of Sp100-rs | NM_033616, NM_001081746 |
| Glul | glutamate-ammonia ligase (glutamine synthetase) | NM_008131 |
| Itpkb | inositol 1,4,5-trisphosphate 3-kinase B | NM_001081175 |
| Stk17b | serine/threonine kinase 17b (apoptosis-inducing) | NM_133810 |
| Ankrd44 | ankyrin repeat domain 44 | NM_001081433 |
| Tns1 | tensin 1 | NM_027884 |
| Fam124b | family with sequence similarity 124, member B | NM_173425 |
| Dock10 | dedicator of cytokinesis 10 | NM_175291 |
| Ptprc | protein tyrosine phosphatase, receptor type, C | NM_001268286, NM_011210, NM_001111316 |
| Rgs2 | regulator of G-protein signaling 2 | NM_009061 |
| Rgs1 | regulator of G-protein signaling 1 | NM_015811 |
| Fcer1g | Fc receptor, IgE, high affinity I, gamma polypeptide | NM_010185 |
| Trdn | triadin | NM_029726 |
| Cdk19 | cyclin-dependent kinase 19 | NM_198164, NM_001168304 |
| Gp49a | glycoprotein 49 A | NM_008147 |
| Lilrb4 | leukocyte immunoglobulin-like receptor, subfamily B, member 4 | NM_013532 |
| Tmem229b | transmembrane protein 229B | NM_001170401, NM_178745 |
| Smpdl3a | sphingomyelin phosphodiesterase, acid-like 3A | NM_020561 |
| Itgb2 | integrin beta 2 | NM_008404 |
| Hmha1 | histocompatibility (minor) HA-1 | NM_027521, NM_001142701 |
| B4galnt1 | beta-1,4-N-acetyl-galactosaminyl transferase 1 | NM_008080, NM_027739 |
| Amd2 /// Amd1 | S-adenosylmethionine decarboxylase 2 /// S-adenosylmethionine decarboxylase 1 | NM_009665, NM_007444 |
| Amd2 /// Amd1 | S-adenosylmethionine decarboxylase 2 /// S-adenosylmethionine decarboxylase 1 | NM_007444, NM_009665 |
| Slc41a2 | solute carrier family 41, member 2 | NM_177388 |
| Glipr1 | GLI pathogenesis-related 1 (glioma) | NM_028608 |
| Ikzf1 | IKAROS family zinc finger 1 | NM_001025597, NM_009578 |
| Glul | glutamate-ammonia ligase (glutamine synthetase) | NM_008131 |
| Spred2 | sprouty-related, EVH1 domain containing 2 | ENSMUST00000093299 /// BC040462 |
| Bcl11a | B cell CLL/lymphoma 11A (zinc finger protein) | NM_016707, NM_001242934, NM_001159289 |
| Lcp2 | lymphocyte cytosolic protein 2 | NM_010696 |
| Atp2a3 | ATPase, Ca++ transporting, ubiquitous | NM_001163336, NM_016745, NM_001163337 |
| Tmem100 | transmembrane protein 100 | NM_026433 |

-continued

| Gene Symbol | Gene Name | Gene Accession Number |
|---|---|---|
| Chad | chondroadherin | NM_007689 |
| Fmnl1 | formin-like 1 | NM_019679, NM_001077698 |
| Plek | pleckstrin | NM_019549 |
| Dock2 | dedicator of cyto-kinesis 2 | NM_033374 |
| Cyfip2 | cytoplasmic FMR1 interacting protein 2 | NM_001252460, NM_001252459, NM_133769 |
| Cd68 | CD68 antigen | NM_009853 |
| Bcl6b | B cell CLL/lymphoma 6, member B | NM_007528 |
| Abr | active BCR-related gene | NM_198894, NM_198018, NM_198895 |
| Evi2a | ecotropic viral integration site 2a | NM_001033711, NM_010161 |
| Ccl9 | chemokine (C-C motif) ligand 9 | NM_011338 |
| Ccl6 | chemokine (C-C motif) ligand 6 | NM_009139 |
| Cd300c | CD300C antigen | NM_199225 |
| Cd7 | CD7 antigen | NM_009854 |
| Pld4 | phospholipase D family, member 4 | NM_178911 |
| Stxbp6 | syntaxin binding protein 6 (amisyn) | NM_144552 |
| Ifi27l2a | interferon, alpha-inducible protein 27 like 2A | NM_029803 |
| Hist1h2bn | histone cluster 1, H2bn | NM_178201 |
| Hist1h2bk | histone cluster 1, H2bk | NM_175665 |
| Hist1h2ac /// Hist1h2ae /// Hist1h2ag /// Hist1h2ah /// Hist1h2an /// Hist1h2ab /// Hist1h2ai /// Hist1h2af /// Hist1h2ad /// Hist1h2ao /// Hist1h2ap | histone cluster 1, H2ac /// histone cluster 1, H2ae /// histone cluster 1, H2ag /// histone cluster 1, H2ah /// histone cluster 1, H2an /// histone cluster 1, H2ab /// histone cluster 1, H2ai /// histone cluster 1, H2af /// histone cluster 1, H2ad /// histone cluster 1, H2ao /// histone cluster 1, H2ap | NM_175661, NM_178185, NM_178188 |
| Hist1h2bb | histone cluster 1, H2bb | NM_175664 |
| Bmp6 | bone morphogenetic protein 6 | NM_007556 |
| Cd180 | CD180 antigen | NM_008533 |
| Gpr137b-ps | G protein-coupled receptor 137B, pseudogene | NR_003568 |
| Hist1h2ak | histone cluster 1, H2ak | NM_178183 |
| Hist1h2ac /// Hist1h2ae /// Hist1h2ah /// Hist1h2an /// Hist1h2ab /// Hist1h2ai /// Hist1h2ad /// Hist1h2ao /// Hist1h2ap /// Hist1h2ag | histone cluster 1, H2ac /// histone cluster 1, H2ae /// histone cluster 1, H2ah /// histone cluster 1, H2an /// histone cluster 1, H2ab /// histone cluster 1, H2ai /// histone cluster 1, H2ad /// histone cluster 1, H2ao /// histone cluster 1, H2ap /// histone cluster 1, H2ag | NM_178185, NM_178184, NM_178188, NM_178186 |
| Hist1h2bf /// Hist1h2bj /// Hist1h2bl /// Hist1h2bn | histone cluster 1, H2bf /// histone cluster 1, H2bj /// histone cluster 1, H2bl /// histone cluster 1, H2bn | NM_178195 |
| Mast4 | microtubule associated serine/threonine kinase family member 4 | NM_175171 |
| Gapt | Grb2-binding adaptor, transmembrane | NM_177713 |
| Gm3002 | predicted gene 3002 | NR_033388 |
| Rnase6 | ribonuclease, RNase A family, 6 | NM_030098 |
| Lcp1 | lymphocyte cytosolic protein 1 | NM_008879, NM_001247984 |
| Gzmb | granzyme B | NM_013542 |
| Rb1 | retinoblastoma 1 | NM_009029 |
| Gpr183 | G protein-coupled receptor 183 | NM_183031 |
| Fyb | FYN binding protein | NM_001278269, NM_011815 |
| Myo10 | myosin X | NM_019472 |
| Ptp4a3 | protein tyrosine phosphatase 4a3 | NM_001166389, NM_008975, NM_001166388 |
| Cyth4 | cytohesin 4 | NM_028195 |
| Lgals1 | lectin, galactose binding, soluble 1 | NM_008495 |
| Nckap1l | NCK associated protein 1 like | NM_153505 |
| Il7r | interleukin 7 receptor | NM_008372 |
| Azin1 | antizyme inhibitor 1 | NM_018745, NM_001102458 |

| Gene Symbol | Gene Name | Gene Accession Number |
|---|---|---|
| Mtss1 | metastasis suppressor 1 | NM_001146180, NM_144800 |
| Sla | src-like adaptor | NM_009192, NM_001029841 |
| Ly6d | lymphocyte antigen 6 complex, locus D | NM_010742 |
| Il2rb | interleukin 2 receptor, beta chain | NM_008368 |
| Rac2 | RAS-related C3 botulinum substrate 2 | NM_009008 |
| Slc38a1 | solute carrier family 38, member 1 | NM_134086, NM_001166456, NM_001166458 |
| Cldn5 | claudin 5 | NM_013805 |
| B4galt4 | UDP-Gal:betaGlcNAc beta 1,4-galactosyltransferase, polypeptide 4 | NM_019804 |
| Tigit | T cell immunoreceptor with Ig and ITIM domains | NM_001146325 |
| Cd200 | CD200 antigen | NM_010818 |
| Tagap | T cell activation Rho GTPase activating protein | NM_145968 |
| H2-DMa | histocompatibility 2, class II, locus DMa | NM_010386 |
| H2-Ab1 | histocompatibility 2, class II antigen A, beta 1 | NM_207105 |
| H2-Eb1 | histocompatibility 2, class II antigen E beta | NM_010382 |
| Amd2 /// Amd1 | S-adenosylmethionine decarboxylase 2 /// S-adenosylmethionine decarboxylase 1 | NM_009665, NM_007444 |
| H2-Aa | histocompatibility 2, class II antigen A, alpha | NM_010378 |
| Hspa1a | heat shock protein 1A | NM_010479 |
| Runx2 | runt related transcription factor 2 | NM_009820, NM_001146038, NM_001145920 |
| Rftn1 | raftlin lipid raft linker 1 | NM_181397 |
| 9430020K01Rik | RIKEN cDNA 9430020K01 gene | NM_001081963 |
| Cd74 | CD74 antigen (invariant polypeptide of major histocompatibility complex, class II antigen-associated) | NM_001042605, NM_010545 |
| Lox | lysyl oxidase | NM_010728 |
| Amd2 /// Amd1 | S-adenosylmethionine decarboxylase 2 /// S-adenosylmethionine decarboxylase 1 | NM_009665, NM_007444 |
| Ehd1 | EH-domain containing 1 | NM_010119 |
| Cybasc3 | cytochrome b, ascorbate dependent 3 | NM_201351 |
| Mpeg1 | macrophage expressed gene 1 | NM_010821 |
| Papss2 | 3'-phosphoadenosine 5'-phosphosulfate synthase 2 | NM_011864, NM_001201470 |
| Ifit3 | interferon-induced protein with tetratricopeptide repeats 3 | NM_010501 |
| Kif11 | kinesin family member 11 | NM_010615 |
| Ctsw | cathepsin W | NM_009985 |
| Fads2 | fatty acid desaturase 2 | NM_019699 |
| AW112010 | expressed sequence AW112010 | NM_001177351 |
| Blnk | B cell linker | NM_008528 |
| Rapgef1 | Rap guanine nucleotide exchange factor (GEF) 1 | NM_054050, NM_001039086, NM_001039087 |
| Dapl1 | death associated protein-like 1 | NM_029723 |
| Itga4 | integrin alpha 4 | NM_010576 |
| Sfpi1 | SFFV proviral integration 1 | NM_011355 |
| Slc28a2 | solute carrier family 28 (sodium-coupled nucleoside transporter), member 2 | NM_172980 |
| Id1 | inhibitor of DNA binding 1 | NM_010495 |
| Rnd3 | Rho family GTPase 3 | NM_028810 |
| Cytip | cytohesin 1 interacting protein | NM_139200 |
| Cd44 | CD44 antigen | NM_001177787, NM_001177785, NM_009851, NM_001039150, NM_001177786 |
| Bcl2l1 | BCL2-like 1 | NM_009743 |
| Stmn2 | stathmin-like 2 | NM_025285 |
| Adh1 | alcohol dehydrogenase 1 (class I) | NM_007409 |
| Cpa3 | carboxypeptidase A3, mast cell | NM_007753 |
| F630111L10Rik | RIKEN cDNA F630111L10 gene | NR_045641 |
| Lrat | lecithin-retinol acyltransferase (phosphatidylcholine-retinol-O-acyltransferase) | NM_023624 |
| Terc | telomerase RNA component | NR_001579 |
| Cd53 | CD53 antigen | NM_007651 |
| Fam102b | family with sequence similarity 102, member B | NM_001163567 |
| 6330407A03Rik | RIKEN cDNA 6330407A03 gene | NR_028126 |
| LOC100862177 /// Gm13304 /// Gm10591 /// | c-C motif chemokine 21c-like /// predicted gene 13304 /// predicted gene 10591 /// chemokine (C-C motif) ligand 21B (leucine) /// c-C motif | NM_001193668, NM_001193666, NM_011335, |

| Gene Symbol | Gene Name | Gene Accession Number |
|---|---|---|
| Ccl21b /// LOC100041593 /// Ccl21c /// Gm1987 /// Ccl21a | chemokine 21c-like /// chemokine (C-C motif) ligand 21C (leucine) /// predicted gene 1987 /// chemokine (C-C motif) ligand 21A (serine) | NM_023052, NM_001270360, NM_011124, NM_001193667 |
| Laptm5 | lysosomal-associated protein transmembrane 5 | NM_010686 |
| Runx3 | runt related transcription factor 3 | NM_019732 |
| Coro2a | coronin, actin binding protein 2A | NM_178893, NM_001164804 |
| Amd2 /// Amd1 | S-adenosylmethionine decarboxylase 2 /// S-adenosylmethionine decarboxylase 1 | NM_009665, NM_007444 |
| BC013712 | cDNA sequence BC013712 | NM_001033308 |
| Cd52 | CD52 antigen | NM_013706 |
| Pion | pigeon homolog (*Drosophila*) | NM_175437 |
| Kit | kit oncogene | NM_001122733, NM_021099 |
| EG665031 | — | ENSMUST00000171624 /// ENSMUST00000115900 /// ENSMUST00000166649 |
| LOC620551 | PRAME family member 12-like /// predicted gene 6468 /// uncharacterized LOC620639 /// predicted gene 6502 /// predicted gene 6509 /// PRAME family member 12-like /// predicted gene 6351 /// PRAME family member 12-like /// predicted gene 7682 /// predicted gene 7982 /// PRAME family member 12-like /// PRAME family member 12-like /// predicted gene 6346 /// predicted gene 6348 | NT_187059 |
| Hvcn1 | hydrogen voltage-gated channel 1 | NM_001042489, NM_028752 |
| Gpr30 | G protein-coupled receptor 30 | NM_029771 |
| Cyth3 | cytohesin 3 | NM_001163548, NM_011182 |
| Alox5ap | arachidonate 5-lipoxygenase activating protein | NM_009663 |
| Rheb | Ras homolog enriched in brain | NM_053075 |
| Prom1 | prominin 1 | NM_001163585, NM_008935, NM_001163582, NM_001163578, NM_001163583, NM_001163584, NM_001163577 |
| Lnx1 | ligand of numb-protein X 1 | NM_001159580, NM_001159579, NM_001159578, NM_001159577, NM_010727 |
| Plac8 | placenta-specific 8 | NM_139198 |
| Selplg | selectin, platelet (p-selectin) ligand | NM_009151 |
| Amd1 | S-adenosylmethionine decarboxylase 1 | NM_009665 |
| Cd8b1 | CD8 antigen, beta chain 1 | NM_009858 |
| Gata2 | GATA binding protein 2 | NM_008090 |
| Gkn3 | gastrokine 3 | NM_026860 |
| Nup210 | nucleoporin 210 | NM_018815 |
| Timp4 | tissue inhibitor of metalloproteinase 4 | NM_080639 |
| Cd4 | CD4 antigen | NM_013488 |
| Cd69 | CD69 antigen | NM_001033122 |
| Dusp16 | dual specificity phosphatase 16 | NM_001048054, NM_130447 |
| Cd79a | CD79A antigen (immunoglobulin-associated alpha) | NM_007655 |
| Tyrobp | TYRO protein tyrosine kinase binding protein | NM_011662 |
| Nkg7 | natural killer cell group 7 sequence | NM_024253 |
| Klk1 /// Klk1b5 | kallikrein 1 /// kallikrein 1-related peptidase b5 | NM_008456, NM_010639 |
| Siglech | sialic acid binding Ig-like lectin H | NM_178706 |
| Fchsd2 | FCH and double SH3 domains 2 | NM_001146010, NM_199012 |
| Itgal | integrin alpha L | NM_001253874, NM_001253873, NM_008400, NM_001253872 |
| Ifitm1 | interferon induced transmembrane protein 1 | NM_001112715, NM_026820 |

-continued

| Gene Symbol | Gene Name | Gene Accession Number |
|---|---|---|
| Lsp1 | lymphocyte specific 1 | NM_001136071, NM_019391 |
| Lair1 | leukocyte-associated Ig-like receptor 1 | NM_001113474, NM_178611 |
| Spib | Spi-B transcription factor (Spi-1/PU.1 related) | NM_019866 |
| Cd37 | CD37 antigen | NM_007645 |
| Mctp2 | multiple C2 domains, transmembrane 2 | NM_001024703 |
| Hbb-b1 /// Hbb-b2 /// Beta-s | hemoglobin, beta adult major chain /// hemoglobin, beta adult minor chain /// hemoglobin subunit beta-1-like | NM_008220, NM_001201391 |
| Hbb-b1 /// Hbb-b2 /// Beta-s | hemoglobin, beta adult major chain /// hemoglobin, beta adult minor chain /// hemoglobin subunit beta-1-like | NM_001201391, NM_008220 |
| Gprc5b | G protein-coupled receptor, family C, group 5, member B | NM_001195774, NM_022420 |
| Igsf6 | immunoglobulin superfamily, member 6 | NM_030691 |
| Coro1a | coronin, actin binding protein 1A | NM_009898 |
| Cox6a2 | cytochrome c oxidase, subunit VI a, polypeptide 2 | NM_009943 |
| Igf2 | insulin-like growth factor 2 | NM_001122736, NM_010514, NM_001122737 |
| Ifitm1 | interferon induced transmembrane protein 1 | NM_001112715 |
| Gm10674 | predicted gene 10674 | NC_000074 |
| Lpl | lipoprotein lipase | NM_008509 |
| Herpud1 | homocysteine-inducible, endoplasmic reticulum stress-inducible, ubiquitin-like domain member 1 | NM_022331 |
| Lrrc36 | leucine rich repeat containing 36 | NM_001170789, NM_001033371, NM_001170788 |
| Plcg2 | phospholipase C, gamma 2 | NM_172285 |
| Irf8 | interferon regulatory factor 8 | NM_008320 |
| Cd209a | CD209a antigen | AF373408 |
| Cd209d | CD209d antigen | ENSMUST00000011445 /// AF373411 |
| Plekha2 | pleckstrin homology domain-containing, family A (phosphoinositide binding specific) member 2 | NM_031257 |
| Ifi30 | interferon gamma inducible protein 30 | NM_023065 |
| Cyba | cytochrome b-245, alpha polypeptide | NM_007806 |
| Dennd4a | DENN/MADD domain containing 4A | NM_001162917 |
| Dennd4a | DENN/MADD domain containing 4A | NM_001162917 |
| Tlr9 | toll-like receptor 9 | NM_031178 |
| Ccr9 | chemokine (C-C motif) receptor 9 | NM_009913, NM_001166625 |
| Filip1 | filamin A interacting protein 1 | NM_001081243 |
| Sh3kbp1 | SH3-domain kinase binding protein 1 | NM_021389, NM_001135728, NM_001135727 |
| Cybb | cytochrome b-245, beta polypeptide | NM_007807 |
| Pls3 | plastin 3 (T-isoform) | NM_001166454, NM_001166453, NM_145629 |
| LOC665406 | Y-linked testis-specific protein 1-like | NT_166399 |
| LOC100041704 | y-linked testis-specific protein 1-like | NT_166345 |

Table 10 lists genes under-represented in V-EC unique to adipose tissue. As used herein, "Table 10" includes Table 10A and Table 10B below.

Table 10A—Genes under-represented in V-EC unique to adipose tissue (28 genes)

Crispld1, Phlpp1, Nr5a2, Adora2a, Aim1, Scgb3a1, Nos2, Sept4, Dgke, Dusp3, Lrrc3b, Itpr3, H2-Ab1, Ifit2, Sox18, Nes, Hspg2, Gba2, Tbx3, Gpr81, Cecr2, Kcna5, Snord33, Thrsp, Dapk2, Jam3, 6230427J02Rik, Gpc4.

| Gene Symbol | Gene Name | Gene Accession Number |
|---|---|---|
| Crispld1 | cysteine-rich secretory protein LCCL domain containing 1 | NM_031402 |
| Phlpp1 | PH domain and leucine rich repeat protein phosphatase 1 | NM_133821 |
| Nr5a2 | nuclear receptor subfamily 5, group A, member 2 | NM_001159769, NM_030676 |
| Adora2a | adenosine A2a receptor | NM_009630 |
| Aim1 | absent in melanoma 1 | NM_172393 |
| Scgb3a1 | secretoglobin, family 3A, member 1 | NM_170727, NM_054037 |
| Nos2 | nitric oxide synthase 2, inducible | NM_010927 |
| Sept4 | septin 4 | NM_011129 |
| Dgke | diacylglycerol kinase, epsilon | NM_019505 |
| Dusp3 | dual specificity phosphatase 3 (vaccinia virus phosphatase VH1-related) | NM_028207 |
| Lrrc3b | leucine rich repeat containing 3B | NM_146052 |
| Itpr3 | inositol 1,4,5-triphosphate receptor 3 | NM_080553 |

-continued

| Gene Symbol | Gene Name | Gene Accession Number |
|---|---|---|
| H2-Ab1 | histocompatibility 2, class II antigen A, beta 1 | NM_207105 |
| Ifit2 | interferon-induced protein with tetratricopeptide repeats 2 | NM_008332 |
| Sox18 | SRY-box containing gene 18 | NM_009236 |
| Nes | nestin | NM_016701 |
| Hspg2 | perlecan (heparan sulfate proteoglycan 2) | NM_008305 |
| Gba2 | glucosidase beta 2 | NM_172692 |
| Tbx3 | T-box 3 | NM_198052, NM_011535 |
| Gpr81 | G protein-coupled receptor 81 | NM_175520 |
| Cecr2 | cat eye syndrome chromosome region, candidate 2 | NM_001128151 |
| Kcna5 | potassium voltage-gated channel, shaker-related subfamily, member 5 | NM_145983 |
| Rpl13a, | ribosomal protein L13A, | NM_009438; |
| Snord33 | small nucleolar RNA, C/D box 33 | NR_001277 |
| Thrsp | thyroid hormone responsive SPOT14 homolog (*Rattus*) | NM_009381 |

-continued

| Gene Symbol | Gene Name | Gene Accession Number |
|---|---|---|
| Dapk2 | death-associated protein kinase 2 | NM_010019 |
| Jam3 | junction adhesion molecule 3 | NM_023277 |
| 6230427J02Rik | RIKEN cDNA 6230427J02 gene | NM_026597 |
| Gpc4 | glypican 4 | NM_008150 |

Table 10B—Genes under-represented in V-EC unique to adipose tissue (63genes)

Snora75, Nr5a2, Rcsd1, Nepn, Aim1, Scgb3a1, Kcnj2, Abca8b, Mboat2, Pgf, F2r, Gm10021///Gm16525, Gm3696, Arc, Apol7c, Gm7735, Robo1, H2-M11, 3110082D06Rik, Ms4a1, AA467197, Arhgef26, Casq2, Ttll7, Clca5, Tnc, Speer4d, Speer8-ps1, Tbx3, Tpst1, Speer4e, A430089I19Rik, Creb5, Gm3994, Vmn1r100, Vmn1r148, Vmn1r122, Vmn1r114, Vmn1r132, Vmn1r158, Vmn1r93, Vmn1r-ps79, Gm10670, Vmn1r117, Vmn1r125, Vmn1r118, Vmn1r101, Vmn1r151, Vmn1r115, Snord115, Ces2e, Epor, Jam3, Tmem35, Mir680-2, Srsy, Ssty1, LOC100041704, LOC100042359, LOC665698, LOC100039147, LOC665128, and LOC100504530.

| Gene Symbol | Gene Name | Gene Accession Number |
|---|---|---|
| Snora75 | small nucleolar RNA, H/ACA box 75 | NC_000067 |
| Nr5a2 | nuclear receptor subfamily 5, group A, member 2 | NM_001159769, NM_030676 |
| Rcsd1 | RCSD domain containing 1 | NM_001038846, NM_178593 |
| Nepn | nephrocan | NM_025684 |
| Aim1 | absent in melanoma 1 | NM_172393 |
| Scgb3a1 | secretoglobin, family 3A, member 1 | NM_054037, NM_170727 |
| Kcnj2 | potassium inwardly-rectifying channel, subfamily J, member 2 | NM_008425 |
| Abca8b | ATP-binding cassette, sub-family A (ABC1), member 8b | NM_013851 |
| Mboat2 | membrane bound O-acyltransferase domain containing 2 | NM_026037, NM_001083341 |
| Pgf | placental growth factor | NM_008827 |
| F2r | coagulation factor II (thrombin) receptor | NM_010169 |
| Gm10021 /// Gm16525 | predicted gene 10021 /// predicted gene, 16525 | NC_000080 |
| Gm3696 | predicted gene 2897 /// predicted gene 3696 | NM_001177714, NM_001177715, NM_001024712 |
| Arc | activity regulated cytoskeletal-associated protein | NM_018790 |
| Apol7c | apolipoprotein L 7c | NM_175391 |
| Gm7735 | predicted gene 7735 | NC_000082 |
| Robo2 | roundabout homolog 2 (*Drosophila*) | NM_175549 |
| H2-M11 | histocompatibility 2, M region locus 11 | NM_177635 |
| 3110082D06Rik | RIKEN cDNA 3110082D06 gene | NM_028474 |
| Ms4a1 | membrane-spanning 4-domains, subfamily A, member 1 | NM_007641 |
| AA467197 | expressed sequence AA467197 | NM_001004174 |
| Arhgef26 | Rho guanine nucleotide exchange factor (GEF) 26 | NM_001081295 |
| Casq2 | calsequestrin 2 | NM_009814 |
| Ttll7 | tubulin tyrosine ligase-like family, member 7 | NM_027594 |
| Clca5 | chloride channel calcium activated 5 | NM_178697 |
| Tnc | tenascin C | NM_011607 |
| Speer4d | spermatogenesis associated glutamate (E)-rich protein 4c /// disks large homolog 5-like /// spermatogenesis associated glutamate (E)-rich protein 4d | NM_025759 |
| Speer8-ps1 | spermatogenesis associated glutamate (E)-rich protein 8, pseudogene 1 | NR_001584 |
| Tbx3 | T-box 3 | NM_011535, NM_198052 |
| Tpst1 | protein-tyrosine sulfotransferase 1 | NM_001130476, NM_013837 |
| Speer4e | spermatogenesis associated glutamate (E)-rich protein 4d /// predicted gene 9758 /// predicted | NM_001122661 |

-continued

| Gene Symbol | Gene Name | Gene Accession Number |
|---|---|---|
| A430089I19Rik | gene 17019 /// spermatogenesis associated glutamate (E)-rich protein 4e RIKEN cDNA A430089I19 gene | NM_177913 |
| Creb5 | cAMP responsive element binding protein 5 | NM_172728 |
| Gm3994 | predicted gene 3994 | NG_016885 |
| Vmn1r100 | vomeronasal 1 receptor 100 | NM_001166844 |
| Vmn1r148 | vomeronasal 1 receptor 148 | NM_030736 |
| Vmn1r122 | vomeronasal 1 receptor 122 | NM_001166714 |
| Vmn1r114 | vomeronasal 1 receptor 114 | NM_001166837 |
| Vmn1r132 | vomeronasal 1 receptor 132 | NM_001122682 |
| Vmn1r158 | vomeronasal 1 receptor 158 | NM_001166841 |
| Vmn1r93 | vomernasal 1 receptor Vmn1r93 | NM_207547 |
| Vmn1r-ps79 | vomeronasal 1 receptor, pseudogene 79 | NR_030707 |
| Gm10670 | predicted gene 10670 | NM_001167161 |
| Vmn1r117 | vomeronasal 1 receptor 117 | NM_001166743 |
| Vmn1r125 | vomeronasal 1 receptor 125 | NM_001166740 |
| Vmn1r118 | vomeronasal 1 receptor 118 | NM_001166742 |
| Vmn1r101 | vomeronasal 1 receptor 101 | NM_001166836 |
| Vmn1r151 | vomeronasal 1 receptor 151 | NM_001166712 |
| Vmn1r115 | vomeronasal 1 receptor 115 | NM_001166745 |
| Snord115 | small nucleolar RNA, C/D Box 115 cluster | |
| Ces2e | carboxylesterase 2E | NM_001163756, NM_172759 |
| Epor | erythropoietin receptor | NM_010149 |
| Jam3 | junction adhesion molecule 3 | NM_023277 |
| Tmem35 | transmembrane protein 35 | NM_026239 |
| Mir680-2 | microRNA 680-2 | mmu-mir-680-2 |
| Srsy | serine-rich, secreted, Y-linked | NC_000087 |
| Ssty1 | spermiogenesis specific transcript on the Y1 | NM_009220 |
| LOC100041704 | y-linked testis-specific protein 1-like | NT_166345 |
| LOC100042359 | y-linked testis-specific protein 1-like | NT_166412 |
| LOC665698 | y-linked testis-specific protein 1-like | NT_161875 |
| LOC100039147 | y-linked testis-specific protein 1-like | NT_166418 |
| LOC665128 | y-linked testis-specific protein 1-like | NT_161892 |
| LOC100504530 | uncharacterized LOC100504530 | NT_161916 |

Table 11 lists genes under-represented in V-EC unique to lymph node. As used herein, "Table 11" includes Table 11A and Table 11B below.

Table 11A—Genes under-represented in V-EC unique to lymph node (181 genes)

Sdpr, Pik3c2b, Glt25d2, Rgs16, Hecw2, Tns1, Serpine2, Inhbb, Prelp, Btg2, Nav1, Cfh, Hmcn1, 1700025G04Rik, Rgl1, Fmo1, Mpzl1, Pcp4l1, Ephx1, H1x, Prox1, Syne1, Sgk1, Sesn1, Dcbld1, Palm, Gadd45b, Ptprb, Pde7b, Enpp3, Marcks, Lyz2, Gm129, Selm, Ramp3, Hba-a1, Hba-a2, Pmp22, Pik3r6, Per1, Mir22, Kcnj2, Sec14l1, B3gnt2, Olfr1396, Alox12, Fam101b, Pitpnc1, Cmpk2, Pxdn, Syne2, Fos, Tnfaip2, Rhob, Ckb, Dip2c, Hist1h2bm, Arrdc3, Plk2, Ppap2a, Arl15, Gpx8, Ptprg, Galnt12, Spata13, Ints9, Stc1, Tsc22d1, Tspan14, Hmbox1, Extl3, Sorbs3, Rb1, Fzd6, Dennd3, Nr4a1, Tenc1, St3gal1, Ly6c1, Ly6c2, Rapgef3, Hes1, Ets2, Adamts1, Cdkn1a, Ddah2, Tmem204, Dusp1, Ptprm, Xdh, Spry4, Synpo, Afap1l1, Fam38b, Unc93b1, Sipa1, Sorbs1, Itih5, Nostrin, Aplnr, Trp53i11, Mertk, Plcb1, Map1lc3a, Lbp, Notch1, Ggta1, Nr4a2, Thbd, Cp, Fam198b, S100a6, Hist2h2aa1, Fabp4, Lmna, Cdc14a, Cyr61, Npr2, Acer2, Id3, Dhrs3, Clstn1, Klf4, Ppbp, Lrrc8c, Cd36, Atp8a1, Sparcl1, Aldh2, Sh2b3, Scarb1, Flt1, Mmrn1, Dysf, Mgll, Fbln2, Lmcd1, Pparg, 8430408G22Rik, Klrb1f, Emp1, Impdh1, Tra2a, Frmd4b, Plxnd1, Mgp, Exoc3l2, Akap13, Tm6sf1, Fosb, Ceacam1, Ltbp4, Lrp3, Galntl4, Myadm, Col4a2, Plat, Gm16486, Dnajb1, Mir27a, Cx3cl1, Cdh13, Snord68, Nrp1, Gas6, 1810011O10Rik, Dlc1, Ier2, Junb, Dok4, Slc7a5, Tafld, Slc44a2, Plscr2, Endod1, Zbtb16, Tgfbr2, Cxx1c, Stard8, Tsc22d3, Sat1

| Gene Symbol | Gene Name | Gene Accession Number |
|---|---|---|
| Sdpr | serum deprivation response | NM_138741 |
| Pik3c2b | phosphoinositide-3-kinase, class 2, beta polypeptide | NM_001099276 |
| Glt25d2 | glycosyltransferase 25 domain containing 2 | NM_177756 |
| Rgs16 | regulator of G-protein signaling 16 | NM_011267 |
| Hecw2 | HECT, C2 and WW domain containing E3 ubiquitin protein ligase 2 | NM_001001883, NM_172655 |
| Tns1 | tensin 1 | NM_027884 |
| Serpine2 | serine (or cysteine) peptidase inhibitor, clade E, member 2 | NM_009255 |
| Inhbb | inhibin beta-B | NM_008381 |
| Prelp | proline arginine-rich end leucine-rich repeat | NM_054077 |
| Btg2 | B cell translocation gene 2, anti-proliferative | NM_007570 |

-continued

| Gene Symbol | Gene Name | Gene Accession Number |
| --- | --- | --- |
| Nav1 | neuron navigator 1 | NM_173437 |
| Cfh | complement component factor h | NM_009888 |
| Hmcn1 | hemicentin 1 | NM_001024720.3 |
| 1700025G04Rik | RIKEN cDNA 1700025G04 gene | NM_197990 |
| Rgl1 | ral guanine nucleotide dissociation stimulator, -like 1 | NM_016846 |
| Fmo1 | flavin containing monooxygenase 1 | NM_010231 |
| Mpzl1 | myelin protein zero-like 1 | NM_001001880, NM_001083897 |
| Pcp4l1 | Purkinje cell protein 4-like 1 | NM_025557 |
| Ephx1 | epoxide hydrolase 1, microsomal | NM_010145 |
| Hlx | H2.0-like homeobox | NM_008250 |
| Prox1 | prospero-related homeobox 1 | NM_008937 |
| Syne1 | synaptic nuclear envelope 1 | NM_001079686, NM_153399 |
| Sgk1 | serum/glucocorticoid regulated kinase 1 | NM_001161849, NM_001161845, NM_011361, NM_001161848, NM_001161850, NM_001161847 |
| Sesn1 | sestrin 1 | NM_001162908, NM_001013370 |
| Dcbld1 | discoidin, CUB and LCCL domain containing 1 | NM_025705 |
| Palm | paralemmin | NM_023128, NM_001161747 |
| Gadd45b | growth arrest and DNA-damage-inducible 45 beta | NM_008655 |
| Ptprb | protein tyrosine phosphatase, receptor type, B | NM_029928 |
| Pde7b | phosphodiesterase 7B | NM_013875 |
| Enpp3 | ectonucleotide pyrophosphatase/phosphodiesterase 3 | NM_134005 |
| Marcks | myristoylated alanine rich protein kinase C substrate | NM_008538 |
| Lyz2 | lysozyme 2 | NM_017372 |
| Gm129 | predicted gene 129 | NM_001033302 |
| Selm | selenoprotein M | NM_053267 |
| Ramp3 | receptor (calcitonin) activity modifying protein 3 | NM_019511 |
| Hba-a1 | hemoglobin alpha, adult chain 1 | NM_008218 |
| Hba-a2 | hemoglobin alpha, adult chain 2 | NM_001083955 |
| Pmp22 | peripheral myelin protein 22 | NM_008885 |
| Pik3r6 | phosphoinositide-3-kinase, regulatory subunit 6 | NM_001004435, NM_001081566 |
| Per1 | period homolog 1 (*Drosophila*) | NM_011065, NM_001159367 |
| Mir22 | microRNA 22 | NR_029739 |
| Kcnj2 | potassium inwardly-rectifying channel, subfamily J, member 2 | NM_008425 |
| Sec14l1 | SEC14-like 1 (*S. cerevisiae*) | NM_028777, NM_001166506, NM_001166507 |
| B3gnt2 | UDP-GlcNAc:betaGal beta-1,3-N-acetylglucosaminyltransferase 2 | NM_001169114, NM_016888 |
| Olfr1396 | olfactory receptor 1396 | NM_146337 |
| Alox12 | arachidonate 12-lipoxygenase | NM_007440 |
| Fam101b | family with sequence similarity 101, member B | NM_029658 |
| Pitpnc1 | phosphatidylinositol transfer protein, cytoplasmic 1 | NM_145823 |
| Cmpk2 | cytidine monophosphate (UMP-CMP) kinase 2, mitochondrial | NM_020557 |
| Pxdn | peroxidasin homolog (*Drosophila*) | NM_181395 |
| Syne2 | synaptic nuclear envelope 2 | NM_001005510.2 |
| Fos | FBJ osteosarcoma oncogene | NM_010234 |
| Tnfaip2 | tumor necrosis factor, alpha-induced protein 2 | NM_009396 |
| Rhob | ras homolog gene family, member B | NM_007483 |
| Ckb | creatine kinase, brain | NM_021273 |
| Dip2c | DIP2 disco-interacting protein 2 homolog C (*Drosophila*) | NM_001081426 |
| Hist1h2bm | histone cluster 1, H2bm | NM_178200 |
| Arrdc3 | arrestin domain containing 3 | NM_001042591 |
| Plk2 | polo-like kinase 2 | NM_152804 |

-continued

| Gene Symbol | Gene Name | Gene Accession Number |
| --- | --- | --- |
| Ppap2a | phosphatidic acid phosphatase type 2A | NM_008903, NM_008247 |
| Arl15 | ADP-ribosylation factor-like 15 | NM_172595 |
| Gpx8 | glutathione peroxidase 8 (putative) | NM_027127 |
| Ptprg | protein tyrosine phosphatase, receptor type, G | NM_008981 |
| Galntl2 | UDP-N-acetyl-alpha-D-galactosamine:polypeptide N-acetylgalactosaminyltransferase-like 2 | NM_030166 |
| Spata13 | spermatogenesis associated 13 | NM_001033272 |
| Ints9 | integrator complex subunit 9 | NM_153414, NM_001253731 |
| Stc1 | stanniocalcin 1 | NM_009285 |
| Tsc22d1 | TSC22 domain family, member 1 | NM_001177751, NM_207652 NM_009366 |
| Tspan14 | tetraspanin 14 | NM_145928 |
| Hmbox1 | homeobox containing 1 | NM_177338 |
| Extl3 | exostoses (multiple)-like 3 | NM_018788 |
| Sorbs3 | sorbin and SH3 domain containing 3 | NM_011366 |
| Rb1 | retinoblastoma 1 | NM_009029 |
| Fzd6 | frizzled homolog 6 (*Drosophila*) | NM_001162494, NM_008056 |
| Dennd3 | DENN/MADD domain containing 3 | NM_001081066 |
| Nr4a1 | nuclear receptor subfamily 4, group A, member 1 | NM_010444 |
| Tenc1 | tensin like C1 domain-containing phosphatase | NM_153533 |
| St3gal1 | ST3 beta-galactoside alpha-2,3-sialyltransferase 1 | NM_009177 |
| Ly6c1 | lymphocyte antigen 6 complex, locus C1 | NM_001252057, NM_001252058, NM_010741 NM_001252056, NM_001252055, |
| Ly6c2 | lymphocyte antigen 6 complex, locus C2 | NM_001099217 |
| Rapgef3 | Rap guanine nucleotide exchange factor (GEF) 3 | NM_144850, NM_001177810 NM_001177811 |
| Hes1 | hairy and enhancer of split 1 (*Drosophila*) | NM_008235 |
| Ets2 | E26 avian leukemia oncogene 2,3' domain | NM_011809 |
| Adamts1 | a disintegrin-like and metallopeptidase (reprolysin type) with thrombospondin type 1 motif, 1 | NM_009621 |
| Cdkn1a | cyclin-dependent kinase inhibitor 1A (P21) | NM_007669, NM_001111099 |
| Ddah2 | dimethylarginine dimethylaminohydrolase 2 | NM_001190449, NM_016765 |
| Tmem204 | transmembrane protein 204 | NM_001001183 |
| Dusp1 | dual specificity phosphatase 1 | NM_013642 |
| Ptprm | protein tyrosine phosphatase, receptor type, M | NM_008984 |
| Xdh | xanthine dehydrogenase | NM_011723 |
| Spry4 | sprouty homolog 4 (*Drosophila*) | NM_011898 |
| Synpo | synaptopodin | NM_177340, NM_001109975 |
| Afap1l1 | actin filament associated protein 1-like 1 | NM_178928 |
| Fam38b | family with sequence similarity 38, member B | NM_001039485 |
| Unc93b1 | unc-93 homolog B1 (*C. elegans*) | NM_019449, NM_001161428 |
| Sipa1 | signal-induced proliferation associated gene 1 | NM_001164481, NM_001164568, NM_001164482, NM_011379, NM_001164480 |
| Sorbs1 | sorbin and SH3 domain containing 1 | NM_178362, NM_001034963 NM_001034962, NM_001034964, NM_009166 |
| Itih5 | inter-alpha (globulin) inhibitor H5 | NM_172471 |
| Nostrin | nitric oxide synthase trafficker | NM_181547 |
| Aplnr | apelin receptor | NM_011784 |
| Trp53i11 | transformation related protein 53 inducible protein 11 | NM_001025246 |
| Mertk | c-mer proto-oncogene tyrosine kinase | NM_008587 |

-continued

| Gene Symbol | Gene Name | Gene Accession Number |
|---|---|---|
| Plcb1 | phospholipase C, beta 1 | NM_019677, NM_001145830 |
| Map1lc3a | microtubule-associated protein 1 light chain 3 alpha | NM_025735 |
| Lbp | lipopolysaccharide binding protein | NM_008489 |
| Notch1 | notch 1 | NM_008714 |
| Ggta1 | glycoprotein galactosyltransferase alpha 1,3 | NM_010283, NM_001145821 |
| Nr4a2 | nuclear receptor subfamily 4, group A, member 2 | NM_013613, NM_001139509 |
| Thbd | thrombomodulin | NM_009378 |
| Cp | ceruloplasmin | NM_001042611, NM_007752 |
| Fam198b | family with sequence similarity 198, member B | NM_133187 |
| S100a6 | S100 calcium binding protein A6 (calcyclin) | NM_011313 |
| Hist2h2aa1 | histone cluster 2, H2aa1 | NM_013549 |
| Fabp4 | fatty acid binding protein 4, adipocyte | NM_024406 |
| Lmna | lamin A | NM_001002011, NM_019390, NM_001111102 |
| Cdc14a | CDC14 cell division cycle 14A | NM_001080818, NM_001173553 |
| Cyr61 | cysteine rich protein 61 | NM_010516 |
| Npr2 | natriuretic peptide receptor 2 | NM_173788 |
| Acer2 | alkaline ceramidase 2 | NM_139306 |
| Id3 | inhibitor of DNA binding 3 | NM_008321 |
| Dhrs3 | dehydrogenase/reductase (SDR family) member 3 | NM_011303, NM_001172424 |
| Clstn1 | calsyntenin 1 | NM_023051 |
| Klf4 | Kruppel-like factor 4 (gut) | NM_010637 |
| Ppbp | pro-platelet basic protein | NM_023785 |
| Lrrc8c | leucine rich repeat containing 8 family, member C | NM_133897 |
| Cd36 | CD36 antigen | NM_007643, NM_001159555, NM_001159556, NM_001159557, NM_001159558 |
| Atp8a1 | ATPase, aminophospholipid transporter (APLT), class I, type 8A, member 1 | NM_009727, NM_001038999 |
| Sparcl1 | SPARC-like 1 | NM_010097 |
| Aldh2 | aldehyde dehydrogenase 2, mitochondrial | NM_009656 |
| Sh2b3 | SH2B adaptor protein 3 | NM_008507 |
| Scarb1 | scavenger receptor class B, member 1 | NM_016741, NM_001205082, NM_001205083 |
| Flt1 | FMS-like tyrosine kinase 1 | NM_010228 |
| Mmrn1 | multimerin 1 | NM_027613, NM_001163507 |
| Dysf | dysferlin | NM_001077694, NM_021469 |
| Mgll | monoglyceride lipase | NM_001166250, NM_001166251, NM_001166249, NM_011844 |
| Fbln2 | fibulin 2 | NM_007992, NM_001081437 |
| Lmcd1 | LIM and cysteine-rich domains 1 | NM_144799 |
| Pparg | peroxisome proliferator activated receptor gamma | NM_011146, NM_001127330 |
| 8430408G22Rik | RIKEN cDNA 8430408G22 gene | NM_145980, NM_001166580 |
| Klrb1f | killer cell lectin-like receptor subfamily B member 1F | NM_153094 |
| Emp1 | epithelial membrane protein 1 | NM_010128 |
| Impdh1 | inosine 5'-phosphate dehydrogenase 1 | NM_011829 |
| Tra2a | transformer 2 alpha homolog (*Drosophila*) | AB052758 |
| Frmd4b | FERM domain containing 4B | NM_145148 |
| Plxnd1 | plexin D1 | NM_026376 |
| Mgp | matrix Gla protein | NM_008597 |
| Exoc3l2 | exocyst complex component 3-like 2 | ENSMUST00000011407 |
| Akap13 | A kinase (PRKA) anchor protein 13 | NM_029332 |
| Tm6sf1 | transmembrane 6 superfamily member 1 | NM_145375 |
| Fosb | FBJ osteosarcoma oncogene B | NM_008036 |

| Gene Symbol | Gene Name | Gene Accession Number |
|---|---|---|
| Ceacam1 | carcinoembryonic antigen-related cell adhesion molecule 1 | NM_001039185, NM_001039186, NM_011926, NM_001039187 |
| Ltbp4 | latent transforming growth factor beta binding protein 4 | NM_175641, NM_001113549 |
| Lrp3 | low density lipoprotein receptor-related protein 3 | NM_001024707 |
| Galntl4 | UDP-N-acetyl-alpha-D-galactosamine:polypeptide N-acetylgalactosaminyltransferase-like 4 | NM_173739 |
| Myadm | myeloid-associated differentiation marker | NM_001093764, NM_001093766, NM_001093765, NM_016969 |
| Col4a2 | collagen, type IV, alpha 2 | NM_009932 |
| Plat | plasminogen activator, tissue | NM_008872 |
| Gm16486 | predicted gene 16486 | XM_912668 |
| Dnajb1 | DnaJ (Hsp40) homolog, subfamily B, member 1 | NM_018808 |
| Mir27a | microRNA 27a | NR_029746 |
| Cx3cl1 | chemokine (C—X3—C motif) ligand 1 | NM_009142 |
| Cdh13 | cadherin 13 | NM_019707 |
| Snord68 | small nucleolar RNA, C/D box 68 | NR_028128 |
| Nrp1 | neuropilin 1 | NM_008737 |
| Gas6 | growth arrest specific 6 | NM_019521 |
| 1810011O10Rik | RIKEN cDNA 1810011O10 gene | NM_026931 |
| Dlc1 | deleted in liver cancer 1 | NM_015802, NM_001194941, NM_001194940 |
| Ier2 | immediate early response 2 | NM_010499 |
| Junb | Jun-B oncogene | NM_008416 |
| Dok4 | docking protein 4 | NM_053246 |
| Slc7a5 | solute carrier family 7 (cationic amino acid transporter, y+ system), member 5 | NM_011404 |
| Taf1d | TATA box binding protein (Tbp)-associated factor, RNA polymerase I, D | BC056964 |
| Slc44a2 | solute carrier family 44, member 2 | NM_152808, NM_001199186 |
| Plscr2 | phospholipid scramblase 2 | NM_008880, NM_001195084 |
| Endod1 | endonuclease domain containing 1 | NM_028013 |
| Zbtb16 | zinc finger and BTB domain containing 16 | NM_001033324 |
| Tgfbr2 | transforming growth factor, beta receptor II | NM_009371, NM_029575 |
| Cxx1c | CAAX box 1 homolog C (human) | NM_028375 |
| Stard8 | START domain containing 8 | NM_199018 |
| Tsc22d3 | TSC22 domain family, member 3 | NM_001077364, NM_010286 |
| Sat1 | spermidine/spermine N1-acetyl transferase 1 | NM_009121 |

Table 11B—Genes under-represented in V-EC unique to lymph node (170genes)

Mtap2, Dgkd, Cxcr7, Phlpp1, Pik3c2b, Ivns1abp, Glt25d2, Hecw2, Rftn2, Epha4, Serpine2, Inhbb, Cfh, Hmcn1, Pcp4l1, Pydc4, AI607873, Ifi204, Ephx1, Prox1, Syne1, Dcbld1, Gm9956, Tmem26, Fam13c, Palm, Tbxa2r, Pde7b, Enpp3, H2afy2, Adarb1, Gipc3, Nts, Ciart, Gatsl3, Pmp22, Pik3r6, Mmd, Emid1, Hlf, Pitpnc1, Pxdn, Syne2, Eml1, Rhob, 6430527G18Rik, Gm10759, Rasgrf2, Gpx8, Ptprg, Gdf10, Spata13, Stc1, Lpar6, Tspan14, Hmbox1, Klf12, Fzd6, Pkhd1l1, Apol9b///Apol9a, Nr4a1, Npr3, Apol9b///Apol9a, Ahsg, Tnk2, Slc12a8, Itgb5, Etv5, Pla1a, Scube3, Ddah2, Xdh, Lama3, Spry4, Afap1l1, Fam38b, Ms4a4d, Fas, I830012O16Rik, Sipa1, Itih5, Aplnr, Stard9, Sema6d, Mertk, Plcb1, Tcf15, Ggta1, Tspan18, Thbd, Acss1, Cables2, Cp, Fam198b, AI504432, Gm129, Cdc14a, Enpep, Npr2, Nr4a3, Acer2, Ppap2b, Dhrs3, Clstn1, Car8, Ptplad2, Zfp69, Gm694, Agrn, Sema3d, Sema3c, Uchl1, Cxcl13, Cd36, Tec, Kdr, Sparcl1, Mlec, Aldh2, Gpr81, Micall2, Cald1, Mmrn1, St3gal5, Dysf, Mgll, Lmcd1, Pparg, Tspan12, Impdh1, Podxl, Frmd4b, Plxnd1, Exoc3l2, Nav2, Kcne3, Xylt1, Ltbp4, Lrp3, Zfp715, Aqp11, Col4a2, Sh3rf1, F2rl3, Cx3cl1, Mtss1l, Cdh13, Foxc2, Nrp1, Col4a1, Gas6, TDRP, Tox3, Dok4, Fxyd6, Myo9a, Uaca, Oaz2, Plscr2, AW551984, Ephb1, Rtp3, Ccrl2, Tgfbr2, Lpar4, A630033H20Rik, Fam70a, Apln, and Bmx.

| Gene Symbol | Gene Name | Gene Accession Number |
|---|---|---|
| Mtap2 | microtubule-associated protein 2 | NM_001039934, NM_008632 |

| Gene Symbol | Gene Name | Gene Accession Number |
| --- | --- | --- |
| Dgkd | diacylglycerol kinase, delta | NM_177646 |
| Cxcr7 | chemokine (C—X—C motif) receptor 7 | NM_007722 |
| Phlpp1 | PH domain and leucine rich repeat protein phosphatase 1 | NM_133821 |
| Pik3c2b | phosphoinositide-3-kinase, class 2, beta polypeptide | NM_001099276 |
| Ivns1abp | influenza virus NS1A binding protein | NM_001039512, NM_001039511, NM_054102 |
| Glt25d2 | glycosyltransferase 25 domain containing 2 | NM_177756 |
| Hecw2 | HECT, C2 and WW domain containing E3 ubiquitin protein ligase 2 | NM_001001883 |
| Rftn2 | raftlin family member 2 | NM_028713 |
| Epha4 | Eph receptor A4 | NM_007936 |
| Serpine2 | serine (or cysteine) peptidase inhibitor, clade E, member 2 | NM_009255 |
| Inhbb | inhibin beta-B | NM_008381 |
| Cfh | complement component factor h | NM_009888 |
| Hmcn1 | hemicentin 1 | NM_001024720 |
| Pcp4l1 | Purkinje cell protein 4-like 1 | NM_025557 |
| Pydc4 | pyrin domain containing 4 | NM_001177349, NM_001177350 |
| AI607873 | expressed sequence AI607873 | NM_001204910 |
| Ifi204 | interferon activated gene 204 | NM_008329 |
| Ephx1 | epoxide hydrolase 1, microsomal | NM_010145 |
| Prox1 | prospero-related homeobox 1 | NM_008937 |
| Syne1 | spectrin repeat containing, nuclear envelope 1 | NM_001079686, NM_022027, NM_153399 |
| Dcbld1 | discoidin, CUB and LCCL domain containing 1 | NM_025705 |
| Gm9956 | predicted gene 9956 | NC_000076 |
| Tmem26 | transmembrane protein 26 | NM_177794 |
| Fam13c | family with sequence similarity 13, member C | NM_001143776, NM_001143777, NM_024244 |
| Palm | paralemmin | NM_001161747, NM_023128 |
| Tbxa2r | thromboxane A2 receptor | NM_009325 |
| Pde7b | phosphodiesterase 7B | NM_013875 |
| Enpp3 | ectonucleotide pyrophosphatase/phosphodiesterase 3 | NM_134005 |
| H2afy2 | H2A histone family, member Y2 | NM_207000 |
| Adarb1 | adenosine deaminase, RNA-specific, B1 | NM_130895, NM_001024837 |
| Gipc3 | GIPC PDZ domain containing family, member 3 | NM_148951 |
| Nts | neurotensin | NM_024435 |
| Ciart | circadian associated repressor of transcription | NM_001033302 |
| Gatsl3 | GATS protein-like 3 | NM_028022 |
| Pmp22 | peripheral myelin protein 22 | NM_008885 |
| Pik3r6 | phosphoinositide-3-kinase, regulatory subunit 6 | NM_001081566, NM_001004435 |
| Mmd | monocyte to macrophage differentiation-associated | NM_026178 |
| Emid1 | EMI domain containing 1 | NM_080595 |
| Fam101b | family with sequence similarity 101, member B | NM_029658 |
| Hlf | hepatic leukemia factor | NM_172563 |
| Pitpnc1 | phosphatidylinositol transfer protein, cytoplasmic 1 | NM_145823 |
| Pxdn | peroxidasin homolog (*Drosophila*) | NM_181395 |
| Syne2 | synaptic nuclear envelope 2 | NM_001005510 |
| Eml1 | echinoderm microtubule associated protein like 1 | NM_001043336, NM_001043335 |
| Rhob | ras homolog gene family, member B | NM_007483 |
| 6430527G18Rik | RIKEN cDNA 6430527G18 gene | NM_145836 |
| Gm10759 | predicted gene 10759 | AY344585 |
| Rasgrf2 | RAS protein-specific guanine nucleotide-releasing factor 2 | NM_009027 |
| Gpx8 | glutathione peroxidase 8 (putative) | NM_027127 |
| Ptprg | protein tyrosine phosphatase, receptor type, G | NM_008981 |
| Gdf10 | growth differentiation factor 10 | NM_145741 |
| Spata13 | spermatogenesis associated 13 | NM_001033272 |
| Stc1 | stanniocalcin 1 | NM_009285 |
| Lpar6 | lysophosphatidic acid receptor 6 | NM_175116 |
| Tspan14 | tetraspanin 14 | NM_145928 |
| Hmbox1 | homeobox containing 1 | NM_177338 |
| Klf12 | Kruppel-like factor 12 | NM_010636 |
| Fzd6 | frizzled homolog 6 (*Drosophila*) | NM_001162494, NM_008056 |

| Gene Symbol | Gene Name | Gene Accession Number |
| --- | --- | --- |
| Pkhd1l1 | polycystic kidney and hepatic disease 1-like 1 | NM_138674 |
| Apol9b /// Apol9a | apolipoprotein L 9b /// apolipoprotein L 9a | NM_173743, NM_001168660, NM_173786, NM_001162883 |
| Nr4a1 | nuclear receptor subfamily 4, group A, member 1 | NM_010444 |
| Npr3 | natriuretic peptide receptor 3 | NM_001039181, NM_001286395, NM_008728 |
| Apol9b /// Apol9a | apolipoprotein L 9b /// apolipoprotein L 9a | NM_173786, NM_001168660, NM_173743, NM_001162883 |
| Ahsg | alpha-2-HS-glycoprotein | NM_013465 |
| Tnk2 | tyrosine kinase, non-receptor, 2 | NM_016788, NM_001110147 |
| Slc12a8 | solute carrier family 12 (potassium/chloride transporters), member 8 | NM_001083902, NM_134251 |
| Itgb5 | integrin beta 5 | NM_001145884, NM_010580 |
| Etv5 | ets variant gene 5 | NM_023794 |
| Pla1a | phospholipase A1 member A | NM_134102 |
| Scube3 | signal peptide, CUB domain, EGF-like 3 | NM_001004366 |
| Ddah2 | dimethylarginine dimethylaminohydrolase 2 | NM_016765, NM_001190449 |
| Xdh | xanthine dehydrogenase | NM_011723 |
| Lama3 | laminin, alpha 3 | NM_010680 |
| Spry4 | sprouty homolog 4 (*Drosophila*) | NM_011898 |
| Afap1l1 | actin filament associated protein 1-like 1 | NM_178928 |
| Fam38b | family with sequence similarity 38, member B | NM_001039485 |
| Ms4a4d | membrane-spanning 4-domains, subfamily A, member 4D | NM_025658 |
| Fas | Fas (TNF receptor superfamily member 6) | NM_007987 |
| I830012O16Rik | RIKEN cDNA I830012O16 gene | NM_001005858 |
| Sipa1 | signal-induced proliferation associated gene 1 | NM_001164482 |
| Itih5 | inter-alpha (globulin) inhibitor H5 | NM_172471 |
| Aplnr | apelin receptor | NM_011784 |
| Stard9 | START domain containing 9 | NC_000068 |
| Sema6d | sema domain, transmembrane domain (TM), and cytoplasmic domain, (semaphorin) 6D | NM_172537, NM_199238, NM_199240, NM_199239, NM_199241 |
| Mertk | c-mer proto-oncogene tyrosine kinase | NM_008587 |
| Plcb1 | phospholipase C, beta 1 | NM_019677, NM_001145830 |
| Tcf15 | transcription factor 15 | NM_009328 |
| Ggta1 | glycoprotein galactosyltransferase alpha 1,3 | NM_001145821, NM_010283 |
| Tspan18 | tetraspanin 18 | NM_183180 |
| Thbd | thrombomodulin | NM_009378 |
| Acss1 | acyl-CoA synthetase short-chain family member 1 | NM_080575 |
| Cables2 | CDK5 and Abl enzyme substrate 2 | NM_145851 |
| Cp | ceruloplasmin | NM_001042611, NM_007752 |
| Fam198b | family with sequence similarity 198, member B | NM_133187 |
| AI504432 | expressed sequence AI504432 | NR_033498 |
| Gm129 | predicted gene 129 | NM_001033302 |
| Cdc14a | CDC14 cell division cycle 14A | NM_001173553, NM_001080818 |
| Enpep | glutamyl aminopeptidase | NM_007934 |
| Npr2 | natriuretic peptide receptor 2 | NM_173788 |
| Nr4a3 | nuclear receptor subfamily 4, group A, member 3 | NM_015743 |
| Acer2 | alkaline ceramidase 2 | NM_139306 |
| Ppap2b | phosphatidic acid phosphatase type 2B | NM_080555 |
| Dhrs3 | dehydrogenase/reductase (SDR family) member 3 | NM_011303, NM_001172424 |
| Clstn1 | calsyntenin 1 | NM_023051 |
| Car8 | carbonic anhydrase 8 | NM_007592 |
| Ptplad2 | protein tyrosine phosphatase-like A domain containing 2 | NM_025760 |
| Zfp69 | zinc finger protein 69 | NM_001005788 |
| Gm694 | predicted gene 694 | NM_001033374 |
| Agrn | agrin | NM_021604 |

-continued

| Gene Symbol | Gene Name | Gene Accession Number |
|---|---|---|
| Sema3d | sema domain, immunoglobulin domain (Ig), short basic domain, secreted, (semaphorin) 3D | NM_028882 |
| Sema3c | sema domain, immunoglobulin domain (Ig), short basic domain, secreted, (semaphorin) 3C | NM_013657 |
| Uchl1 | ubiquitin carboxy-terminal hydrolase L1 | NM_011670 |
| Cxcl13 | chemokine (C—X—C motif) ligand 13 | NM_018866 |
| Cd36 | CD36 antigen | NM_001159558, NM_001159557, NM_001159556, NM_007643, NM_001159555 |
| Tec | tec protein tyrosine kinase | NM_001113461, NM_001113464, NM_001113460 |
| Kdr | kinase insert domain protein receptor | NM_010612 |
| Sparcl1 | SPARC-like 1 | NM_010097 |
| Mlec | malectin | NM_175403 |
| Aldh2 | aldehyde dehydrogenase 2, mitochondrial | NM_009656 |
| Gpr81 | G protein-coupled receptor 81 | NM_175520 |
| Micall2 | MICAL-like 2 | NM_174850 |
| Cald1 | caldesmon 1 | NM_145575 |
| Mmrn1 | multimerin 1 | NM_001163507, NM_027613 |
| St3gal5 | ST3 beta-galactoside alpha-2,3-sialyltransferase 5 | NM_001035228, NM_011375 |
| Dysf | dysferlin | NM_001077694, NM_021469 |
| Mgll | monoglyceride lipase | NM_001166251, NM_001166249, NM_011844 |
| Lmcd1 | LIM and cysteine-rich domains 1 | NM_144799 |
| Pparg | peroxisome proliferator activated receptor gamma | NM_001127330, NM_011146 |
| Tspan12 | tetraspanin 12 | NM_173007 |
| Impdh1 | inosine 5'-phosphate dehydrogenase 1 | NM_011829 |
| Podxl | podocalyxin-like | NM_013723 |
| Frmd4b | FERM domain containing 4B | NM_145148 |
| Plxnd1 | plexin D1 | NM_026376 |
| Exoc3l2 | exocyst complex component 3-like 2 | XM_006540475 |
| Nav2 | neuron navigator 2 | NM_001111016, NM_175272 |
| Kcne3 | potassium voltage-gated channel, Isk-related subfamily, gene 3 | NM_001190871, NM_001190869, NM_001190950, NM_020574, NM_001190870 |
| Xylt1 | xylosyltransferase 1 | NM_175645 |
| Ltbp4 | latent transforming growth factor beta binding protein 4 | NM_001113549, NM_175641 |
| Lrp3 | low density lipoprotein receptor-related protein 3 | NM_001024707 |
| Zfp715 | zinc finger protein 715 | NM_027264 |
| Aqp11 | aquaporin 11 | NM_175105 |
| Col4a2 | collagen, type IV, alpha 2 | NM_009932 |
| Sh3rf1 | SH3 domain containing ring finger 1 | NM_021506 |
| F2rl3 | coagulation factor II (thrombin) receptor-like 3 | NM_007975 |
| Cx3cl1 | chemokine (C—X3—C motif) ligand 1 | NM_009142 |
| Mtss1l | metastasis suppressor 1-like | NM_198625 |
| Cdh13 | cadherin 13 | NM_019707 |
| Foxc2 | forkhead box C2 | NM_013519 |
| Nrp1 | neuropilin 1 | NM_008737 |
| Col4a1 | collagen, type IV, alpha 1 | NM_009931 |
| Gas6 | growth arrest specific 6 | NM_019521 |
| TDRP | testis development related protein | NM_173744 |
| Tox3 | TOX high mobility group box family member 3 | NM_172913 |
| Dok4 | docking protein 4 | NM_053246 |
| Fxyd6 | FXYD domain-containing ion transport regulator 6 | NM_022004 |
| Myo9a | myosin IXa | NM_173018 |
| Uaca | uveal autoantigen with coiled-coil domains and ankyrin repeats | NM_028283 |
| Oaz2 | ornithine decarboxylase antizyme 2 | NM_010952 |
| Plscr2 | phospholipid scramblase 2 | NM_008880, NM_001195084 |
| AW551984 | expressed sequence AW551984 | NM_001199556, NM_178737 |

| Gene Symbol | Gene Name | Gene Accession Number |
| --- | --- | --- |
| Ephb1 | Eph receptor B1 | NM_001168296, NM_173447 |
| Rtp3 | receptor transporter protein 3 | NM_153100 |
| Ccrl2 | chemokine (C-C motif) receptor-like 2 | NM_017466 |
| Tgfbr2 | transforming growth factor, beta receptor II | NM_029575, NM_009371 |
| Lpar4 | lysophosphatidic acid receptor 4 | NM_175271 |
| A630033H20Rik | RIKEN cDNA A630033H20 gene | NM_175442, NM_001122596, NM_001122595 |
| Fam70a | family with sequence similarity 70, member A | NM_172930 |
| Apln | apelin | NM_013912 |
| Bmx | BMX non-receptor tyrosine kinase | NM_009759 |

In some embodiments, Table 11 excludes Pmp22.

Table 12 lists genes under-represented in V-EC shared by lymph node and skin. As used herein, "Table 12" includes Table 12A and Table 12B below.

Table 12A—Genes under-represented in V-EC shared by lymph node and skin (50 genes)

Itpkb, Sox17, Tns1, Cxcr4, Atp1b1, Arhgap18, Timp3, Gm9766, Car4, Cd7, Rsad2, Hist1h2ai, Hist1h3h, Hist1h2bn, Hist1h2ao, Gm11277, Hist1h2bk, Hist1h2bj, Hist1h2af, Hist1h3g, Hist1h2ad, Hist1h3d, Hist1h2bb, Hist1h3b, Hist1h2bl, Hist1h2ak, Hist1h3i, Hist1h2an, Hist1h2ah, Hist1h2ag, Hist1h3e, Hist1h2bf, Hist1h3c, Hist1h3a, Itga1, Hspa1a, Rapgef1, Hist2h3c1, Hist2h3b, Gja5, Laptm5, Aqp7, Gja4, Mlec, A130022J15Rik, D630042P16Rik, P2ry2, Hbb-b2, Cd97, Pdgfd.

| Gene Symbol | Gene Name | Gene Accession Number |
| --- | --- | --- |
| Itpkb | inositol 1,4,5-trisphosphate 3-kinase B | NM_001081175 |
| Sox17 | SRY-box containing gene 17 | NM_011441 |
| Tns1 | tensin 1 | NM_027884 |
| Cxcr4 | chemokine (C—X—C motif) receptor 4 | NM_009911 |
| Atp1b1 | ATPase, Na+/K+ transporting, beta 1 polypeptide | NM_009721 |
| Arhgap18 | Rho GTPase activating protein 18 | NM_176837 |
| Timp3 | tissue inhibitor of metalloproteinase 3 | NM_011595 |
| Gm9766 | predicted gene 9766 | NM_001204983 |
| Car4 | carbonic anhydrase 4 | NM_007607 |
| Cd7 | CD7 antigen | NM_009854 |
| Rsad2 | radical S-adenosyl methionine domain containing 2 | NM_021384 |
| Hist1h2ai | histone cluster 1, H2ai | NM_178182 |
| Hist1h3h | histone cluster 1, H3h | NM_178206 |
| Hist1h2bn | histone cluster 1, H2bn | NM_178201 |
| Hist1h2ao | histone cluster 1, H2ao | NM_001177544 |
| Hist1h2br | histone cluster 1 H2br | NM_001110555 |
| Hist1h2bk | histone cluster 1, H2bk | NM_175665 |
| Hist1h2bj | histone cluster 1, H2bj | NM_178198 |
| Hist1h2af | histone cluster 1, H2af | NM_175661 |
| Hist1h3g | histone cluster 1, H3g | NM_145073 |
| Hist1h2ad | histone cluster 1, H2ad | NM_178188 |
| Hist1h3d | histone cluster 1, H3d | NM_178204 |
| Hist1h2bb | histone cluster 1, H2bb | NM_175664 |
| Hist1h3b | histone cluster 1, H3b | NM_178203 |
| Hist1h2bl | histone cluster 1, H2bl | NM_178199 |
| Hist1h2ak | histone cluster 1, H2ak | NM_178183 |
| Hist1h3i | histone cluster 1, H3i | NM_178207 |
| Hist1h2an | histone cluster 1, H2an | NM_178184 |
| Hist1h2ah | histone cluster 1, H2ah | NM_175659 |
| Hist1h2ag | histone cluster 1, H2ag | NM_178186 |
| Hist1h3e | histone cluster 1, H3e | NM_178205 |
| Hist1h2bf | histone cluster 1, H2bf | NM_178195 |
| Hist1h3c | histone cluster 1, H3c | NM_175653 |
| Hist1h3a | histone cluster 1, H3a | NM_013550 |
| Itga1 | integrin alpha 1 | NM_001033228 |
| Hspa1a | heat shock protein 1A | NM_010479 |
| Rapgef1 | Rap guanine nucleotide exchange factor (GEF) 1 | NM_001039086, NM_001039087, NM_054050 |
| Hist2h3c1 | histone cluster 2, H3c1 | NM_178216 |
| Hist2h3b | histone cluster 2, H3b | NM_178215 |
| Gja5 | gap junction protein, alpha 5 | NM_008121 |
| Laptm5 | lysosomal-associated protein transmembrane 5 | NM_010686 |
| Aqp7 | aquaporin 7 | NM_007473 |
| Gja4 | gap junction protein, alpha 4 | NM_008120 |
| Mlec | malectin | NM_175403 |

-continued

| Gene Symbol | Gene Name | Gene Accession Number |
|---|---|---|
| Eogt | EGF domain-specific O-linked N-acetylglucosamine (GlcNAc) transferase | NM_175313 |
| D630042P16Rik | RIKEN cDNA D630042P16 gene | NM_175525 |
| P2ry2 | purinergic receptor P2Y, G-protein coupled 2 | NM_008773 |
| Hbb-b2 | hemoglobin, beta adult minor chain | NM_016956 |
| Cd97 | CD97 antigen | NM_001163030, NM_011925, NM_001163029, NM_001163031 |
| Pdgfd | platelet-derived growth factor, D polypeptide | NM_027924 |

Table 12B—Genes under-represented in V-EC shared by lymph node and skin (39 genes)

Sox17, St8sia4, Atp1b1, Tgfb2, Arhgap18, Lama4, Gm9766, Car4, Jup, Lgals3bp, Jag2, Ppap2a, Arl15, Itga1, Gpihbp1, Cdc42ep1, Pdgfb, Atp13a3, Rps6ka2, Rasgrp3, Slc9a3r2, Ablim3, Car3, BC028528, Sdc3, Aqp7, Fscn1, Mlec, Mest, Slc6a6, Irak2, Klrb1f, Eogt, D630042P16Rik, Irf7, D8Ertd82e, Cd97, Pdgfd, and Gpc4.

| Gene Symbol | Gene Name | Gene Accession Number |
|---|---|---|
| Sox17 | SRY-box containing gene 17 | NM_011441 |
| St8sia4 | ST8 alpha-N-acetyl-neuraminide alpha-2,8-sialyltransferase 4 | NM_009183 |
| Atp1b1 | ATPase, Na+/K+ transporting, beta 1 polypeptide | NM_009721 |
| Tgfb2 | transforming growth factor, beta 2 | NM_009367 |
| Arhgap18 | Rho GTPase activating protein 18 | NM_176837 |
| Lama4 | laminin, alpha 4 | NM_010681 |
| Gm9766 | predicted gene 9766 | NM_001204983 |
| Car4 | carbonic anhydrase 4 | NM_007607 |
| Jup | junction plakoglobin | NM_010593 |
| Lgals3bp | lectin, galactoside-binding, soluble, 3 binding protein | NM_011150 |
| Jag2 | jagged 2 | NM_010588 |
| Ppap2a | phosphatidic acid phosphatase type 2A | NM_008903, NM_008247 |
| Arl15 | ADP-ribosylation factor-like 15 | NM_172595 |
| Itga1 | integrin alpha 1 | NM_001033228 |
| Gpihbp1 | GPI-anchored HDL-binding protein 1 | NM_026730 |
| Cdc42ep1 | CDC42 effector protein (Rho GTPase binding) 1 | NM_027219 |
| Pdgfb | platelet derived growth factor, B polypeptide | NM_011057 |
| Atp13a3 | ATPase type 13A3 | NM_001128094, NM_001128096 |
| Rps6ka2 | ribosomal protein S6 kinase, polypeptide 2 | NM_011299 |
| Rasgrp3 | RAS, guanyl releasing protein 3 | NM_001166493, NM_207246 |
| Slc9a3r2 | solute carrier family 9 (sodium/hydrogen exchanger), member 3 regulator 2 | NM_023055, NM_023449 |
| Ablim3 | actin binding LIM protein family, member 3 | NM_001164491, NM_198649 |
| Car3 | carbonic anhydrase 3 | NM_007606 |
| BC028528 | cDNA sequence BC028528 | NM_153513 |
| Sdc3 | syndecan 3 | NM_011520 |
| Aqp7 | aquaporin 7 | NM_007473 |
| Fscn1 | fascin homolog 1, actin bundling protein (*Strongylocentrotus purpuratus*) | NM_007984 |
| Mlec | malectin | NM_175403 |
| Mest | mesoderm specific transcript | NM_001252292, NM_001252293, NM_008590 |
| Slc6a6 | solute carrier family 6 (neurotransmitter transporter, taurine), member 6 | NM_009320 |
| Irak2 | interleukin-1 receptor-associated kinase 2 | NM_001113553 |
| Klrb1f | killer cell lectin-like receptor subfamily B member 1F | NM_153094 |
| Eogt | EGF domain-specific O-linked N-acetylglucosamine (GlcNAc) transferase | NM_175313 |
| D630042P16Rik | RIKEN cDNA D630042P16 gene | NM_175525 |
| Irf7 | interferon regulatory factor 7 | NM_001252600, NM_001252601, NM_016850 |
| D8Ertd82e | DNA segment, Chr 8, ERATO Doi 82, expressed | NM_172911 |
| Cd97 | CD97 antigen | NM_001163031, NM_001163029, |

| Gene Symbol | Gene Name | Gene Accession Number |
|---|---|---|
| Pdgfd | platelet-derived growth factor, D polypeptide | NM_011925, NM_001163030 NM_027924 |
| Gpc4 | glypican 4 | NM_008150 |

Table 13 lists genes under-represented in V-EC shared by lymph node and adipose tissue. As used herein, "Table 13" includes Table 13A and Table 13B below.

Table 13A—Genes under-represented in V-EC shared by lymph node and adipose tissue (26genes)

Prdm1, Unc5b, Lamb1, Jag2, Akr1c14, Mef2c, Esm1, Nid2, Lpar6, Lama3, Mcc, Rasgrp2, Rapgef4, Sema6d, Snord57, Tspan18, BC028528, Ppap2b, Tpst1, Unc119b, D8Ertd82e, Mtss11, Col4a1, Sipa1l2, Oaz2-ps, Lpar4.

| Gene Symbol | Gene Name | Gene Accession Number |
|---|---|---|
| Prdm1 | PR domain containing 1, with ZNF domain | NM_007548 |
| Unc5b | unc-5 homolog B (*C. elegans*) | NM_029770 |
| Lamb1 | laminin B1 | NM_008482 |
| Jag2 | jagged 2 | NM_010588 |
| Akr1c14 | aldo-keto reductase family 1, member C14 | NM_134072 |
| Mef2c | myocyte enhancer factor 2C | NM_025282, NM_001170537 |
| Esm1 | endothelial cell-specific molecule 1 | NM_023612 |
| Nid2, | nidogen 2 | NM_008695 |
| Lpar6, Rb1 | lysophosphatidic acid receptor 6, retinoblastoma 1 | NM_175116, NM_009029 |
| Lama3 | laminin, alpha 3 | NM_010680 |
| Mcc | mutated in colorectal cancers | NM_001085373, NM_001085374 |
| Rasgrp2 | RAS, guanyl releasing protein 2 | NM_011242 |
| Rapgef4 | Rap guanine nucleotide exchange factor (GEF) 4 | NM_001204167, NM_001204165, NM_019688, NM_001204166 |
| Sema6d | sema domain, transmembrane domain (TM), and cytoplasmic domain, (semaphorin) 6D | NM_172537, NM_199238, NM_199239, NM_199240, NM_199241 |
| Snord57 | small nucleolar RNA, C/D box 57 | NR_028528 |
| Tspan18 | tetraspanin 18 | NM_183180 |
| BC028528 | cDNA sequence BC028528 | BC028528 |
| Ppap2b | phosphatidic acid phosphatase type 2B | NM_080555 |
| Tpst1 | protein-tyrosine sulfotransferase 1 | NM_001130476, NM_013837 |
| Unc119b | unc-119 homolog B (*C. elegans*) | NM_175352 |
| D8Ertd82e | DNA segment, Chr 8, ERATO Doi 82, expressed | NM_172911 |
| Mtss11 | metastasis suppressor 1-like | NM_198625 |
| Col4a1 | collagen, type IV, alpha 1 | NM_009931 |
| Sipa1l2 | signal-induced proliferation-associated 1 like 2 | NM_001081337 |
| Oaz2 | ornithine decarboxylase antizyme 2 | NM_010952 |
| Lpar4 | lysophosphatidic acid receptor 4 | NM_175271 |

Table 13B—Genes under-represented in V-EC shared by lymph node and adipose tissue (20genes)

Prdm1, Ramp3, Olfr1396, Alox12, Lamb1, Fut8, Tnfaip2, Nid2, Mcc, Slc1a1, Rapgef4, Trp53i11, Nes, Cldn15, Arap2, Prickle2, Sez6l2, Sipa1l2, Cd109, and Magix.

| Gene Symbol | Gene Name | Gene Accession Number |
|---|---|---|
| Prdm1 | PR domain containing 1, with ZNF domain | NM_007548 |
| Ramp3 | receptor (calcitonin) activity modifying protein 3 | NM_019511 |
| Olfr1396 | olfactory receptor 1396 | NM_146337 |
| Alox12 | arachidonate 12-lipoxygenase | NM_007440 |
| Lamb1 | laminin B1 | NM_008482 |
| Fut8 | fucosyltransferase 8 | NM_016893, NM_001252614 |
| Tnfaip2 | tumor necrosis factor, alpha-induced protein 2 | NM_009396 |
| Nid2 | nidogen 2 | NM_008695 |
| Mcc | mutated in colorectal cancers | NM_001085374, NM_001085373 |
| Slc1a1 | solute carrier family 1 (neuronal/epithelial high affinity glutamate transporter, system Xag), member 1 | NM_009199 |
| Rapgef4 | Rap guanine nucleotide exchange factor (GEF) 4 | NM_019688, NM_001204165, NM_001204166 |
| Trp53i11 | transformation related protein 53 inducible protein 11 | NM_001025246 |
| Nes | nestin | NM_016701 |
| Cldn15 | claudin 15 | NM_021719 |
| Arap2 | ArfGAP with RhoGAP domain, ankyrin repeat and PH domain 2 | NM_178407 |
| Prickle2 | prickle homolog 2 (*Drosophila*) | NM_001134461 |
| Sez6l2 | seizure related 6 homolog like 2 | NM_001252567, NM_001252566, NM_144926 |

-continued

| Gene Symbol | Gene Name | Gene Accession Number |
|---|---|---|
| Sipa1l2 | signal-induced proliferation-associated 1 like 2 | NM_001081337 |
| Cd109 | CD109 antigen | NM_153098 |
| Magix | MAGI family member, X-linked | NM_018832 |

Table 14 lists genes under-represented in V-EC shared by skin and adipose tissue. As used herein, "Table 14" includes Table 14A and Table 14B below.

Table 14A—Genes under-represented in V-EC shared by skin and adipose tissue (14genes)

Ccl3, Ly86, Myo10, Col8a1, H2-Aa, Cd74, AW112010, St8sia6, Adh1, Mest, Timp4, Ercc1, Vwa3a, Eps8l2.

| Gene Symbol | Gene Name | Gene Accession Number |
|---|---|---|
| Ccl3 | chemokine (C-C motif) ligand 3 | NM_011337 |
| Ly86 | lymphocyte antigen 86 | NM_010745 |
| Myo10 | myosin X | NM_019472 |
| Col8a1 | collagen, type VIII, alpha 1 | NM_007739 |
| H2-Aa | histocompatibility 2, class II antigen A, alpha | NM_010378 |
| Cd74 | CD74 antigen (invariant polypeptide of major histocompatibility complex, class II antigen-associated) | NM_010545, NM_001042605 |
| AW112010 | expressed sequence AW112010 | NM_001177351 |
| St8sia6 | ST8 alpha-N-acetyl-neuraminide alpha-2,8-sialyltransferase 6 | NM_145838 |
| Adh1 | alcohol dehydrogenase 1 (class I) | NM_007409 |
| Mest, | mesoderm specific transcript, coatomer protein | NM_008590, |
| Copg2 | complex, subunit gamma 2 | NM_001252293, NM_001252292 |
| Timp4 | tissue inhibitor of metalloproteinase 4 | NM_080639 |
| Ercc1 | excision repair cross-complementing rodent repair deficiency, complementation group 1 | NM_007948, NM_001127324 |
| Vwa3a | von Willebrand factor A domain containing 3A | NM_177697 |
| Eps8l2 | EPS8-like 2 | NM_133191 |

Table 14B—Genes under-represented in V-EC shared by skin and adipose tissue (33genes)

Crispld1, A530040E14Rik, Sell, Coro6, Ccdc85a, Ccl3, Cd79b, Ly86, Chrm3, Rgnef, Lrrc3b, Ptger4, Col8a1, Rasgrp2, Dll4, St8sia6, Cecr2, Ercc1, Snord116, Thrsp, A530040E14Rik, Sema7a, LOC100504530, LOC100042196, LOC100040223, Ssty2, LOC100039753, Gm20823, LOC100039552, Gm20867, LOC665746, LOC100042196, and LOC100040235.

| Gene Symbol | Gene Name | Gene Accession Number |
|---|---|---|
| Crispld1 | cysteine-rich secretory protein LCCL domain containing 1 | NM_031402 |
| A530040E14Rik | RIKEN cDNA A530040E14 gene | NC_000067 |
| Sell | selectin, lymphocyte | NM_001164059, NM_011346 |
| Coro6 | coronin 6 | NM_139129, NM_139128, NM_139130 |
| Ccdc85a | coiled-coil domain containing 85A | NM_181577, NM_001166661 |
| Ccl3 | chemokine (C-C motif) ligand 3 | NM_011337 |
| Cd79b | CD79B antigen | NM_008339 |
| Ly86 | lymphocyte antigen 86 | NM_010745 |
| Chrm3 | cholinergic receptor, muscarinic 3, cardiac | NM_033269 |
| Rgnef | Rho-guanine nucleotide exchange factor | NM_012026 |
| Lrrc3b | leucine rich repeat containing 3B | NM_146052 |
| Ptger4 | prostaglandin E receptor 4 (subtype EP4) | NM_008965, NM_001136079 |
| Col8a1 | collagen, type VIII, alpha 1 | NM_007739 |
| Rasgrp2 | RAS, guanyl releasing protein 2 | NM_011242 |
| Dll4 | delta-like 4 (*Drosophila*) | NM_019454 |
| St8sia6 | ST8 alpha-N-acetyl-neuraminide alpha-2,8-sialyltransferase 6 | NM_145838 |
| Cecr2 | cat eye syndrome chromosome region, candidate 2 | NM_001128151 |
| Ercc1 | excision repair cross-complementing rodent repair deficiency, complementation group 1 | NM_001127324, NM_007948 |
| Snord116 | small nucleolar RNA, C/D box 116 | AF241256 |
| Thrsp | thyroid hormone responsive SPOT14 homolog (*Rattus*) | NM_009381 |
| A530040E14Rik | RIKEN cDNA A530040E14 gene | NC_000067 |
| Sema7a | sema domain, immunoglobulin domain (Ig), and GPI membrane anchor, (semaphorin) 7A | NM_011352 |
| LOC100504530 | uncharacterized LOC100504530 | NT_161916 |
| LOC100042196 | y-linked testis-specific protein 1-like | NT_166409 |
| LOC100040223 | predicted gene, 20831 | NM_001103152 |
| Ssty2 | spermiogenesis specific transcript on the Y 2 | NM_023546 |
| LOC100039753 | — | — |

| Gene Symbol | Gene Name | Gene Accession Number |
|---|---|---|
| Gm20823 | predicted gene, 20823 | NM_001160143 |
| LOC100039552 | y-linked testis-specific protein 1-like | NT_166418 |
| Gm20867 | predicted gene, 20867 | NM_001160142 |
| LOC665746 | y-linked testis-specific protein 1-like | NT_161879 |
| LOC100042196 | y-linked testis-specific protein 1-like | NT_166409 |
| LOC100040235 | Y-linked testis-specific protein 1-like | NW_001034079 |

In some embodiments, Table 14 excludes Sell.

Tables 1-14 above show results of analyses of over- and under-represented genes that are either shared or uniquely over- or under-expressed in V-ECs compared to NV-ECs of adipose tissue, lymph node and skin. Italicized genes are known to be surface expressed, genes in bold have been validated either at the mRNA level (qRT-PCR) or protein level (IHC and/or FACS). It should be appreciated that the various aspects and embodiments of the disclosure contemplate using the genes (including mRNA and/or protein) listed in Tables 1-14, as well as corresponding human genes (i.e., genes which exhibit similar sequence and functionality in the respective tissue).

One of skill in the art will readily be able to obtain amino acid sequences of microvessel (e.g. venular) endothelial cell polypeptides, and the genomic and mRNA sequences encoding them, from publicly available databases, such as those available at the National Center for Biotechnology Information (NCBI), e.g., Gene, GenBank, Proteins, etc. For example, the Nucleotide database provides sequence information (e.g., accession numbers for reference sequences (in the RefSeq database)) and functional information, which can be obtained, e.g., by searching on a name or Accession Number for a nucleic acid or protein of interest. Tables 1-14 provide list of the official symbol and Accession Numbers of certain differentially expressed microvessel (e.g., venular) genes of interest.

Discussion

The work described herein capitalizes on methods to develop and exploit a proprietary discovery platform that will lead to a new generation of anti-inflammatory drugs that specifically target venular endothelium, either globally or exclusively in a selected tissue. This strategy is in stark contrast to other currently prevalent strategies that are largely based on systemic administration of anti-inflammatory drugs. One of the key anticipated benefits of the strategy is the reduction of adverse side effects in uninvolved tissue during anti-inflammatory treatment. In the following, we provide some examples of molecules and strategies that may be employed based on putative candidate genes disclosed herein.

Among the genes that over-represented in V-ECs compared to NV-ECs and shared between venules in multiple (or all) tissues (Table 1), at least some genes are likely to play a role in the maintenance of venular phenotype and function. For example, ZFP521 is a strong candidate transcriptional regulator that might be involved in the maintenance of the venular phenotype. Indeed, data described herein demonstrates the absence of DARC expression on venules from Zfp521 ko mice (FIG. 22). Accordingly, without wishing to be bound by theory, it is believed that transcriptional regulator Zfp521 plays a role in maintenance of the venular phenotype, and that modulating Zfp521 expression and/or activity will modulate the venuleness of endothelial cells and/or microvessels in which they reside. RasGef1a is a member of the GEF family, which is known to regulate the activity of GTPases that are involved in key cellular processes, including cell growth, differentiation and movement, which each could contribute to the maintenance of venular phenotype.

Among the genes that are uniquely over-represented in V-ECs compared to NV-ECs in the skin (Table 2), 7 genes are predicted to be surface molecules, 2 genes are predicted to be transcription regulators, 4 are predicted to have enzymatic activity and 3 are predicted to have kinase activity. Each of these genes will be validated and evaluated as potential target for specific drugs to treat inflammatory skin diseases, such as psoriasis or atopic dermatitis.

Numerous surface molecules are disclosed herein and more are likely to be found as we apply our strategy to additional tissues. These molecules can be used to design novel strategies to deliver drugs to a specific vascular bed such as skin (Table 3), adipose tissue (Table 4) or lymph node (Table 5). For example, Fcer1a is a surface receptor for IgE, which we unexpectedly discovered to be specifically expressed by venules in visceral adipose tissue, but not in skin or lymph nodes (Table 3). Inflammation in visceral fat precipitated by high fat diet and obesity is thought to be a critical event in the pathogenesis of metabolic syndrome, hypertension, CVHD and type 2 diabetes. Selective targeting of adipose tissue venules with anti-inflammatory drugs offers the opportunity to dampen local inflammation and its detrimental sequalae with minimal off-target activity in other tissues.

The lists of genes that are shared by 2 (or more) different tissues allows for the development of drugs that will target only 2 (or more) tissues such as adipose tissue and skin without exerting uncontrolled systemic effects (Table 7).

The work described herein also contemplates that the genes that are over-represented in NV-ECs (Tables 8-14) may exert activities in NV-ECs that antagonize their ability to support inflammation. Inducing the expression of such genes in V-EC could be an alternative anti-inflammatory strategy. In addition, inhibition of genes that interfere with endothelial pro-inflammatory activity could be exploited to enhance effector cell recruitment during immunotherapy of malignancies or chronic infections.

In conclusion, inflammatory diseases are a major public health problem with few treatment options that are often poorly efficacious or fraught with significant side effects or both, leaving a substantial unmet need to develop better drugs to treat and prevent inflammatory diseases. None of the existing anti-inflammatory drugs specifically targets endothelial cells, let alone venules. Use of the methods described herein to isolate segmental endothelial cells from a variety of relevant tissues allows for the identification, for the first time, of candidate genes that represent an entirely novel class of targets for anti-inflammatory therapeutics. Such therapeutics may be small molecules, biologics, nucleotide-based agents or targeted carriers that selectively deliver one or more of these pharmacologically active agents to a relevant population of postcapillary venules. These agents would be employed for anti-inflammatory treatment of a variety of inflammatory disorders.

Example 2: Two-phased Approach to Discover Novel Anti-Inflammatory Molecules

Disclosed herein is a two-phased approach to discover novel anti-inflammatory molecules. An initial target identification phase (ongoing) will be followed by a drug screen phase.

Phase 1—Target Identification

A. Identification of Candidate Master Regulators of Global and Tissue-Specific Venular and Non-Venular EC Phenotype.

Restricted expression of genes to venular or non-venular ECs can be validated at the transcript level by qRT-PCR and/or at the proteomic level by IHC or flow cytometry.

B. Validation of Candidate Regulators of EC Specialization In Vitro and In Vivo.

The function of candidate genes and the pathways that are involved in the maintenance of the venular phenotype can be validated in both healthy and inflamed tissues, using in vitro and in vivo techniques including, but not limited to, RNA interference, transgenic and knockout mice, and transfection of cultured endothelial cells in flow-chamber assays.

RNA Interference siRNAs can be used to downregulate the expression of candidate gene products. This assay can be performed in vitro on cultured ECs or using cationic lipid-based nanoparticles as carriers for in vivo injections. If potent siRNAs against specific genes of interest are not already published, systematic screens followed by in vitro validation using EC cultures and/or transfected cell lines can be performed.

Transgenic and Knockout Mice

Transgenic and knockout mice can be used when available. The first and second approaches described above can be coupled to homing and/or IVM experiments to address the adhesive properties of the venular endothelium to confirm the implication of candidate regulators in the maintenance of venular phenotype in vivo.

Transfection of Cultured Endothelial Cells in Flow-chamber Assays

Transfection of cultured endothelial cells in flow-chamber assays can be performed to either induce or inhibit leukocyte adhesiveness on monolayers of early passage HUVEC (Human Umbilical Vein Endothelial Cells) or HCAEC (Human Coronary Artery Endothelial Cells).

Small Molecule Inhibitors

Small molecule inhibitors for a given candidate gene disclosed herein can be tested in vivo and in vitro.

C. Confirmation of Restricted Expression of Candidate Genes to Global and/or Tissue Specific Venules in Human Tissues.

In parallel, expression of candidate genes in human ECs can be investigated. In particular, V-ECs and NV-ECs can be sorted based on DARC expression, from fresh healthy human tissues such as adipose tissue and skin. qRT-PCR analysis can be performed to confirm the expression of genes of interest identified in mouse tissues.

Phase 2—Drug Screening

A. Development of Biochemical and/or Cell Based Screening Assays and Screening of Libraries for Small Molecules and/or Biological Agents.

Individual screening assays can be developed depending upon the nature and likely function of proteins of interest. Disclosed herein are a number of transcriptional regulators and enzymes already identified that will be further investigated. The decision of whether cell-based or cell-free assays should be employed will be made on a case-by-case basis.

B. Validation of Molecules in Secondary and Tertiary Assays In Vitro and In Vivo.

Agents that show specific activity can be tested for their ability to attenuate EC adhesiveness for leukocytes. Both in vitro and in vivo assays can be employed.

C. Development of Tissue-Selective Targeting Strategies Aimed to Deliver Therapeutic Payloads to Venules in Distinct Organs.

The work described herein identified a number of putative surface molecules that appear to be selectively expressed in venules or non-venules of a given tissue. These markers are of interest to specifically target anti-inflammatory drugs (e.g. corticosteroid-laden nanoparticles) to these tissues. Thus, fluorescent immunoreagents or nanoparticles conjugated to MAbs or other ligands specific for these candidate targets can be used to analyze the accumulation of targeted reagents (relative to appropriate controls) in tissues after i.v. infusion. Molecular targets in which cross-linking leads to internalization are likely to be effective endothelial cell targeting agents. Multi-photon intravital microscopy technology can be used to make such determinations by direct in situ imaging.

REFERENCES

1. Halin C, Rodrigo Mora J, Sumen C, von Andrian U H. In vivo imaging of lymphocyte trafficking. Annu Rev Cell Dev Biol. 2005; 21:581-603
2. Ley K, Gaehtgens P. Endothelial, not hemodynamic, differences are responsible for preferential leukocyte rolling in rat mesenteric venules. Circulation Research. 1991; 69:1034-1041
3. von Andrian U H, Mackay C R. T-cell function and migration. Two sides of the same coin. New Engl Jour Med. 2000; 343(14):1020-1034
4. Luster A. D., Alon R., von Andrian U H Immune cell migration in inflammation: present and future therapeutic targets. Nature Immunology. 2005; 6(12):1182-1190
5. Peiper S C, Wang Z-x, Neote K, et al. The Duffy antigen/receptor for chemokines (DARC) is expressed in endothelial cells of Duffy negative individuals who lack the erythrocyte receptor. J Exp Med. 1995; 181: 1311-1317
6. Hadley T J, Lu Z H, Wasniowska K, et al. Postcapillary Venule Endothelial Cells in Kidney Express a Multispecific Chemokine Receptor That Is Structurally and Functionally identical to the erythroid isoform, which is the Duffy Blood Group Antigen. J Clin Invest. 1994; 94:985-991

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of decreasing venuleness in a subject in need thereof, comprising:
    administering to the subject an effective amount of an agent that decreases expression of Zfp521.

2. The method according to claim 1, wherein Zfp521 is differentially expressed in skin venule endothelial cells compared to skin non-venule endothelial cells, or wherein Zfp521 is differentially expressed in adipose tissue venule endothelial cells compared to adipose tissue non-venule endothelial cells, or
    wherein Zfp521 is differentially expressed in lymph node venule endothelial cells compared to lymph node non-venule endothelial cells.

* * * * *